US012350364B2

(12) United States Patent
Jeffries et al.

(10) Patent No.: US 12,350,364 B2
(45) Date of Patent: Jul. 8, 2025

(54) LIPID BODY COMPOSITIONS, PRODUCTS MADE THEREFROM, METHODS OF MAKING SAME, AND METHODS OF USE

(71) Applicant: Xylome Corporation, Madison, WI (US)

(72) Inventors: Thomas W. Jeffries, Madison, WI (US); Thomas J. Kelleher, Thousand Oaks, CA (US); David Z. Mokry, Madison, WI (US); Richard Taylor, Madison, WI (US); Austin Gluth, Stoughton, WI (US); Merrill S. Goldenberg, Thousand Oaks, CA (US)

(73) Assignee: Xylome Corporation, Madison, WI (US)

( * ) Notice: Subject to any disclaimer, the term of this patent is extended or adjusted under 35 U.S.C. 154(b) by 533 days.

(21) Appl. No.: 17/776,485

(22) PCT Filed: Nov. 13, 2020

(86) PCT No.: PCT/US2020/060443

§ 371 (c)(1),
(2) Date: May 12, 2022

(87) PCT Pub. No.: WO2021/097230

PCT Pub. Date: May 20, 2021

(65) Prior Publication Data

US 2022/0401349 A1 Dec. 22, 2022

Related U.S. Application Data

(60) Provisional application No. 63/073,679, filed on Sep. 2, 2020, provisional application No. 62/935,878, filed on Nov. 15, 2019.

(51) Int. Cl.

| | |
|---|---|
| ***A61K 36/06*** | (2006.01) |
| ***A61K 8/55*** | (2006.01) |
| ***A61K 8/9728*** | (2017.01) |
| ***A61Q 19/00*** | (2006.01) |
| ***C12N 15/81*** | (2006.01) |

(52) U.S. Cl.

CPC ............ *A61K 8/9728* (2017.08); *A61K 8/553* (2013.01); *A61Q 19/00* (2013.01); *A61K 2800/56* (2013.01)

(58) Field of Classification Search

None

See application file for complete search history.

(56) References Cited

U.S. PATENT DOCUMENTS

| | | | | |
|---|---|---|---|---|
| 5,004,611 | A | 4/1991 | Leigh | |
| 5,545,398 | A | 8/1996 | Perricone | |
| 8,524,292 | B2 | 9/2013 | Kopas | |
| 10,662,448 | B2 | 5/2020 | Jeffries | |
| 2005/0079210 | A1 | 4/2005 | Gupta | |
| 2007/0196914 | A1* | 8/2007 | Murray | A61P 17/06 435/243 |
| 2013/0217083 | A1 | 8/2013 | VanWinkle-Swift | |
| 2013/0289289 | A1 | 10/2013 | Franzosi et al. | |
| 2014/0024714 | A1 | 1/2014 | Wijesundera et al. | |
| 2018/0245109 | A1 | 8/2018 | Jeffries et al. | |
| 2019/0105248 | A1* | 4/2019 | Yang | A61K 8/14 |

FOREIGN PATENT DOCUMENTS

| | | | | |
|---|---|---|---|---|
| WO | WO 2011/127118 A1 | 10/2011 | | |
| WO | WO-2017066569 A1 * | 4/2017 | | A23D 7/001 |

OTHER PUBLICATIONS

Kimura et al., Inhibition of Lipid Accumulation and Lipid Body Formation in Oleaginous Yeast by Effective Components in Spices, Carvacrol, Eugenol, Thymol, and Piperine, Journal of Agricultural and Food Chemistry (Year: 2006).*

Impact of wall material physicochemical characteristics on the stability of encapsulated phytochemicals: A review, Labuschagne (Year: 2018).*

Lauric Acid (the main constituent of coconut oil), May, Paul, University of Bristol (Year: 2012).*

Comparative genomics of biotechnologically important yeasts, Riley et al. (Year: 2016).*

International Search Report and Written Opinion for PCT Application PCT/US2020/060443 dated Feb. 19, 2021.

Alving, C.R., and S. C. Kinsy, "The preparation and properties of liposomes in LA and LAC states" *Immunochemistry*, vol. 8, No. 4, pp. 325-343, 1971, doi: 10.1016/0019-2791(71)90155-8.

Angerbauer, C., Siebenhofer, M., Mittelbach, M. & Guebitz, G.M. Conversion of sewage sludge into lipids by Lipomyces starkeyi for biodiesel production. *Bioresource Technology* 99, 3051-3056 (2008).

Andrews, B.A. & Asenjo, J.A. Enzymatic lysis and disruption of microbial cells. *Trends in Biotechnology* 5, 273-277 (1987).

Andrews, B.A. & Asenjo, J.A. Continuous-culture studies of synthesis and regulation of extracellular beta(1-3) glucanase and protease enzymes from Oerskovia xanthineolytica. *Biotechnol Bioeng* 30, 628-637 (1987).

Aono, R., Hammura, M., Yamamoto, M. & Asano, T. Isolation of extracellular 28- and 42-kilodalton beta-1,3-glucanases and comparison of three beta-1,3-glucanases produced by Bacillus circulans IAM1165. *Appl Environ Microbiol* 61, 122-129 (1995).

(Continued)

*Primary Examiner* — Tracy Liu
*Assistant Examiner* — Samantha J Knight
(74) *Attorney, Agent, or Firm* — Daniel A. Blasiole; DeWitt LLP

(57) ABSTRACT

The invention provides lipid bodies isolated from yeast, compositions comprising the lipid bodies, products made from the lipid bodies, methods of making the lipid bodies, and methods of using the lipid bodies. The lipid bodies of the invention have an exceptionally large size and high internal neutral lipid content, providing a number of advantages for a variety of practical applications.

32 Claims, 20 Drawing Sheets

Specification includes a Sequence Listing.

(56) References Cited

OTHER PUBLICATIONS

Athenstaedt, K. YALI0E32769g (DGA1) and YALI0E16797g (LRO1) encode major triacylglycerol synthases of the oleaginous yeast *Yarrowia lipolytica. Biochimica Et Biophysica Acta-Molecular and Cell Biology of Lipids* 1811, 587-596 (2011).
Bangham A.D., M. W. Hill, and N. G. A. Miller, *Preparation and use of liposomes as models of biological membranes* (Korn, Edward D.). 1974, pp. 1-68.
Barcia-Vieitez, R. & Ramos-Martinez, J.I. The Regulation of the Oxidative Phase of the Pentose Phosphate Pathway: New Answers to Old Problems. *Iubmb Life* 66, 775-779 (2014).
Bartolo-Aguilar, Y. et al. Autolysis of Pichia pastoris induced by cold. *AMB Express* 7, 9 (2017).
Becker, J. et al. Metabolic flux engineering of L-lysine production in *Corynebacterium glutamicum*—over expression and modification of G6P dehydrogenase. *Journal of Biotechnology* 132, 99-109 (2007).
Beer, M.U., Arrigoni, E. & Amado, R. Extraction of oat gum from oat bran: Effects of process on yield, molecular weight distribution, viscosity and (1->3)(1->4)-beta-D-glucan content of the gum. *Cereal Chemistry* 73, 58-62 (1996).
Beopoulos, A. et al. Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts. *Applied Microbiology and Biotechnology* 93, 1523-1537 (2012).
Bhutada G, Kavšček M, Hofer F, Gogg-Fassolter G, Schweiger M, Darnhofer B, Kordiš D, Birner-Gruenberger R, Natter K. Characterization of a lipid droplet protein from Yarrowia lipolytica that is required for its oleaginous phenotype. *Biochim Biophys Acta Mol Cell Biol Lipids*. Oct. 2018; 1863(10):1193-1205.
Bignell, G.R., Bruce, I.J. & Evans, I.H. Amylolytic enzymes of *Lipomyces starkeyi*: purification and size-determination. *Biotechnology Letters* 22, 1713-1718 (2000).
Bligh and Dyer. A rapid method of total lipid extraction and purification. *Canadian Journal of Biochemistry and Physiology* 37(8):911-7 (1959).
Boulton, C.A. & Ratledge, C. Use of transition studies in continuous cultures of *Lipomyces starkeyi*, an oleaginous yeast, to investigate the physiology of lipid accumulation. *Journal of general microbiology* 129, 2871-2876 (1983).
Bougis P., H. Rochat, G. Pieroni, and R. Verger, "Penetration of phospholipid Monolayers by cardiotoxins" (in English), *Biochemistry*, Article vol. 20, No. 17, pp. 4915-4920, 1981.
Braidman I. and G. Gregoriadis, "Preparation of glucocerebroside beta-glucosidase for entrapment in liposomes and treatment of patients with adult Gauchers disease " *Biochemical Society Transactions*, vol. 4, No. 2, pp. 259-261, 1976.
Calvey, C.H., Willis, L.B. & Jeffries, T.W. An optimized transformation protocol for *Lipomyces starkeyi. Current Genetics* 60, 223-230 (2014).
Calvey, C.H., Su, Y.K., Willis, L.B., McGee, M. & Jeffries, T.W. Nitrogen limitation, oxygen limitation, and lipid accumulation in *Lipomyces starkeyi. Bioresource Technology* 200, 780-788 (2016).
Cannella, D. & Jorgensen, H. Do New Cellulolytic Enzyme Preparations Affect the Industrial Strategies for High Solids Lignocellulosic Ethanol Production? *Biotechnology and Bioengineering* 111, 59-68 (2014).
Cardenas, J. & Da Silva, N.A. Engineering cofactor and transport mechanisms in *Saccharomyces cerevisiae* for enhanced acetyl-CoA and polyketide biosynthesis. *Metabolic Engineering* 36, 80-89 (2016).
Chen, L., Zhou, X.S., Fan, W.M. & Zhang, Y.X. Expression, purification and characterization of a recombinant *Lipomyces starkeyi* dextranase in *Pichia pastoris. Protein Expression and Purification* 58, 87-93 (2008).
Choi, J.W. & Da Silva, N.A. Improving polyketide and fatty acid synthesis by engineering of the yeast acetyl-CoA carboxylase. *Journal of Biotechnology* 187, 56-59 (2014).
Collett, J.R., Meyer, S. & Jones, S. Preliminary economics for hydrocarbon fuel production from cellulosic sugars. (2014).
Connell G. H. and C. E. Skinner, "The external surface of the human body as a habitat for nonfermenting nonpigmented yeasts " *Journal of Bacteriology*, vol. 66, No. 6, pp. 627-633, 1953.
Connell G. H., C. E. Skinner, and R. C. Hurd, "*Lipomyces starkeyi* on the skin surface of the human body" *Mycologia*, vol. 46, No. 1, pp. 12-15, 1954.
Courchesne, N.M.D., Parisien, A., Wang, B. & Lan, C.Q. Enhancement of lipid production using biochemical, genetic and transcription factor engineering approaches. *J Biotechnol* 141, 31-41 (2009).
Demel R. A., S. C. Kinsky, C. B. Kinsky, and Vandeenen. L.L.M., "Effects of temperature and cholesterol on glucose permeability of liposomes prepared with natural and synthetic lecithins" *Biochimica Et Biophysica Acta*, vol. 150, No. 4, pp. 655-665, 1968.
Dewi, R., Mubarik, N. & Suhartono, M. Medium optimization of beta-glucanase production by *Bacillus subtilis* SAHA 32.6 used as biological control of oil palm pathogen. *Emirates Journal of Food and Agriculture* 28, 116-125 (2016).
Doi, K. & Doi, A. Cloning and expression in *Escherichia coli* of the gene for an Arthrobacter beta-(1----3)-glucanase. *J Bacteriol* 168, 1272-1276 (1986).
D. T. Downing, J. S. Strauss, and P. E. Pochi, "Variability in the chemical composition of human skin surface lipids," *J Invest Dermatol*, vol. 53, No. 5, pp. 322-327, Nov. 1969, doi: 10.1038/jid.1969.157.
Egbaria K. and N. Weiner, "Liposomes as topical drug delivery system" *Advanced Drug Delivery Reviews*, vol. 5, No. 3, pp. 287-300, 1990.
Esposito, S. Nitrogen Assimilation, Abiotic Stress and Glucose 6-Phosphate Dehydrogenase: The Full Circle of Reductants. *Plants-Basel* 5 (2016).
Evans, C.T. & Ratledge, C. Possible regulatory roles of ATP-citrate lyase, malic enzyme and AMP deaminate in lipid accumulation by *Rhodosporidium toruloides* CBS-14. *Canadian Journal of Microbiology* 31, 1000-1005 (1985).
Ferracini-Santos, L. & Sato, H.H. Production of alkaline protease from *Cellulosimicrobium cellulans. Braz J Microbiol* 40, 54-60 (2009).
Ferrer, P. et al. Nucleotide sequence of a beta-1,3-glucanase isoenzyme IIA gene of Oerskovia xanthineolytica LL G109 (Cellulomonas cellulans) and initial characterization of the recombinant enzyme expressed in Bacillus subtilis. *Journal of Bacteriology* 178, 4751-4757 (1996).
Ferrer, P. et al. Molecular cloning of a lytic beta-1,3-glucanase gene from Oerskovia xanthineolytica LLG109. A beta-1,3-glucanase able to selectively permeabilize the yeast cell wall. *Annals of the New York Academy of Sciences* 782, 555-565 (1996).
Ferrer, P. Revisiting the Cellulosimicrobium cellulans yeast-lytic beta-1,3-glucanases toolbox: a review. *Microb Cell Fact* 5, 10 (2006).
Fifield R., "Liposomes—bags of biological potential " *New Scientist*, vol. 88, No. 1223, pp. 150-153, 1980.
Fishman Y. and N. Citri, "L-Asparaginase entrapped in liposomes—preparation and properties" *FEBS Letters*, vol. 60, No. 1, pp. 17-20, 1975.
Flores, C.L., and Gancedo, C. *Yarrowia lipolytica* mutants devoid of pyruvate carboxylase activity show an unusual growth phenotype, *Eukaryot. Cell* 4 (2005) 356-364.
Gallagher, A.M., Kelly, C.T. & Fogarty, W.M. A novel extracellular carbohydrase produced by *Lipomyces tetrasporus. Applied Microbiology and Biotechnology* 35, 455-460 (1991).
Ganceviciene R., A. I. Liakou, A. Theodoridis, E. Makrantonaki, and C. C. Zouboulis, "Skin anti-aging strategies," (in eng), *Dermatoendocrinol*, vol. 4, No. 3, pp. 308-319, 2012.
Garay, L.A. et al. Eighteen new oleaginous yeast species. *Journal of industrial microbiology & biotechnology* 43, 887-900 (2016).
Garber AT, Segall J. The SPS4 gene of *Saccharomyces cerevisiae* encodes a major sporulation-specific Mrna. *Mol Cell Biol*. Dec. 1986;6(12):4478-85.
Gershenwald J. E., A. C. Halpern, and V. K. Sondak, "Melanoma Prevention-Avoiding Indoor Tanning and Minimizing Overexpo-

(56) References Cited

OTHER PUBLICATIONS sure to the Sun," *Jama-Journal of the American Medical Association*, vol. 316, No. 18, pp. 1913-1914, Nov. 2016.
Gibson, D.G et al. Enzymatic assembly of DNA molecules up to several hundred kilobases. *Nature Methods* 6, 343-U341 (2009).
Gietz, R. D., and R.A. Woods, Transformation of yeast by lithium acetate/single stranded carrier DNA/polyethylene glycol method. *Methods in Enzymology* 350:87-96 (2002).
Gomma, A.E., Lee, S.K., Sun, S.M., Yang, S.H. & Chung, G. Improvement in Oil Production by Increasing Malonyl-CoA and Glycerol-3-Phosphate Pools in *Scenedesmus quadricauda. Indian Journal of Microbiology* 55, 447-455 (2015).
Goon D. E., S. Kadir, N. Ab Latip, S. Ab Rahim, and M. Mazlan, "Palm Oil in Lipid-Based Formulations and Drug Delivery Systems," *Biomolecules*, vol. 9, No. 2, Feb. 2019.
Gong, Z.W. et al. Co-fermentation of cellobiose and xylose by *Lipomyces starkeyi* for lipid production. *Bioresource Technology* 117, 20-24 (2012).
Gorner, C. et al. Genetic engineering and production of modified fatty acids by the non-conventional oleaginous yeast *Trichosporon oleaginosus* ATCC 20509. *Green Chemistry* 18, 2037-2046 (2016).
Hamid, A.A., Mokhtar, N.F., Taha, E.M., Omar, O. & Yusoff, W.M.W. The role of ATP citrate lyase, malic enzyme and fatty acid synthase in the regulation of lipid accumulation in *Cunninghamella* sp 2A1. *Annals of Microbiology* 61, 463-468 (2011).
Hammond, E.G., Johnson, L.A., Su, C., Wang, T. & White, P.J. Soybean oil. Bailey's Industrial Oil and Fat Products (2005).
Hashida M., S. Kawakami, and F. Yamashita, "Lipid carrier systems for targeted drug and gene delivery," (in English), *Chem. Pharm. Bull*., Review vol. 53, No. 8, pp. 871-880, Aug. 2005.
Holdsworth, J.E. & Ratledge, C. Lipid turnover in oleaginous yeasts. *Journal of General Microbiology* 134, 339-346 (1988).
Holdsworth, J.E., Veenhuis, M. & Ratledge, C. Enzyme activities in oleaginous yeasts accumulating and utilizing exogenous or endogenous lipids. *Journal of General Microbiology* 134, 2907-2915 (1988).
Huang, C. et al. Bioconversion of Corncob Acid Hydrolysate into Microbial Oil by the Oleaginous Yeast Lipomyces starkeyi. *Applied Biochemistry and Biotechnology* 172, 2197-2204 (2014).
Ingebrigtsen, L. & Brandl, M. Determination of the size distribution of liposomes by SEC fractionation, and PCS analysis and enzymatic assay of lipid content. *AAPS PharmSciTech* 3, E7-E7 (2002).
Jeffries, T.W. Effects of nitrate on fermentation of xylose and glucose by *Pachysolen tannophilus. Bio-Technology* 1, 503-506 (1983).
Jeffries T.W., Eveleigh D.E., Macmillan J.D., Parrish F.W., & Reese E.T. (1977) Enzymatic hydrolysis of walls of yeast cells and germinated fungal spores. *Biochimica Et Biophysica Acta* 499(1):10-23.
Jeffries, T.W. & Macmillan, J.D. Action patterns of (1→3)-β-d-glucanases from *Oerskovia xanthineolytica* on laminaran, lichenan, and yeast glucan. *Carbohydr. Res*. 95, 87-100 (1981).
Jiang Z. X. and J. Delacruz, "Appearance benefits of skin moisturization," *Skin Research and Technology*, vol. 17, No. 1, pp. 51-55, Feb. 2011.
Kafi R. et al., "Improvement of naturally aged skin with vitamin A (retinol)," *Archives of Dermatology*, vol. 143, No. 5, pp. 606-612, May 2007.
Kandror, O., Bretschneider, N., Kreydin, E., Cavalieri, D. & Goldberg, A.L. Yeast adapt to near-freezing temperatures by STRE/Msn2,4-dependent induction of trehalose synthesis and certain molecular chaperones. *Molecular Cell* 13, 771-781 (2004).
Kaneko, T., Kitamura, K. & Yamamoto, Y. Susceptibilities of Yeasts to Yeast Cell Wall Lytic Enzyme of Arthrobacter luteus. *Agricultural and Biological Chemistry* 37, 2295-2302 (2014).
Kang, H.K. et al. Cloning and characterization of a dextranase gene from *Lipomyces starkeyi* and its expression in *Saccharomyces cerevisiae. Yeast* 22, 1239-1248 (2005).
Kildegaard, K.R. et al. Engineering and systems-level analysis of *Saccharomyces cerevisiae* for production of 3-hydroxypropionic acid via malonyl-CoA reductase-dependent pathway. *Microbial Cell Factories* 15 (2016).
Kim, Y. et al. Composition of corn dry-grind ethanol by-products: DDGS, wet cake, and thin stillage. *Bioresource Technology* 99, 5165-5176 (2008).
Kitamura, K., Kaneko, T. & Yamamoto, Y. Lysis of viable yeast cells by enzymes of Arthrobacter luteus. *Arch Biochem Biophys* 145, 402-404 (1971).
Kruger, J.S. et al. Recovery of Fuel-Precursor Lipids from Oleaginous Yeast. *ACS Sustainable Chemistry & Engineering* 6, 2921-2931 (2018).
Kvorning S. A. and E. Kirk, "The correlation between the clinical appearance of the skin and the skin lipid secretion in middle-aged and old individuals" *Journals of Gerontology*, vol. 4, No. 2, pp. 113-120, 1949.
Lee, S.Y. et al. Demonstration of two independent dextranase and amylase active sites on a single enzyme elaborated by *Lipomyces starkeyi* KSM 22. *Journal of Microbiology and Biotechnology* 13, 313-316 (2003).
Leiva-Candia, D.E. et al. The potential for agro-industrial waste utilization using oleaginous yeast for the production of biodiesel. *Fuel* 123, 33-42 (2014).
Li, Z. et al. Overexpression of malic enzyme (ME) of *Mucor circinelloides* improved lipid accumulation in engineered *Rhodotorula glutinis. Appl Microbiol Biotechnol* (2013).
Liu, L.P. et al. Efficient microbial oil production on crude glycerol by Lipomyces starkeyi AS 2.1560 and its kinetics. *Process Biochemistry* 58, 230-238 (2017).
Lodder, J., Acomina & Kreger-Van Rij, N.J.W. The yeasts—a taxonomic study. (1952). (Book).
Lopezberestein G., "Liposomes as carriers of antimicrobial agents " *Antimicrobial Agents and Chemotherapy*, vol. 31, No. 5, pp. 675-678, May 1987.
Mann, J.W., Jeffries, T.W. & Macmillan, J.D. Production and ecological significance of yeast cell wall-degrading enzymes from oerskovia. *Appl Environ Microbiol* 36, 594-605 (1978).
Marchand, G. et al. Alternative methods for genetic transformation of Pseudozyma antarctica, a basidiomycetous yeast-like fungus. *Journal of Microbiological Methods* 70, 519-527 (2007).
Mayer L. D., M. B. Bally, M. J. Hope, and p. R. Cullis, "Techniques for encapsulating bioactive agents into liposomes" *Chemistry and Physics of Lipids*, vol. 40, No. 2-4, pp. 333-345, Jun.-Jul. 1986.
McClements D. J., *Nanoparticle- and microparticle-based delivery systems. Encapsulation, protection and release of active compounds* (Nanoparticle- and microparticle-based delivery systems. Encapsulation, protection and release of active compounds.). 2015, pp. xxvi-546. (Book).
McNeil, B.A. & Stuart, D.T. Lipomyces starkeyi: an emerging cell factory for production of lipids, oleochemicals and biotechnology applications. *World Journal of Microbiology & Biotechnology* 34 (2018).
Michelon, M., de Matos de Borba, T., da Silva Rafael, R., Burkert, C.A.V. & de Medeiros Burkert, J.F. Extraction of carotenoids from Phaffia rhodozyma: A comparison between different techniques of cell disruption. *Food Science and Biotechnology* 21, 1-8 (2012).
Mitra, D. et al. Value-added oil and animal feed production from corn-ethanol stillage using the oleaginous fungus Mucor circinelloides. *Bioresource Technology* 107, 368-375 (2012).
Moritz, B., Striegel, K., De Graaf, A.A. & Sahm, H. Kinetic properties of the glucose-6-phosphate and 6-phosphogluconate dehydrogenases from *Corynebacterium glutamicum* and their application for predicting pentose phosphate pathway flux in vivo. *European journal of biochemistry / FEBS* 267, 3442-3452 (2000).
Naganuma, T., Uzuka, Y., Tanaka, K. & Iizuka, H. Differences in enzyme activities of *Lipomyces starkeyi* between cells accumulating lipid and proliferating cells. *Journal of basic microbiology* 27, 35-42 (1987).
Nakabayashi, M. et al. Structure of the gene encoding laminaripentaose-producing β-1,3-glucanase (LPHase) of *Streptomyces matensis* DIC-108. *Journal of Fermentation and Bioengineering* 85, 459-464 (1998).

(56) References Cited

OTHER PUBLICATIONS

Nisha, A., Sankar, K.U. & Venkateswaran, G. Supercritical CO2 extraction of Mortierella alpina single cell oil: Comparison with organic solvent extraction. *Food Chemistry* 133, 220-226 (2012).
Ochsenreitheri, K., Gluck, C., Stressler, T., Fischer, L. & Syldatk, C. Production Strategies and Applications of Microbial Single Cell Oils. *Frontiers in Microbiology* 7 (2016).
Oguro, Y. et al. Multicopy integration and expression of heterologous genes in the oleaginous yeast, *Lipomyces starkeyi*. Bio*science Biotechnology and Biochemistry* 79, 512-515 (2015).
Ohnishi, J., Katahira, R., Mitsuhashi, S., Kakita, S. & Ikeda, M. A novel gnd mutation leading to increased L-lysine production in *Corynebacterium glutamicum. FEMS Microbiology Letters* 242, 265-274 (2005).
Okada, T. et al. Structure of the gene encoding β-1,3-glucanase B of Bacillus circulans WL-12. *Journal of Fermentation and Bioengineering* 80, 229-236 (1995).
Pan, L.-X. et al. Isolation of the oleaginous yeasts from the soil and studies of their lipid-producing capacities. *Food Technol. Biotechnol* 47, 215-220 (2009).
Papanikolaou, S., Chevalot, I., Komaitis, M., Aggelis, G. & Marc, I. Kinetic profile of the cellular lipid composition in an oleaginous *Yarrowia lipolytica* capable of producing a cocoa-butter substitute from industrial fats. *Antonie Van Leeuwenhoek International Journal of General and Molecular Microbiology* 80, 215-224 (2001).
Patel H. M. and B. E. Ryman, "Oral administration of insulin by encapsulation within liposomes" *FEBS Letters*, vol. 62, No. 1, pp. 60-63, 1976.
Punpeng, B., Nakata, Y., Goto, M., Teramoto, Y. & Hayashida, S. A novel raw-starch digesting yeast alpha amylase from *Lipomyces starkeyi. Journal of Fermentation and Bioengineering* 73, 108-111 (1992).
Rangasamy, D. & Ratledge, C. Genetic Enhancement of Fatty Acid Synthesis by Targeting Rat Liver ATP:Citrate Lyase into Plastids of Tobacco. *Plant Physiology* 122, 1231-1238 (2000).
Ratledge, C. Lipid biotechnology—a wonderland for the microbial physiologist. *Journal of the American Oil Chemists Society* 64, 1647-1656 (1987).
Ratledge, C. Regulation of lipid accumulation in oleaginous microorganisms. *Biochemical Society Transactions* 30, 1047-1050 (2002).
Ratledge, C. Fatty acid biosynthesis in microorganisms being used for Single Cell Oil production. *Biochimie* 86, 807-815 (2004).
Ratledge, C. The role of malic enzyme as the provider of NADPH in oleaginous microorganisms: a reappraisal and unsolved problems. *Biotechnol. Lett*. 36, 1557-1568 (2014).
Rhie G. E. et al., "Aging- and photoaging-dependent changes of enzymic and nonenzymic antioxidants in the epidermis and dermis of human skin in vivo," *Journal of Investigative Dermatology*, vol. 117, No. 5, pp. 1212-1217, Nov. 2001.
Riley R, et al. (2016) Comparative genomics of biotechnologically important yeasts. *Proceedings of the National Academy of Sciences* 113(35):9882-9887.
Rippa, M., Giovannini, P.P., Barrett, M.P., Dallocchio, F. & Hanau, S. 6-phosphogluconate dehydrogenase: the mechanism of action investigated by a comparison of the enzyme from different species. *Biochimica Et Biophysica Acta-Protein Structure and Molecular Enzymology* 1429, 83-92 (1998).
Ruenwai, R., Cheevadhanarak, S. & Laoteng, K. Overexpression of acetyl-CoA carboxylase gene of *Mucor rouxii* enhanced fatty acid content in *Hansenula polymorpha*. Mol Biotechnol 42, 327-332 (2009).
Ryu, S.J. et al. Purification and partial characterization of a novel glucanhydrolase from *Lipomyces starkeyi* KSM 22 and its use for inhibition of insoluble glucan formation. *Bioscience Biotechnology and Biochemistry* 64, 223-228 (2000).
Saenge, C., Cheirsilp, B., Suksaroge, T.T. & Bourtoom, T. Potential use of oleaginous red yeast *Rhodotorula glutinis* for the bioconversion of crude glycerol from biodiesel plant to lipids and carotenoids. *Process Biochemistry* 46, 210-218 (2011).
Schwendener, R.A. & Schott, H. Liposome formulations of hydrophobic drugs. *Methods in molecular biology* (*Clifton, N.J.*) 605, 129-138 (2010).
Severa, G., Kumar, G. & Cooney, M.J. Corecovery of Lipids and Fermentable Sugars from Rhodosporidium toruloides Using Ionic Liquid Cosolvents: Application of Recycle to Batch Fermentation. *Biotechnology Progress* 30, 1239-1242 (2014).
Shi, S.B., Chen, Y., Siewers, V. & Nielsen, J. Improving Production of Malonyl Coenzyme A-Derived Metabolites by Abolishing Snf1-Dependent Regulation of Acc1. *Mbio* 5 (2014).
Shindo Y., E. Witt, D. Han, W. Epstein, and L. Packer, "Enzymic and non-enzymic antioxidants in epidermis and dermis of human skin," (in eng), *J Invest Dermatol*, vol. 102, No. 1, pp. 122-124, Jan. 1994, doi: 10.1111/1523-1747.
Shrestha, K.L. et al. Characterization and identification of essential residues of the glycoside hydrolase family 64 laminaripentaose-producing-beta-1, 3-glucanase. *Protein Eng Des Sel* 24, 617-625 (2011).
Sikl, D., Masler, L. & Bauer, S. Extracellular polysaccharides of *Lipomyces starkeyi* Lodder et Kreuger van Rij. Isolation and structural features of galactomannan *Collection of Czechoslovak Chemical Communications* 33, 1157-1164 (1968).
Sitepu, et al. An improved high-throughput Nile red fluorescence assay for estimating intracellular lipids in a variety of yeast species. *Journal of Microbiological Methods* 91:321-328 (2012).
Sitepu, I.R. et al. Oleaginous yeasts for biodiesel: Current and future trends in biology and production. *Biotechnology Advances* 32, 1336-1360 (2014).
Signori, L. et al. Assessing an effective feeding strategy to optimize crude glycerol utilization as sustainable carbon source for lipid accumulation in oleaginous yeasts. *Microbial Cell Factories* 15 (2016).
Spier, F., Buffon, J.G. & Burkert, C.A.V. Bioconversion of Raw Glycerol Generated from the Synthesis of Biodiesel by Different Oleaginous Yeasts: Lipid Content and Fatty Acid Profile of Biomass. *Indian Journal of Microbiology* 55, 415-422 (2015).
Steyn, A.J.C., Marmur, J. & Pretorius, I.S. Cloning, sequence analysis and expression in yeasts of a cDNA-containing a *Lipomyces kononenkoae* alpha-amylase encoding gene. *Gene* 166, 65-71 (1995).
Szoka F. J. and D. Papahadjopoulos, "Comparative properties and methods of lipid vesicles liposomes" in Mullins, L. J., (Annual Review of Biophysics and Bioengineering, 1980, pp. P467-508.
Tai, M. & Stephanopoulos, G. Engineering the push and pull of lipid biosynthesis in oleaginous yeast *Yarrowia lipolytica* for biofuel production. *Metabolic Engineering* 15, 1-9 (2013).
Tanabe, Y. & Oda, M. Molecular characterization of endo-1,3-beta-glucanase from Cellulosimicrobium cellulans: effects of carbohydrate-binding module on enzymatic function and stability. *Biochim Biophys Acta* 1814, 1713-1719 (2011).
Tang, W., Zhang, S., Wang, Q., Tan, H. & Zhao, Z.K. The isocitrate dehydrogenase gene of oleaginous yeast *Lipomyces starkeyi* is linked to lipid accumulation. *Can J Microbiol* 55, 1062-1069 (2009).
Tang, X.L., Feng, H.X. & Chen, W.N. Metabolic engineering for enhanced fatty acids synthesis in *Saccharomyces cerevisiae. Metabolic Engineering* 16, 95-102 (2013).
Tang, X.L. & Chen, W.N. Investigation of fatty acid accumulation in the engineered *Saccharomyces cerevisiae* under nitrogen limited culture condition. *Bioresource Technology* 162, 200-206 (2014).
Tchakouteu, S.S. et al. Lipid production by yeasts growing on biodiesel-derived crude glycerol: strain selection and impact of substrate concentration on the fermentation efficiency. *Journal of Applied Microbiology* 118, 911-927 (2015).
Tentsova A. I., N. S. Kovaleva, E. A. Yarova, and N. N. Ivkov, "Liposomes and the possibilities of their use in pharmacy and pharmacology" *Farmatsiya* (*Moscow*), vol. 25, No. 3, pp. 82-85, 1976. (English Copy Not Available).
Uzuka, Yasuyuki; Kanamori, Takeshi; Koga, Tetsuro; Tanaka, Kentaro; Naganuma, Takafumi. Isolation and Chemical Composition of Intracellular Oil Globules from the Yeast *Lipomyces starkeyi. J. Gen. Appl. Microbiol*., 21, 157-168 (1975).
Van Rossum, H.M., Kozak, B.U., Pronk, J.T. & van Maris, A.J.A. Engineering cytosolic acetyl-coenzyme A supply in *Saccharomyces*

(56) References Cited

OTHER PUBLICATIONS

*cerevisiae*: Pathway stoichiometry, free-energy conservation and redox-cofactor balancing. *Metabolic Engineering* 36, 99-115 (2016).
Velasco, P., Sieiro, A.M., Ibarguren, I., Ramosmartinez, J.I. & Barcia, R. The Modulation of the Oxidative Phase of the Pentose-Phosphate Pathway in Mouse Liver. *International Journal of Biochemistry & Cell Biology* 27, 1015-1019 (1995).
Vicente, G. et al. Direct transformation of fungal biomass from submerged cultures into biodiesel. *Energy & Fuels* 24, 3173-3178 (2010).
Wältermann M, Steinbüchel A. Neutral lipid bodies in prokaryotes: recent insights into structure, formation, and relationship to eukaryotic lipid depots. *J Bacteriol*. Jun. 2005;187(11):3607-19.
Wang, Z.P., Xu, H.M., Wang, G.Y., Chi, Z. & Chi, Z.M. Disruption of the MIG1 gene enhances lipid biosynthesis in the oleaginous yeast *Yarrowia lipolytica* ACA-DC 50109. *Biochimica Et Biophysica Acta-Molecular and Cell Biology of Lipids* 1831, 675-682 (2013).
Wang, W. et al. Fatty alcohol production in Lipomyces starkeyi and Yarrowia lipolytica. *Biotechnology for Biofuels* 9 (2016).
Wang, J.C., Xu, R.H., Wang, R.L., Haque, M.E. & Liu, A.Z. Overexpression of ACC gene from oleaginous yeast *Lipomyces starkeyi* enhanced the lipid accumulation in *Saccharomyces cerevisiae* with increased levels of glycerol 3-phosphate substrates. *Bioscience Biotechnology and Biochemistry* 80, 1214-1222 (2016).
Watanabe, T. et al. Expression in *Escherichia coli*of theBacillus circulans WL-12 Structural Gene for β-1,3-Glucanase A. *Agricultural and Biological Chemistry* 53, 1759-1767 (2014).
Wei, T., Sufang, Z., Qian, W., Haidong, T. & Zongbao Kent, Z. The isocitrate dehydrogenase gene of oleaginous yeast *Lipomyces starkeyi* is linked to lipid accumulation. *Canadian Journal of Microbiology* 55, 1062-1069 (2009).
Wenning, L., Yu, T., David, F., Nielsen, J. & Siewers, V. Establishing very long-chain fatty alcohol and wax ester biosynthesis in *Saccharomyces cerevisiae. Biotechnology and Bioengineering* 114, 1025-1035 (2017).
Wilkie, A.C., Riedesel, K.J. & Owens, J.M. Stillage characterization and anaerobic treatment of ethanol stillage from conventional and cellulosic feedstocks. *Biomass & Bioenergy* 19, 63-102 (2000).
Wynn, J.P., Hamid, A.B.A. & Ratledge, C. The role of malic enzyme in the regulation of lipid accumulation in filamentous fungi. *Microbiology—Uk* 145, 1911-1917 (1999).
Xavier, M.C.A., Coradini, A.L.V., Deckmann, A.C. & Franco, T.T. Lipid production from hemicellulose hydrolysate and acetic acid by *Lipomyces starkeyi* and the ability of yeast to metabolize inhibitors. *Biochemical Engineering Journal* 118, 11-19 (2017).
Xuan, J.W., Fournier, P. & Gaillardin, C. Cloning of the Lys5 gene encoding saccharopine dehydrogenase from the yeast *Yarrowia lipolytica. Current Genetics* 14, 15-21 (1988).
Yen, H.-W., Yang, Y.-C. & Yu, Y.-H. Using crude glycerol and thin stillage for the production of microbial lipids through the cultivation of *Rhodotorula glutinis. Journal of Bioscience and Bioengineering* 114, 453-456 (2012).
Yu, X.C., Dong, T., Zheng, Y.B., Miao, C. & Chen, S.L. Investigations on cell disruption of oleaginous microorganisms: Hydrochloric acid digestion is an effective method for lipid extraction. *European Journal of Lipid Science and Technology* 117, 730-737 (2015).
Yu, X.C., Zheng, Y.B., Dorgan, K.M. & Chen, S.L. Oil production by oleaginous yeasts using the hydrolysate from pretreatment of wheat straw with dilute sulfuric acid. *Bioresource Technology* 102, 6134-6140 (2011).
Zha, J., Shen, M.H., Hu, M.L., Song, H. & Yuan, Y.J. Enhanced expression of genes involved in initial xylose metabolism and the oxidative pentose phosphate pathway in the improved xylose-utilizing *Saccharomyces cerevisiae* through evolutionary engineering. *Journal of Industrial Microbiology & Biotechnology* 41, 27-39 (2014).
Zhang, Y., Adams, I.P. & Ratledge, C. Malic enzyme: the controlling activity for lipid production? Overexpression of malic enzyme in *Mucor circinelloides* leads to a 2.5-fold increase in lipid accumulation. *Microbiology-Sgm* 153, 2013-2025 (2007).
Zhang, Y., Wang, Z.Y., He, X.P., Liu, N. & Zhang, B.R. New industrial brewing yeast strains with ILV2 disruption and LSD1 expression. *International Journal of Food Microbiology* 123, 18-24 (2008).
Zhang, M., Galdieri, L. & Vancura, A. The Yeast AMPK Homolog SNF1 Regulates Acetyl Coenzyme A Homeostasis and Histone Acetylation. *Molecular and Cellular Biology* 33, 4701-4717 (2013).
Zhao, X., Kong, X.L., Hua, Y.Y., Feng, B. & Zhao, Z.B. Medium optimization for lipid production through co-fermentation of glucose and xylose by the oleaginous yeast *Lipomyces starkeyi. European Journal of Lipid Science and Technology* 110, 405-412 (2008).
Zhou, Y.J.J. et al. Production of fatty acid-derived oleochemicals and biofuels by synthetic yeast cell factories. *Nature Communications* 7 (2016).
Zhu, Z.W. et al. A multi-omic map of the lipid-producing yeast Rhodosporidium toruloides, *Nature Communications*, vol. 3 (2012).

* cited by examiner

400x 45.5 Average Age
28-65 Age Range
27.6 Average uses per person
579 Exposures
0 Number of adverse events and skin irritations

SEQUENCE LISTING

```
<160> NUMBER OF SEQ ID NOS: 43

<210> SEQ ID NO 1
<211> LENGTH: 1387
<212> TYPE: DNA
<213> ORGANISM: Lipomyces starkeyi
<220> FEATURE:
<221> NAME/KEY: Intron
<222> LOCATION: (42)..(89)
<220> FEATURE:
<221> NAME/KEY: Intron
<222> LOCATION: (168)..(220)
<220> FEATURE:
<221> NAME/KEY: Intron
<222> LOCATION: (747)..(799)

<400> SEQUENCE: 1

atgagtgaga aggcagagat cgaggttccg ccgcaaaaat cgtgagtacg tcggatgctt      60

gcttaggaca gatgctgatt gctatttagg acattccctc gcagtgtgca cttcgctcca     120

cttcatattc cactggagag acgcctacag actttggcag tcttattgta agtctcgtct     180

accttacggt gacatggagt cgctaatgat atgagggtag ccacactgtc gcgctaccat     240

actgcatcgg tctgttcttt ctcatgctcg cgttccctcc tttttggcca ttattggtaa     300
```

```
tgtatgtcat atacgcatac gggttcgacc actcgagctc gaacggagag atctcccgcc    360

ggcgatcgcc gctgtttcga agactcccgt tgttcaggct gtattgtgat tacttcccca    420

tccacattca ccgggaggtt ccgctcgagc cgacgtttcc tggtcgcctt cgcgaaccga    480

gtggccttgt cgagcggtgg attgcgaaga tgttcggcgt gcaggacgct gttgtcgagg    540

gaaatgaatc tgacgttaag gccacggcca acggcaatgg gacgacgaaa gaaatcggac    600

cgacgtatgt tttcggctat catccgcatg gaattgttag cttgggtgcg tttggtgcta    660

ttggtacgga aggcgctgga tgggagaagc tctttcctgg gatcccggtg tcactgctga    720

ctctcgaaac aaatttcagc cttccagtag gttgatgttt gggtttgtct gccatgggat    780

agtactaata acagattagt tttacagaga gtatttgctg tcacttggga ttgcttcagt    840

atctcgacgg tcttgtacca atctcctcaa acacgaccaa tccatctgca tcgttatcgg    900

cggcgcccaa gagtcgctct tagcggaacc aggcactcta gatctgatcc tcgttaaacg    960

tcgcggtttt gtcaaacttg caatgtcaac ggcgcgggta tctgaccaac cgatttgtct   1020

tgttccgatc ctcagtttcg gcgagaacga cgtgtacgac caagtccgcg gggaccgatc   1080

gtcgaagttg tataagatcc agacttttat caagaaagcg gccgggttta cgctaccatt   1140

gatgtatgcg cgcggtatat ttaattacga ctttgggctg atgccgtacc gcaggcaaat   1200

gacgctcgtg gtcggcaagc cgattgcagt gccgtacgtg gcccagccta cggaggctga   1260

aatcgaagtg tatcacaagc agtacatgga tgaattgagg aggttatggg acacgtataa   1320

ggacgactat tttgtagacc acaagggcaa gggggtcaag aattccgaga tgcgttttgt   1380

ggagtaa                                                             1387
```

```
<210> SEQ ID NO 2
<211> LENGTH: 410
<212> TYPE: PRT
<213> ORGANISM: Lipomyces starkeyi

<400> SEQUENCE: 2

Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser Ser
65                  70                  75                  80

Asn Gly Glu Ile Ser Arg Arg Arg Ser Pro Leu Phe Arg Arg Leu Pro
                85                  90                  95

Leu Phe Arg Leu Tyr Cys Asp Tyr Phe Pro Ile His Ile His Arg Glu
            100                 105                 110

Val Pro Leu Glu Pro Thr Phe Pro Gly Arg Leu Arg Glu Pro Ser Gly
        115                 120                 125

Leu Val Glu Arg Trp Ile Ala Lys Met Phe Gly Val Gln Asp Ala Val
    130                 135                 140

Val Glu Gly Asn Glu Ser Asp Val Lys Ala Thr Ala Asn Gly Asn Gly
145                 150                 155                 160

Thr Thr Lys Glu Ile Gly Pro Thr Tyr Val Phe Gly Tyr His Pro His
                165                 170                 175
```

```
Gly Ile Val Ser Leu Gly Ala Phe Gly Ala Ile Gly Thr Glu Gly Ala
            180                 185                 190

Gly Trp Glu Lys Leu Phe Pro Gly Ile Pro Val Ser Leu Leu Thr Leu
        195                 200                 205

Glu Thr Asn Phe Ser Leu Pro Phe Tyr Arg Glu Tyr Leu Leu Ser Leu
    210                 215                 220

Gly Ile Ala Ser Val Ser Arg Arg Ser Cys Thr Asn Leu Leu Lys His
225                 230                 235                 240

Asp Gln Ser Ile Cys Ile Val Ile Gly Gly Ala Gln Glu Ser Leu Leu
                245                 250                 255

Ala Glu Pro Gly Thr Leu Asp Leu Ile Leu Val Lys Arg Arg Gly Phe
            260                 265                 270

Val Lys Leu Ala Met Ser Thr Ala Arg Val Ser Asp Gln Pro Ile Cys
        275                 280                 285

Leu Val Pro Ile Leu Ser Phe Gly Glu Asn Asp Val Tyr Asp Gln Val
    290                 295                 300

Arg Gly Asp Arg Ser Ser Lys Leu Tyr Lys Ile Gln Thr Phe Ile Lys
305                 310                 315                 320

Lys Ala Ala Gly Phe Thr Leu Pro Leu Met Tyr Ala Arg Gly Ile Phe
                325                 330                 335

Asn Tyr Asp Phe Gly Leu Met Pro Tyr Arg Arg Gln Met Thr Leu Val
            340                 345                 350

Val Gly Lys Pro Ile Ala Val Pro Tyr Val Ala Gln Pro Thr Glu Ala
        355                 360                 365

Glu Ile Glu Val Tyr His Lys Gln Tyr Met Asp Glu Leu Arg Arg Leu
    370                 375                 380

Trp Asp Thr Tyr Lys Asp Asp Tyr Phe Val Asp His Lys Gly Lys Gly
385                 390                 395                 400

Val Lys Asn Ser Glu Met Arg Phe Val Glu
                405                 410


<210> SEQ ID NO 3
<211> LENGTH: 1879
<212> TYPE: DNA
<213> ORGANISM: Lipomyces starkeyi
<220> FEATURE:
<221> NAME/KEY: Intron
<222> LOCATION: (439)..(493)
<220> FEATURE:
<221> NAME/KEY: Intron
<222> LOCATION: (861)..(911)
<220> FEATURE:
<221> NAME/KEY: Intron
<222> LOCATION: (1301)..(1349)
<220> FEATURE:
<221> NAME/KEY: Intron
<222> LOCATION: (1625)..(1675)

<400> SEQUENCE: 3

atgtcgaccg ctgcacaatc tgatacagac aacgaggata tatcgactgt cgatttggtt      60

gactctcgtg cagatactca cacatcttca aatgttatgt tgcaacagca aaaatcgcgt     120

cggagactaa tcgggaaaga cgccgagcca agaacacagc atccgtctgg aggcaaatcg     180

gagaaggagg agttgacgaa gccggatgac tcaaagggac ccataaaatt aagtcacata     240

tacccgatac atgccgttag ccgaggcagt attctgtcac gagagtcgac aactcctaca     300

ccgagttttg ttgggtttcg aaacttagcc atgatagtgc tagggaagtt acagtattca     360

ttattctttt ggtgcgatcg ggctaacatt ccgacagccg tcagcaatct tcgattggtg     420
```

```
attgaaaatt actcaaaggt atgcctgctc gacagaaata attgtggctg tatgacgagc    480
tgactttgaa cagtacggcg ttctgatccg attcgcccga ctcggtattt cacaaaagga    540
cattctgtat tgcatattct tgaccgctac catcccgctg cacctattta ttgctattgt    600
cattgaaaga ctagttgcga ttccgacggt aaactacgtc gcttcgctca gcgagagcga    660
ggataaaaaa cgctccaacc ccaaaatggg acggaagggg ggcagtatat cgattttgcg    720
tcctaagcca aaatatatgt ggcgcctgat cgtcctattg cattcaataa acgcaatggc    780
ttgcttgtgg gttacgactg ttgttgttta caattctatt tatcatcccc ttattgggac    840
agcttgtgaa tttcatgcag gtgagctata ctctaatttg tggtacgcat tgtaccgcta    900
acaagttgac agtgattgtg tgtcttaagg tcgcatcgtt tgcgcttacc aatcgcgatc    960
ttcgggagtc gatgctgaac tctcaacctg tgccagccat atacaacttg gccccttatc   1020
caaaaaactt aaccctcaag aacttgtcat acttttggtg ggcgccgact cttgtttatc   1080
aacctgtcta tccgcgatcg ccttcattcc ggcctttgtt ttttgtcaag cggattctgg   1140
agatggtggg cctatcattt ttaatatggt tcttgtcagc tcaatatgct gtgccgacgc   1200
tagaaaatag tttggtgcat tttcacagtt tgcaattcat gggaattatg gagcgactca   1260
tgaagcttgc tagcattagc atggctattt ggcttgctgg gtatgttcgg atagcaactt   1320
tggtctcgtg atgataaact aatttcgtta gtttttctg catttttcag tctggactca   1380
atgcgcttgc ggaggtaatg cggtttggtg acagagcctt ttacgacgac tggtggaaca   1440
gcaaatctgt gggagagtat tggcgtctgt ggaataagcc ggttacgaat tacttccggc   1500
gtcatattta cgtaccgctt gtgcgccgcg ggtggaattc tgcgacagcc agtgtcatgg   1560
tatttttcgt cagcgcggtg ttgcatgagc tagttgttgg agttccgacg cataacgtaa   1620
ttgggtacga ttgcctttat atagtatgaa aattgctgtt aactgagtta ataacagagt   1680
tgcattctcg tcgatgattc tacaaatccc actcatacaa gtaaccgcgc ctctggagaa   1740
gatgcatgga cctacatctg gaataatagg gaactgtatc ttttggttta gcttcttcat   1800
cggtcagcct ctgggcgtgc tactttacta ttttgcgtgg aacgttagta tgagcaaagt   1860
aaagatggtc gagagctag                                                1879
```

<210> SEQ ID NO 4
<211> LENGTH: 555
<212> TYPE: PRT
<213> ORGANISM: Lipomyces starkeyi

<400> SEQUENCE: 4

```
Met Ser Thr Ala Ala Gln Ser Asp Thr Asp Asn Glu Asp Ile Ser Thr
1               5                   10                  15

Val Asp Leu Val Asp Ser Arg Ala Asp Thr His Thr Ser Ser Asn Val
            20                  25                  30

Met Leu Gln Gln Gln Lys Ser Arg Arg Arg Leu Ile Gly Lys Asp Ala
        35                  40                  45

Glu Pro Arg Thr Gln His Pro Ser Gly Gly Lys Ser Glu Lys Glu Glu
    50                  55                  60

Leu Thr Lys Pro Asp Asp Ser Lys Gly Pro Ile Lys Leu Ser His Ile
65                  70                  75                  80

Tyr Pro Ile His Ala Val Ser Arg Gly Ser Ile Leu Ser Arg Glu Ser
                85                  90                  95

Thr Thr Pro Thr Pro Ser Phe Val Gly Phe Arg Asn Leu Ala Met Ile
            100                 105                 110
```

-continued

```
Val Leu Gly Lys Leu Gln Tyr Ser Leu Phe Phe Trp Cys Asp Arg Ala
        115                 120                 125

Asn Ile Pro Thr Ala Val Ser Asn Leu Arg Leu Val Ile Glu Asn Tyr
    130                 135                 140

Ser Lys Tyr Gly Val Leu Ile Arg Phe Ala Arg Leu Gly Ile Ser Gln
145                 150                 155                 160

Lys Asp Ile Leu Tyr Cys Ile Phe Leu Thr Ala Thr Ile Pro Leu His
                165                 170                 175

Leu Phe Ile Ala Ile Val Ile Glu Arg Leu Val Ala Ile Pro Thr Val
            180                 185                 190

Asn Tyr Val Ala Ser Leu Ser Glu Ser Glu Asp Lys Lys Arg Ser Asn
        195                 200                 205

Pro Lys Met Gly Arg Lys Gly Gly Ser Ile Ser Ile Leu Arg Pro Lys
    210                 215                 220

Pro Lys Tyr Met Trp Arg Leu Ile Val Leu Leu His Ser Ile Asn Ala
225                 230                 235                 240

Met Ala Cys Leu Trp Val Thr Thr Val Val Val Tyr Asn Ser Ile Tyr
                245                 250                 255

His Pro Leu Ile Gly Thr Ala Cys Glu Phe His Ala Val Ile Val Cys
            260                 265                 270

Leu Lys Val Ala Ser Phe Ala Leu Thr Asn Arg Asp Leu Arg Glu Ser
        275                 280                 285

Met Leu Asn Ser Gln Pro Val Pro Ala Ile Tyr Asn Leu Ala Pro Tyr
    290                 295                 300

Pro Lys Asn Leu Thr Leu Lys Asn Leu Ser Tyr Phe Trp Trp Ala Pro
305                 310                 315                 320

Thr Leu Val Tyr Gln Pro Val Tyr Pro Arg Ser Pro Ser Phe Arg Pro
                325                 330                 335

Leu Phe Phe Val Lys Arg Ile Leu Glu Met Val Gly Leu Ser Phe Leu
            340                 345                 350

Ile Trp Phe Leu Ser Ala Gln Tyr Ala Val Pro Thr Leu Glu Asn Ser
        355                 360                 365

Leu Val His Phe His Ser Leu Gln Phe Met Gly Ile Met Glu Arg Leu
    370                 375                 380

Met Lys Leu Ala Ser Ile Ser Met Ala Ile Trp Leu Ala Gly Phe Phe
385                 390                 395                 400

Cys Ile Phe Gln Ser Gly Leu Asn Ala Leu Ala Glu Val Met Arg Phe
                405                 410                 415

Gly Asp Arg Ala Phe Tyr Asp Asp Trp Trp Asn Ser Lys Ser Val Gly
            420                 425                 430

Glu Tyr Trp Arg Leu Trp Asn Lys Pro Val Thr Asn Tyr Phe Arg Arg
        435                 440                 445

His Ile Tyr Val Pro Leu Val Arg Arg Gly Trp Asn Ser Ala Thr Ala
    450                 455                 460

Ser Val Met Val Phe Phe Val Ser Ala Val Leu His Glu Leu Val Val
465                 470                 475                 480

Gly Val Pro Thr His Asn Val Ile Gly Val Ala Phe Ser Ser Met Ile
                485                 490                 495

Leu Gln Ile Pro Leu Ile Gln Val Thr Ala Pro Leu Glu Lys Met His
            500                 505                 510

Gly Pro Thr Ser Gly Ile Ile Gly Asn Cys Ile Phe Trp Phe Ser Phe
        515                 520                 525
```

-continued

```
Phe Ile Gly Gln Pro Leu Gly Val Leu Leu Tyr Tyr Phe Ala Trp Asn
    530                 535                 540

Val Ser Met Ser Lys Val Lys Met Val Glu Ser
545                 550                 555
```

<210> SEQ ID NO 5
<211> LENGTH: 1930
<212> TYPE: DNA
<213> ORGANISM: Lipomyces starkeyi
<220> FEATURE:
<221> NAME/KEY: Intron
<222> LOCATION: (67)..(121)
<220> FEATURE:
<221> NAME/KEY: Intron
<222> LOCATION: (398)..(447)
<220> FEATURE:
<221> NAME/KEY: Intron
<222> LOCATION: (598)..(652)
<220> FEATURE:
<221> NAME/KEY: Intron
<222> LOCATION: (852)..(902)

<400> SEQUENCE: 5

```
atggctccta aatcgtcgac tcgtgtgcca ttgtcggtta aagggcccat tgattgtcca      60

tatgaggtaa ttccagatca actctgagat gctgtccaac tactaacaaa ccatgattca     120

gggcaaagaa atgctcaacc tgccgcagtt caaccgagga acagctttca cagcagagga     180

acgtgacctg tttaatcttg tggggaatct tcccgctgcc ctgcagactc tgcagaatca     240

agtcgacaga gcgtacgatc agtattcctc gatctcgacg gctttgggga agaatacctt     300

tttgatgagt ttaaaggtgc aaaatgaggt cctgtatttt aagttgttgc aggatcattt     360

gaaggagatg tttagtataa tttacacgcc gactgaggta ggatcaaatt tagttttgtt     420

ggtaagatat tgctgaacga tgagtagagt gaagctattg agcattattc gagactgttt     480

agacgcccgg agggctgctt tctgaacatc aaccaccctg agtatatcga acggtctctg     540

gcggcgtggg gtacagagga ggacattgac tatatcatcg ttagtgacgg cgaggaggta     600

tgacatgatt ttgttctaga gttttcgaaa tgcactcatg ccggttatgc agatcctcgg     660

aattggcgat caaggagtcg gagctatcgg aatctcaagt gcaaaagctg tgcttatgac     720

tctatgcgcc ggcgtccatc catcgagatg cattccagtc gcgcttgatg ttggcacgga     780

taacgagcag ttgctcgagg atgagctata ccttggcaat aggcacaaca gagtccgcgg     840

cgggcgatat ggtgagctga tcgaatattc taagctttcg tgacgtgcta atttatttat     900

agataaattt gtggacgatt ttgtgcaatg tgtcaagaaa ctgtatcctc gtgcggttct     960

ccactttgag gatttcggac tacctaatgc cagaagacta ctcgacacct acagaccacg    1020

actagcgtgc tttaatgacg atgttcaggg tactggcgct gtcactttgg ccgcactctc    1080

atcagccgtc cgggtggccg gaattgactt ccgagacctc agaacggtga tctttggagc    1140

gggaacagca ggaactggca tcgcggatca gctgcgcgac tttctcaaca cacaagggat    1200

ttccaagcaa caagttatcg atcatatttg gcttgttgac aagccaggat tgcttcttaa    1260

atcaatgcat gataaactta catcagcgca acgtccgtac gctgcgtcgg acgatcgttg    1320

gaaagagatc gacaccaagt cattgtcaga aatcgtgaag aaagtgaagc cgcatgtgtt    1380

gattgggtgc tccacgaagc caaaagcatt caacgaagca gttcttcgtg agatggccaa    1440

acacgttgaa cggccgattg tctttcccct gagcaatccc acgcgactac acgaagcgac    1500

gccggcggag atttttaagt acacggacgg taaggcgctg gtggccaccg gttcgccgtt    1560

tgatcctgtc gatggcaagg aaattgccga gaacaataac tgtttcgtgt accctggtat    1620
```

-continued

```
tggcatgggg tcgatcttga gcagggccga tagagtcaca gagacgatga ttgcggcagt   1680

cgtgaaggag cttgcgtcgt tggcgccgtc ggagaaagat cctactggcg cactcttgcc   1740

tgatgtggca gatattagag atatttctgc gaagatcgcg actgcagtag tgttgcaagc   1800

gttagaggag ggaactgcga gagtggaaga gattgaaggt atcaaagttc cacgagacag   1860

agatcactgc ctggaatggg tcaaagagca gatgtggaaa cctgagtata gaccattgag   1920

aaaggtgtga                                                          1930


<210> SEQ ID NO 6
<211> LENGTH: 572
<212> TYPE: PRT
<213> ORGANISM: Lipomyces starkeyi

<400> SEQUENCE: 6

Met Ala Pro Lys Ser Ser Thr Arg Val Pro Leu Ser Val Lys Gly Pro
1               5                   10                  15

Ile Asp Cys Pro Tyr Glu Gly Lys Glu Met Leu Asn Leu Pro Gln Phe
            20                  25                  30

Asn Arg Gly Thr Ala Phe Thr Ala Glu Glu Arg Asp Leu Phe Asn Leu
        35                  40                  45

Val Gly Asn Leu Pro Ala Ala Leu Gln Thr Leu Gln Asn Gln Val Asp
    50                  55                  60

Arg Ala Tyr Asp Gln Tyr Ser Ser Ile Ser Thr Ala Leu Gly Lys Asn
65                  70                  75                  80

Thr Phe Leu Met Ser Leu Lys Val Gln Asn Glu Val Leu Tyr Phe Lys
                85                  90                  95

Leu Leu Gln Asp His Leu Lys Glu Met Phe Ser Ile Ile Tyr Thr Pro
            100                 105                 110

Thr Glu Ser Glu Ala Ile Glu His Tyr Ser Arg Leu Phe Arg Arg Pro
        115                 120                 125

Glu Gly Cys Phe Leu Asn Ile Asn His Pro Glu Tyr Ile Glu Arg Ser
    130                 135                 140

Leu Ala Ala Trp Gly Thr Glu Glu Asp Ile Asp Tyr Ile Ile Val Ser
145                 150                 155                 160

Asp Gly Glu Glu Ile Leu Gly Ile Gly Asp Gln Gly Val Gly Ala Ile
                165                 170                 175

Gly Ile Ser Ser Ala Lys Ala Val Leu Met Thr Leu Cys Ala Gly Val
            180                 185                 190

His Pro Ser Arg Cys Ile Pro Val Ala Leu Asp Val Gly Thr Asp Asn
        195                 200                 205

Glu Gln Leu Leu Glu Asp Glu Leu Tyr Leu Gly Asn Arg His Asn Arg
    210                 215                 220

Val Arg Gly Gly Arg Tyr Asp Lys Phe Val Asp Asp Phe Val Gln Cys
225                 230                 235                 240

Val Lys Lys Leu Tyr Pro Arg Ala Val Leu His Phe Glu Asp Phe Gly
                245                 250                 255

Leu Pro Asn Ala Arg Arg Leu Leu Asp Thr Tyr Arg Pro Arg Leu Ala
            260                 265                 270

Cys Phe Asn Asp Asp Val Gln Gly Thr Gly Ala Val Thr Leu Ala Ala
        275                 280                 285

Leu Ser Ser Ala Val Arg Val Ala Gly Ile Asp Phe Arg Asp Leu Arg
    290                 295                 300

Thr Val Ile Phe Gly Ala Gly Thr Ala Gly Thr Gly Ile Ala Asp Gln
```

```
305                 310                 315                 320

Leu Arg Asp Phe Leu Asn Thr Gln Gly Ile Ser Lys Gln Gln Val Ile
                325                 330                 335

Asp His Ile Trp Leu Val Asp Lys Pro Gly Leu Leu Leu Lys Ser Met
            340                 345                 350

His Asp Lys Leu Thr Ser Ala Gln Arg Pro Tyr Ala Ala Ser Asp Asp
        355                 360                 365

Arg Trp Lys Glu Ile Asp Thr Lys Ser Leu Ser Glu Ile Val Lys Lys
    370                 375                 380

Val Lys Pro His Val Leu Ile Gly Cys Ser Thr Lys Pro Lys Ala Phe
385                 390                 395                 400

Asn Glu Ala Val Leu Arg Glu Met Ala Lys His Val Glu Arg Pro Ile
                405                 410                 415

Val Phe Pro Leu Ser Asn Pro Thr Arg Leu His Glu Ala Thr Pro Ala
            420                 425                 430

Glu Ile Phe Lys Tyr Thr Asp Gly Lys Ala Leu Val Ala Thr Gly Ser
        435                 440                 445

Pro Phe Asp Pro Val Asp Gly Lys Glu Ile Ala Glu Asn Asn Asn Cys
    450                 455                 460

Phe Val Tyr Pro Gly Ile Gly Met Gly Ser Ile Leu Ser Arg Ala Asp
465                 470                 475                 480

Arg Val Thr Glu Thr Met Ile Ala Ala Val Val Lys Glu Leu Ala Ser
                485                 490                 495

Leu Ala Pro Ser Glu Lys Asp Pro Thr Gly Ala Leu Leu Pro Asp Val
            500                 505                 510

Ala Asp Ile Arg Asp Ile Ser Ala Lys Ile Ala Thr Ala Val Val Leu
        515                 520                 525

Gln Ala Leu Glu Glu Gly Thr Ala Arg Val Glu Glu Ile Glu Gly Ile
    530                 535                 540

Lys Val Pro Arg Asp Arg Asp His Cys Leu Glu Trp Val Lys Glu Gln
545                 550                 555                 560

Met Trp Lys Pro Glu Tyr Arg Pro Leu Arg Lys Val
                565                 570
```

<210> SEQ ID NO 7
<211> LENGTH: 1936
<212> TYPE: DNA
<213> ORGANISM: Lipomyces starkeyi
<220> FEATURE:
<221> NAME/KEY: Intron
<222> LOCATION: (164)..(224)
<220> FEATURE:
<221> NAME/KEY: Intron
<222> LOCATION: (326)..(382)

<400> SEQUENCE: 7

```
atggcttcct cagttcctca agctcccgtc acttccctac tctcggaggc tcgcggtaag      60

accgtacagc gtgataataa tgaattaccc ggtgctcgtt ccattgacac cgaggctacg     120

ttccagcatt ggatctacga catggttatc tggagtttat caggtgtgta caccgtatgc     180

tttaattagc aagccgatac tgccatatta acttgcgcat tcagtcgtgt tcgatctatt     240

tttccgtgaa atccgcccga ggggcgcata ccgaatcccg agacatggtc cgattatctt     300

tgttgccgct ccgcacgcca atcaggtgag tcttggccgc aatgatacca tcatacgacg     360

tatggagcta acacgaagac agtttattga ccccatcatg ctcatgcgtc aaattcgaat     420

tgaagcaggt cgcagaatat cgtttctggc ggccgaaagt tcaatgcacc gcaaattcgt     480
```

-continued

```
cggcactgtc gctcgatcag tttcttcaat tccggttgct agagctcagg acttggcgtc    540
tcacggaact ggtttgatct atattgaaga taaggagaag ccgttggtta tcaagggcca    600
gggaaccaag tttatgaagg aatgcagtca aggcgggttg ataatgttgg cgaagtcact    660
tggcagcgcc gagattgata gcatcgtgtc tgatgtcgag ttgattttgc gccggccttt    720
caaggaggag aaagccatcg agtatttatt ttccggtccg tccaagttta aaaaagcgcc    780
aaaggtcgac cagtcacaga tgtaccagaa ggtcttcgaa agactgaatg acggtggatg    840
tatcggtatc tttcccgaag gcggttcaca tgaccgacca gacttattac cactaaaagc    900
cggtgtcgcg gttatggctc ttggtgccct agagcagaac ccagagtgcg acatcagaat    960
tgtcccttgc ggtatgaact acttccaccc tcacaaattc cgatcacgag cagttattga   1020
gtttggtcct ccacttaacg ttcccaagga gcttgtcaag acgtacagtg aaggaaataa   1080
gagagattct atacaccagc tcttggaaat gattcatagc gcgttgttgg ctgttactgt   1140
tacctcgccg gattacgaca cattgatggt tattcaagcg gctcgacgac tatacaaacc   1200
cgcacacaag aaaatcccgc tatcgttggt tatcgagatg aatcggcggt tagtcatagg   1260
gtatacacat tacaaggacg atccacggat tattcatctt cgggaagccg ttgcgaacta   1320
taacaagcag ttgagacatt tgggaatcct ggatcatcag gttgagtacg caacattgcc   1380
aataccggag attgtcggaa aattagtcta ccggtcgctg aaactattta ttctggcatt   1440
gggcgctctg cccggagcta ttcttttcgc accggtattc atcgcgacca agatgatttc   1500
caagaagaag gcagccgaag cgttgaaggc gtcgaccgtg aagatcgctg ccagggatgt   1560
tgtcgcgaca tggaagattc tcgtagcgct gggtctcgcg ccgacgctat actggttcta   1620
cgcacttttg gcgacatggg cgacgtggaa gtacgatctt gttcctcaag tgcgaccggt   1680
gtggctcgtg actcttgcgg ctatgattat tttcccggcg atcacgtacg ctgcacttag   1740
aattggagag atcggaatgg atattttcaa gtcattaaag ccgcttgtga catgcttgaa   1800
cccgaataat ttgaacacga ttgcgaagtt gcggattacg agagaggaat tgtcgaagga   1860
agtcaccgag atgattaatt cattaggccc ggatgtcttt ccagagttcg actctcaccg   1920
gttaatgcag agttag                                                   1936
```

<210> SEQ ID NO 8
<211> LENGTH: 605
<212> TYPE: PRT
<213> ORGANISM: Lipomyces starkeyi

<400> SEQUENCE: 8

```
Met Ala Ser Ser Val Pro Gln Ala Pro Val Thr Ser Leu Leu Ser Glu
1               5                   10                  15

Ala Arg Gly Lys Thr Val Gln Arg Asp Asn Asn Glu Leu Pro Gly Ala
            20                  25                  30

Arg Ser Ile Asp Thr Glu Ala Thr Phe Gln His Trp Ile Tyr Asp Met
        35                  40                  45

Val Ile Trp Ser Leu Ser Val Val Phe Asp Leu Phe Phe Arg Glu Ile
    50                  55                  60

Arg Pro Arg Gly Ala Tyr Arg Ile Pro Arg His Gly Pro Ile Ile Phe
65                  70                  75                  80

Val Ala Ala Pro His Ala Asn Gln Phe Ile Asp Pro Ile Met Leu Met
                85                  90                  95

Arg Gln Ile Arg Ile Glu Ala Gly Arg Arg Ile Ser Phe Leu Ala Ala
            100                 105                 110
```

-continued

```
Glu Ser Ser Met His Arg Lys Phe Val Gly Thr Val Ala Arg Ser Val
        115                 120                 125

Ser Ser Ile Pro Val Ala Arg Ala Gln Asp Leu Ala Ser His Gly Thr
    130                 135                 140

Gly Leu Ile Tyr Ile Glu Asp Lys Glu Lys Pro Leu Val Ile Lys Gly
145                 150                 155                 160

Gln Gly Thr Lys Phe Met Lys Glu Cys Ser Gln Gly Gly Leu Ile Met
                165                 170                 175

Leu Ala Lys Ser Leu Gly Ser Ala Glu Ile Asp Ser Ile Val Ser Asp
            180                 185                 190

Val Glu Leu Ile Leu Arg Arg Pro Phe Lys Glu Glu Lys Ala Ile Glu
        195                 200                 205

Tyr Leu Phe Ser Gly Pro Ser Lys Phe Lys Lys Ala Pro Lys Val Asp
    210                 215                 220

Gln Ser Gln Met Tyr Gln Lys Val Phe Glu Arg Leu Asn Asp Gly Gly
225                 230                 235                 240

Cys Ile Gly Ile Phe Pro Glu Gly Gly Ser His Asp Arg Pro Asp Leu
                245                 250                 255

Leu Pro Leu Lys Ala Gly Val Ala Val Met Ala Leu Gly Ala Leu Glu
            260                 265                 270

Gln Asn Pro Glu Cys Asp Ile Arg Ile Val Pro Cys Gly Met Asn Tyr
        275                 280                 285

Phe His Pro His Lys Phe Arg Ser Arg Ala Val Ile Glu Phe Gly Pro
    290                 295                 300

Pro Leu Asn Val Pro Lys Glu Leu Val Lys Thr Tyr Ser Glu Gly Asn
305                 310                 315                 320

Lys Arg Asp Ser Ile His Gln Leu Leu Glu Met Ile His Ser Ala Leu
                325                 330                 335

Leu Ala Val Thr Val Thr Ser Pro Asp Tyr Asp Thr Leu Met Val Ile
            340                 345                 350

Gln Ala Ala Arg Arg Leu Tyr Lys Pro Ala His Lys Lys Ile Pro Leu
        355                 360                 365

Ser Leu Val Ile Glu Met Asn Arg Arg Leu Val Ile Gly Tyr Thr His
    370                 375                 380

Tyr Lys Asp Asp Pro Arg Ile Ile His Leu Arg Glu Ala Val Ala Asn
385                 390                 395                 400

Tyr Asn Lys Gln Leu Arg His Leu Gly Ile Leu Asp His Gln Val Glu
                405                 410                 415

Tyr Ala Thr Leu Pro Ile Pro Glu Ile Val Gly Lys Leu Val Tyr Arg
            420                 425                 430

Ser Leu Lys Leu Phe Ile Leu Ala Leu Gly Ala Leu Pro Gly Ala Ile
        435                 440                 445

Leu Phe Ala Pro Val Phe Ile Ala Thr Lys Met Ile Ser Lys Lys Lys
    450                 455                 460

Ala Ala Glu Ala Leu Lys Ala Ser Thr Val Lys Ile Ala Ala Arg Asp
465                 470                 475                 480

Val Val Ala Thr Trp Lys Ile Leu Val Ala Leu Gly Leu Ala Pro Thr
                485                 490                 495

Leu Tyr Trp Phe Tyr Ala Leu Leu Ala Thr Trp Ala Thr Trp Lys Tyr
            500                 505                 510

Asp Leu Val Pro Gln Val Arg Pro Val Trp Leu Val Thr Leu Ala Ala
        515                 520                 525
```

-continued

```
Met Ile Ile Phe Pro Ala Ile Thr Tyr Ala Ala Leu Arg Ile Gly Glu
    530                 535                 540

Ile Gly Met Asp Ile Phe Lys Ser Leu Lys Pro Leu Val Thr Cys Leu
545                 550                 555                 560

Asn Pro Asn Asn Leu Asn Thr Ile Ala Lys Leu Arg Ile Thr Arg Glu
                565                 570                 575

Glu Leu Ser Lys Glu Val Thr Glu Met Ile Asn Ser Leu Gly Pro Asp
            580                 585                 590

Val Phe Pro Glu Phe Asp Ser His Arg Leu Met Gln Ser
        595                 600                 605


<210> SEQ ID NO 9
<211> LENGTH: 6932
<212> TYPE: DNA
<213> ORGANISM: Lipomyces starkeyi
<220> FEATURE:
<221> NAME/KEY: Intron
<222> LOCATION: (124)..(189)
<220> FEATURE:
<221> NAME/KEY: Intron
<222> LOCATION: (2833)..(2889)
<220> FEATURE:
<221> NAME/KEY: Intron
<222> LOCATION: (2972)..(3027)
<220> FEATURE:
<221> NAME/KEY: Intron
<222> LOCATION: (4522)..(4569)

<400> SEQUENCE: 9

atgtctgctg cggccagtag cctcccctcc cactttatcg gccttaacac cgtcgatgtg     60

gcggccaata gccccgttaa ggattttgtc cagaatcatg gtggtcacac cgtcatcact    120

tccgtacgtg accgatctgt ttcctctttg atctttgtcg catcatgact gacgatctaa    180

tccatttagg ttctcatagc gaacaacggt atcgccgctg tcaaggaaat ccgcagtgtc    240

cggaaatggg cctacgagac tttcggcgac gagcgcgcca tctccttcac cgtcatggcc    300

acgcctgagg atctcaaggc aaacgcggat tacatccgca tggcagatca gtacgtcgaa    360

gttcccggcg ggacaaacaa caacaatttc gccaacgtcg agctcatcgt cgatatcgcc    420

gagcgcatga acgtccacgc cgtctgggcc ggctggggac atgcctccga aaacccaaag    480

ctcccagagt ctctcgcgca gtcgccaaag aagatcgtct tcatcggccc gcccggatcc    540

gccatgcggt ctctcggtga caagatctcg tccaccatag ttgcccagca cgcaaaagtc    600

ccctgtattc cctggtctgg aaccggcgtg gacgaagtcc agattgattc tgttagcggt    660

ctcgtcaccg tgtccgatga gatatacgca aagggttgta cttccaccgc ggaagaggct    720

ctcgagaagg cccgcatcat cggcttcccc gtcatgatca aggcttccga aggtggcggt    780

ggcaaaggta ttcgaaaggt cgagagcgag gacaacttcc attctttgta cagccaggtt    840

gccaatgagg tccctggatc tcccatcttc gtcatgaagc ttgccggcaa cgcgcgacat    900

cttgaggtcc aattgcttgc cgatcaatac ggaaacaaca tctctctctt tggcagagat    960

tgctcagtcc agcgtcgtca ccagaagatt atcgaagagg cgcctgtcac tgttgccaac   1020

cccgcaacat tctcggcaat ggaacacgcc gctgttcgac ttggccagct tgtcggctat   1080

gtctccgccg gtacagtcga gtacctctac tctcacgacg acgacaaatt ctacttcttg   1140

gagctcaatc cccgtcttca ggtagagcat cctactaccg agatggtcac cggtgtcaac   1200

ttacccgccg ctcagctcca aatcgcgatg ggtgtgtctc tccaccgaat cagagatatc   1260

cggctcttct acggcgtcga tcctcacact tcgaccgaaa tcgactttga tttctccaag   1320
```

-continued

```
gagggctctc ttcaaactca gcgccgtcca gtgcccaagg gccacaccac ggcctgccga   1380
atcacgtccg aagatcctgg cgaaggtttc aaaccatcta gtggtgtcat gcacgaactg   1440
aactttagat cgagctccaa tgtctggggt tacttctccg tcggaaatca gggcggaatc   1500
cactcgttct ccgattccca gttcggtcat atctttgcat tcggcgaaaa cagaagcgcg   1560
agtcgcaagc acatggttgt cgcgttgaag gaattgtcta ttcgtggtga cttccgcact   1620
acggtcgaat atctcattaa gctgcttgag actcctgatt tcgagtctaa caagatcacc   1680
accggatggc tcgatgagct aatttccaag aagctcaccg ccgagcgccc tgatcctgtc   1740
gtcgctgttg tctgcggcgc tgtcacgaag gcacatcttg cttcagaggc ttgcttccag   1800
gagtacaaga attccctaga gaagggccag gtcccgtcga aggacatcct aaagactttg   1860
ttccctgtcg actttatcta cgagggcagc cgatacaagt tcactgtcac gcgatcgtcc   1920
atggatttgt atcagatttt catcaacggt tccaagtgcc tggtcggtgt caaatcactc   1980
agtgacggtg gtcttttggt tttgctcgga ggcaagtccc acaatgtgta ctggaaggac   2040
gaagttggaa ccaccagact cagtgtcgac tccaagactt gcttgttgga gcaggagaat   2100
gatcctaccc agctccgcac tccttccccc ggtaagctcg tcaagttctt ggtcgagaac   2160
ggtgagcacg tcaagactgg acagccgttt gctgaagttg aggtcatgaa gatgtacatg   2220
cccctgattg ctcaggagga cggtatcgtg caattgatca agcagcctgg agctactctc   2280
gaggctggcg atattctcgg cattttagct ctagatgatc catcccgcgt caaacacgcc   2340
aagcccttcg agggtcaact gcctgatttc ggttcgccat tggttctagg cagcaagcct   2400
tcgcagcgat tcaatctgtt gctaagcacc ctcaggaaca ttctggctgg ttttgacaac   2460
caggtcttgt tggcgtcgac tctcaaggat ctgagccaag tattaaagga cgacgcgctg   2520
ccctatagtg agtggaacgc tcagttctcc gcccttcaca gtcgtatccc gcagaagctc   2580
gacgcgactc tttccagtct tatcgagcgc tccaagtcca aggacgctga attcccggca   2640
aagttgctgt tgcgcgctat tgagcgattt gctgaagagt tcatccagcc gcaggatcta   2700
tttgtcttca agcaacaggt cgagcctctt gttaccattg ctacgagata ccaggctggt   2760
ttgaaagcac atgagtatgg tgtcattgct gaattgttgg agcagtattt ggctgtcgag   2820
aaattgtttt cggtgagccg cacacttttc tgttgctgtt atggacgggc cgcgtactaa   2880
catttgtagg gcgccaatat tcgggatgag gatgtttttc tcagacttag agatgaaaat   2940
aaggatgata ttttcaaggt tgtcatgact ggtatgttaa tttgttgtcg cgccggcttt   3000
cgagtaccag tatgttgatg tcactagtat tctctcacgg tcgcgttgga gctaagaaca   3060
acctcatcct cgcaatttta gccgcacttc gatccgacag atctgaggtt tccgaggtcg   3120
ctaaatactt gcggcctgct ctcaagacat taacggagct tgactcaggt gtcactgccc   3180
ctgtggctct caaggctcgt gaactattga tccagtgcgc acttccatct ctcgaggagc   3240
gaaccgccca gctcgaacat atattgcgct cgtctgttgt tgagtcgcga tacggtgagg   3300
tgggctttga gcacagtgct cccagaattg acgtcttgaa ggaggtcatt gactcgcaat   3360
acatcgtttt tgacgttctg ccaaagtttt tcgcgcactc ggatcgttat gtcaccttag   3420
ccgcactcga gctctacgtc cgtcgcgctt atcgcgcgta taacgtcatg agcatggagt   3480
accacaacga aggcgatctt gtgcccgtcg tcacgttcaa gtttttgctt gccgctattg   3540
gcaatcccgc ttacaacatc gtcggacagg gtgctccgtc aggcgattcg cgcattgatt   3600
tccagcgtgc tgcggcggtt tcggatctca catttatgat gagcaagtcc gacagcgagt   3660
ccttgcgatc cggtgtgatt gttcccgtgg ctgatattgc tgatattgac gaagttctcc   3720
```

-continued

```
ctcgtgcttt ggattacctc ccacagcgag ccggtgcggg atcgggaggc ttctccttct   3780
cggctaaatc tgatttggac tcgaagcgac gaccagcacc gccaaagcca gagtctttga   3840
gcaatatctg caacgttttg atccgcaaga cggcaaaaac cgacgacgct gcacttgtct   3900
cggatatcaa gttcatcgtc gatgagtaca aggaggagtt cttgcttcga tctattcgac   3960
gagttacatt cgtttgcggc cgcgaggacg gttcgtatcc tggttatttt acgttccgcg   4020
gtcctgacta cgtcgaggac gagagtatcc gacatattga gcctgcgttg gcgtaccagc   4080
ttgagttggg acgtttgtcg aactttaact ataagccgat tttcacggat aaccgcaaca   4140
ttcacgtcta ccaggccatc ggcaaggacg ttcctagcga caagcgtttc ttcgtgagag   4200
gtatcgtcag acccggccgt ctacgtgatg aaattccgac gtcggaatac cttatctctg   4260
aaaccgaccg actgatgtcg gacattttgg acgctctcga ggttatcggt cctaataaca   4320
cggatatgaa ccacatttc atcaactttt cgcccatttt ccatttggta ccggaagagg   4380
tcgaggcagc atttggacag ttcttggaga gatttggacg cagattgtgg agattgagag   4440
tgactggtgc ggagatccgg attatgtgca ccgacccgga gactaatgtg ccgtacccct   4500
tgcgtgcgat tatcacgaat ggtgagtatc tttcatactt tttttcggc tgctgctaat   4560
tttcgttagt gtccggctat gtcgtccaga gtgagttgta cacggaggtc aagaatgata   4620
agggccaatg ggtgttcaag tcgttgggta agccaggtaa catgcacttg cgctcgatca   4680
cgactccata cgcgaccaag gaatggctac agccgaagag atacaaggca cacttgatgg   4740
gcacgacatt cgtgtacgat ttcccagagc ttttcaacca agctattcgt gctagttggc   4800
gtgcagcgca gcagcagtcg cccgagaatg tgcttacgta caaggagctt atcatggatg   4860
acagtggaga gttgtcggag gtttctcgag agccaggtgc gaatacttgc ggaatggttg   4920
cctggttgtt cacggcgctc actcccgaat atccaacggg ccgtcaattc atcgtggtcg   4980
ccaatgatat cacttacaag attggctcct tcggtcctca ggaggataag tacttccaca   5040
ctgtgaccca gctcgccgtc aaacttggca ttccccgaat ctatctctct gcaaactctg   5100
gtgcgcgaat tggcgttgcg gacgaatttg tgtcattgtt ctcggtcgcc tggaatgatt   5160
cttccaatcc tgaaaaggga ttcaagtact tgtacctcac gcctgcgatc tacaacggtc   5220
tttcggacgc ggccaagaag actgtgctta ccgaacgcat tgttgaggag ggcgaggagc   5280
gatatgttat caccaccatt atcggcgctg aagacggtct tggtgtcgag tgtcttcgtg   5340
gatcgggtct cattgccggc gctacttcga aggcttataa agacattttc acgattactt   5400
tggtcacttg ccgttcggtt ggtattggtg cttatctcgt ccgtctcgga cagcgtgcga   5460
tccagattga gggccagcct atcatactta ctggtgctcc tgcgatcaac aaactccttg   5520
gtcgggaagt ttacagttcg aatttgcagc tcggtggcac gcagatcatg tacaagaacg   5580
gtgtatcgca tcttaccgct aatgatgacc ttgctggtgt catgaagatt atcgagtgga   5640
tgtcatacgt accgtataag aaaggtggtc agctgccaat ttatccatca tcagatacct   5700
gggatcgtga tgtcacttat actcctccca aacaggtccc gtacgatgtc cgatggctga   5760
tcgctggtcg cgaggacgag gagggcggtt tcgagtacgg tttgttcgac aaagactcgt   5820
tccaggagac ccttagcggc tgggctcgaa ctgtcgttgt cggtcgtgcg cggttaggcg   5880
gcatccctgt cggcgtaatt ggcgttgaag tccgctcggt cgagaacatt ttccccgccg   5940
atcctgccaa tcccgattcg acagaaatgg tcgtccagga agccggccag gtttggtacc   6000
ccaactcggc atttaagact gctcaggcga ttaacgattt caaccacggt gaggagcttc   6060
```

-continued

```
cgctcgtaat cctcgccaac tggagaggtt tctctggcgg tcagcgtgat atgtacaacg   6120

aggtcttgaa gtacggttcg ttcatcgtgg atgcgctcgt tggttacaag cagcctattt   6180

tcgtctacat tccgccgcat gcagagctcc gtggtggttc atgggttgtt atcgatccca   6240

ccatcaactc tgatcagatg gagatgtacg cggatgacga ggcacgtgct ggtgtgttgg   6300

agcccgaggg tatggttggc atcaagtacc gtcgtgaccg tctcttggag accatgactc   6360

gtctcgaccc ggtctatgcc tcgctcaagc gccaggccga caagaaagat ctcgctccgg   6420

caatcgctca ggatctcaaa gtcaagttga gcgaacggga aagcacattg atgccaatct   6480

accgacagat cagcttacag ttcgccgact tgcatgaccg ggcaggacga atgaaggcga   6540

agggaactat ccgtgaagtc cttcactggc gtgaggctag acgtttcttc tactggcgtg   6600

ttagacgtcg tgttggcgag agctatattc ttcgtgatct ggaggctgct aacccgaaat   6660

cgacgagact agaacgcgtc gcgcgattga agtcttggta tgctgaggct ggtatcaacg   6720

aatcttccga cgcagacgtc gcaagctgga tcgagaagtc tggtgccgct atcaccagca   6780

aagtcaaaca ggttagaaag gatgcaaaga tccaggactt gttggctctt gtgcgcgcgg   6840

ataaggatgt cgctttgcag ggcctggttg agtccctcaa ggctttgtct actgaggaac   6900

gggatgcgat tttcaagcag gcttctaatt aa                                 6932
```

<210> SEQ ID NO 10
<211> LENGTH: 2234
<212> TYPE: PRT
<213> ORGANISM: Lipomyces starkeyi

<400> SEQUENCE: 10

```
Met Ser Ala Ala Ala Ser Ser Leu Pro Ser His Phe Ile Gly Leu Asn
1               5                   10                  15

Thr Val Asp Val Ala Ala Asn Ser Pro Val Lys Asp Phe Val Gln Asn
            20                  25                  30

His Gly Gly His Thr Val Ile Thr Ser Val Leu Ile Ala Asn Asn Gly
        35                  40                  45

Ile Ala Ala Val Lys Glu Ile Arg Ser Val Arg Lys Trp Ala Tyr Glu
    50                  55                  60

Thr Phe Gly Asp Glu Arg Ala Ile Ser Phe Thr Val Met Ala Thr Pro
65                  70                  75                  80

Glu Asp Leu Lys Ala Asn Ala Asp Tyr Ile Arg Met Ala Asp Gln Tyr
                85                  90                  95

Val Glu Val Pro Gly Gly Thr Asn Asn Asn Asn Phe Ala Asn Val Glu
            100                 105                 110

Leu Ile Val Asp Ile Ala Glu Arg Met Asn Val His Ala Val Trp Ala
        115                 120                 125

Gly Trp Gly His Ala Ser Glu Asn Pro Lys Leu Pro Glu Ser Leu Ala
    130                 135                 140

Gln Ser Pro Lys Lys Ile Val Phe Ile Gly Pro Pro Gly Ser Ala Met
145                 150                 155                 160

Arg Ser Leu Gly Asp Lys Ile Ser Ser Thr Ile Val Ala Gln His Ala
                165                 170                 175

Lys Val Pro Cys Ile Pro Trp Ser Gly Thr Gly Val Asp Glu Val Gln
            180                 185                 190

Ile Asp Ser Val Ser Gly Leu Val Thr Val Ser Asp Glu Ile Tyr Ala
        195                 200                 205

Lys Gly Cys Thr Ser Thr Ala Glu Glu Ala Leu Glu Lys Ala Arg Ile
    210                 215                 220
```

-continued

```
Ile Gly Phe Pro Val Met Ile Lys Ala Ser Glu Gly Gly Gly Gly Lys
225                 230                 235                 240

Gly Ile Arg Lys Val Glu Ser Glu Asp Asn Phe His Ser Leu Tyr Ser
                245                 250                 255

Gln Val Ala Asn Glu Val Pro Gly Ser Pro Ile Phe Val Met Lys Leu
            260                 265                 270

Ala Gly Asn Ala Arg His Leu Glu Val Gln Leu Leu Ala Asp Gln Tyr
        275                 280                 285

Gly Asn Asn Ile Ser Leu Phe Gly Arg Asp Cys Ser Val Gln Arg Arg
    290                 295                 300

His Gln Lys Ile Ile Glu Glu Ala Pro Val Thr Val Ala Asn Pro Ala
305                 310                 315                 320

Thr Phe Ser Ala Met Glu His Ala Ala Val Arg Leu Gly Gln Leu Val
                325                 330                 335

Gly Tyr Val Ser Ala Gly Thr Val Glu Tyr Leu Tyr Ser His Asp Asp
            340                 345                 350

Asp Lys Phe Tyr Phe Leu Glu Leu Asn Pro Arg Leu Gln Val Glu His
        355                 360                 365

Pro Thr Thr Glu Met Val Thr Gly Val Asn Leu Pro Ala Ala Gln Leu
    370                 375                 380

Gln Ile Ala Met Gly Val Ser Leu His Arg Ile Arg Asp Ile Arg Leu
385                 390                 395                 400

Phe Tyr Gly Val Asp Pro His Thr Ser Thr Glu Ile Asp Phe Asp Phe
                405                 410                 415

Ser Lys Glu Gly Ser Leu Gln Thr Gln Arg Arg Pro Val Pro Lys Gly
            420                 425                 430

His Thr Thr Ala Cys Arg Ile Thr Ser Glu Asp Pro Gly Glu Gly Phe
        435                 440                 445

Lys Pro Ser Ser Gly Val Met His Glu Leu Asn Phe Arg Ser Ser Ser
    450                 455                 460

Asn Val Trp Gly Tyr Phe Ser Val Gly Asn Gln Gly Gly Ile His Ser
465                 470                 475                 480

Phe Ser Asp Ser Gln Phe Gly His Ile Phe Ala Phe Gly Glu Asn Arg
                485                 490                 495

Ser Ala Ser Arg Lys His Met Val Val Ala Leu Lys Glu Leu Ser Ile
            500                 505                 510

Arg Gly Asp Phe Arg Thr Thr Val Glu Tyr Leu Ile Lys Leu Leu Glu
        515                 520                 525

Thr Pro Asp Phe Glu Ser Asn Lys Ile Thr Thr Gly Trp Leu Asp Glu
    530                 535                 540

Leu Ile Ser Lys Lys Leu Thr Ala Glu Arg Pro Asp Pro Val Val Ala
545                 550                 555                 560

Val Val Cys Gly Ala Val Thr Lys Ala His Leu Ala Ser Glu Ala Cys
                565                 570                 575

Phe Gln Glu Tyr Lys Asn Ser Leu Glu Lys Gly Gln Val Pro Ser Lys
            580                 585                 590

Asp Ile Leu Lys Thr Leu Phe Pro Val Asp Phe Ile Tyr Glu Gly Ser
        595                 600                 605

Arg Tyr Lys Phe Thr Val Thr Arg Ser Ser Met Asp Leu Tyr Gln Ile
    610                 615                 620

Phe Ile Asn Gly Ser Lys Cys Leu Val Gly Val Lys Ser Leu Ser Asp
625                 630                 635                 640
```

-continued

```
Gly Gly Leu Leu Val Leu Leu Gly Gly Lys Ser His Asn Val Tyr Trp
                645                 650                 655

Lys Asp Glu Val Gly Thr Thr Arg Leu Ser Val Asp Ser Lys Thr Cys
            660                 665                 670

Leu Leu Glu Gln Glu Asn Asp Pro Thr Gln Leu Arg Thr Pro Ser Pro
        675                 680                 685

Gly Lys Leu Val Lys Phe Leu Val Glu Asn Gly Glu His Val Lys Thr
    690                 695                 700

Gly Gln Pro Phe Ala Glu Val Glu Val Met Lys Met Tyr Met Pro Leu
705                 710                 715                 720

Ile Ala Gln Glu Asp Gly Ile Val Gln Leu Ile Lys Gln Pro Gly Ala
                725                 730                 735

Thr Leu Glu Ala Gly Asp Ile Leu Gly Ile Leu Ala Leu Asp Asp Pro
            740                 745                 750

Ser Arg Val Lys His Ala Lys Pro Phe Glu Gly Gln Leu Pro Asp Phe
        755                 760                 765

Gly Ser Pro Leu Val Leu Gly Ser Lys Pro Ser Gln Arg Phe Asn Leu
    770                 775                 780

Leu Leu Ser Thr Leu Arg Asn Ile Leu Ala Gly Phe Asp Asn Gln Val
785                 790                 795                 800

Leu Leu Ala Ser Thr Leu Lys Asp Leu Ser Gln Val Leu Lys Asp Asp
                805                 810                 815

Ala Leu Pro Tyr Ser Glu Trp Asn Ala Gln Phe Ser Ala Leu His Ser
            820                 825                 830

Arg Ile Pro Gln Lys Leu Asp Ala Thr Leu Ser Ser Leu Ile Glu Arg
        835                 840                 845

Ser Lys Ser Lys Asp Ala Glu Phe Pro Ala Lys Leu Leu Leu Arg Ala
    850                 855                 860

Ile Glu Arg Phe Ala Glu Glu Phe Ile Gln Pro Gln Asp Leu Phe Val
865                 870                 875                 880

Phe Lys Gln Gln Val Glu Pro Leu Val Thr Ile Ala Thr Arg Tyr Gln
                885                 890                 895

Ala Gly Leu Lys Ala His Glu Tyr Gly Val Ile Ala Glu Leu Leu Glu
            900                 905                 910

Gln Tyr Leu Ala Val Glu Lys Leu Phe Ser Gly Ala Asn Ile Arg Asp
        915                 920                 925

Glu Asp Val Phe Leu Arg Leu Arg Asp Glu Asn Lys Asp Asp Ile Phe
    930                 935                 940

Lys Val Val Met Thr Val Phe Ser His Gly Arg Val Gly Ala Lys Asn
945                 950                 955                 960

Asn Leu Ile Leu Ala Ile Leu Ala Ala Leu Arg Ser Asp Arg Ser Glu
                965                 970                 975

Val Ser Glu Val Ala Lys Tyr Leu Arg Pro Ala Leu Lys Thr Leu Thr
            980                 985                 990

Glu Leu Asp Ser Gly Val Thr Ala  Pro Val Ala Leu Lys  Ala Arg Glu
        995                 1000                1005

Leu Leu  Ile Gln Cys Ala Leu  Pro Ser Leu Glu Glu  Arg Thr Ala
    1010                1015                1020

Gln Leu  Glu His Ile Leu Arg  Ser Ser Val Val Glu  Ser Arg Tyr
    1025                1030                1035

Gly Glu  Val Gly Phe Glu His  Ser Ala Pro Arg Ile  Asp Val Leu
    1040                1045                1050

Lys Glu  Val Ile Asp Ser Gln  Tyr Ile Val Phe Asp  Val Leu Pro
```

```
    1055                1060                1065

Lys Phe  Phe Ala His Ser Asp  Arg Tyr Val Thr Leu  Ala Ala Leu
    1070                1075                1080

Glu Leu  Tyr Val Arg Arg Ala  Tyr Arg Ala Tyr Asn  Val Met Ser
    1085                1090                1095

Met Glu  Tyr His Asn Glu Gly  Asp Leu Val Pro Val  Val Thr Phe
    1100                1105                1110

Lys Phe  Leu Leu Ala Ala Ile  Gly Asn Pro Ala Tyr  Asn Ile Val
    1115                1120                1125

Gly Gln  Gly Ala Pro Ser Gly  Asp Ser Arg Ile Asp  Phe Gln Arg
    1130                1135                1140

Ala Ala  Ser Val Ser Asp Leu  Thr Phe Met Met Ser  Lys Ser Asp
    1145                1150                1155

Ser Glu  Ser Leu Arg Ser Gly  Val Ile Val Pro Val  Ala Asp Ile
    1160                1165                1170

Ala Asp  Ile Asp Glu Val Leu  Pro Arg Ala Leu Asp  Tyr Leu Pro
    1175                1180                1185

Gln Arg  Ala Gly Ala Gly Ser  Gly Gly Phe Ser Phe  Ser Ala Lys
    1190                1195                1200

Ser Asp  Leu Asp Ser Lys Arg  Arg Pro Ala Pro Pro  Lys Pro Glu
    1205                1210                1215

Ser Leu  Ser Asn Ile Cys Asn  Val Leu Ile Arg Lys  Thr Ala Lys
    1220                1225                1230

Thr Asp  Asp Ala Ala Leu Val  Ser Asp Ile Lys Phe  Ile Val Asp
    1235                1240                1245

Glu Tyr  Lys Glu Glu Phe Leu  Leu Arg Ser Ile Arg  Arg Val Thr
    1250                1255                1260

Phe Val  Cys Gly Arg Glu Asp  Gly Ser Tyr Pro Gly  Tyr Phe Thr
    1265                1270                1275

Phe Arg  Gly Pro Asp Tyr Val  Glu Asp Glu Ser Ile  Arg His Ile
    1280                1285                1290

Glu Pro  Ala Leu Ala Tyr Gln  Leu Glu Leu Gly Arg  Leu Ser Asn
    1295                1300                1305

Phe Asn  Tyr Lys Pro Ile Phe  Thr Asp Asn Arg Asn  Ile His Val
    1310                1315                1320

Tyr Gln  Ala Ile Gly Lys Asp  Val Pro Ser Asp Lys  Arg Phe Phe
    1325                1330                1335

Val Arg  Gly Ile Val Arg Pro  Gly Arg Leu Arg Asp  Glu Ile Pro
    1340                1345                1350

Thr Ser  Glu Tyr Leu Ile Ser  Glu Thr Asp Arg Leu  Met Ser Asp
    1355                1360                1365

Ile Leu  Asp Ala Leu Glu Val  Ile Gly Pro Asn Asn  Thr Asp Met
    1370                1375                1380

Asn His  Ile Phe Ile Asn Phe  Ser Pro Ile Phe His  Leu Val Pro
    1385                1390                1395

Glu Glu  Val Glu Ala Ala Phe  Gly Gln Phe Leu Glu  Arg Phe Gly
    1400                1405                1410

Arg Arg  Leu Trp Arg Leu Arg  Val Thr Gly Ala Glu  Ile Arg Ile
    1415                1420                1425

Met Cys  Thr Asp Pro Glu Thr  Asn Val Pro Tyr Pro  Leu Arg Ala
    1430                1435                1440

Ile Ile  Thr Asn Val Ser Gly  Tyr Val Val Gln Ser  Glu Leu Tyr
    1445                1450                1455
```

```
Thr Glu Val Lys Asn Asp Lys Gly Gln Trp Val Phe Lys Ser Leu
    1460                1465                1470

Gly Lys Pro Gly Asn Met His Leu Arg Ser Ile Thr Thr Pro Tyr
    1475                1480                1485

Ala Thr Lys Glu Trp Leu Gln Pro Lys Arg Tyr Lys Ala His Leu
    1490                1495                1500

Met Gly Thr Thr Phe Val Tyr Asp Phe Pro Glu Leu Phe Asn Gln
    1505                1510                1515

Ala Ile Arg Ala Ser Trp Arg Ala Ala Gln Gln Gln Ser Pro Glu
    1520                1525                1530

Asn Val Leu Thr Tyr Lys Glu Leu Ile Met Asp Asp Ser Gly Glu
    1535                1540                1545

Leu Ser Glu Val Ser Arg Glu Pro Gly Ala Asn Thr Cys Gly Met
    1550                1555                1560

Val Ala Trp Leu Phe Thr Ala Leu Thr Pro Glu Tyr Pro Thr Gly
    1565                1570                1575

Arg Gln Phe Ile Val Val Ala Asn Asp Ile Thr Tyr Lys Ile Gly
    1580                1585                1590

Ser Phe Gly Pro Gln Glu Asp Lys Tyr Phe His Thr Val Thr Gln
    1595                1600                1605

Leu Ala Val Lys Leu Gly Ile Pro Arg Ile Tyr Leu Ser Ala Asn
    1610                1615                1620

Ser Gly Ala Arg Ile Gly Val Ala Asp Glu Phe Val Ser Leu Phe
    1625                1630                1635

Ser Val Ala Trp Asn Asp Ser Ser Asn Pro Glu Lys Gly Phe Lys
    1640                1645                1650

Tyr Leu Tyr Leu Thr Pro Ala Ile Tyr Asn Gly Leu Ser Asp Ala
    1655                1660                1665

Ala Lys Lys Thr Val Leu Thr Glu Arg Ile Val Glu Glu Gly Glu
    1670                1675                1680

Glu Arg Tyr Val Ile Thr Thr Ile Ile Gly Ala Glu Asp Gly Leu
    1685                1690                1695

Gly Val Glu Cys Leu Arg Gly Ser Gly Leu Ile Ala Gly Ala Thr
    1700                1705                1710

Ser Lys Ala Tyr Lys Asp Ile Phe Thr Ile Thr Leu Val Thr Cys
    1715                1720                1725

Arg Ser Val Gly Ile Gly Ala Tyr Leu Val Arg Leu Gly Gln Arg
    1730                1735                1740

Ala Ile Gln Ile Glu Gly Gln Pro Ile Ile Leu Thr Gly Ala Pro
    1745                1750                1755

Ala Ile Asn Lys Leu Leu Gly Arg Glu Val Tyr Ser Ser Asn Leu
    1760                1765                1770

Gln Leu Gly Gly Thr Gln Ile Met Tyr Lys Asn Gly Val Ser His
    1775                1780                1785

Leu Thr Ala Asn Asp Asp Leu Ala Gly Val Met Lys Ile Ile Glu
    1790                1795                1800

Trp Met Ser Tyr Val Pro Tyr Lys Lys Gly Gly Gln Leu Pro Ile
    1805                1810                1815

Tyr Pro Ser Ser Asp Thr Trp Asp Arg Asp Val Thr Tyr Thr Pro
    1820                1825                1830

Pro Lys Gln Val Pro Tyr Asp Val Arg Trp Leu Ile Ala Gly Arg
    1835                1840                1845
```

```
Glu Asp  Glu Glu Gly Gly Phe  Glu Tyr Gly Leu Phe  Asp Lys Asp
    1850                 1855                 1860

Ser Phe  Gln Glu Thr Leu Ser  Gly Trp Ala Arg Thr  Val Val Val
    1865                 1870                 1875

Gly Arg  Ala Arg Leu Gly Gly  Ile Pro Val Gly Val  Ile Gly Val
    1880                 1885                 1890

Glu Val  Arg Ser Val Glu Asn  Ile Phe Pro Ala Asp  Pro Ala Asn
    1895                 1900                 1905

Pro Asp  Ser Thr Glu Met Val  Val Gln Glu Ala Gly  Gln Val Trp
    1910                 1915                 1920

Tyr Pro  Asn Ser Ala Phe Lys  Thr Ala Gln Ala Ile  Asn Asp Phe
    1925                 1930                 1935

Asn His  Gly Glu Glu Leu Pro  Leu Val Ile Leu Ala  Asn Trp Arg
    1940                 1945                 1950

Gly Phe  Ser Gly Gly Gln Arg  Asp Met Tyr Asn Glu  Val Leu Lys
    1955                 1960                 1965

Tyr Gly  Ser Phe Ile Val Asp  Ala Leu Val Gly Tyr  Lys Gln Pro
    1970                 1975                 1980

Ile Phe  Val Tyr Ile Pro Pro  His Ala Glu Leu Arg  Gly Gly Ser
    1985                 1990                 1995

Trp Val  Val Ile Asp Pro Thr  Ile Asn Ser Asp Gln  Met Glu Met
    2000                 2005                 2010

Tyr Ala  Asp Asp Glu Ala Arg  Ala Gly Val Leu Glu  Pro Glu Gly
    2015                 2020                 2025

Met Val  Gly Ile Lys Tyr Arg  Arg Asp Arg Leu Leu  Glu Thr Met
    2030                 2035                 2040

Thr Arg  Leu Asp Pro Val Tyr  Ala Ser Leu Lys Arg  Gln Ala Asp
    2045                 2050                 2055

Lys Lys  Asp Leu Ala Pro Ala  Ile Ala Gln Asp Leu  Lys Val Lys
    2060                 2065                 2070

Leu Ser  Glu Arg Glu Ser Thr  Leu Met Pro Ile Tyr  Arg Gln Ile
    2075                 2080                 2085

Ser Leu  Gln Phe Ala Asp Leu  His Asp Arg Ala Gly  Arg Met Lys
    2090                 2095                 2100

Ala Lys  Gly Thr Ile Arg Glu  Val Leu His Trp Arg  Glu Ala Arg
    2105                 2110                 2115

Arg Phe  Phe Tyr Trp Arg Val  Arg Arg Arg Val Gly  Glu Ser Tyr
    2120                 2125                 2130

Ile Leu  Arg Asp Leu Glu Ala  Ala Asn Pro Lys Ser  Thr Arg Leu
    2135                 2140                 2145

Glu Arg  Val Ala Arg Leu Lys  Ser Trp Tyr Ala Glu  Ala Gly Ile
    2150                 2155                 2160

Asn Glu  Ser Ser Asp Ala Asp  Val Ala Ser Trp Ile  Glu Lys Ser
    2165                 2170                 2175

Gly Ala  Ala Ile Thr Ser Lys  Val Lys Gln Val Arg  Lys Asp Ala
    2180                 2185                 2190

Lys Ile  Gln Asp Leu Leu Ala  Leu Val Arg Ala Asp  Lys Asp Val
    2195                 2200                 2205

Ala Leu  Gln Gly Leu Val Glu  Ser Leu Lys Ala Leu  Ser Thr Glu
    2210                 2215                 2220

Glu Arg  Asp Ala Ile Phe Lys  Gln Ala Ser Asn
    2225                 2230
```

```
<210> SEQ ID NO 11
<211> LENGTH: 1121
<212> TYPE: DNA
<213> ORGANISM: Lipomyces starkeyi
<220> FEATURE:
<221> NAME/KEY: Intron
<222> LOCATION: (42)..(94)

<400> SEQUENCE: 11

atgcttaacc tcaaagtatc tgttatcggt tctggcaact ggtaggcgcc tcctttttca     60

attcattaaa ttgctttact gactgtctcc ataggggcag cgccattgcg aaaatagtgg    120

ccgagaacgc ggctgagaac agcgacattt tcgagaccga cgttcgcatg tgggttttcg    180

aggagcttgt tgctggccag aagctcaccg aaattatcaa tacccagcac gagaacgtca    240

agtacttgcc aggcatcaaa ctgccgtcca acgtcgtggc tgtgccagac cttttggacg    300

ccgtcaagga tgccaacctc ttagtcttca acgtgcctca tcagtttctt ccacggatat    360

gtagccagct gaaaggcaaa gtgccgtcca ccgtcagagc tgtgtcttgc atcaaaggtg    420

tcgaggtttc tggcgatggc atcaccatca tcgcagacta tatctctcag gaactcggca    480

tttactgcgg tgccttgtct ggcgccaatc ttgctcccga agttgcgcaa gagaaatttt    540

ccgagacgac aatcgcgtac aaagttcccg atccaagcga ctccattgac gcacgcgtcg    600

taaggacgct cttccacaga ccttacttcc acgtaaacgt cgttggtgat gtcgccggtg    660

tgtctctttg tggtgcttta aaaaacattg tggcattggc atcaggattt gtagacggaa    720

tggcatgggg cgataatgcc aaggctgcca ttattcgaag aggattgtta gagatgacca    780

agtttggccg tgaattcttc ccggaatgca atgccagtac cttcaccgaa gaatcatgtg    840

gtgttgccga tgtcattact tcctgctctg gtgggcgcaa taacaagctt ggtgcggcga    900

tgattaagac caggcgaccc atttttgagc ttgaggaaga gttgctcaag ggtcagaagg    960

ctcaaggagt tacgactgcc caggaggtgc acgaattttt ggagcggcgg ggcaagttgg   1020

aagacttccc tcttttcacc gcagtccacg acattatttt caacggactc gacagctatg   1080

ctctgccgca gattctcgaa gatgtcgagc agaagttcta a                       1121


<210> SEQ ID NO 12
<211> LENGTH: 355
<212> TYPE: PRT
<213> ORGANISM: Lipomyces starkeyi

<400> SEQUENCE: 12

Met Leu Asn Leu Lys Val Ser Val Ile Gly Ser Gly Asn Trp Gly Ser
1               5                   10                  15

Ala Ile Ala Lys Ile Val Ala Glu Asn Ala Ala Glu Asn Ser Asp Ile
            20                  25                  30

Phe Glu Thr Asp Val Arg Met Trp Val Phe Glu Glu Leu Val Ala Gly
        35                  40                  45

Gln Lys Leu Thr Glu Ile Ile Asn Thr Gln His Glu Asn Val Lys Tyr
    50                  55                  60

Leu Pro Gly Ile Lys Ser Pro Ser Asn Val Val Ala Val Pro Asp Leu
65                  70                  75                  80

Leu Asp Ala Val Lys Asp Ala Asn Leu Leu Val Phe Asn Val Pro His
                85                  90                  95

Gln Phe Leu Pro Arg Ile Cys Ser Gln Ser Lys Gly Lys Val Pro Ser
            100                 105                 110

Thr Val Arg Ala Val Ser Cys Ile Lys Gly Val Glu Val Ser Gly Asp
        115                 120                 125
```

```
Gly Ile Thr Ile Ile Ala Asp Tyr Ile Ser Gln Glu Leu Gly Ile Tyr
    130                 135                 140

Cys Gly Ala Leu Ser Gly Ala Asn Leu Ala Pro Glu Val Ala Gln Glu
145                 150                 155                 160

Lys Phe Ser Glu Thr Thr Ile Ala Tyr Lys Val Pro Asp Pro Ser Asp
                165                 170                 175

Ser Ile Asp Ala Arg Val Val Arg Thr Leu Phe His Arg Pro Tyr Phe
            180                 185                 190

His Val Asn Val Val Gly Asp Val Ala Gly Val Ser Leu Cys Gly Ala
        195                 200                 205

Leu Lys Asn Ile Val Ala Leu Ala Ser Gly Phe Val Asp Gly Met Ala
    210                 215                 220

Trp Gly Asp Asn Ala Lys Ala Ala Ile Ile Arg Arg Gly Leu Leu Glu
225                 230                 235                 240

Met Thr Lys Phe Gly Arg Glu Phe Phe Pro Glu Cys Asn Ala Ser Thr
                245                 250                 255

Phe Thr Glu Glu Ser Cys Gly Val Ala Asp Val Ile Thr Ser Cys Ser
            260                 265                 270

Gly Gly Arg Asn Asn Lys Leu Gly Ala Ala Met Ile Lys Thr Arg Arg
        275                 280                 285

Pro Ile Phe Glu Leu Glu Glu Glu Leu Leu Lys Gly Gln Lys Ala Gln
    290                 295                 300

Gly Val Thr Thr Ala Gln Glu Val His Glu Phe Leu Glu Arg Arg Gly
305                 310                 315                 320

Lys Leu Glu Asp Phe Pro Leu Phe Thr Ala Val His Asp Ile Ile Phe
                325                 330                 335

Asn Gly Leu Asp Ser Tyr Ala Ser Pro Gln Ile Leu Glu Asp Val Glu
            340                 345                 350

Gln Lys Phe
        355
```

<210> SEQ ID NO 13
<211> LENGTH: 1832
<212> TYPE: DNA
<213> ORGANISM: Lipomyces starkeyi
<220> FEATURE:
<221> NAME/KEY: Intron
<222> LOCATION: (45)..(294)
<220> FEATURE:
<221> NAME/KEY: Intron
<222> LOCATION: (368)..(416)

<400> SEQUENCE: 13

```
atggctgata ctatcatctc ttccacgaag gcctccgaca ctgggtatgt gtgctctctc     60

ctaatcattc gcagccgcgc tctgccggcg cgagcagtcg gacggccttc ctccgtctac    120

tcgataagcc cgagttgtta gctacagcac ctcaattcat tcgttgatga cttctgacta    180

ttcgaggatt atcacgaatg acttacagag cattgcgtgt gaattgattg tgttaatcgc    240

cgatggagat gtgaaggact tatctgtacg atcatttttg ctaacaatgt ctagtgccgt    300

cccactacct ccgaactcga tcattgtggt cctgggagca tctggtgatc ttgcgaaaaa    360

gaagacagta cgttactatt atttggttgc ttatatgccg atagctgatc gaatagtacc    420

cggcgttgtt cggcttatat cgctatggat tgttgccaaa gaatgtcaag atcgtcggtt    480

atgcgcgcac aaagatggac gatgcagact acaagaagcg catatcgtca tatatgaaga    540

ctcctaccga gactatcgag acgcagttga aggagttcct ggcgatgacg tcgtacgtat    600
```

-continued

```
caggacagta cgaccaagac gaaggcttca ttagcttgac gaagcatata gaggaactcg    660

aaggcgatgt cgaggagcgt taccgtctat tttacatggc gctcccgcct aatgttttca    720

ttcctgtcgc ccagcacctt aagaagaact gctaccccaa gtctggcggt gcgagaatca    780

tcattgaaaa gccattcggt cacgatctgg ccagctcacg agagttgcag acagctcttc    840

agccgatttg gactgaagac gaaattttcc gtatcgacca ctacctcggc aaggagatgg    900

ttaagaacat tttgattctg cggtttggca atgagttctt tggcgctgcc tggaacaaga    960

accatgtgtc gtcagtccag attactttca aggagccctt cggcaccgag ggtcgtggtg   1020

gttacttcga tcagtttggt attattcgag acgttatgca gaaccatttg ctccaggttc   1080

tcacgatgat cgccatggag cggcccgttt cattctctgc cgaggacatc cgtgacgaaa   1140

aagttcgtgt actacgggcc atgccaatca ttgatcccaa gaacgttgtc atcggccagt   1200

acgataagtc cctcgatggt accaagccga gctaccagga cgacgccacc gttcccaagg   1260

gctcgcgctg cccaacattc gctgcaattg tgatgtacat caagaacgac cgatgggacg   1320

gtgtcccgtt tattctcaag gccggcaagg cgctcgatgc cgccaaagtc gaggttcgtg   1380

ttcagttcaa ggacgtcacg tccggcattt tcaaggatat accccgaaac gagcttgtcc   1440

tgcgaattca gcctgacgag gccgtgtacg tcaaaatgaa caccaagctc cctggtttaa   1500

ccatgaagac ttccgtcacc gagcttgacc tgacctacaa gcgccggttc tcggacctca   1560

agattcctga agcgtacgag gccctcatcc tcgatgcgat caatggtgac cactccaact   1620

ttgttcgaga cgatgagctc gacgcgtcct ggaagatttt cactccattt ctgcactacc   1680

tcgatgagaa caccgatatc gtaccggcca aatatcctta cggttcgcga gggccggctt   1740

tccttgatga ctttcttgcg tcgtacgggt acgcacgcga gcagcatggc atgtaccagt   1800

ggcctacaac caaggtcaat ggcaacttgt aa                                 1832
```

```
<210> SEQ ID NO 14
<211> LENGTH: 510
<212> TYPE: PRT
<213> ORGANISM: Lipomyces starkeyi

<400> SEQUENCE: 14

Met Ala Asp Thr Ile Ile Ser Ser Thr Lys Ala Ser Asp Thr Gly Ala
1               5                   10                  15

Val Pro Leu Pro Pro Asn Ser Ile Ile Val Val Ser Gly Ala Ser Gly
            20                  25                  30

Asp Leu Ala Lys Lys Lys Thr Tyr Pro Ala Leu Phe Gly Leu Tyr Arg
        35                  40                  45

Tyr Gly Leu Leu Pro Lys Asn Val Lys Ile Val Gly Tyr Ala Arg Thr
    50                  55                  60

Lys Met Asp Asp Ala Asp Tyr Lys Lys Arg Ile Ser Ser Tyr Met Lys
65                  70                  75                  80

Thr Pro Thr Glu Thr Ile Glu Thr Gln Leu Lys Glu Phe Ser Ala Met
                85                  90                  95

Thr Ser Tyr Val Ser Gly Gln Tyr Asp Gln Asp Glu Gly Phe Ile Ser
            100                 105                 110

Leu Thr Lys His Ile Glu Glu Leu Glu Gly Asp Val Glu Glu Arg Tyr
        115                 120                 125

Arg Leu Phe Tyr Met Ala Leu Pro Pro Asn Val Phe Ile Pro Val Ala
    130                 135                 140

Gln His Leu Lys Lys Asn Cys Tyr Pro Lys Ser Gly Gly Ala Arg Ile
```

```
145                 150                 155                 160

Ile Ile Glu Lys Pro Phe Gly His Asp Ser Ala Ser Ser Arg Glu Leu
                165                 170                 175

Gln Thr Ala Leu Gln Pro Ile Trp Thr Glu Asp Glu Ile Phe Arg Ile
            180                 185                 190

Asp His Tyr Leu Gly Lys Glu Met Val Lys Asn Ile Leu Ile Ser Arg
        195                 200                 205

Phe Gly Asn Glu Phe Phe Gly Ala Ala Trp Asn Lys Asn His Val Ser
    210                 215                 220

Ser Val Gln Ile Thr Phe Lys Glu Pro Phe Gly Thr Glu Gly Arg Gly
225                 230                 235                 240

Gly Tyr Phe Asp Gln Phe Gly Ile Ile Arg Asp Val Met Gln Asn His
                245                 250                 255

Leu Leu Gln Val Leu Thr Met Ile Ala Met Glu Arg Pro Val Ser Phe
            260                 265                 270

Ser Ala Glu Asp Ile Arg Asp Glu Lys Val Arg Val Leu Arg Ala Met
        275                 280                 285

Pro Ile Ile Asp Pro Lys Asn Val Val Ile Gly Gln Tyr Asp Lys Ser
    290                 295                 300

Leu Asp Gly Thr Lys Pro Ser Tyr Gln Asp Asp Ala Thr Val Pro Lys
305                 310                 315                 320

Gly Ser Arg Cys Pro Thr Phe Ala Ala Ile Val Met Tyr Ile Lys Asn
                325                 330                 335

Asp Arg Trp Asp Gly Val Pro Phe Ile Leu Lys Ala Gly Lys Ala Leu
            340                 345                 350

Asp Ala Ala Lys Val Glu Val Arg Val Gln Phe Lys Asp Val Thr Ser
        355                 360                 365

Gly Ile Phe Lys Asp Ile Pro Arg Asn Glu Leu Val Ser Arg Ile Gln
    370                 375                 380

Pro Asp Glu Ala Val Tyr Val Lys Met Asn Thr Lys Leu Pro Gly Leu
385                 390                 395                 400

Thr Met Lys Thr Ser Val Thr Glu Leu Asp Ser Thr Tyr Lys Arg Arg
                405                 410                 415

Phe Ser Asp Leu Lys Ile Pro Glu Ala Tyr Glu Ala Leu Ile Leu Asp
            420                 425                 430

Ala Ile Asn Gly Asp His Ser Asn Phe Val Arg Asp Asp Glu Leu Asp
        435                 440                 445

Ala Ser Trp Lys Ile Phe Thr Pro Phe Ser His Tyr Leu Asp Glu Asn
    450                 455                 460

Thr Asp Ile Val Pro Ala Lys Tyr Pro Tyr Gly Ser Arg Gly Pro Ala
465                 470                 475                 480

Phe Leu Asp Asp Phe Leu Ala Ser Tyr Gly Tyr Ala Arg Glu Gln His
                485                 490                 495

Gly Met Tyr Gln Trp Pro Thr Thr Lys Val Asn Gly Asn Leu
            500                 505                 510
```

```
<210> SEQ ID NO 15
<211> LENGTH: 1831
<212> TYPE: DNA
<213> ORGANISM: Lipomyces starkeyi
<220> FEATURE:
<221> NAME/KEY: Intron
<222> LOCATION: (10)..(234)
<220> FEATURE:
<221> NAME/KEY: Intron
<222> LOCATION: (332)..(393)
```

```
<220> FEATURE:
<221> NAME/KEY: Intron
<222> LOCATION: (846)..(901)
<220> FEATURE:
<221> NAME/KEY: Intron
<222> LOCATION: (1168)..(1227)

<400> SEQUENCE: 15

atgggtcagg taagtcaatt ctgctatttt acgtccactc attcgagcag cgccaatttc     60

ttactgtttg cgattggaat tgattatcaa attcctttat gtgtttcagt gatcgaaata    120

tggcgcgctt gcttggtaac cgaagatgat gcgctagtcc caattgggtt agcgtctttt    180

cttaacgggt ctctcttctc cgaccgtggc agcctcgcta acacccaagg acagaacttg    240

atcctcaacg ctgctgacca cggctacaca gtggttgctt tcaatcgtac tgtttccaag    300

gttgatcact tccttgccaa tgaagccaag ggtatgttaa tttgagctaa atttggctca    360

attgagtgtg gaggttgacg ccgattggaa taggcaagag cgttgttggt gctcactcca    420

ttgcggagct ctgcgccaag ttgaagaagc cccgtcgagt tattcttctc gttaaggctg    480

gtaaggctgt tgacgatttc attgacttgc tcttgccaca catggagcct ggtgacatca    540

tcatcgacgg tggtaactct tatttccccg actccaaccg ccgctgcaag gagctggctg    600

ctaagggctt cctctttgtc ggctctggcg tttccggtgg tgaggagggt gcccgctatg    660

gtcccagttt gatgcctggt ggtaacgagg ctgcctggcc gtacatcaag aacatcttcc    720

aggatattgc tgccaagtct gacggtgagc cttgctgcga ctgggtcggt gacgaaggcg    780

ctggtcactt cgtcaagatg gtgcacaatg gtattgagta tggtgatatg cagttgattt    840

gcgaggtatg ttggtagttt agtggtccct ccaattaaac acgcattaac aattcctcta    900

ggcgtacgat attttgaagc gcggtgctgg attcaccgac aaggagattg gcgatgtttt    960

cactcagtgg aacaagggtg tccttgactc tttcttgatc gagattacgc gtgacatttt   1020

gtacttcaat gacgacgatg gaactcctct cgttgagaag attctcgaca ctgccggtca   1080

gaagggtacc ggcaagtgga ctgccattaa cgctctcgac cttggtatgc ccgttacctt   1140

gatcggcgag gctgtcttcg ctcgaacgta agctgatagg tctcctatat tgaatgcttt   1200

gaggcaaaaa gactaatctc tggtcagttt gtccgctatc aagcccgaac gtgtccgcgc   1260

cagcaagatc ttgaccggcc ctgtccccgc cttcaagggt gacaagaagg aacttgtcga   1320

ccaactcgag caggctctct atgcttccaa gattatctcc tatgcgcagg gtttcatgtt   1380

gatcagagag gctggccgag agtacggctg gacgttgaat aaccccgcca ttgcccttat   1440

gtggagaggt ggttgcatta tccggtctgt cttcttggcg gatatcaccc gtgcctaccg   1500

ccagaaacct gacttggaga accttctatt cgacgaattc ttccacaccg ccattgacaa   1560

ggcacagcca tcgtggcgcc agacggttgc caatgctgct ctctggggta ttcccactcc   1620

cgctttctct accgctcttt ccttctacga cggttacagg agcgagagac ttccggccaa   1680

tcttctccag gcacagcgtg actacttcgg tgctcacacc ttccacatct tgcccgaatt   1740

ctcgagcgag aagtacccta aggatactga cgtccatgtt aactggactg gcagaggtgg   1800

caatgtttct gcctccacct accttgctta a                                  1831


<210> SEQ ID NO 16
<211> LENGTH: 475
<212> TYPE: PRT
<213> ORGANISM: Lipomyces starkeyi

<400> SEQUENCE: 16
```

-continued

Met Gly Gln Asn Leu Ile Leu Asn Ala Ala Asp His Gly Tyr Thr Val
1               5                   10                  15

Val Ala Phe Asn Arg Thr Val Ser Lys Val Asp His Phe Leu Ala Asn
            20                  25                  30

Glu Ala Lys Gly Lys Ser Val Val Gly Ala His Ser Ile Ala Glu Leu
        35                  40                  45

Cys Ala Lys Leu Lys Lys Pro Arg Arg Val Ile Leu Leu Val Lys Ala
    50                  55                  60

Gly Lys Ala Val Asp Asp Phe Ile Asp Leu Leu Leu Pro His Met Glu
65                  70                  75                  80

Pro Gly Asp Ile Ile Ile Asp Gly Gly Asn Ser Tyr Phe Pro Asp Ser
                85                  90                  95

Asn Arg Arg Cys Lys Glu Leu Ala Ala Lys Gly Phe Leu Phe Val Gly
            100                 105                 110

Ser Gly Val Ser Gly Gly Glu Glu Gly Ala Arg Tyr Gly Pro Ser Leu
        115                 120                 125

Met Pro Gly Gly Asn Glu Ala Ala Trp Pro Tyr Ile Lys Asn Ile Phe
    130                 135                 140

Gln Asp Ile Ala Ala Lys Ser Asp Gly Glu Pro Cys Cys Asp Trp Val
145                 150                 155                 160

Gly Asp Glu Gly Ala Gly His Phe Val Lys Met Val His Asn Gly Ile
                165                 170                 175

Glu Tyr Gly Asp Met Gln Leu Ile Cys Glu Ala Tyr Asp Ile Leu Lys
            180                 185                 190

Arg Gly Ala Gly Phe Thr Asp Lys Glu Ile Gly Asp Val Phe Thr Gln
        195                 200                 205

Trp Asn Lys Gly Val Leu Asp Ser Phe Leu Ile Glu Ile Thr Arg Asp
    210                 215                 220

Ile Leu Tyr Phe Asn Asp Asp Asp Gly Thr Pro Leu Val Glu Lys Ile
225                 230                 235                 240

Leu Asp Thr Ala Gly Gln Lys Gly Thr Gly Lys Trp Thr Ala Ile Asn
                245                 250                 255

Ala Leu Asp Leu Gly Met Pro Val Thr Leu Ile Gly Glu Ala Val Phe
            260                 265                 270

Ala Arg Thr Leu Ser Ala Ile Lys Pro Glu Arg Val Arg Ala Ser Lys
        275                 280                 285

Ile Leu Thr Gly Pro Val Pro Ala Phe Lys Gly Asp Lys Lys Glu Leu
    290                 295                 300

Val Asp Gln Leu Glu Gln Ala Leu Tyr Ala Ser Lys Ile Ile Ser Tyr
305                 310                 315                 320

Ala Gln Gly Phe Met Leu Ile Arg Glu Ala Gly Arg Glu Tyr Gly Trp
                325                 330                 335

Thr Leu Asn Asn Pro Ala Ile Ala Leu Met Trp Arg Gly Gly Cys Ile
            340                 345                 350

Ile Arg Ser Val Phe Leu Ala Asp Ile Thr Arg Ala Tyr Arg Gln Lys
        355                 360                 365

Pro Asp Leu Glu Asn Leu Leu Phe Asp Glu Phe Phe His Thr Ala Ile
    370                 375                 380

Asp Lys Ala Gln Pro Ser Trp Arg Gln Thr Val Ala Asn Ala Ala Leu
385                 390                 395                 400

Trp Gly Ile Pro Thr Pro Ala Phe Ser Thr Ala Leu Ser Phe Tyr Asp
                405                 410                 415

Gly Tyr Arg Ser Glu Arg Leu Pro Ala Asn Leu Leu Gln Ala Gln Arg

-continued

```
            420                 425                 430

Asp Tyr Phe Gly Ala His Thr Phe His Ile Leu Pro Glu Phe Ser Ser
        435                 440                 445

Glu Lys Tyr Pro Lys Asp Thr Asp Val His Val Asn Trp Thr Gly Arg
    450                 455                 460

Gly Gly Asn Val Ser Ala Ser Thr Tyr Leu Ala
465                 470                 475


<210> SEQ ID NO 17
<211> LENGTH: 5159
<212> TYPE: DNA
<213> ORGANISM: Lipomyces starkeyi
<220> FEATURE:
<221> NAME/KEY: Intron
<222> LOCATION: (63)..(216)
<220> FEATURE:
<221> NAME/KEY: Intron
<222> LOCATION: (244)..(365)
<220> FEATURE:
<221> NAME/KEY: Intron
<222> LOCATION: (827)..(882)

<400> SEQUENCE: 17

atgacttcgg tttcagacga agagagagcg cgcactcaca cattggtatt ggagctcttg      60

gcgtaagtct tctacccttg gtccaagttt tcccaatttg gcagttagcc ctaaatgctg     120

ggctgggcga tctcgacacg agaagctgta atatcgacta cagcaaggat agaaaacata     180

taggagcaag agctaatagt tattctttcc tgacagtcat cagttcgcat atcctgtaca     240

atggtaagct tcccattctt tcccaccact tcaaagacgc tgtcatgtca tgtgctcgat     300

catgttgacc tcgtacattg atttgttca cccaaaggca atatgctgac aggtggatgg     360

tgaaggattg atacacaaga tgccctcttg ggggaagaaa agatcgagcg attcgtcgag     420

attgggccat cgaacacact cactggactg gctaaacaaa ctatccaaac gaaatatcaa     480

gaccatgaca ctgccctgtc aatccaaagg cagcttttaa gcatcaaaca gactgagagt     540

gacatctact atgcaactgg agaggccgtg gaggtgccaa aacaagcacc tgctaaaacc     600

gacgcaaaac ctactgctcc agctccgtcg ccagagcctg ctgcaaccgc gcccgcgcca     660

tctgctccct cgcccgcacc gagtggagct ggtgccagat cgattgcaac agctgaggat     720

gtcccagtga agtcagaaga tatagttctt actattattg ctcaaaagtt gaagaagtcc     780

accaaggata tttcgctcag cagtaatatc aaagcgctcg ttggaggtat gaaatccatc     840

gaatgaaact tcagtgacat aaaactgatt tgaatatttt aggtcgctca actttggaga     900

atgagattgt cggagacctc cttagtgaat tcggcaacct acctgaaaga tccgaggaac     960

tcagtttgac cgagctggga gaaaccctta acagcgcaaa tgctcaaaga cgactcggca    1020

agcagacaaa taccctagta caacgtctta ttgctgcgtc aatgccggga gattttagca    1080

tgacaagggt cagaaaatat cttgaggatc gttggggctt tcaagctggc cgccaagatt    1140

ccgtgcttct atctgcaatt ccctcgcctc ctaaaaaccg acttggggat ccaaaggaag    1200

tcaatgctta tctggattca ttggttaagg agtatgcgca agccgctgga ttggcactgg    1260

aagaagcacc acagcagcag cagcagtctg ccgtccaagt caatccggaa gccataaatg    1320

ctgttgttcg gagacaagag caactggcag aacagcagct caaagtctac gctcaatttc    1380

tggatgttga tctccatgct gatggcaagt ctgcagagca atcggaaagc gccatgtcgg    1440

ctcttcagaa acagttagat ttgtgggtag ctgaacatgg tgaggcgtat gctagtggta    1500

tcactccagt ctttgatgcc aagaagcttc gagagtactc ctcttactgg acttgggcct    1560
```

-continued

```
tgcaagacct cacagctact ttctacgata tcagtcgcgg aacattaaaa gtcgaccctg   1620
aggtgattga tgatatttct taccggctgg ccaacaaatc aagcccaccg ttagtggact   1680
caatcagata cctgttgacg caatgtcatg atgaaaaatc aaaggccttc taccaactcc   1740
ttctcaatac tgttgcgcag tcaattggat ctattcccgt tttcaagacc tccacgaatt   1800
tccttggccc tcgaacaact atcgacgagc tgggcaatat cacatactct gaacacccga   1860
ggtctgaaga cggatcaaag gagcatttgg gtgaaccgac tcgtcttcca catattaaac   1920
gcaagaatga caaagaatgg acattcgatt cggcaacgac cgcattgtac aacaaagcta   1980
tcgatcaaat ctcaagcaca ggtctctcac tcgccaataa aacgattctc ctaactggag   2040
ccggaacgaa ctccatcggt gaagagcttc tgaaaggcct tctcgctggt ggtgcacaag   2100
tcattgttac gaccaatagc ttttcatcca agacagctct caagtatcag aagatctacc   2160
agggtcacgg ctctaaaggg tccaaactgg ttttggttcc atttaaccaa ggtagccagc   2220
aggatgtcga atctctggtt gattatatct acaaccagaa acaaggcctc ggttgggatc   2280
ttgatgttgt catcccattc gccgcaattt ctgttacagg gcgacaaata gacgagattg   2340
actccaagag tgagatagca cagcgtatca tgctgacaaa tactattcga cttctcggag   2400
ctatcaagag acataaggag gctgcaggct accgaacccg gcccacccat gctatacttc   2460
ccctgtcacc caaccatggt gtctttggtg gtgatggtct atactctgag tcgaagatgg   2520
cactcgaaag tctgttcgca aaatggcatt ctgaaggttg gagcgattat ctctccatct   2580
gtggtacttc aatcggttgg actcgcggca ccggtctgat gcatcagaac gatacagtgg   2640
ccgagggcgt cgaaaaactt ggcgtgagaa cattctcccg accagaaatg gctctctgca   2700
ttctcgcctt attgagtcgt cctttggtcg agttttctca agaagaaccc ctgtacgccg   2760
acttcagcgg tggtatggat aaagtaccag atttcccgag tgagttgaac gcgatccagg   2820
ataacatcaa aagcctgagc gagatccgaa gagctgttgc agcggaatta gcgcttgaca   2880
acggatctga tcttaaagcg acaaagtcag ccaaaaatga acaggatgcc ataaaaaaac   2940
gtgcgaagat cgagcttgga tttccgacct tgccaaacta tgaaacagag attcagccgc   3000
tccgctccca attggattcc atggtctcgc ttgaacacac tgttgtgatt gtaggctttt   3060
cggagctagg accttgcgga aattctcgta ctcgctggga aatggaagcc tatgatgaac   3120
tctcgctcga aggatgcacc gaaatggctt ggatcatggg cctcataaaa tattccaagg   3180
cctctggtaa taaaccagcc ggatggatcg atgtcaagac aaaagagccc gttgaggaat   3240
ttgacgtgaa aaagcgttac gagtcatata ttcgcgagca tacgggcatt cgactaattg   3300
agccgactct tttcgacaag tacaatcctg aaaagaagca aatgactcaa gagattgtcg   3360
tccaagaaga tcttgcacca ttcgaaacat ctaaggatgc tgcactcagc tttaagagag   3420
aacacggaga caaggtggaa atattcccag gcgtggagtc tgactcttac agtgtcgtca   3480
tgaaaaaggg ggcagtgata catgttccca aggccgtgaa gttcagacaa actgtcgcgg   3540
cacagattcc tacaggatgg gatccacgga cgtatggcat ttcagacgat attatcaacc   3600
aggtcgatcc ggtcacctta tatacacttg taacaactgt cgaaggcctt ctttcagcgg   3660
gtatcacgga tccttacgag atctacaagt acatccatgt ctccgaactt ggcaattgct   3720
ttggaagcgg tttgggtggt acaaactcct cagaaaagat gtaccgggat cggttggcag   3780
acaagcctgt gcagaatgat atcttgcaag agacattttt gaacacagtt ggagcttggg   3840
tgaacatgct cttgctctca tcaagtggac caaacaagac atccgttgga gcctgcgcaa   3900
```

-continued

```
cttctgtgga atcacttgac acagcctacg atctcattct tgctggcaag gcaaagatgt   3960

gtttcgttgg tagcgttgac gagttctcag aatacacgtc tttggagttt tcgaacatga   4020

aagcaactat caatgccgag acggagcgtg aggctggtcg ggacccgaag gagatgtcac   4080

gtcctgcagc ctcttcaagg aaaggtttca tggaatccca cggcgctggt ctccatatag   4140

cttgcacggc aaagcttgcc attgagatgg gactgcctat atatggtgtc atcgccttca   4200

caggcatctc cagtgacaag gtcggccgct ctgttcccgc tccgggcaag ggagtcctgt   4260

caaatgcaag agaatcgaca gctgggttcc catcgccact tcttgatatc gaatatcgtc   4320

gacgacagat tgatatacga cgacagcaaa tcaccaactt cagagaggtg gagctcagta   4380

accttgagga cacgattctg catcttatgg ccaataataa tcatttcaat gcatctgaat   4440

atcgagcata tatggtcaag cagattgatc tcaaattcca gatgcaggaa caagatatgc   4500

ttgcctcctt tggaaatcac ttttggcgta accaccctga gatcgcaccc atcaagggag   4560

cgttggcaac ctggggtctt agtgtcgacg atgtgaccgt ggcttctttc cacggaacct   4620

caactgtcct gaacgagaag aacgagtgct ctattatcca aaaccagctt tctcatctcg   4680

gacgtaccaa aggaagtcgc actctcggtg tattccagaa gagcgtcacc gggcacccga   4740

aaggtcctgc aagttcctgg atgctcaatg gctgcctgca gatcatgagc acggggctcg   4800

tgccaggaaa ccgaaatcta gataatttgg atcccgggtt tgaacagtac gatcatatca   4860

cgttcctgaa ccagaatgtt caaacggctg gcatcaaggc cttctctttg acctcatttg   4920

gcttcggcca gaagggtggt caggtgattg gtgtgcaccc caaatatctg tttgcgacaa   4980

ttccgaagga tgtgttcgac gactacgcga agaggttgaa gaagaggcgg gcgattgcga   5040

ctgtcgcatt ccatgaggca ttgctcgaga ataacatgtt tgtggcgaag gacgaccccgc  5100

cgtacgatgt tgtacaggag atgaagacgc tactggatcc aaatgctagg tgggagtag    5159
```

<210> SEQ ID NO 18
<211> LENGTH: 1608
<212> TYPE: PRT
<213> ORGANISM: Lipomyces starkeyi

<400> SEQUENCE: 18

```
Met Thr Ser Val Ser Asp Glu Glu Arg Ala Arg Thr His Thr Leu Val
1               5                   10                  15

Leu Glu Leu Leu Ala His Gln Phe Ala Tyr Pro Val Gln Trp Ile Asp
            20                  25                  30

Thr Gln Asp Ala Leu Leu Gly Glu Glu Lys Ile Glu Arg Phe Val Glu
        35                  40                  45

Ile Gly Pro Ser Asn Thr Leu Thr Gly Ser Ala Lys Gln Thr Ile Gln
    50                  55                  60

Thr Lys Tyr Gln Asp His Asp Thr Ala Ser Ser Ile Gln Arg Gln Leu
65                  70                  75                  80

Leu Ser Ile Lys Gln Thr Glu Ser Asp Ile Tyr Tyr Ala Thr Gly Glu
                85                  90                  95

Ala Val Glu Val Pro Lys Gln Ala Pro Ala Lys Thr Asp Ala Lys Pro
            100                 105                 110

Thr Ala Pro Ala Pro Ser Pro Glu Pro Ala Ala Thr Ala Pro Ala Pro
        115                 120                 125

Ser Ala Pro Ser Pro Ala Pro Ser Gly Ala Gly Ala Arg Ser Ile Ala
    130                 135                 140

Thr Ala Glu Asp Val Pro Val Lys Ser Glu Asp Ile Val Leu Thr Ile
145                 150                 155                 160
```

```
Ile Ala Gln Lys Leu Lys Lys Ser Thr Lys Asp Ile Ser Leu Ser Ser
                165                 170                 175

Asn Ile Lys Ala Leu Val Gly Gly Arg Ser Thr Leu Glu Asn Glu Ile
            180                 185                 190

Val Gly Asp Leu Leu Ser Glu Phe Gly Asn Leu Pro Glu Arg Ser Glu
        195                 200                 205

Glu Leu Ser Leu Thr Glu Ser Gly Glu Thr Leu Asn Ser Ala Asn Ala
    210                 215                 220

Gln Arg Arg Leu Gly Lys Gln Thr Asn Thr Leu Val Gln Arg Leu Ile
225                 230                 235                 240

Ala Ala Ser Met Pro Gly Asp Phe Ser Met Thr Arg Val Arg Lys Tyr
                245                 250                 255

Leu Glu Asp Arg Trp Gly Phe Gln Ala Gly Arg Gln Asp Ser Val Leu
            260                 265                 270

Leu Ser Ala Ile Pro Ser Pro Pro Lys Asn Arg Leu Gly Asp Pro Lys
        275                 280                 285

Glu Val Asn Ala Tyr Ser Asp Ser Leu Val Lys Glu Tyr Ala Gln Ala
    290                 295                 300

Ala Gly Leu Ala Ser Glu Glu Ala Pro Gln Gln Gln Gln Gln Ser Ala
305                 310                 315                 320

Val Gln Val Asn Pro Glu Ala Ile Asn Ala Val Val Arg Arg Gln Glu
                325                 330                 335

Gln Ser Ala Glu Gln Gln Leu Lys Val Tyr Ala Gln Phe Ser Asp Val
            340                 345                 350

Asp Leu His Ala Asp Gly Lys Ser Ala Glu Gln Ser Glu Ser Ala Met
        355                 360                 365

Ser Ala Leu Gln Lys Gln Leu Asp Leu Trp Val Ala Glu His Gly Glu
    370                 375                 380

Ala Tyr Ala Ser Gly Ile Thr Pro Val Phe Asp Ala Lys Lys Leu Arg
385                 390                 395                 400

Glu Tyr Ser Ser Tyr Trp Thr Trp Ala Leu Gln Asp Leu Thr Ala Thr
                405                 410                 415

Phe Tyr Asp Ile Ser Arg Gly Thr Leu Lys Val Asp Pro Glu Val Ile
            420                 425                 430

Asp Asp Ile Ser Tyr Arg Ser Ala Asn Lys Ser Ser Pro Pro Leu Val
        435                 440                 445

Asp Ser Ile Arg Tyr Ser Leu Thr Gln Cys His Asp Glu Lys Ser Lys
    450                 455                 460

Ala Phe Tyr Gln Leu Leu Leu Asn Thr Val Ala Gln Ser Ile Gly Ser
465                 470                 475                 480

Ile Pro Val Phe Lys Thr Ser Thr Asn Phe Leu Gly Pro Arg Thr Thr
                485                 490                 495

Ile Asp Glu Ser Gly Asn Ile Thr Tyr Ser Glu His Pro Arg Ser Glu
            500                 505                 510

Asp Gly Ser Lys Glu His Leu Gly Glu Pro Thr Arg Leu Pro His Ile
        515                 520                 525

Lys Arg Lys Asn Asp Lys Glu Trp Thr Phe Asp Ser Ala Thr Thr Ala
    530                 535                 540

Leu Tyr Asn Lys Ala Ile Asp Gln Ile Ser Ser Thr Gly Leu Ser Leu
545                 550                 555                 560

Ala Asn Lys Thr Ile Leu Leu Thr Gly Ala Gly Thr Asn Ser Ile Gly
                565                 570                 575
```

```
Glu Glu Leu Ser Lys Gly Leu Leu Ala Gly Gly Ala Gln Val Ile Val
            580                 585                 590

Thr Thr Asn Ser Phe Ser Ser Lys Thr Ala Leu Lys Tyr Gln Lys Ile
        595                 600                 605

Tyr Gln Gly His Gly Ser Lys Gly Ser Lys Ser Val Leu Val Pro Phe
    610                 615                 620

Asn Gln Gly Ser Gln Gln Asp Val Glu Ser Ser Val Asp Tyr Ile Tyr
625                 630                 635                 640

Asn Gln Lys Gln Gly Leu Gly Trp Asp Leu Asp Val Val Ile Pro Phe
                645                 650                 655

Ala Ala Ile Ser Val Thr Gly Arg Gln Ile Asp Glu Ile Asp Ser Lys
            660                 665                 670

Ser Glu Ile Ala Gln Arg Ile Met Ser Thr Asn Thr Ile Arg Leu Leu
        675                 680                 685

Gly Ala Ile Lys Arg His Lys Glu Ala Ala Gly Tyr Arg Thr Arg Pro
    690                 695                 700

Thr His Ala Ile Leu Pro Ser Ser Pro Asn His Gly Val Phe Gly Gly
705                 710                 715                 720

Asp Gly Leu Tyr Ser Glu Ser Lys Met Ala Leu Glu Ser Ser Phe Ala
                725                 730                 735

Lys Trp His Ser Glu Gly Trp Ser Asp Tyr Leu Ser Ile Cys Gly Thr
            740                 745                 750

Ser Ile Gly Trp Thr Arg Gly Thr Gly Ser Met His Gln Asn Asp Thr
        755                 760                 765

Val Ala Glu Gly Val Glu Lys Leu Gly Val Arg Thr Phe Ser Arg Pro
    770                 775                 780

Glu Met Ala Leu Cys Ile Leu Ala Leu Leu Ser Arg Pro Leu Val Glu
785                 790                 795                 800

Phe Ser Gln Glu Glu Pro Ser Tyr Ala Asp Phe Ser Gly Gly Met Asp
                805                 810                 815

Lys Val Pro Asp Phe Pro Ser Glu Leu Asn Ala Ile Gln Asp Asn Ile
            820                 825                 830

Lys Ser Ser Ser Glu Ile Arg Arg Ala Val Ala Ala Glu Leu Ala Leu
        835                 840                 845

Asp Asn Gly Ser Asp Leu Lys Ala Thr Lys Ser Ala Lys Asn Glu Gln
    850                 855                 860

Asp Ala Ile Lys Lys Arg Ala Lys Ile Glu Leu Gly Phe Pro Thr Leu
865                 870                 875                 880

Pro Asn Tyr Glu Thr Glu Ile Gln Pro Leu Arg Ser Gln Leu Asp Ser
                885                 890                 895

Met Val Ser Leu Glu His Thr Val Val Ile Val Gly Phe Ser Glu Leu
            900                 905                 910

Gly Pro Cys Gly Asn Ser Arg Thr Arg Trp Glu Met Glu Ala Tyr Asp
        915                 920                 925

Glu Leu Ser Leu Glu Gly Cys Thr Glu Met Ala Trp Ile Met Gly Leu
    930                 935                 940

Ile Lys Tyr Ser Lys Ala Ser Gly Asn Lys Pro Ala Gly Trp Ile Asp
945                 950                 955                 960

Val Lys Thr Lys Glu Pro Val Glu Glu Phe Asp Val Lys Lys Arg Tyr
                965                 970                 975

Glu Ser Tyr Ile Arg Glu His Thr Gly Ile Arg Leu Ile Glu Pro Thr
            980                 985                 990

Leu Phe Asp Lys Tyr Asn Pro Glu  Lys Lys Gln Met Thr  Gln Glu Ile
```

-continued

```
        995                 1000                1005

Val Val  Gln Glu Asp Leu Ala  Pro Phe Glu Thr Ser  Lys Asp Ala
    1010                 1015                 1020

Ala Leu  Ser Phe Lys Arg Glu  His Gly Asp Lys Val  Glu Ile Phe
    1025                 1030                 1035

Pro Gly  Val Glu Ser Asp Ser  Tyr Ser Val Val Met  Lys Lys Gly
    1040                 1045                 1050

Ala Val  Ile His Val Pro Lys  Ala Val Lys Phe Arg  Gln Thr Val
    1055                 1060                 1065

Ala Ala  Gln Ile Pro Thr Gly  Trp Asp Pro Arg Thr  Tyr Gly Ile
    1070                 1075                 1080

Ser Asp  Asp Ile Ile Asn Gln  Val Asp Pro Val Thr  Leu Tyr Thr
    1085                 1090                 1095

Leu Val  Thr Thr Val Glu Gly  Leu Leu Ser Ala Gly  Ile Thr Asp
    1100                 1105                 1110

Pro Tyr  Glu Ile Tyr Lys Tyr  Ile His Val Ser Glu  Leu Gly Asn
    1115                 1120                 1125

Cys Phe  Gly Ser Gly Leu Gly  Gly Thr Asn Ser Ser  Glu Lys Met
    1130                 1135                 1140

Tyr Arg  Asp Arg Leu Ala Asp  Lys Pro Val Gln Asn  Asp Ile Leu
    1145                 1150                 1155

Gln Glu  Thr Phe Leu Asn Thr  Val Gly Ala Trp Val  Asn Met Leu
    1160                 1165                 1170

Leu Leu  Ser Ser Ser Gly Pro  Asn Lys Thr Ser Val  Gly Ala Cys
    1175                 1180                 1185

Ala Thr  Ser Val Glu Ser Leu  Asp Thr Ala Tyr Asp  Leu Ile Leu
    1190                 1195                 1200

Ala Gly  Lys Ala Lys Met Cys  Phe Val Gly Ser Val  Asp Glu Phe
    1205                 1210                 1215

Ser Glu  Tyr Thr Ser Leu Glu  Phe Ser Asn Met Lys  Ala Thr Ile
    1220                 1225                 1230

Asn Ala  Glu Thr Glu Arg Glu  Ala Gly Arg Asp Pro  Lys Glu Met
    1235                 1240                 1245

Ser Arg  Pro Ala Ala Ser Ser  Arg Lys Gly Phe Met  Glu Ser His
    1250                 1255                 1260

Gly Ala  Gly Leu His Ile Ala  Cys Thr Ala Lys Leu  Ala Ile Glu
    1265                 1270                 1275

Met Gly  Ser Pro Ile Tyr Gly  Val Ile Ala Phe Thr  Gly Ile Ser
    1280                 1285                 1290

Ser Asp  Lys Val Gly Arg Ser  Val Pro Ala Pro Gly  Lys Gly Val
    1295                 1300                 1305

Ser Ser  Asn Ala Arg Glu Ser  Thr Ala Gly Phe Pro  Ser Pro Leu
    1310                 1315                 1320

Leu Asp  Ile Glu Tyr Arg Arg  Arg Gln Ile Asp Ile  Arg Arg Gln
    1325                 1330                 1335

Gln Ile  Thr Asn Phe Arg Glu  Val Glu Leu Ser Asn  Leu Glu Asp
    1340                 1345                 1350

Thr Ile  Ser His Leu Met Ala  Asn Asn Asn His Phe  Asn Ala Ser
    1355                 1360                 1365

Glu Tyr  Arg Ala Tyr Met Val  Lys Gln Ile Asp Leu  Lys Phe Gln
    1370                 1375                 1380

Met Gln  Glu Gln Asp Met Leu  Ala Ser Phe Gly Asn  His Phe Trp
    1385                 1390                 1395
```

-continued

```
Arg Asn  His Pro Glu Ile Ala  Pro Ile Lys Gly Ala  Leu Ala Thr
    1400                 1405                 1410

Trp Gly  Leu Ser Val Asp Asp  Val Thr Val Ala Ser  Phe His Gly
    1415                 1420                 1425

Thr Ser  Thr Val Ser Asn Glu  Lys Asn Glu Cys Ser  Ile Ile Gln
    1430                 1435                 1440

Asn Gln  Leu Ser His Leu Gly  Arg Thr Lys Gly Ser  Arg Thr Leu
    1445                 1450                 1455

Gly Val  Phe Gln Lys Ser Val  Thr Gly His Pro Lys  Gly Pro Ala
    1460                 1465                 1470

Ser Ser  Trp Met Leu Asn Gly  Cys Ser Gln Ile Met  Ser Thr Gly
    1475                 1480                 1485

Leu Val  Pro Gly Asn Arg Asn  Leu Asp Asn Leu Asp  Pro Gly Phe
    1490                 1495                 1500

Glu Gln  Tyr Asp His Ile Thr  Phe Ser Asn Gln Asn  Val Gln Thr
    1505                 1510                 1515

Ala Gly  Ile Lys Ala Phe Ser  Leu Thr Ser Phe Gly  Phe Gly Gln
    1520                 1525                 1530

Lys Gly  Gly Gln Val Ile Gly  Val His Pro Lys Tyr  Ser Phe Ala
    1535                 1540                 1545

Thr Ile  Pro Lys Asp Val Phe  Asp Asp Tyr Ala Lys  Arg Leu Lys
    1550                 1555                 1560

Lys Arg  Arg Ala Ile Ala Thr  Val Ala Phe His Glu  Ala Leu Leu
    1565                 1570                 1575

Glu Asn  Asn Met Phe Val Ala  Lys Asp Asp Pro Pro  Tyr Asp Val
    1580                 1585                 1590

Val Gln  Glu Met Lys Thr Leu  Ser Asp Pro Asn Ala  Arg Trp Glu
    1595                 1600                 1605
```

<210> SEQ ID NO 19
<211> LENGTH: 6132
<212> TYPE: DNA
<213> ORGANISM: Lipomyces starkeyi
<220> FEATURE:
<221> NAME/KEY: Intron
<222> LOCATION: (5030)..(5080)

<400> SEQUENCE: 19

```
atgagggatc gattttttca acatatcggc acgacggcgg ccagtgatga gctgttacct      60

caggagtcac tggtagagct tatcacagac tttctggact tcaaatcaaa gcttttgctt     120

aattggccag gtgccgatag aacatccagg cagaggcttc ttcgagcttt gctcgaccat     180

ctggagagaa atgtccttac agatgacatc cacaccattg cggcgatatc gtccgacgac     240

cccgagcgac ctgctaaaat cattcgatca tactactctg cgtgccatgc atcaggtcgc     300

cccatagcca agcgccagtc tgcactgctg gattccgttt cgagtggtga ctccaagttg     360

tacgccgtgc tcggtggtca aggaatcact actgcttatc tggatgagct gcgcgaaatc     420

catacaatgt atcacagttt cttggtagat tatatcgaga cattggggga gttcttgaaa     480

tcccttgcat cccagccaga tgtgtctcga tattacccag aaggcctgga tatcatcaac     540

tggctgcgaa acccggaagc aacaccagat gtaagctacc ttgcttcatc ccgagtcagc     600

ttccctatta ttggcatact ccagctcgcg caatatatgg tcagcctgaa ggttttgggt     660

caaaatccct caactttcaa tcccagtctt agcggcatag ctggccactc tcaggggttg     720

gtcattgctg cagtaatcgc tggcgctgtc gactggtcgt ctttcatcga cttgagtcgt     780
```

acagccgtgg agatactgtt ttcgattgga gttgtcagcc agcagatcta tcctgagaca 840
tcaccagacc caaagatagt ctccgattct atctccaatg atgaaggcac cccttcctct 900
atgctcagca ttcgtggcat ctccgaagct caagtccagg agcacgtgga tgtgtccaac 960
aaatctctac ccgaagatag aaagatttcg attgctctag caaatgggcc acgtaatttc 1020
gtggttgctg gacctgccac atccttgtgt gggctgaacg cacgtttgag gcggtttaaa 1080
gtgtccgcag aagtcgacca gaaccgaatc ccatcaaagg agcgaaaatc gactctcacg 1140
aaccactttc tccctataag tgtgcctttc cacaccaact atctacttcc tgcacttccg 1200
atcttgagaa agcgtctcgg ccatatttc ctacccagta acagtctgca aattccggta 1260
tacgacacaa acactggcga agaccttagc gccttgggta gtgagaatct acttgatagg 1320
ctagtatacc tgatcacagt cgcccctgtt cgctggctca aggcttcaac ctgtgaatcg 1380
gcgtctcata tcgttgactt tggtcctgga ggcagttccg gtattggcgt cgttactagc 1440
cacaacaagc aaggaacggg tgttcgtgtt atgatggctg gcgctttagc tggaaaatcc 1500
tccgaagtcg gttacaaggc cgaacttttc agttggaaca aagcttccat tgtggatagc 1560
aagaattggg caagaagctt tagcccaaga ctgattcggg cgaccgatgg gcaaattcac 1620
ctcgagacca aaatgagcaa gcttttacac atgccaccca tcatggttgc tggcatgacg 1680
ccaactactg tatcctggag atttgtttca gctaccatca atgctggata tcacattgag 1740
ttagctggcg gaggctaccg tgacgaagcc atgttgacaa cagccttgaa caacatcgtg 1800
gctacgattc cacctggacg aggagtttgc atcaacatca tatatgtcga cccccgtgca 1860
gtagcatggc agatcccact tctggagaag ctccatgcgg aaggaatacc aattgatggt 1920
ttgaccattg gcgctggagt gccttcagtc gagatttccc aaagctatat caacgacctt 1980
ggattgaaat atattgcctt caaacctggt tcggtcaatt caatcaagca ggttattagc 2040
attgctaaag ccaattccac cttccccgtc attttgcagt ggactggcgg ccgagccgga 2100
ggccatcact ctttcgaaga cttccacacg ccgattttgg aagtctatgg ccagatccgc 2160
gattgcgaaa atattattct cgtcgctggt agtggctttg gctcagctga ggatgcttat 2220
ccatacttca ctggagcatg gtccaaggct ttcggttatc cccccatgcc ctttgatggt 2280
gtgttgcttg gaagtcgcat gatgacggca aaggaagcct ccaccagtgt ggggtccaag 2340
aagaagatcg ttgagactga cggtcttcct gatggccaat gggagaaaac attcaaaggc 2400
gcagctggag gtgtgattac tgtcatctca gagatgggag agccaatgca cgttctagca 2460
actcgcggta tgagattctg ggctgaaatg gacactatct tcaagatgcc caaggatcag 2520
atggttgcta cgctacagaa gagaagcagc tacatcatca aaaagctcaa cgacgacttc 2580
caaaaagttt ggttcggcaa gaacacggct gaggaagctg tgctactgaa ggagatgact 2640
tatcacgaag tagttgcccg aatggtcgag ctgatgtata tcagtgcaag gggtgtatgg 2700
atcgataagt cattgaagac ccttacaggt gacttcattc gtcgggttga ggaaagattc 2760
gcaacgagca gcggcagtgg attcgttctt tcggattatg ccgacctcga tgctcctcaa 2820
gtggtgctgg acacccttgt caaaacctac cccgatatca gtgatgatat cattactcct 2880
ttggatgttc agttcttctt gtcgctctgt ctgcgtccag gcaagaaacc agttcctttt 2940
gttccggtcc tcgatgaaaa cttgtcattc tatttcaaga aagattcgct gtggcagtct 3000
gagaaccttt gggcggttgt tggtaatgat gcagatcgta cacagatctt gcacggaccg 3060
gtagcagctc aacattcgaa gacctacgac gaacctgtcc aggacatcct cgacggcatc 3120

-continued

```
aagaatgggc tggtttcttc attgctcaaa gaagcttaca atggagagat caggaatctt   3180
cccgttcaga aggctccatt ggaaataacg ccacaagctc attggtctga ctccgaacgc   3240
aatgtgtcta tcaccgagtc ttcagagtca gtcgtctacg caatctcttc ggcgcgtgat   3300
gatttaccct cgccaagttc gtggtataga atgatcgcag gtgaccaata cacatggcgt   3360
tatgcgctcc tcagttcaga aactgtcatt tccggcaaca agcggttacc aaaccctatt   3420
cgcaaaatct gcacgccttc cagtgacctt cgtgtaactg ttgaaaacca taccgagcca   3480
tcgaaaatgg ttatcaccat ccaagctgca tcagatacgg agaaccccga tactgttgtg   3540
aagataaggt tgcagggatc ctgcatagtt gctgattgca tattgagtcc aacaactact   3600
catgtatcgc caaccttgcg attggcgttc tcataccacc cggatgcggt gtacgcgccg   3660
atacgggaga actcagatgg cttactcgat gaggtttcag aattctacag aaaactttgg   3720
tttggcgatg aacaactcga ctttgatgcg cagcctaccc aagatttctc gggagaaaca   3780
atgaccatta ctcgggaggc aatcagctct tttctccaag ccaccggcag tagttgcgag   3840
acataccgta gccgcgcaaa tcaggaactg cctgcacctt tggactttgg cattgttatt   3900
gcttggaaag ctctcctgaa accaatcttt ttgagaaaga atggtggcaa tattctcaag   3960
cttgtacatc tctccaacaa gttcaagcgt gtggatggag cagcttcttt aagcgctggc   4020
gacaaagtgt cgacttcttc ccgcatcaca gcggttcgca ttcaggatgc aggcaaagtg   4080
gttgaggtac ttgcggtcat taccaaggat ggaagtcctg tgatggaagt tgtctcgcaa   4140
ttcatgtatc gcggaaaata cactgacttc gaaacaactt ttgaacgaaa agttgaagtc   4200
ccgatgcagg tccatttggg ttcacgaaag gacgtcgcaa tcctcaaatc caagccttgg   4260
ttccaattaa ccaaccccga ctccgaattg ttggacagga ccttcatttt ccgtctcgaa   4320
actacgcaag tgaagtctac cgctactgct ggcaccgttt tggtggttgg cactgtttct   4380
gagaagcacg ctacagatgg tgaacgctca gtagcttcaa tcaactatac tactgcgctc   4440
tcctccgtca atcccatttt gcgctatctc aacacgcatg gtagcggagt cgaaggtcct   4500
gttttgctcg aaaatgcaat tccagttcat ggtgccagtg gaattccact caagaggccg   4560
atgtctagcg ctgcttatgc aaaggtctcc ggggattaca atcctatcca cgtgtcgaac   4620
acctttgcat tgctcgccaa cttaccaggc tcgattgttc atggcatgca tacaagctct   4680
gccattggat cattgcttga aacttggact gccaaaggtc gcgtgggcgc agtgcgcagt   4740
tttgaagctt cttttgtcgg tatggttctt ccggatgatc tggtagatgt cgagttttgg   4800
catacggcta tgatgaaagg ccgcaaagtg atcaagatta cagccaagaa gacagacagt   4860
ggtgagatgg tgttgaaggg cgaagccgag gtggaggaac agagatctgc ctacctgttc   4920
accggccagg gttcacagga acccaacatg ggcatggacc tttatgcaag cagcccaatt   4980
gctcgatctg tgtgggatat tgccgacaag ttctacttga agacttatgg ttcgttatcc   5040
tttcctgtat acgataccca gttattaatt ctttttctag gttttgagat cacaaagatc   5100
gtcagagaga atcccaagga gatgactatt cattttggag gcgtcaatgg cagacgtatt   5160
cgccagaact acctttcatt gactctgcaa actactggtg atgacggtca gccaatcttg   5220
gagaaagtct tcaaggacat caacgaggac tcagagtcct acactttcaa gtcgcccaag   5280
ggtcttctcc atgcaacgca gttcacgcaa gcggctatta ccctggtaga actcgcacgg   5340
tacaaggaca tggaagcccg aggtcttatt tcggagaatt acaactttgc gggccactcc   5400
cttggagagt atccagccct agcatcattc gcacaaataa tgtcgattga gcagttagtc   5460
gcaatttgtt tctaccgtgg tatggcgatg caagttaccg tcaaacgtga cgagcaaggc   5520
```

```
gcttcagact actccttgtg tgctgtcaac ccgagtcgag tttcaaagac tttcaacgaa   5580

aagatgttgc gcttcattac caagaccatt tcgcaacaga ctgggtggct tctggagatt   5640

gtgaatttca acatctcaaa cagacaatat gtctgtgcag gagaactcat agcactcgat   5700

tgtcttacga aactacttga ccgcatcgca aagggcctga atgtcgactg gatcaatcga   5760

cctggaagtg gattagatgg taagactgtg ttcttatcaa ctgtccgttc catcatacaa   5820

gaggcacaag caaagaaaac acgcgtcgaa ttgaaacgag gtacgggcat tacacctctg   5880

gaaggcattg acgtgccgtt ccactcgact ctccttcgtc caggtgttgc cacattccgt   5940

gactttttgg catcaaagat tgatccgtca aatatcgatg cgaaaaagct cgttaataaa   6000

tgggtcccta atctcacagg gaagccattt aggaatgacc ggaagtattt tgaatatgtc   6060

tacaatctta cagggtctgt gcctcttcag aagctgttgg gagaatggag ggaaatagat   6120

ttggttatgt ag                                                       6132


<210> SEQ ID NO 20
<211> LENGTH: 2026
<212> TYPE: PRT
<213> ORGANISM: Lipomyces starkeyi

<400> SEQUENCE: 20

Met Arg Asp Arg Phe Phe Gln His Ile Gly Thr Thr Ala Ala Ser Asp
1               5                   10                  15

Glu Ser Leu Pro Gln Glu Ser Ser Val Glu Leu Ile Thr Asp Phe Ser
            20                  25                  30

Asp Phe Lys Ser Lys Leu Leu Leu Asn Trp Pro Gly Ala Asp Arg Thr
        35                  40                  45

Ser Arg Gln Arg Leu Leu Arg Ala Leu Leu Asp His Ser Glu Arg Asn
    50                  55                  60

Val Leu Thr Asp Asp Ile His Thr Ile Ala Ala Ile Ser Ser Asp Asp
65                  70                  75                  80

Pro Glu Arg Pro Ala Lys Ile Ile Arg Ser Tyr Tyr Ser Ala Cys His
                85                  90                  95

Ala Ser Gly Arg Pro Ile Ala Lys Arg Gln Ser Ala Ser Ser Asp Ser
            100                 105                 110

Val Ser Ser Gly Asp Ser Lys Leu Tyr Ala Val Leu Gly Gly Gln Gly
        115                 120                 125

Ile Thr Thr Ala Tyr Ser Asp Glu Ser Arg Glu Ile His Thr Met Tyr
    130                 135                 140

His Ser Phe Leu Val Asp Tyr Ile Glu Thr Leu Gly Glu Phe Leu Lys
145                 150                 155                 160

Ser Leu Ala Ser Gln Pro Asp Val Ser Arg Tyr Tyr Pro Glu Gly Ser
                165                 170                 175

Asp Ile Ile Asn Trp Ser Arg Asn Pro Glu Ala Thr Pro Asp Val Ser
            180                 185                 190

Tyr Leu Ala Ser Ser Arg Val Ser Phe Pro Ile Ile Gly Ile Leu Gln
        195                 200                 205

Leu Ala Gln Tyr Met Val Ser Ser Lys Val Leu Gly Gln Asn Pro Ser
    210                 215                 220

Thr Phe Asn Pro Ser Leu Ser Gly Ile Ala Gly His Ser Gln Gly Leu
225                 230                 235                 240

Val Ile Ala Ala Val Ile Ala Gly Ala Val Asp Trp Ser Ser Phe Ile
                245                 250                 255
```

-continued

```
Asp Leu Ser Arg Thr Ala Val Glu Ile Ser Phe Ser Ile Gly Val Val
            260                 265                 270

Ser Gln Gln Ile Tyr Pro Glu Thr Ser Pro Asp Pro Lys Ile Val Ser
        275                 280                 285

Asp Ser Ile Ser Asn Asp Glu Gly Thr Pro Ser Ser Met Leu Ser Ile
    290                 295                 300

Arg Gly Ile Ser Glu Ala Gln Val Gln Glu His Val Asp Val Ser Asn
305                 310                 315                 320

Lys Ser Leu Pro Glu Asp Arg Lys Ile Ser Ile Ala Leu Ala Asn Gly
                325                 330                 335

Pro Arg Asn Phe Val Val Ala Gly Pro Ala Thr Ser Leu Cys Gly Ser
            340                 345                 350

Asn Ala Arg Leu Arg Arg Phe Lys Val Ser Ala Glu Val Asp Gln Asn
        355                 360                 365

Arg Ile Pro Ser Lys Glu Arg Lys Ser Thr Leu Thr Asn His Phe Leu
    370                 375                 380

Pro Ile Ser Val Pro Phe His Thr Asn Tyr Leu Leu Pro Ala Leu Pro
385                 390                 395                 400

Ile Leu Arg Lys Arg Leu Gly His Ile Phe Leu Pro Ser Asn Ser Ser
                405                 410                 415

Gln Ile Pro Val Tyr Asp Thr Asn Thr Gly Glu Asp Leu Ser Ala Leu
            420                 425                 430

Gly Ser Glu Asn Leu Leu Asp Arg Leu Val Tyr Ser Ile Thr Val Ala
        435                 440                 445

Pro Val Arg Trp Leu Lys Ala Ser Thr Cys Glu Ser Ala Ser His Ile
    450                 455                 460

Val Asp Phe Gly Pro Gly Gly Ser Ser Gly Ile Gly Val Val Thr Ser
465                 470                 475                 480

His Asn Lys Gln Gly Thr Gly Val Arg Val Met Met Ala Gly Ala Leu
                485                 490                 495

Ala Gly Lys Ser Ser Glu Val Gly Tyr Lys Ala Glu Leu Phe Ser Trp
            500                 505                 510

Asn Lys Ala Ser Ile Val Asp Ser Lys Asn Trp Ala Arg Ser Phe Ser
        515                 520                 525

Pro Arg Ser Ile Arg Ala Thr Asp Gly Gln Ile His Leu Glu Thr Lys
    530                 535                 540

Met Ser Lys Leu Leu His Met Pro Pro Ile Met Val Ala Gly Met Thr
545                 550                 555                 560

Pro Thr Thr Val Ser Trp Arg Phe Val Ser Ala Thr Ile Asn Ala Gly
                565                 570                 575

Tyr His Ile Glu Leu Ala Gly Gly Gly Tyr Arg Asp Glu Ala Met Leu
            580                 585                 590

Thr Thr Ala Leu Asn Asn Ile Val Ala Thr Ile Pro Pro Gly Arg Gly
        595                 600                 605

Val Cys Ile Asn Ile Ile Tyr Val Asp Pro Arg Ala Val Ala Trp Gln
    610                 615                 620

Ile Pro Leu Ser Glu Lys Leu His Ala Glu Gly Ile Pro Ile Asp Gly
625                 630                 635                 640

Leu Thr Ile Gly Ala Gly Val Pro Ser Val Glu Ile Ser Gln Ser Tyr
                645                 650                 655

Ile Asn Asp Leu Gly Leu Lys Tyr Ile Ala Phe Lys Pro Gly Ser Val
            660                 665                 670

Asn Ser Ile Lys Gln Val Ile Ser Ile Ala Lys Ala Asn Ser Thr Phe
```

-continued

```
        675                 680                 685

Pro Val Ile Leu Gln Trp Thr Gly Gly Arg Ala Gly Gly His His Ser
    690                 695                 700

Phe Glu Asp Phe His Thr Pro Ile Leu Glu Val Tyr Gly Gln Ile Arg
705                 710                 715                 720

Asp Cys Glu Asn Ile Ile Leu Val Ala Gly Ser Gly Phe Gly Ser Ala
                725                 730                 735

Glu Asp Ala Tyr Pro Tyr Phe Thr Gly Ala Trp Ser Lys Ala Phe Gly
            740                 745                 750

Tyr Pro Pro Met Pro Phe Asp Gly Val Leu Leu Gly Ser Arg Met Met
        755                 760                 765

Thr Ala Lys Glu Ala Ser Thr Ser Val Gly Ser Lys Lys Lys Ile Val
    770                 775                 780

Glu Thr Asp Gly Leu Pro Asp Gly Gln Trp Glu Lys Thr Phe Lys Gly
785                 790                 795                 800

Ala Ala Gly Gly Val Ile Thr Val Ile Ser Glu Met Gly Glu Pro Met
                805                 810                 815

His Val Leu Ala Thr Arg Gly Met Arg Phe Trp Ala Glu Met Asp Thr
            820                 825                 830

Ile Phe Lys Met Pro Lys Asp Gln Met Val Ala Thr Leu Gln Lys Arg
        835                 840                 845

Ser Ser Tyr Ile Ile Lys Lys Leu Asn Asp Asp Phe Gln Lys Val Trp
    850                 855                 860

Phe Gly Lys Asn Thr Ala Glu Glu Ala Val Leu Ser Lys Glu Met Thr
865                 870                 875                 880

Tyr His Glu Val Val Ala Arg Met Val Glu Ser Met Tyr Ile Ser Ala
                885                 890                 895

Arg Gly Val Trp Ile Asp Lys Ser Leu Lys Thr Leu Thr Gly Asp Phe
            900                 905                 910

Ile Arg Arg Val Glu Glu Arg Phe Ala Thr Ser Ser Gly Ser Gly Phe
        915                 920                 925

Val Leu Ser Asp Tyr Ala Asp Leu Asp Ala Pro Gln Val Val Ser Asp
    930                 935                 940

Thr Leu Val Lys Thr Tyr Pro Asp Ile Ser Asp Asp Ile Ile Thr Pro
945                 950                 955                 960

Leu Asp Val Gln Phe Phe Leu Ser Leu Cys Ser Arg Pro Gly Lys Lys
                965                 970                 975

Pro Val Pro Phe Val Pro Val Leu Asp Glu Asn Leu Ser Phe Tyr Phe
            980                 985                 990

Lys Lys Asp Ser Ser Trp Gln Ser  Glu Asn Leu Trp Ala  Val Val Gly
        995                 1000                1005

Asn Asp  Ala Asp Arg Thr Gln  Ile Leu His Gly Pro  Val Ala Ala
    1010                1015                1020

Gln His  Ser Lys Thr Tyr Asp  Glu Pro Val Gln Asp  Ile Leu Asp
    1025                1030                1035

Gly Ile  Lys Asn Gly Ser Val  Ser Ser Leu Leu Lys  Glu Ala Tyr
    1040                1045                1050

Asn Gly  Glu Ile Arg Asn Leu  Pro Val Gln Lys Ala  Pro Leu Glu
    1055                1060                1065

Ile Thr  Pro Gln Ala His Trp  Ser Asp Ser Glu Arg  Asn Val Ser
    1070                1075                1080

Ile Thr  Glu Ser Ser Glu Ser  Val Val Tyr Ala Ile  Ser Ser Ala
    1085                1090                1095
```

-continued

```
Arg Asp  Asp Leu Pro Ser Pro  Ser Ser Trp Tyr Arg  Met Ile Ala
    1100                 1105                 1110

Gly Asp  Gln Tyr Thr Trp Arg  Tyr Ala Leu Leu Ser  Ser Glu Thr
    1115                 1120                 1125

Val Ile  Ser Gly Asn Lys Arg  Leu Pro Asn Pro Ile  Arg Lys Ile
    1130                 1135                 1140

Cys Thr  Pro Ser Ser Asp Leu  Arg Val Thr Val Glu  Asn His Thr
    1145                 1150                 1155

Glu Pro  Ser Lys Met Val Ile  Thr Ile Gln Ala Ala  Ser Asp Thr
    1160                 1165                 1170

Glu Asn  Pro Asp Thr Val Val  Lys Ile Arg Leu Gln  Gly Ser Cys
    1175                 1180                 1185

Ile Val  Ala Asp Cys Ile Leu  Ser Pro Thr Thr Thr  His Val Ser
    1190                 1195                 1200

Pro Thr  Leu Arg Leu Ala Phe  Ser Tyr His Pro Asp  Ala Val Tyr
    1205                 1210                 1215

Ala Pro  Ile Arg Glu Asn Ser  Asp Gly Leu Leu Asp  Glu Val Ser
    1220                 1225                 1230

Glu Phe  Tyr Arg Lys Leu Trp  Phe Gly Asp Glu Gln  Leu Asp Phe
    1235                 1240                 1245

Asp Ala  Gln Pro Thr Gln Asp  Phe Ser Gly Glu Thr  Met Thr Ile
    1250                 1255                 1260

Thr Arg  Glu Ala Ile Ser Ser  Phe Leu Gln Ala Thr  Gly Ser Ser
    1265                 1270                 1275

Cys Glu  Thr Tyr Arg Ser Arg  Ala Asn Gln Glu Ser  Pro Ala Pro
    1280                 1285                 1290

Leu Asp  Phe Gly Ile Val Ile  Ala Trp Lys Ala Leu  Ser Lys Pro
    1295                 1300                 1305

Ile Phe  Leu Arg Lys Asn Gly  Gly Asn Ile Leu Lys  Leu Val His
    1310                 1315                 1320

Leu Ser  Asn Lys Phe Lys Arg  Val Asp Gly Ala Ala  Ser Leu Ser
    1325                 1330                 1335

Ala Gly  Asp Lys Val Ser Thr  Ser Ser Arg Ile Thr  Ala Val Arg
    1340                 1345                 1350

Ile Gln  Asp Ala Gly Lys Val  Val Glu Val Leu Ala  Val Ile Thr
    1355                 1360                 1365

Lys Asp  Gly Ser Pro Val Met  Glu Val Val Ser Gln  Phe Met Tyr
    1370                 1375                 1380

Arg Gly  Lys Tyr Thr Asp Phe  Glu Thr Thr Phe Glu  Arg Lys Val
    1385                 1390                 1395

Glu Val  Pro Met Gln Val His  Leu Gly Ser Arg Lys  Asp Val Ala
    1400                 1405                 1410

Ile Leu  Lys Ser Lys Pro Trp  Phe Gln Leu Thr Asn  Pro Asp Ser
    1415                 1420                 1425

Glu Leu  Leu Asp Arg Thr Phe  Ile Phe Arg Leu Glu  Thr Thr Gln
    1430                 1435                 1440

Val Lys  Ser Thr Ala Thr Ala  Gly Thr Val Leu Val  Val Gly Thr
    1445                 1450                 1455

Val Ser  Glu Lys His Ala Thr  Asp Gly Glu Arg Ser  Val Ala Ser
    1460                 1465                 1470

Ile Asn  Tyr Thr Thr Ala Leu  Ser Ser Val Asn Pro  Ile Leu Arg
    1475                 1480                 1485
```

-continued

```
Tyr Leu  Asn Thr His Gly Ser  Gly Val Glu Gly Pro  Val Leu Leu
    1490                 1495                 1500

Glu Asn  Ala Ile Pro Val His  Gly Ala Ser Gly Ile  Pro Leu Lys
    1505                 1510                 1515

Arg Pro  Met Ser Ser Ala Ala  Tyr Ala Lys Val Ser  Gly Asp Tyr
    1520                 1525                 1530

Asn Pro  Ile His Val Ser Asn  Thr Phe Ala Leu Leu  Ala Asn Leu
    1535                 1540                 1545

Pro Gly  Ser Ile Val His Gly  Met His Thr Ser Ser  Ala Ile Gly
    1550                 1555                 1560

Ser Leu  Leu Glu Thr Trp Thr  Ala Lys Gly Arg Val  Gly Ala Val
    1565                 1570                 1575

Arg Ser  Phe Glu Ala Ser Phe  Val Gly Met Val Leu  Pro Asp Asp
    1580                 1585                 1590

Ser Val  Asp Val Glu Phe Trp  His Thr Ala Met Met  Lys Gly Arg
    1595                 1600                 1605

Lys Val  Ile Lys Ile Thr Ala  Lys Lys Thr Asp Ser  Gly Glu Met
    1610                 1615                 1620

Val Leu  Lys Gly Glu Ala Glu  Val Glu Glu Gln Arg  Ser Ala Tyr
    1625                 1630                 1635

Ser Phe  Thr Gly Gln Gly Ser  Gln Glu Pro Asn Met  Gly Met Asp
    1640                 1645                 1650

Leu Tyr  Ala Ser Ser Pro Ile  Ala Arg Ser Val Trp  Asp Ile Ala
    1655                 1660                 1665

Asp Lys  Phe Tyr Leu Lys Thr  Tyr Gly Phe Glu Ile  Thr Lys Ile
    1670                 1675                 1680

Val Arg  Glu Asn Pro Lys Glu  Met Thr Ile His Phe  Gly Gly Val
    1685                 1690                 1695

Asn Gly  Arg Arg Ile Arg Gln  Asn Tyr Leu Ser Leu  Thr Ser Gln
    1700                 1705                 1710

Thr Thr  Gly Asp Asp Gly Gln  Pro Ile Leu Glu Lys  Val Phe Lys
    1715                 1720                 1725

Asp Ile  Asn Glu Asp Ser Glu  Ser Tyr Thr Phe Lys  Ser Pro Lys
    1730                 1735                 1740

Gly Leu  Leu His Ala Thr Gln  Phe Thr Gln Ala Ala  Ile Thr Ser
    1745                 1750                 1755

Val Glu  Leu Ala Arg Tyr Lys  Asp Met Glu Ala Arg  Gly Leu Ile
    1760                 1765                 1770

Ser Glu  Asn Tyr Asn Phe Ala  Gly His Ser Leu Gly  Glu Tyr Pro
    1775                 1780                 1785

Ala Leu  Ala Ser Phe Ala Gln  Ile Met Ser Ile Glu  Gln Leu Val
    1790                 1795                 1800

Ala Ile  Cys Phe Tyr Arg Gly  Met Ala Met Gln Val  Thr Val Lys
    1805                 1810                 1815

Arg Asp  Glu Gln Gly Ala Ser  Asp Tyr Ser Leu Cys  Ala Val Asn
    1820                 1825                 1830

Pro Ser  Arg Val Ser Lys Thr  Phe Asn Glu Lys Met  Leu Arg Phe
    1835                 1840                 1845

Ile Thr  Lys Thr Ile Ser Gln  Gln Thr Gly Trp Leu  Ser Glu Ile
    1850                 1855                 1860

Val Asn  Phe Asn Ile Ser Asn  Arg Gln Tyr Val Cys  Ala Gly Glu
    1865                 1870                 1875

Leu Ile  Ala Leu Asp Cys Leu  Thr Lys Leu Leu Asp  Arg Ile Ala
```

```
    1880                1885                1890

Lys Gly  Ser Asn Val Asp Trp  Ile Asn Arg Pro Gly  Ser Gly Leu
    1895                1900                1905

Asp Gly  Lys Thr Val Phe Leu  Ser Thr Val Arg Ser  Ile Ile Gln
    1910                1915                1920

Glu Ala  Gln Ala Lys Lys Thr  Arg Val Glu Leu Lys  Arg Gly Thr
    1925                1930                1935

Gly Ile  Thr Pro Ser Glu Gly  Ile Asp Val Pro Phe  His Ser Thr
    1940                1945                1950

Leu Leu  Arg Pro Gly Val Ala  Thr Phe Arg Asp Phe  Leu Ala Ser
    1955                1960                1965

Lys Ile  Asp Pro Ser Asn Ile  Asp Ala Lys Lys Leu  Val Asn Lys
    1970                1975                1980

Trp Val  Pro Asn Leu Thr Gly  Lys Pro Phe Arg Asn  Asp Arg Lys
    1985                1990                1995

Tyr Phe  Glu Tyr Val Tyr Asn  Leu Thr Gly Ser Val  Pro Leu Gln
    2000                2005                2010

Lys Ser  Leu Gly Glu Trp Arg  Glu Ile Asp Leu Val  Met
    2015                2020                2025
```

<210> SEQ ID NO 21
<211> LENGTH: 1996
<212> TYPE: DNA
<213> ORGANISM: Lipomyces starkeyi
<220> FEATURE:
<221> NAME/KEY: Intron
<222> LOCATION: (385)..(436)

<400> SEQUENCE: 21

```
atgtctcctc cttctgccga cgccaacatc acacgcttcg cgccgccaac cgcgccagcg     60

tcgccgctgc cggcgtacca gctcttccac aacaagacgc gtgcgttcgt ttatggcctg    120

cagccgcgtg cttgccaggg tatgctcgat ttcgacttca tctgcaagcg cacgaccccg    180

tcggtcgccg ctatcatcta tcctttcggc ggccagtttg tgtctaagat gtattggggc    240

acgaaggaga ccctcctccc tgtctaccag agcgccaaga aggccgcaga gaagcatccc    300

gaagtcgacg tcgtcgtcaa ctttgcctct tcccgatccg tctactcctc aacgatggag    360

cttctggaat taccccagat tagggtgtgt tttggtctaa gtttacttac tcaattgatg    420

ctaatatact gattagacaa ttgcgatcat tgcggaaggt gtgcctgagc gtcgcgctcg    480

cgagattctt ttcaaggcca aggaaaaggg cgtcgtcatc atcggccctg ctactgtcgg    540

cggtatcaaa cctggctgct ttaagatcgg caacaccggc ggtatgatgg acaacatcgt    600

tgcctccaaa ctctaccgac ctggatccgt cggctacgtc tccaagtccg gtggtatgtc    660

taacgaactc aataacatca tctctcagac caccgatggt gtctacgaag gtgtcgctat    720

tggcggtgac cgttatcccg gcaccacctt catcgaccac ctcctccgct acgaggccga    780

tcccgattgt aagatcctgg tgttgcttgg tgaggttggt ggtgttgagg aataccgcgt    840

catcgatgct gtcaagtctg gcacgatcac aaagccaatt gtcgcctggg ccatcggcac    900

ttgcgcatct atgttcacga ctgaggttca gtttggccac gctggttcgt tcgccaactc    960

ccagctcgag actgctaagg ccaagaatgc cgccatgaag gccgccggtt tttacgttcc   1020

tgacaccttc gaggatatgc cagatgtctt gggtgatctc tacaagagtc tcgtcaagaa   1080

gggtgtcatt gttccgaagc ccgagcccga gcctccaaag atcccgattg actacgcctg   1140

ggcccaggaa cttggcctca tccgtaagcc ggccgcgttc atctcgacca tttctgacga   1200
```

```
tcgtggccaa gagctgctct acgccggcat gcccattacc gacgtcttca aggagaatat   1260

tggcatcggt ggcgtcatgt cgcttctgtg gttccgtcgt cgtctgcccg actacgcttc   1320

caagttcctc gagatggtcc ttatgctcac tgcagaccac ggaccagctg tctcaggcgc   1380

catgaacacc atcatcacta ctcgtgctgg caaggacttg atctccgctc tcgtgtccgg   1440

tctgttgacc atcggtgagc gattcggtgg tgcgctcgac ggcgccgctc aggaattcac   1500

caatgcgttc gacaagggcc tttcgccccg ccagtttgtc gacaccatgc gcaagcagaa   1560

caagctcatc cccggtattg gccacaagat caagtcccgc aacaatccag atatgcgggt   1620

tgagttagtc aaggaatttg cccgcaacag cttcccatcc accaaacttc tcgactacgc   1680

gctcgccgtc gagactgtta ccacttccaa gaaggacaac ttgatcctca acgtcgacgg   1740

ctgtgtcgcc gtctgcttca tcgatttgat ccgccactgc ggtgctttca cccctgaaga   1800

agctgaagac tacctgaaga tgggagttct gaacggcctg ttcgttcttg gccgatccat   1860

tggtttgatc gcgcactatc tggatcagaa gcgcctgcgc actggcttgt acagacaccc   1920

ttgggatgat attacatatc tgctccccag tgttgactct ttgggcggca gcagtcgcgt   1980

tgaagtcacg gtctag                                                  1996
```

<210> SEQ ID NO 22
<211> LENGTH: 647
<212> TYPE: PRT
<213> ORGANISM: Lipomyces starkeyi

<400> SEQUENCE: 22

```
Met Ser Pro Pro Ser Ala Asp Ala Asn Ile Thr Arg Phe Ala Pro Pro
1               5                   10                  15

Thr Ala Pro Ala Ser Pro Leu Pro Ala Tyr Gln Leu Phe His Asn Lys
            20                  25                  30

Thr Arg Ala Phe Val Tyr Gly Leu Gln Pro Arg Ala Cys Gln Gly Met
        35                  40                  45

Leu Asp Phe Asp Phe Ile Cys Lys Arg Thr Thr Pro Ser Val Ala Ala
    50                  55                  60

Ile Ile Tyr Pro Phe Gly Gly Gln Phe Val Ser Lys Met Tyr Trp Gly
65                  70                  75                  80

Thr Lys Glu Thr Leu Leu Pro Val Tyr Gln Ser Ala Lys Lys Ala Ala
                85                  90                  95

Glu Lys His Pro Glu Val Asp Val Val Val Asn Phe Ala Ser Ser Arg
            100                 105                 110

Ser Val Tyr Ser Ser Thr Met Glu Leu Leu Glu Leu Pro Gln Ile Arg
        115                 120                 125

Thr Ile Ala Ile Ile Ala Glu Gly Val Pro Glu Arg Arg Ala Arg Glu
    130                 135                 140

Ile Leu Phe Lys Ala Lys Glu Lys Gly Val Val Ile Ile Gly Pro Ala
145                 150                 155                 160

Thr Val Gly Gly Ile Lys Pro Gly Cys Phe Lys Ile Gly Asn Thr Gly
                165                 170                 175

Gly Met Met Asp Asn Ile Val Ala Ser Lys Leu Tyr Arg Pro Gly Ser
            180                 185                 190

Val Gly Tyr Val Ser Lys Ser Gly Gly Met Ser Asn Glu Leu Asn Asn
        195                 200                 205

Ile Ile Ser Gln Thr Thr Asp Gly Val Tyr Glu Gly Val Ala Ile Gly
    210                 215                 220
```

-continued

```
Gly Asp Arg Tyr Pro Gly Thr Thr Phe Ile Asp His Leu Leu Arg Tyr
225                 230                 235                 240

Glu Ala Asp Pro Asp Cys Lys Ile Leu Val Leu Leu Gly Glu Val Gly
                245                 250                 255

Gly Val Glu Glu Tyr Arg Val Ile Asp Ala Val Lys Ser Gly Thr Ile
            260                 265                 270

Thr Lys Pro Ile Val Ala Trp Ala Ile Gly Thr Cys Ala Ser Met Phe
        275                 280                 285

Thr Thr Glu Val Gln Phe Gly His Ala Gly Ser Phe Ala Asn Ser Gln
    290                 295                 300

Leu Glu Thr Ala Lys Ala Lys Asn Ala Ala Met Lys Ala Ala Gly Phe
305                 310                 315                 320

Tyr Val Pro Asp Thr Phe Glu Asp Met Pro Asp Val Leu Gly Asp Leu
                325                 330                 335

Tyr Lys Ser Leu Val Lys Lys Gly Val Ile Val Pro Lys Pro Glu Pro
            340                 345                 350

Glu Pro Pro Lys Ile Pro Ile Asp Tyr Ala Trp Ala Gln Glu Leu Gly
        355                 360                 365

Leu Ile Arg Lys Pro Ala Ala Phe Ile Ser Thr Ile Ser Asp Asp Arg
    370                 375                 380

Gly Gln Glu Leu Leu Tyr Ala Gly Met Pro Ile Thr Asp Val Phe Lys
385                 390                 395                 400

Glu Asn Ile Gly Ile Gly Gly Val Met Ser Leu Leu Trp Phe Arg Arg
                405                 410                 415

Arg Leu Pro Asp Tyr Ala Ser Lys Phe Leu Glu Met Val Leu Met Leu
            420                 425                 430

Thr Ala Asp His Gly Pro Ala Val Ser Gly Ala Met Asn Thr Ile Ile
        435                 440                 445

Thr Thr Arg Ala Gly Lys Asp Leu Ile Ser Ala Leu Val Ser Gly Leu
    450                 455                 460

Leu Thr Ile Gly Glu Arg Phe Gly Gly Ala Leu Asp Gly Ala Ala Gln
465                 470                 475                 480

Glu Phe Thr Asn Ala Phe Asp Lys Gly Leu Ser Pro Arg Gln Phe Val
                485                 490                 495

Asp Thr Met Arg Lys Gln Asn Lys Leu Ile Pro Gly Ile Gly His Lys
            500                 505                 510

Ile Lys Ser Arg Asn Asn Pro Asp Met Arg Val Glu Leu Val Lys Glu
        515                 520                 525

Phe Ala Arg Asn Ser Phe Pro Ser Thr Lys Leu Leu Asp Tyr Ala Leu
    530                 535                 540

Ala Val Glu Thr Val Thr Thr Ser Lys Lys Asp Asn Leu Ile Leu Asn
545                 550                 555                 560

Val Asp Gly Cys Val Ala Val Cys Phe Ile Asp Leu Ile Arg His Cys
                565                 570                 575

Gly Ala Phe Thr Pro Glu Glu Ala Glu Asp Tyr Leu Lys Met Gly Val
            580                 585                 590

Leu Asn Gly Leu Phe Val Leu Gly Arg Ser Ile Gly Leu Ile Ala His
        595                 600                 605

Tyr Leu Asp Gln Lys Arg Leu Arg Thr Gly Leu Tyr Arg His Pro Trp
    610                 615                 620

Asp Asp Ile Thr Tyr Leu Leu Pro Ser Val Asp Ser Leu Gly Gly Ser
625                 630                 635                 640

Ser Arg Val Glu Val Thr Val
```

645

<210> SEQ ID NO 23
<211> LENGTH: 1540
<212> TYPE: DNA
<213> ORGANISM: Lipomyces starkeyi
<220> FEATURE:
<221> NAME/KEY: Intron
<222> LOCATION: (445)..(496)

<400> SEQUENCE: 23
atgtccgcaa agtccatcca cgaggccgac ggaaaggcac tactctctta cttcctccca 60
cggtcaccgc tgctcacaaa ggaaggtact tcgaccgagt tcgtgcctgc tccaccgcgt 120
ctcgcgtcgc tcaccttccc tgacgactcc ccagcaaccg ttaaggccgt cctagatgct 180
gcagaatcga cctacgggtg gctgcttgcg ccgggtgcga agttcgtcgc caagcctgac 240
caattgatca agcgtcgtgg caagtccggt ctgctctcgc ttaacgtcac ctggcaacag 300
gctcgcgact ggatcacagt ccgcgctggt aagaagcttg ttgtcgaggg catccctggc 360
tacctgcgta ctttccttgt cgagcctttc gttccccatc cgcaagagac ggaatactac 420
atcaacatca actctgttcg tgaagtacgt attgtttgat cgcaactccg gggtgttatc 480
aatctaactt ttgtagggcg actggatttt gttttatcac gagggtggtg tcgatgtcgg 540
tgacgttgac tccaaggcct ctaagctgtt gatcccggtc gatctcgaca aggagtaccc 600
gacgaatgct actataatct ccactctcct ctccaaagtg ccagaggcac agcacgctac 660
gcttgtcgac ttcatcaacc gcctgtacgc cgtctatgtc gacctgcaat tcacgtacct 720
cgagattaac ccactcgtcg tcatcccgac cgcgtctggc gtcgaggtcc actatcttga 780
tctcgcggcc aagctcgacc aaacagcgga gttcgagtgc ggcgccaagt gggcaggtgc 840
ccgcgctcct actgcgctcg gaatcactcc ggccaagaac ggcgcctcga tcaacatcga 900
tgccggtccc ccaatggttt tccctgcgcc gtttggtcgt gagctttcgg acgaggaggc 960
ctacatcgcc gagcttgatg ccaaaaccgg tgcgtcgctc aagcttactg tgctcaatcc 1020
actaggccgc gtgtggacac tcgtcgcggg cggcggtgcg tccgtcgtgt acgccgatgc 1080
catcgcgtct gccggctacg ctaacgacat tgccaactac ggtgaatact ctggtgcacc 1140
taccgagacg caaacttacg agtacgcgaa gactgtgctg gatctgatga cccgcggtac 1200
tcccgtcgaa ggtggtaagg tcctgttcat tggcggtggt atcgcgaact tcacacaggt 1260
cggctcgaca ttcaagggca taattcgcgc gttcaaggac taccagtccc aactccacct 1320
ccatggcgtg aagatgtacg tccgccgcgg tgggcctaac tggcaggaag gtctccgtct 1380
gatcaaatcc tgcggcgagg agctctctat ccctatggag gtctacggac cagacatgca 1440
cgtatctggt attgtccctc tcgcactgct caaaaagcga cctgctggca tctatccgtt 1500
tggctcttct gccagcagca gtgccgtcag tgtgctgtaa 1540

<210> SEQ ID NO 24
<211> LENGTH: 495
<212> TYPE: PRT
<213> ORGANISM: Lipomyces starkeyi

<400> SEQUENCE: 24

Met Ser Ala Lys Ser Ile His Glu Ala Asp Gly Lys Ala Leu Leu Ser
1 5 10 15

Tyr Phe Leu Pro Arg Ser Pro Leu Leu Thr Lys Glu Gly Thr Ser Thr
20 25 30

```
Glu Phe Val Pro Ala Pro Pro Arg Leu Ala Ser Leu Thr Phe Pro Asp
        35                  40                  45

Asp Ser Pro Ala Thr Val Lys Ala Val Leu Asp Ala Ala Glu Ser Thr
    50                  55                  60

Tyr Gly Trp Leu Leu Ala Pro Gly Ala Lys Phe Val Ala Lys Pro Asp
65                  70                  75                  80

Gln Leu Ile Lys Arg Arg Gly Lys Ser Gly Leu Leu Ser Leu Asn Val
                85                  90                  95

Thr Trp Gln Gln Ala Arg Asp Trp Ile Thr Val Arg Ala Gly Lys Lys
            100                 105                 110

Leu Val Val Glu Gly Ile Pro Gly Tyr Leu Arg Thr Phe Leu Val Glu
        115                 120                 125

Pro Phe Val Pro His Pro Gln Glu Thr Glu Tyr Tyr Ile Asn Ile Asn
    130                 135                 140

Ser Val Arg Glu Gly Asp Trp Ile Leu Phe Tyr His Glu Gly Gly Val
145                 150                 155                 160

Asp Val Gly Asp Val Asp Ser Lys Ala Ser Lys Leu Leu Ile Pro Val
                165                 170                 175

Asp Leu Asp Lys Glu Tyr Pro Thr Asn Ala Thr Ile Ile Ser Thr Leu
            180                 185                 190

Leu Ser Lys Val Pro Glu Ala Gln His Ala Thr Leu Val Asp Phe Ile
        195                 200                 205

Asn Arg Leu Tyr Ala Val Tyr Val Asp Leu Gln Phe Thr Tyr Leu Glu
    210                 215                 220

Ile Asn Pro Leu Val Val Ile Pro Thr Ala Ser Gly Val Glu Val His
225                 230                 235                 240

Tyr Leu Asp Leu Ala Ala Lys Leu Asp Gln Thr Ala Glu Phe Glu Cys
                245                 250                 255

Gly Ala Lys Trp Ala Gly Ala Arg Ala Pro Thr Ala Leu Gly Ile Thr
            260                 265                 270

Pro Ala Lys Asn Gly Ala Ser Ile Asn Ile Asp Ala Gly Pro Pro Met
        275                 280                 285

Val Phe Pro Ala Pro Phe Gly Arg Glu Leu Ser Asp Glu Glu Ala Tyr
    290                 295                 300

Ile Ala Glu Leu Asp Ala Lys Thr Gly Ala Ser Leu Lys Leu Thr Val
305                 310                 315                 320

Leu Asn Pro Leu Gly Arg Val Trp Thr Leu Val Ala Gly Gly Gly Ala
                325                 330                 335

Ser Val Val Tyr Ala Asp Ala Ile Ala Ser Ala Gly Tyr Ala Asn Asp
            340                 345                 350

Ile Ala Asn Tyr Gly Glu Tyr Ser Gly Ala Pro Thr Glu Thr Gln Thr
        355                 360                 365

Tyr Glu Tyr Ala Lys Thr Val Leu Asp Leu Met Thr Arg Gly Thr Pro
    370                 375                 380

Val Glu Gly Gly Lys Val Leu Phe Ile Gly Gly Gly Ile Ala Asn Phe
385                 390                 395                 400

Thr Gln Val Gly Ser Thr Phe Lys Gly Ile Ile Arg Ala Phe Lys Asp
                405                 410                 415

Tyr Gln Ser Gln Leu His Leu His Gly Val Lys Met Tyr Val Arg Arg
            420                 425                 430

Gly Gly Pro Asn Trp Gln Glu Gly Leu Arg Leu Ile Lys Ser Cys Gly
        435                 440                 445

Glu Glu Leu Ser Ile Pro Met Glu Val Tyr Gly Pro Asp Met His Val
```

```
    450                 455                 460

Ser Gly Ile Val Pro Leu Ala Leu Leu Lys Lys Arg Pro Ala Gly Ile
465                 470                 475                 480

Tyr Pro Phe Gly Ser Ser Ala Ser Ser Ser Ala Val Ser Val Leu
                485                 490                 495


<210> SEQ ID NO 25
<211> LENGTH: 1827
<212> TYPE: DNA
<213> ORGANISM: Lipomyces starkeyi
<220> FEATURE:
<221> NAME/KEY: Intron
<222> LOCATION: (51)..(162)
<220> FEATURE:
<221> NAME/KEY: Intron
<222> LOCATION: (241)..(296)
<220> FEATURE:
<221> NAME/KEY: Intron
<222> LOCATION: (436)..(492)

<400> SEQUENCE: 25

atgccaaggg tcttcatcgg tgcactggat gccggcacca cgtctacaag gtgaggactg     60

ggccatttga gccgaggacg tcgtgcacgc tcacgctcac ccggccatat cctctgggaa    120

ctctttgaaa ggttccgtta gtgcatatgc taacaaccgc agattcatta tatttgacga    180

tgctggtagg ccttacgcta cacaccagat tgaattcgag cagcattatc cacatgctgg    240

gtgagttgcg ctgttaaata cgccttctgg aaaacaatac gctgaccgag taatagctgg    300

cacgagcaat acccttacga gattatcaag tgcgcgaatg actgtattga gggcgctgtc    360

aagaagtttg tcgcagatgg atacaatgtc tccgacataa aggcggttgg aattacaaac    420

cagcgtgaat ccactgtaaa tccttgttcc ttcttacaga tattaagaac agtctaacaa    480

aaaataacat aggtcgtctg ggattctgag acggggaagc cactgtataa tgcaattgct    540

tggcctgaca cgcgtactgc gcgactagta catcacttca agaacaagaa cggcgccgaa    600

gacctagtgc gaatctgcgg tctgccactg tctacctatc cgtccgcgct caagctggtg    660

tggctgttag aaaacgttca cggcgtccag gaggcacgaa agcgtggaac tttgatgttc    720

ggtaccgttg acacctggtt agtgtacaat ctgaccggtg gcggtaagac tggaaccgac    780

accaggtttg tgacagatac caccaatgcc tcgcgaacta tgttcctaaa tattaactct    840

ctcaagtacg atgatttcct ccttgatttc tttggagttt ctcaaggagt gagactccct    900

gacgttgtgt gctccgcaga cgacaaagct tacggtaata tcgcttccgg tgtcctcgct    960

ggtgtaccaa ttgcgtcgtg tctcggtgac cagtcagccg cgttggtcgg acagcgggcg   1020

ttcagtgtgg gcatgggcaa gaacacgtac ggaactggtt tgttcttgct gtacaacact   1080

ggtgaggagc cagtcttctc gaagaacggt ctcttaacca ctgtcggata tcatttcaag   1140

ggaaagaagc ctatatacgc tctggaaggg tccattgctg tcggtggcgc tgcagttaag   1200

ttcttgcgag ataatttacg gttgatttcg ttctccgatg aggtcgggca attggcagcg   1260

aaggtccccg acgctggtgg ggtcattttt gtcacggcct tctcgggact gttcgcgcct   1320

tactggattg acgataccca gggaaccatc tacggtatca cgaactacac aaccaaagaa   1380

cacattgctc gagcaaccat tgaggccacc tgttatcaga ctagagcagt tttggaagct   1440

atggctaagg attctggcta cgagttgaag acgctcaagg tcgacggtgg catgagtaac   1500

tcggatatat gcatgcaaat ccaatccgac attattggca ttgacgtcgt tcggccggag   1560

tatagggaga ctaccgcatt gggggcagcc attgcagcag gttttgcagt tggagtctat   1620
```

agtagctttg aggagttgaa gcgagtgaac acggatggag agaccacatt caagccttcc 1680
atcactgaga agaagcgcga gaagttgtat aacctctggc agcgtgctgt atcgcgatgt 1740
ggtggttggt tgcgggatga ggatgacgac tctgagattg aggaggagac aagagttggg 1800
gatgggaccc aaaagcagtt tgcatag 1827

<210> SEQ ID NO 26
<211> LENGTH: 533
<212> TYPE: PRT
<213> ORGANISM: Lipomyces starkeyi

<400> SEQUENCE: 26

Met Pro Arg Val Phe Ile Gly Ala Leu Asp Ala Gly Thr Thr Ser Thr
1 5 10 15

Arg Phe Ile Ile Phe Asp Asp Ala Gly Arg Pro Tyr Ala Thr His Gln
20 25 30

Ile Glu Phe Glu Gln His Tyr Pro His Ala Gly Trp His Glu Gln Tyr
35 40 45

Pro Tyr Glu Ile Ile Lys Cys Ala Asn Asp Cys Ile Glu Gly Ala Val
50 55 60

Lys Lys Phe Val Ala Asp Gly Tyr Asn Val Ser Asp Ile Lys Ala Val
65 70 75 80

Gly Ile Thr Asn Gln Arg Glu Ser Thr Val Val Trp Asp Ser Glu Thr
85 90 95

Gly Lys Pro Leu Tyr Asn Ala Ile Ala Trp Pro Asp Thr Arg Thr Ala
100 105 110

Arg Leu Val His His Phe Lys Asn Lys Asn Gly Ala Glu Asp Leu Val
115 120 125

Arg Ile Cys Gly Leu Pro Leu Ser Thr Tyr Pro Ser Ala Leu Lys Leu
130 135 140

Val Trp Leu Leu Glu Asn Val His Gly Val Gln Glu Ala Arg Lys Arg
145 150 155 160

Gly Thr Leu Met Phe Gly Thr Val Asp Thr Trp Leu Val Tyr Asn Leu
165 170 175

Thr Gly Gly Gly Lys Thr Gly Thr Asp Thr Arg Phe Val Thr Asp Thr
180 185 190

Thr Asn Ala Ser Arg Thr Met Phe Leu Asn Ile Asn Ser Leu Lys Tyr
195 200 205

Asp Asp Phe Leu Leu Asp Phe Phe Gly Val Ser Gln Gly Val Arg Leu
210 215 220

Pro Asp Val Val Cys Ser Ala Asp Asp Lys Ala Tyr Gly Asn Ile Ala
225 230 235 240

Ser Gly Val Leu Ala Gly Val Pro Ile Ala Ser Cys Leu Gly Asp Gln
245 250 255

Ser Ala Ala Leu Val Gly Gln Arg Ala Phe Ser Val Gly Met Gly Lys
260 265 270

Asn Thr Tyr Gly Thr Gly Leu Phe Leu Leu Tyr Asn Thr Gly Glu Glu
275 280 285

Pro Val Phe Ser Lys Asn Gly Leu Leu Thr Thr Val Gly Tyr His Phe
290 295 300

Lys Gly Lys Lys Pro Ile Tyr Ala Leu Glu Gly Ser Ile Ala Val Gly
305 310 315 320

Gly Ala Ala Val Lys Phe Leu Arg Asp Asn Leu Arg Leu Ile Ser Phe
325 330 335

-continued

```
Ser Asp Glu Val Gly Gln Leu Ala Ala Lys Val Pro Asp Ala Gly Gly
            340                 345                 350

Val Ile Phe Val Thr Ala Phe Ser Gly Leu Phe Ala Pro Tyr Trp Ile
        355                 360                 365

Asp Asp Thr Gln Gly Thr Ile Tyr Gly Ile Thr Asn Tyr Thr Thr Lys
    370                 375                 380

Glu His Ile Ala Arg Ala Thr Ile Glu Ala Thr Cys Tyr Gln Thr Arg
385                 390                 395                 400

Ala Val Leu Glu Ala Met Ala Lys Asp Ser Gly Tyr Glu Leu Lys Thr
                405                 410                 415

Leu Lys Val Asp Gly Gly Met Ser Asn Ser Asp Ile Cys Met Gln Ile
            420                 425                 430

Gln Ser Asp Ile Ile Gly Ile Asp Val Val Arg Pro Glu Tyr Arg Glu
        435                 440                 445

Thr Thr Ala Leu Gly Ala Ala Ile Ala Ala Gly Phe Ala Val Gly Val
    450                 455                 460

Tyr Ser Ser Phe Glu Glu Leu Lys Arg Val Asn Thr Asp Gly Glu Thr
465                 470                 475                 480

Thr Phe Lys Pro Ser Ile Thr Glu Lys Lys Arg Glu Lys Leu Tyr Asn
                485                 490                 495

Leu Trp Gln Arg Ala Val Ser Arg Cys Gly Gly Trp Leu Arg Asp Glu
            500                 505                 510

Asp Asp Asp Ser Glu Ile Glu Glu Glu Thr Arg Val Gly Asp Gly Thr
        515                 520                 525

Gln Lys Gln Phe Ala
    530
```

<210> SEQ ID NO 27
<211> LENGTH: 1842
<212> TYPE: DNA
<213> ORGANISM: Lipomyces starkeyi
<220> FEATURE:
<221> NAME/KEY: Intron
<222> LOCATION: (66)..(177)
<220> FEATURE:
<221> NAME/KEY: Intron
<222> LOCATION: (256)..(311)
<220> FEATURE:
<221> NAME/KEY: Intron
<222> LOCATION: (451)..(507)

<400> SEQUENCE: 27

```
atgactaccg attccatgcc aagggtcttc atcggtgcac tggatgccgg caccacgtct      60

acaaggtgag gactgggcca tttgagccga ggacgtcgtg cacgctcacg ctcacccggc     120

catatcctct gggaactctt tgaaaggttc cgttagtgca tatgctaaca accgcagatt     180

cattatattt gacgatgctg gtaggcctta cgctacacac cagattgaat tcgagcagca     240

ttatccacat gctgggtgag ttgcgctgtt aaatacgcct tctggaaaac aatacgctga     300

ccgagtaata gctggcacga gcaataccct tacgagatta tcaagtgcgc gaatgactgt     360

attgagggcg ctgtcaagaa gtttgtcgca gatggataca atgtctccga cataaaggcg     420

gttggaatta caaaccagcg tgaatccact gtaaatcctt gttccttctt acagatatta     480

agaacagtct aacaaaaaat aacataggtc gtctgggatt ctgagacggg gaagccactg     540

tataatgcaa ttgcttggcc tgacacgcgt actgcgcgac tagtacatca cttcaagaac     600

aagaacggcg ccgaagacct agtgcgaatc tgcggtctgc cactgtctac ctatccgtcc     660

gcgctcaagc tggtgtggct gttagaaaac gttcacggcg tccaggaggc acgaaagcgt     720
```

```
ggaactttga tgttcggtac cgttgacacc tggttagtgt acaatctgac cggtggcggt    780

aagactggaa ccgacaccag gtttgtgaca gataccacca atgcctcgcg aactatgttc    840

ctaaatatta actctctcaa gtacgatgat ttcctccttg atttctttgg agtttctcaa    900

ggagtgagac tccctgacgt tgtgtgctcc gcagacgaca aagcttacgg taatatcgct    960

tccggtgtcc tcgctggtgt accaattgcg tcgtgtctcg gtgaccagtc agccgcgttg   1020

gtcggacagc gggcgttcag tgtgggcatg ggcaagaaca cgtacggaac tggtttgttc   1080

ttgctgtaca acactggtga ggagccagtc ttctcgaaga acggtctctt aaccactgtc   1140

ggatatcatt tcaagggaaa gaagcctata tacgctctgg aagggtccat tgctgtcggt   1200

ggcgctgcag ttaagttctt gcgagataat ttacggttga tttcgttctc cgatgaggtc   1260

gggcaattgg cagcgaaggt ccccgacgct ggtggggtca tttttgtcac ggccttctcg   1320

ggactgttcg cgccttactg gattgacgat acccagggaa ccatctacgg tatcacgaac   1380

tacacaacca aagaacacat tgctcgagca accattgagg ccacctgtta tcagactaga   1440

gcagttttgg aagctatggc taaggattct ggctacgagt tgaagacgct caaggtcgac   1500

ggtggcatga gtaactcgga tatatgcatg caaatccaat ccgacattat tggcattgac   1560

gtcgttcggc cggagtatag ggagactacc gcattggggg cagccattgc agcaggtttt   1620

gcagttggag tctatagtag ctttgaggag ttgaagcgag tgaacacgga tggagagacc   1680

acattcaagc cttccatcac tgagaagaag cgcgagaagt tgtataacct ctggcagcgt   1740

gctgtatcgc gatgtggtgg ttggttgcgg gatgaggatg acgactctga gattgaggag   1800

gagacaagag ttggggatgg gacccaaaag cagtttgcat ag                      1842
```

<210> SEQ ID NO 28
<211> LENGTH: 538
<212> TYPE: PRT
<213> ORGANISM: Lipomyces starkeyi

<400> SEQUENCE: 28

```
Met Thr Thr Asp Ser Met Pro Arg Val Phe Ile Gly Ala Leu Asp Ala
1               5                   10                  15

Gly Thr Thr Ser Thr Arg Phe Ile Ile Phe Asp Asp Ala Gly Arg Pro
            20                  25                  30

Tyr Ala Thr His Gln Ile Glu Phe Glu Gln His Tyr Pro His Ala Gly
        35                  40                  45

Trp His Glu Gln Tyr Pro Tyr Glu Ile Ile Lys Cys Ala Asn Asp Cys
    50                  55                  60

Ile Glu Gly Ala Val Lys Lys Phe Val Ala Asp Gly Tyr Asn Val Ser
65                  70                  75                  80

Asp Ile Lys Ala Val Gly Ile Thr Asn Gln Arg Glu Ser Thr Val Val
                85                  90                  95

Trp Asp Ser Glu Thr Gly Lys Pro Leu Tyr Asn Ala Ile Ala Trp Pro
            100                 105                 110

Asp Thr Arg Thr Ala Arg Leu Val His His Phe Lys Asn Lys Asn Gly
        115                 120                 125

Ala Glu Asp Leu Val Arg Ile Cys Gly Leu Pro Leu Ser Thr Tyr Pro
    130                 135                 140

Ser Ala Leu Lys Leu Val Trp Leu Leu Glu Asn Val His Gly Val Gln
145                 150                 155                 160

Glu Ala Arg Lys Arg Gly Thr Leu Met Phe Gly Thr Val Asp Thr Trp
                165                 170                 175
```

-continued

```
Leu Val Tyr Asn Leu Thr Gly Gly Gly Lys Thr Gly Thr Asp Thr Arg
            180                 185                 190

Phe Val Thr Asp Thr Thr Asn Ala Ser Arg Thr Met Phe Leu Asn Ile
        195                 200                 205

Asn Ser Leu Lys Tyr Asp Asp Phe Leu Leu Asp Phe Phe Gly Val Ser
    210                 215                 220

Gln Gly Val Arg Leu Pro Asp Val Val Cys Ser Ala Asp Asp Lys Ala
225                 230                 235                 240

Tyr Gly Asn Ile Ala Ser Gly Val Leu Ala Gly Val Pro Ile Ala Ser
                245                 250                 255

Cys Leu Gly Asp Gln Ser Ala Ala Leu Val Gly Gln Arg Ala Phe Ser
            260                 265                 270

Val Gly Met Gly Lys Asn Thr Tyr Gly Thr Gly Leu Phe Leu Leu Tyr
        275                 280                 285

Asn Thr Gly Glu Glu Pro Val Phe Ser Lys Asn Gly Leu Leu Thr Thr
    290                 295                 300

Val Gly Tyr His Phe Lys Gly Lys Lys Pro Ile Tyr Ala Leu Glu Gly
305                 310                 315                 320

Ser Ile Ala Val Gly Gly Ala Ala Val Lys Phe Leu Arg Asp Asn Leu
                325                 330                 335

Arg Leu Ile Ser Phe Ser Asp Glu Val Gly Gln Leu Ala Ala Lys Val
            340                 345                 350

Pro Asp Ala Gly Gly Val Ile Phe Val Thr Ala Phe Ser Gly Leu Phe
        355                 360                 365

Ala Pro Tyr Trp Ile Asp Asp Thr Gln Gly Thr Ile Tyr Gly Ile Thr
    370                 375                 380

Asn Tyr Thr Thr Lys Glu His Ile Ala Arg Ala Thr Ile Glu Ala Thr
385                 390                 395                 400

Cys Tyr Gln Thr Arg Ala Val Leu Glu Ala Met Ala Lys Asp Ser Gly
                405                 410                 415

Tyr Glu Leu Lys Thr Leu Lys Val Asp Gly Gly Met Ser Asn Ser Asp
            420                 425                 430

Ile Cys Met Gln Ile Gln Ser Asp Ile Ile Gly Ile Asp Val Val Arg
        435                 440                 445

Pro Glu Tyr Arg Glu Thr Thr Ala Leu Gly Ala Ala Ile Ala Ala Gly
    450                 455                 460

Phe Ala Val Gly Val Tyr Ser Ser Phe Glu Glu Leu Lys Arg Val Asn
465                 470                 475                 480

Thr Asp Gly Glu Thr Thr Phe Lys Pro Ser Ile Thr Glu Lys Lys Arg
                485                 490                 495

Glu Lys Leu Tyr Asn Leu Trp Gln Arg Ala Val Ser Arg Cys Gly Gly
            500                 505                 510

Trp Leu Arg Asp Glu Asp Asp Asp Ser Glu Ile Glu Glu Glu Thr Arg
        515                 520                 525

Val Gly Asp Gly Thr Gln Lys Gln Phe Ala
    530                 535
```

<210> SEQ ID NO 29
<211> LENGTH: 2057
<212> TYPE: DNA
<213> ORGANISM: Lipomyces starkeyi
<220> FEATURE:
<221> NAME/KEY: Intron
<222> LOCATION: (409)..(462)
<220> FEATURE:

-continued

<221> NAME/KEY: Intron
<222> LOCATION: (579)..(637)
<220> FEATURE:
<221> NAME/KEY: Intron
<222> LOCATION: (981)..(1028)

<400> SEQUENCE: 29
atgtcatttc gccaggcatt gttctcagct acccggactc atcgtgtgct gcttcgctcc 60
gttgccgcgg gcgggatcct gagcaccaca gcgttcttcc tctcgaacac agactcgttc 120
ggctcaatac accaccaggc tgagcaggac gtgccattga actatcctgt cccggccccc 180
tttgccttgc ccccgtcccg agaagaacag atcaagaagt tggaaaccga acagttcgac 240
ttgctgatca taggcggtgg agctaccggt gccggctgcg cattggatgc cgtcagcaga 300
ggattaaagg tcgcgttggt tgagcgtgat gactttgcat gtggtacaag tagtaggagt 360
acgaagcttg tacacggtgg tgtgagatac ttggagaaag cattctgggt aggtgacaat 420
cacagctatg gcatgacatg aacgctaaca gcgtgatttc agaacctcga ctatgagcag 480
tacaaattgg tcaaggaggc acttgctgag cgtgctactt tcttgaaaat tgcgcctcat 540
ttgagtttcc cgctcccaat catggtccct gtctacaagt atgtctatag gccattttga 600
tctataagct taatcaatct aataatgcat tgcgtaggtg gtggcaagtc ccatattact 660
gggctggaac caagatgtac gatcttattg ctggaaagga gaacatggaa tcaagttact 720
tcatgggccg tggtaagacc ctcgagaact tcccaatgct taagcctcag aacttgaagg 780
gtgccattgt ctactacgac ggtagtcaca atgactcgcg aatgaacact gctatcgctc 840
tcactgctgc tcagaaaggt gccgttatcc tgaaccacat ggaggttaca gagttgtcca 900
aggacgcgtc tggtcgcgtc aatggtgctg ttgtccgcga caatgacggt actgctggga 960
agatccaggt tgatgctaag gtatgttgtg gagatacaat ttatatagtg cttgctgacc 1020
tgtttcaggg tgttattaac gcgaccggtc cgttcgcgga ccggatccgt cagctcgata 1080
ctcctgttgc gatcgacatc gtcgctccat catccggtgt gcatgtgatt cttcctgact 1140
actactgctc tcccagcatg ggtttgatcg acccagctac ttctgatgga cgagtagttt 1200
tctttcttcc atggcaaggc catactcttg ccggtacaac cgactctcct accacagtca 1260
cgaaggatcc tattccttcc gaggacgaga taagctggat cttgaacgaa attcaacact 1320
acgttgccga tgatattacc gttcgccggg aagatgttct tgccgcttgg agcggtatcc 1380
gtccattagt ccgcgaccca cgtgctaaga acacagagtc gctggtccgc aaccatttga 1440
tcaccctttc cgacagtggt ctcttgactg tcgctggcgg caagtggact acctatcgag 1500
aaatggcaga agacactgtc aacacctctg tcaaagagtt cggtcttgag ccgaccgccc 1560
catgtggaac caaggatatc aagcttgtcg ggggctgaggg atacagaaaa ctcatgttca 1620
ttcacttgat ccagacattt ggcattgaga ctggcatagc caagcatctt gctgacaact 1680
atggagatcg tgcgtacgac gtcgtcaggc tttcagccac tacgggcgag agatggccca 1740
caagaggtgt caagctgtcg ccagcttatc cgtacattga tggcgagatc cgttacgcag 1800
ttcagcacga gtatgctcga acggctgtcg acgtgctgtc gcgacgcatc cgtctcgcgt 1860
tcttgaactc caaggctgcg ttggagagct tgcccaaggt catcgatatc atggccgaag 1920
agttgaagtg ggacaaggcg cgtcaggaca aggagtggga tgacaccatc aggttcttgt 1980
acagcatggg tctccagaac gggaagtact tctcgagagc ggacgttgag agcggaaaaa 2040
caaaaatgtt gggttaa 2057

<210> SEQ ID NO 30
<211> LENGTH: 631
<212> TYPE: PRT
<213> ORGANISM: Lipomyces starkeyi

<400> SEQUENCE: 30

Met Ser Phe Arg Gln Ala Leu Phe Ser Ala Thr Arg Thr His Arg Val
1 5 10 15

Leu Leu Arg Ser Val Ala Ala Gly Gly Ile Leu Ser Thr Thr Ala Phe
20 25 30

Phe Leu Ser Asn Thr Asp Ser Phe Gly Ser Ile His His Gln Ala Glu
35 40 45

Gln Asp Val Pro Leu Asn Tyr Pro Val Pro Ala Pro Phe Ala Leu Pro
50 55 60

Pro Ser Arg Glu Glu Gln Ile Lys Lys Leu Glu Thr Glu Gln Phe Asp
65 70 75 80

Leu Leu Ile Ile Gly Gly Gly Ala Thr Gly Ala Gly Cys Ala Leu Asp
85 90 95

Ala Val Ser Arg Gly Leu Lys Val Ala Leu Val Glu Arg Asp Asp Phe
100 105 110

Ala Cys Gly Thr Ser Ser Arg Ser Thr Lys Leu Val His Gly Gly Val
115 120 125

Arg Tyr Leu Glu Lys Ala Phe Trp Asn Leu Asp Tyr Glu Gln Tyr Lys
130 135 140

Leu Val Lys Glu Ala Leu Ala Glu Arg Ala Thr Phe Leu Lys Ile Ala
145 150 155 160

Pro His Leu Ser Phe Pro Leu Pro Ile Met Val Pro Val Tyr Lys Trp
165 170 175

Trp Gln Val Pro Tyr Tyr Trp Ala Gly Thr Lys Met Tyr Asp Leu Ile
180 185 190

Ala Gly Lys Glu Asn Met Glu Ser Ser Tyr Phe Met Gly Arg Gly Lys
195 200 205

Thr Leu Glu Asn Phe Pro Met Leu Lys Pro Gln Asn Leu Lys Gly Ala
210 215 220

Ile Val Tyr Tyr Asp Gly Ser His Asn Asp Ser Arg Met Asn Thr Ala
225 230 235 240

Ile Ala Leu Thr Ala Ala Gln Lys Gly Ala Val Ile Leu Asn His Met
245 250 255

Glu Val Thr Glu Leu Ser Lys Asp Ala Ser Gly Arg Val Asn Gly Ala
260 265 270

Val Val Arg Asp Asn Asp Gly Thr Ala Gly Lys Ile Gln Val Asp Ala
275 280 285

Lys Gly Val Ile Asn Ala Thr Gly Pro Phe Ala Asp Arg Ile Arg Gln
290 295 300

Leu Asp Thr Pro Val Ala Ile Asp Ile Val Ala Pro Ser Ser Gly Val
305 310 315 320

His Val Ile Leu Pro Asp Tyr Tyr Cys Ser Pro Ser Met Gly Leu Ile
325 330 335

Asp Pro Ala Thr Ser Asp Gly Arg Val Val Phe Phe Leu Pro Trp Gln
340 345 350

Gly His Thr Leu Ala Gly Thr Thr Asp Ser Pro Thr Thr Val Thr Lys
355 360 365

Asp Pro Ile Pro Ser Glu Asp Glu Ile Ser Trp Ile Leu Asn Glu Ile
370 375 380

```
Gln His Tyr Val Ala Asp Asp Ile Thr Val Arg Arg Glu Asp Val Leu
385                 390                 395                 400

Ala Ala Trp Ser Gly Ile Arg Pro Leu Val Arg Asp Pro Arg Ala Lys
                405                 410                 415

Asn Thr Glu Ser Leu Val Arg Asn His Leu Ile Thr Leu Ser Asp Ser
            420                 425                 430

Gly Leu Leu Thr Val Ala Gly Gly Lys Trp Thr Thr Tyr Arg Glu Met
        435                 440                 445

Ala Glu Asp Thr Val Asn Thr Ser Val Lys Glu Phe Gly Leu Glu Pro
    450                 455                 460

Thr Ala Pro Cys Gly Thr Lys Asp Ile Lys Leu Val Gly Ala Glu Gly
465                 470                 475                 480

Tyr Arg Lys Leu Met Phe Ile His Leu Ile Gln Thr Phe Gly Ile Glu
                485                 490                 495

Thr Gly Ile Ala Lys His Leu Ala Asp Asn Tyr Gly Asp Arg Ala Tyr
            500                 505                 510

Asp Val Val Arg Leu Ser Ala Thr Thr Gly Glu Arg Trp Pro Thr Arg
        515                 520                 525

Gly Val Lys Leu Ser Pro Ala Tyr Pro Tyr Ile Asp Gly Glu Ile Arg
    530                 535                 540

Tyr Ala Val Gln His Glu Tyr Ala Arg Thr Ala Val Asp Val Leu Ser
545                 550                 555                 560

Arg Arg Ile Arg Leu Ala Phe Leu Asn Ser Lys Ala Ala Leu Glu Ser
                565                 570                 575

Leu Pro Lys Val Ile Asp Ile Met Ala Glu Glu Leu Lys Trp Asp Lys
            580                 585                 590

Ala Arg Gln Asp Lys Glu Trp Asp Asp Thr Ile Arg Phe Leu Tyr Ser
        595                 600                 605

Met Gly Leu Gln Asn Gly Lys Tyr Phe Ser Arg Ala Asp Val Glu Ser
    610                 615                 620

Gly Lys Thr Lys Met Leu Gly
625                 630
```

<210> SEQ ID NO 31
<211> LENGTH: 2199
<212> TYPE: DNA
<213> ORGANISM: Lipomyces starkeyi
<220> FEATURE:
<221> NAME/KEY: Intron
<222> LOCATION: (408)..(459)

<400> SEQUENCE: 31

```
tggactcgaa agtgtccgcg cgcgcggcag cacttgccgg ccatctctcc atgagaaatt     60

cgtcggccga gagcaaggat acgtctatcc ttggacttgg aaatccaatg gcatctatgg    120

ccgtggaacg cacaaaggcg tcattcccga ttcgtgagct cacctatttt ctcgatggcg    180

gcaaggagat gaccgcagta aaggagcgaa tgatgactga gctggaacgt gatccggtct    240

tccaaaacgt ggacttttat gatcttacaa aggaacaatt acgcgagcgt actatgtcta    300

aaattgccag gttgatccat tatatcacgt ctgagcggga ggaaatttca cacttgcggt    360

tttcgctcgt tggcctcatc gatatgggtt tgctcaccag aacagggtaa gtaagtatct    420

ccttattatt gcattgacgg gtgctaatga aggtgtagtg tccactacgc tttgttcttc    480

ggctctctgc gaggctcggc atcgccgaaa cagttttcgt actggatctc acaaggagcc    540

gccgagatga agggcatggt tggctgcttt tgcatgaccg agctggcgca cggcagcaac    600
```

-continued

```
gtcgccggtc tcgagactac cgccacattt gacgagcgaa cggacgagtt tatcatccat    660
actccacata tcggcgcaac caagtggtgg ataggtggtg ccgctcatac agcaacacac    720
acggtctgct ttgctagatt gatagtgaag ggtaaagatt acggagtcaa gtcatttgtc    780
gttccactcc gtgatccgaa gacatacgac cttaaaccag gcgtcagcat cggcgacatc    840
ggcaagaaga tgggtcgtga cggcattgat aatggctggg ttcagttctc gtatgtgcga    900
attccacgac agttcatgtt gatgaaacac agcaaagttg accgtcacgg aaatgtcact    960
cagcccccac ttgagcagct tgcgtatggt gcgttggttg ttggccgcgt ctcaatggtc   1020
gccgactcgg ctcagatgag caagcgtttt gtgacgattg ctcttagata cgctgccgtc   1080
agacggcaat ttacgtcgaa gaagggtgaa gttgagacga agattttgga ttacgcatta   1140
catcagcggc gactgctacc gctacttgct cagactttcg cgatgcagtt cagttcggat   1200
gaaatgtcgg ccatgcaccg ggcattgatg cggaagattg attcaactga tcctagtgac   1260
ctgaaggcta tggcggttgt gattgaagag ttgaaggaag tattcaccac tagtgccggt   1320
ttgaaggctt tcactacctg ggcttgtgct gagacgattg atcagacgcg tcaggcatgc   1380
ggtgggcatg gatactctgc atatagtggt ttcggacaag catacaatga ctgggttgtg   1440
caatgtacct gggagggaga caataacatt ctcgcgcttt ctgccggccg cggtcttgtt   1500
cagcgctatc tggacgtcca gagaggttcc aaagcccctc cacaaacgga atatctcaac   1560
aagctcgcca gactcaagtt cgcacaggca gggtcgcgcc agattgactc tgccgcggtt   1620
ctttccgaag cttgggaggc tgttgcggct gctgttgtat cgaaggctgg cgaatcattc   1680
atcgcgctaa gaaagaaagg tctttctgcc gacgaggcat ttgaggagac atcacagcag   1740
cgcttccttg ctgctagaat ccataccaaa tgctttttgg tcttgaagtt ttttgaccgc   1800
atttcctcct ccggaccgga gatcaaaccg gttttgactg atctctctta tctgtatgcg   1860
atgtggtcca tcgagaatga cgccggacta tttctccaag ccgaattctt cacatccgag   1920
caaattgacg acattcgtga actgtgcaac ttatactgcc gcaaagtccg cgagcaggct   1980
gtcccaatta ctgatgcgtt caacttgagt gatttcttca tcaactctgc tatcggcaga   2040
tatgatggca atgtctacga gaattatttt acgcaggtta agaggcagaa tccatcaaag   2100
ccacaagctc catatttcga gaaagtgata aagccgtttg tgcacagggt tgctgaagta   2160
gaagttgatg ctgaggagtt agatgaggat gaggcgtag                          2199
```

```
<210> SEQ ID NO 32
<211> LENGTH: 715
<212> TYPE: PRT
<213> ORGANISM: Lipomyces starkeyi

<400> SEQUENCE: 32

Met Asp Ser Lys Val Ser Ala Arg Ala Ala Ala Leu Ala Gly His Leu
1               5                   10                  15

Ser Met Arg Asn Ser Ser Ala Glu Ser Lys Asp Thr Ser Ile Leu Gly
            20                  25                  30

Leu Gly Asn Pro Met Ala Ser Met Ala Val Glu Arg Thr Lys Ala Ser
        35                  40                  45

Phe Pro Ile Arg Glu Leu Thr Tyr Phe Leu Asp Gly Gly Lys Glu Met
    50                  55                  60

Thr Ala Val Lys Glu Arg Met Met Thr Glu Leu Glu Arg Asp Pro Val
65                  70                  75                  80

Phe Gln Asn Val Asp Phe Tyr Asp Leu Thr Lys Glu Gln Leu Arg Glu
                85                  90                  95
```

```
Arg Thr Met Ser Lys Ile Ala Arg Leu Ile His Tyr Ile Thr Ser Glu
            100                 105                 110

Arg Glu Glu Ile Ser His Leu Arg Phe Ser Leu Val Gly Leu Ile Asp
        115                 120                 125

Met Gly Leu Leu Thr Arg Thr Gly Val His Tyr Ala Leu Phe Phe Gly
    130                 135                 140

Ser Leu Arg Gly Ser Ala Ser Pro Lys Gln Phe Ser Tyr Trp Ile Ser
145                 150                 155                 160

Gln Gly Ala Ala Glu Met Lys Gly Met Val Gly Cys Phe Cys Met Thr
                165                 170                 175

Glu Leu Ala His Gly Ser Asn Val Ala Gly Leu Glu Thr Thr Ala Thr
            180                 185                 190

Phe Asp Glu Arg Thr Asp Glu Phe Ile Ile His Thr Pro His Ile Gly
        195                 200                 205

Ala Thr Lys Trp Trp Ile Gly Gly Ala Ala His Thr Ala Thr His Thr
    210                 215                 220

Val Cys Phe Ala Arg Leu Ile Val Lys Gly Lys Asp Tyr Gly Val Lys
225                 230                 235                 240

Ser Phe Val Val Pro Leu Arg Asp Pro Lys Thr Tyr Asp Leu Lys Pro
                245                 250                 255

Gly Val Ser Ile Gly Asp Ile Gly Lys Lys Met Gly Arg Asp Gly Ile
            260                 265                 270

Asp Asn Gly Trp Val Gln Phe Ser Tyr Val Arg Ile Pro Arg Gln Phe
        275                 280                 285

Met Leu Met Lys His Ser Lys Val Asp Arg His Gly Asn Val Thr Gln
    290                 295                 300

Pro Pro Leu Glu Gln Leu Ala Tyr Gly Ala Leu Val Val Gly Arg Val
305                 310                 315                 320

Ser Met Val Ala Asp Ser Ala Gln Met Ser Lys Arg Phe Val Thr Ile
                325                 330                 335

Ala Leu Arg Tyr Ala Ala Val Arg Arg Gln Phe Thr Ser Lys Lys Gly
            340                 345                 350

Glu Val Glu Thr Lys Ile Leu Asp Tyr Ala Leu His Gln Arg Arg Leu
        355                 360                 365

Leu Pro Leu Leu Ala Gln Thr Phe Ala Met Gln Phe Ser Ser Asp Glu
    370                 375                 380

Met Ser Ala Met His Arg Ala Leu Met Arg Lys Ile Asp Ser Thr Asp
385                 390                 395                 400

Pro Ser Asp Leu Lys Ala Met Ala Val Val Ile Glu Glu Leu Lys Glu
                405                 410                 415

Val Phe Thr Thr Ser Ala Gly Leu Lys Ala Phe Thr Thr Trp Ala Cys
            420                 425                 430

Ala Glu Thr Ile Asp Gln Thr Arg Gln Ala Cys Gly Gly His Gly Tyr
        435                 440                 445

Ser Ala Tyr Ser Gly Phe Gly Gln Ala Tyr Asn Asp Trp Val Val Gln
    450                 455                 460

Cys Thr Trp Glu Gly Asp Asn Asn Ile Leu Ala Leu Ser Ala Gly Arg
465                 470                 475                 480

Gly Leu Val Gln Arg Tyr Leu Asp Val Gln Arg Gly Ser Lys Ala Pro
                485                 490                 495

Pro Gln Thr Glu Tyr Leu Asn Lys Leu Ala Arg Leu Lys Phe Ala Gln
            500                 505                 510
```

```
Ala Gly Ser Arg Gln Ile Asp Ser Ala Ala Val Leu Ser Glu Ala Trp
        515                 520                 525

Glu Ala Val Ala Ala Ala Val Val Ser Lys Ala Gly Glu Ser Phe Ile
    530                 535                 540

Ala Leu Arg Lys Lys Gly Leu Ser Ala Asp Glu Ala Phe Glu Glu Thr
545                 550                 555                 560

Ser Gln Gln Arg Phe Leu Ala Ala Arg Ile His Thr Lys Cys Phe Leu
                565                 570                 575

Val Leu Lys Phe Phe Asp Arg Ile Ser Ser Ser Gly Pro Glu Ile Lys
            580                 585                 590

Pro Val Leu Thr Asp Leu Ser Tyr Leu Tyr Ala Met Trp Ser Ile Glu
        595                 600                 605

Asn Asp Ala Gly Leu Phe Leu Gln Ala Glu Phe Phe Thr Ser Glu Gln
    610                 615                 620

Ile Asp Asp Ile Arg Glu Leu Cys Asn Leu Tyr Cys Arg Lys Val Arg
625                 630                 635                 640

Glu Gln Ala Val Pro Ile Thr Asp Ala Phe Asn Leu Ser Asp Phe Phe
                645                 650                 655

Ile Asn Ser Ala Ile Gly Arg Tyr Asp Gly Asn Val Tyr Glu Asn Tyr
            660                 665                 670

Phe Thr Gln Val Lys Arg Gln Asn Pro Ser Lys Pro Gln Ala Pro Tyr
        675                 680                 685

Phe Glu Lys Val Ile Lys Pro Phe Val His Arg Val Ala Glu Val Glu
    690                 695                 700

Val Asp Ala Glu Glu Leu Asp Glu Asp Glu Ala
705                 710                 715
```

<210> SEQ ID NO 33
<211> LENGTH: 2787
<212> TYPE: DNA
<213> ORGANISM: Lipomyces starkeyi
<220> FEATURE:
<221> NAME/KEY: Intron
<222> LOCATION: (182)..(228)
<220> FEATURE:
<221> NAME/KEY: Intron
<222> LOCATION: (2091)..(2142)

<400> SEQUENCE: 33

```
atgccgcacg aactacgatt tgacggtcaa accgttgtca ttacaggtgc cggcggcggt     60

ctagggaggg catacgcttt atttttcgga tcccgcggcg ctaatgttgt cgttaacgat    120

ttgggctcta gttccaaggg cgaaggccac tcgacaaagg cagctgacgt tgtagtggaa    180

ggtgagcttg cattactgtc aatgttgtgt ggaacaattc taatgtagaa atagaaatta    240

agaaggctgg aggaaacgct gttccgaatt acgattcggt cgaattcggt gacagaattg    300

ttgagaccgc gattaaagca ttcggcagcg tgcatgtgct aatcaacaat gccggcatac    360

tgcgtgatat ctcgttcaag aacatgaaag acgcagattg ggacttgatc caacttgtac    420

atctcaaggg cgcgtacaaa accacgaaag ccgcctggcc agtattccgc aaacaaaagt    480

tcggccgaat tatcaacact gcttctgcgg cgggcttgta cggaagtttc gggcaggcca    540

attattcggc tgcgaaactc ggattggttg gattcacaga gactttggcc aaggaagggg    600

ccaaatacgg catttttgct aacgtgatag cgcctatggc ggccagcaga atgacacaga    660

cggtcatgcc cgaggatctg ttgagcatgc tgaagcccga atgggttgtt cctctcgttt    720

cgtaccttac acacaaggac acggacgata ccggcggaat ctacgaggtt ggcgcagggt    780
```

-continued

```
tcgtttcaaa gcttcgctgg gagcgatcaa atggcgctct tttcaagact gatgacagtt     840
tcacacccgc atcgatcctt gcgcgatggt ctgagattca ggacttcgag tccaaaacac     900
cacagtaccc gactggccca aatgacttca tgacgcttct cgagtcggca cgtgaactgc     960
catccaacaa acaaggcgac gtccccgttg acgtgaagga caaagtcgtc attgtcaccg    1020
gctccggcgg cggtcttggt cgcgcatacg ctcttttatt cgctaagctc ggtgctaagc    1080
ttgttatcaa cgatgtcggc gacccaaatg gtacggttaa tgaaattaac aagctctatg    1140
gcgaaggcac tgcaatatct gatcgtcatt ccgtcgagga aggagacgca gtcgtcaaga    1200
cagcagttga ccactttgga accgtgcatg tagtcgtcaa caatgccgga atcttgcgtg    1260
acaagtcctt cgctagtatg actgacgacc tgtgggatca agtcatagcc gtccacttgc    1320
gcggtacata taagattacc aaggcagctt ggccatactt cttgaagcaa aaattcggac    1380
gaatcgtcaa cactacttcg acgtctggta tatacggcaa ttttggtcag gctaactacg    1440
ctactgccaa atgcgcaata attggcttca caaaaacaat tgcattggaa ggaaagaaat    1500
acaacatttt cgcgaatgcg attgccccca atgctggtac caatatgact cgtactattt    1560
tgcctgagga gattgtgcag gctttcaagc cggactatgt agcgcctctt gccgtcctct    1620
tgtcctctga cagggcccct gttactggcg aaatctttga gaccggctct ggttggatcg    1680
gaaatacaag atggcagcgg accggcggcg ttggattccc tgtcgacaag ccgcttacac    1740
ctgaggccat ccaggagaat tggcgaaga tcactgactt tagtgacggc cgtgcgactt     1800
acccgaagac cacacaagag agcatgggtg cgattctcga gaatatgtcg aacaaaacct    1860
cagtatcatc gtcatcggct tcggagcaga caggccccga ttttcatttc agttatgaaa    1920
ctagagatct aatcctatat aacctcggag ttggtgcgaa ggcgtccgaa ttgaagtacg    1980
tgtttgaagg tgcggatgat ttcacagtct tgcctaccta cggtgttgtt ccatactttg    2040
gcgcatctgg ttcattagac ttcagcgagc ttgttcccaa ctttaacccg gtatggtttt    2100
acccattctc ttcacgacga ttttgatact aactttacta agatgatgct tctccatggc    2160
gagcaatatc tggaaatcaa atcctggcca cttcccacgt cgggtgggag gctcgtttcc    2220
aaagcccgtc taattgaagt tcttgacaag ggcaaggctg cctgcgttat cactggtact    2280
gagacaaatg acgccgagac aggaaagcca gttttctaca atgagtcgac catcgtcctt    2340
cgcggttccg gtggttttgg cggacctagc aagggcaagg accgaggtgc tgctacagct    2400
gccaacactc cgcccaagcg tgcgcccgat ttcgttgctg tagtcaagac tactgaagac    2460
caagcagcca tctatcgatt gtccggcgat tataacccac ttcacattga ccctgagttc    2520
gcggcagtcg gtaagttccc gaaaccaatc ctacacggtc tttgcacgtt tggtattgct    2580
ggaaaacaga tatatgacaa gttcggaatg ttcaagaaca ttaaggttcg tttcgctggt    2640
cacgttttcc cgggcgagac attaaaggtt gagatgtgga agcttggcgg tggcaagatt    2700
attttccaga caactgttat tgaacgaaat acagttgcta tatcgtcggc tgctgtggag    2760
ttaataactg atacatcgaa gttgtag                                        2787
```

<210> SEQ ID NO 34
<211> LENGTH: 870
<212> TYPE: PRT
<213> ORGANISM: Lipomyces starkeyi

<400> SEQUENCE: 34

```
Met Pro His Glu Leu Arg Phe Asp Gly Gln Thr Val Val Ile Thr Gly
1               5                   10                  15
```

-continued

```
Ala Gly Gly Gly Leu Gly Arg Ala Tyr Ala Leu Phe Phe Gly Ser Arg
            20                  25                  30

Gly Ala Asn Val Val Val Asn Asp Leu Gly Ser Ser Ser Lys Gly Glu
        35                  40                  45

Gly His Ser Thr Lys Ala Ala Asp Val Val Val Glu Glu Ile Glu Ile
    50                  55                  60

Lys Lys Ala Gly Gly Asn Ala Val Pro Asn Tyr Asp Ser Val Glu Phe
65                  70                  75                  80

Gly Asp Arg Ile Val Glu Thr Ala Ile Lys Ala Phe Gly Ser Val His
                85                  90                  95

Val Leu Ile Asn Asn Ala Gly Ile Ser Arg Asp Ile Ser Phe Lys Asn
            100                 105                 110

Met Lys Asp Ala Asp Trp Asp Leu Ile Gln Leu Val His Leu Lys Gly
        115                 120                 125

Ala Tyr Lys Thr Thr Lys Ala Ala Trp Pro Val Phe Arg Lys Gln Lys
    130                 135                 140

Phe Gly Arg Ile Ile Asn Thr Ala Ser Ala Ala Gly Leu Tyr Gly Ser
145                 150                 155                 160

Phe Gly Gln Ala Asn Tyr Ser Ala Ala Lys Leu Gly Leu Val Gly Phe
                165                 170                 175

Thr Glu Thr Leu Ala Lys Glu Gly Ala Lys Tyr Gly Ile Phe Ala Asn
            180                 185                 190

Val Ile Ala Pro Met Ala Ala Ser Arg Met Thr Gln Thr Val Met Pro
        195                 200                 205

Glu Asp Ser Leu Ser Met Ser Lys Pro Glu Trp Val Val Pro Leu Val
    210                 215                 220

Ser Tyr Leu Thr His Lys Asp Thr Asp Asp Thr Gly Gly Ile Tyr Glu
225                 230                 235                 240

Val Gly Ala Gly Phe Val Ser Lys Leu Arg Trp Glu Arg Ser Asn Gly
                245                 250                 255

Ala Leu Phe Lys Thr Asp Asp Ser Phe Thr Pro Ala Ser Ile Leu Ala
            260                 265                 270

Arg Trp Ser Glu Ile Gln Asp Phe Glu Ser Lys Thr Pro Gln Tyr Pro
        275                 280                 285

Thr Gly Pro Asn Asp Phe Met Thr Leu Leu Glu Ser Ala Arg Glu Ser
    290                 295                 300

Pro Ser Asn Lys Gln Gly Asp Val Pro Val Asp Val Lys Asp Lys Val
305                 310                 315                 320

Val Ile Val Thr Gly Ser Gly Gly Gly Leu Gly Arg Ala Tyr Ala Leu
                325                 330                 335

Leu Phe Ala Lys Leu Gly Ala Lys Leu Val Ile Asn Asp Val Gly Asp
            340                 345                 350

Pro Asn Gly Thr Val Asn Glu Ile Asn Lys Leu Tyr Gly Glu Gly Thr
        355                 360                 365

Ala Ile Ser Asp Arg His Ser Val Glu Glu Gly Asp Ala Val Val Lys
    370                 375                 380

Thr Ala Val Asp His Phe Gly Thr Val His Val Val Val Asn Asn Ala
385                 390                 395                 400

Gly Ile Leu Arg Asp Lys Ser Phe Ala Ser Met Thr Asp Asp Ser Trp
                405                 410                 415

Asp Gln Val Ile Ala Val His Leu Arg Gly Thr Tyr Lys Ile Thr Lys
            420                 425                 430

Ala Ala Trp Pro Tyr Phe Leu Lys Gln Lys Phe Gly Arg Ile Val Asn
```

```
        435                 440                 445

Thr Thr Ser Thr Ser Gly Ile Tyr Gly Asn Phe Gly Gln Ala Asn Tyr
    450                 455                 460

Ala Thr Ala Lys Cys Ala Ile Ile Gly Phe Thr Lys Thr Ile Ala Leu
465                 470                 475                 480

Glu Gly Lys Lys Tyr Asn Ile Phe Ala Asn Ala Ile Ala Pro Asn Ala
                485                 490                 495

Gly Thr Asn Met Thr Arg Thr Ile Leu Pro Glu Glu Ile Val Gln Ala
            500                 505                 510

Phe Lys Pro Asp Tyr Val Ala Pro Leu Ala Val Leu Leu Ser Ser Asp
        515                 520                 525

Arg Ala Pro Val Thr Gly Glu Ile Phe Glu Thr Gly Ser Gly Trp Ile
    530                 535                 540

Gly Asn Thr Arg Trp Gln Arg Thr Gly Gly Val Gly Phe Pro Val Asp
545                 550                 555                 560

Lys Pro Leu Thr Pro Glu Ala Ile Gln Glu Asn Trp Ala Lys Ile Thr
                565                 570                 575

Asp Phe Ser Asp Gly Arg Ala Thr Tyr Pro Lys Thr Thr Gln Glu Ser
            580                 585                 590

Met Gly Ala Ile Leu Glu Asn Met Ser Asn Lys Thr Ser Val Ser Ser
        595                 600                 605

Ser Ser Ala Ser Glu Gln Thr Gly Pro Asp Phe His Phe Ser Tyr Glu
    610                 615                 620

Thr Arg Asp Leu Ile Leu Tyr Asn Leu Gly Val Gly Ala Lys Ala Ser
625                 630                 635                 640

Glu Leu Lys Tyr Val Phe Glu Gly Ala Asp Asp Phe Thr Val Leu Pro
                645                 650                 655

Thr Tyr Gly Val Val Pro Tyr Phe Gly Ala Ser Gly Ser Leu Asp Phe
            660                 665                 670

Ser Glu Leu Val Pro Asn Phe Asn Pro Met Met Leu Leu His Gly Glu
        675                 680                 685

Gln Tyr Ser Glu Ile Lys Ser Trp Pro Leu Pro Thr Ser Gly Gly Arg
    690                 695                 700

Leu Val Ser Lys Ala Arg Leu Ile Glu Val Leu Asp Lys Gly Lys Ala
705                 710                 715                 720

Ala Cys Val Ile Thr Gly Thr Glu Thr Asn Asp Ala Glu Thr Gly Lys
                725                 730                 735

Pro Val Phe Tyr Asn Glu Ser Thr Ile Val Leu Arg Gly Ser Gly Gly
            740                 745                 750

Phe Gly Gly Pro Ser Lys Gly Lys Asp Arg Gly Ala Ala Thr Ala Ala
        755                 760                 765

Asn Thr Pro Pro Lys Arg Ala Pro Asp Phe Val Ala Val Val Lys Thr
    770                 775                 780

Thr Glu Asp Gln Ala Ala Ile Tyr Arg Leu Ser Gly Asp Tyr Asn Pro
785                 790                 795                 800

Leu His Ile Asp Pro Glu Phe Ala Ala Val Gly Lys Phe Pro Lys Pro
                805                 810                 815

Ile Leu His Gly Leu Cys Thr Phe Gly Ile Ala Gly Lys Gln Ile Tyr
            820                 825                 830

Asp Lys Phe Gly Met Phe Lys Asn Ile Lys Val Arg Phe Ala Gly His
        835                 840                 845

Val Phe Pro Gly Glu Thr Leu Lys Val Glu Met Trp Lys Leu Gly Gly
    850                 855                 860
```

Gly Lys Ile Ile Phe Gln
865 870

<210> SEQ ID NO 35
<211> LENGTH: 2485
<212> TYPE: DNA
<213> ORGANISM: Lipomyces starkeyi

<400> SEQUENCE: 35
atgccattgg cgtctccatc ggacagcagc agccatcggc ccgttagaca ggctgtgagt 60
agcgaacact gaacagcagc ttcagcatgc ccgagtcacc gacaactaat tgcacaagtg 120
tcgcgcgctg cgagcgttac gcccaaactg gtacgaagga aaccgcgtca gggccattgc 180
ccagcctcgg gaggtgggcc tggcgaatgt gcggcgttgc gcgacggttg tgccgagtgc 240
tgcaccaagc tgcgtccctg acaacgctcc caagtgcctg gtcgcgtccc tgagcgcgcc 300
ctataacttg ctctccccgc ctcccgtctt ctcctcttgt ccagctcttc cattcttcac 360
caaagcagca tcttcaatcc atcctcaagc aatggccact gccgattctt taccttctgg 420
cgccgtcaca cccgccagcg agcgtctctc aagacccctc gacagcattg atatccctca 480
caagcgggta accaagatat gctgcctcgg cgctggttat gtcggtatgt tcctcttcct 540
ttcttaaatc tgtcgccaat cctatgttct acattcgccg atcttgacaa tatcgcacgc 600
gacttggaga ttgtgccatg tggccaaact gcaagtaggt agcgacataa acaaatcttt 660
ttggtcgacc aacgtaattg gctggccatg acgacgcttg ctgcgcgtct ttcgtctttt 720
gccaatcttt tcaatcaatt gtactaacga agtctaacag gcggccccac ctgcgccgta 780
attgcctaca agtgccctca tatcactgtc actatcgtgg acttgaacca ggcccgcatt 840
gatgcctgga actccgatga cctgcccatc tacgagcctg gtctcgacga ggttgtcaag 900
gccgtccgtg gcaagaacct tttcttctct actgacgtcg acactgctat caaggaggct 960
gatctgatct tcgtctccgt caacaccccc accaagaaat ctggtgttgg taagggcttc 1020
gcagcagact tggggtgagc attaatttg tctgtgaacg gcgacgaagc aattgctaac 1080
agagagccag ttatgttgag tctgccacgc gtcacattgc caaggtcgct gtgtctgaca 1140
agattgttgt cgagaagtcg accgttcctt gccgcactgc ccagtccatg cgcaagatcc 1200
tcgactccaa cggcaagccc ggtgcccgat ttgacattct ctccaaccct gagttcttgg 1260
ctgagggtac tgccatccgt gacctcttcg caccggaccg tgtcttgatc ggttcgcttg 1320
acactgccaa cggtcgttct gccgccgcaa gccttgctga tgtgtatgga aattgggtcc 1380
cccgaaagca ggtgatcacc atgaacttat ggtcgtctga gctctctaag cttgctgcca 1440
atgctctcct tgctcagcgt atctcgtcca tcaatgcact ttccgccatc tgtgaggcta 1500
ctggcgccga cgtcgacgag gtctcatacg ctgttggtct cgactcccgt attggcccca 1560
agttcttgaa ggcgtccgtc ggtttcggtg gttcgtgctt ccagaaggac atcctcaacc 1620
tggtttacct ctctgagtct ctccaccttc ctgatgtcgc cgagtactgg cgtcaggttg 1680
tcgagatgaa cgagtcccag aagcggcgct ttacccagca catcatctct tcgctcttca 1740
acactctcac gggcaagcgt ctcgctgttc tcggctttgc tttcaagaaa gacactggtg 1800
acacccgcga gtccgctgcg atcactttga tcaagtactt ccgccaggag caggctaaga 1860
ttgctattta cgaccccaag gtcgaggaat cccagatctg gtacgatctt gcagagccgg 1920
gcgtcgtcga cgatgtcacc gctctcaaga agcaagtcac tatcacctcg tctgcgtacg 1980
aggccgccga aggcgccgac gccgtcgtta tctgtaccga atgggacgag ttccgggata 2040

```
ccaagctcga ctatgagaag atctacgcga ccatgaacaa gcctgcgttc atttttgatg   2100

gcagattgat cctcaatcag aagaagctcg agaagatcgg tttcaaggtg gagtgcattg   2160

gtcgaagtcg gttagaggag tcattcgagt aaagactggg tgtagtgcag ataaagtctg   2220

tatgtatcaa ctgggagggg cggaacgatt tctattatat aatagcatat aaatgttttg   2280

tattgcgtat tggctcgcta aatgtgtatg tagatttggc ggatagacag aagaatttgg   2340

taattttttt cagttattgt gtttgagcac ttgtttgtta gggagtaatg ttgtatctat   2400

ctatcatttc tttcatagat atttgtctta tcatactcgt gatatattaa tataattgtt   2460

tcattaggtc agtgccgttc agtga                                        2485
```

<210> SEQ ID NO 36
<211> LENGTH: 486
<212> TYPE: PRT
<213> ORGANISM: Lipomyces starkeyi

<400> SEQUENCE: 36

```
Met Pro Leu Ala Ser Pro Ser Asp Ser Ser Ser His Arg Pro Val Arg
1               5                   10                  15

Gln Ala Arg Val Thr Lys Ile Cys Cys Leu Gly Ala Gly Tyr Val Gly
            20                  25                  30

Gly Pro Thr Cys Ala Val Ile Ala Tyr Lys Cys Pro His Ile Thr Val
        35                  40                  45

Thr Ile Val Asp Leu Asn Gln Ala Arg Ile Asp Ala Trp Asn Ser Asp
    50                  55                  60

Asp Leu Pro Ile Tyr Glu Pro Gly Leu Asp Glu Val Val Lys Ala Val
65                  70                  75                  80

Arg Gly Lys Asn Leu Phe Phe Ser Thr Asp Val Asp Thr Ala Ile Lys
                85                  90                  95

Glu Ala Asp Leu Ile Phe Val Ser Val Asn Thr Pro Thr Lys Lys Ser
            100                 105                 110

Gly Val Gly Lys Gly Phe Ala Ala Asp Leu Gly Tyr Val Glu Ser Ala
        115                 120                 125

Thr Arg His Ile Ala Lys Val Ala Val Ser Asp Lys Ile Val Val Glu
    130                 135                 140

Lys Ser Thr Val Pro Cys Arg Thr Ala Gln Ser Met Arg Lys Ile Leu
145                 150                 155                 160

Asp Ser Asn Gly Lys Pro Gly Ala Arg Phe Asp Ile Leu Ser Asn Pro
                165                 170                 175

Glu Phe Leu Ala Glu Gly Thr Ala Ile Arg Asp Leu Phe Ala Pro Asp
            180                 185                 190

Arg Val Leu Ile Gly Ser Leu Asp Thr Ala Asn Gly Arg Ser Ala Ala
        195                 200                 205

Ala Ser Leu Ala Asp Val Tyr Gly Asn Trp Val Pro Arg Lys Gln Val
    210                 215                 220

Ile Thr Met Asn Leu Trp Ser Ser Glu Leu Ser Lys Leu Ala Ala Asn
225                 230                 235                 240

Ala Leu Leu Ala Gln Arg Ile Ser Ser Ile Asn Ala Leu Ser Ala Ile
                245                 250                 255

Cys Glu Ala Thr Gly Ala Asp Val Asp Glu Val Ser Tyr Ala Val Gly
            260                 265                 270

Leu Asp Ser Arg Ile Gly Pro Lys Phe Leu Lys Ala Ser Val Gly Phe
        275                 280                 285
```

Gly Gly Ser Cys Phe Gln Lys Asp Ile Leu Asn Leu Val Tyr Leu Ser
290 295 300

Glu Ser Leu His Leu Pro Asp Val Ala Glu Tyr Trp Arg Gln Val Val
305 310 315 320

Glu Met Asn Glu Ser Gln Lys Arg Arg Phe Thr Gln His Ile Ile Ser
325 330 335

Ser Leu Phe Asn Thr Leu Thr Gly Lys Arg Leu Ala Val Leu Gly Phe
340 345 350

Ala Phe Lys Lys Asp Thr Gly Asp Thr Arg Glu Ser Ala Ala Ile Thr
355 360 365

Leu Ile Lys Tyr Phe Arg Gln Glu Gln Ala Lys Ile Ala Ile Tyr Asp
370 375 380

Pro Lys Val Glu Glu Ser Gln Ile Trp Tyr Asp Leu Ala Glu Pro Gly
385 390 395 400

Val Val Asp Asp Val Thr Ala Leu Lys Lys Gln Val Thr Ile Thr Ser
405 410 415

Ser Ala Tyr Glu Ala Ala Glu Gly Ala Asp Ala Val Val Ile Cys Thr
420 425 430

Glu Trp Asp Glu Phe Arg Asp Thr Lys Leu Asp Tyr Glu Lys Ile Tyr
435 440 445

Ala Thr Met Asn Lys Pro Ala Phe Ile Phe Asp Gly Arg Leu Ile Leu
450 455 460

Asn Gln Lys Lys Leu Glu Lys Ile Gly Phe Lys Val Glu Cys Ile Gly
465 470 475 480

Arg Ser Arg Ala Val Gln
485

<210> SEQ ID NO 37
<211> LENGTH: 1302
<212> TYPE: DNA
<213> ORGANISM: Lipomyces starkeyi

<400> SEQUENCE: 37
atgaagtttc ttattgcgac gcagcctttc acaggtcacg taaaccccat gcaaccggtt 60
gcccaggaac tggtgcaacg cggccacgag gtcgtatggc taacaggcga ggaattccgg 120
tccaaggttg agctctgtgg tgcacgtttc atggcaacgg aaaaatctaa agtcttcgac 180
gccgttcctc tcactcctga cgacggggct actggactgg ctgcagcagt atctatattg 240
cgccgtctct ttatcgatcg catagtggcc caggtaacag attaccgcca agtactagat 300
gtatttgctg ccgatgctct tctactggat ctctgttcta tgggtgcgca gactctcaat 360
gatttgggtg ggccggtgta cgcaacgctt ggaatcaatc ctcttgtgac agcggaccct 420
gaaattccga tgtggggtac ggggaagccc ccggctgcaa cgattgtcga tcgtatgatc 480
aacaggttca cgcatttcat gtcgaggaga attttctact caaagctcac aggatatgta 540
aatatgcagc ggaaaattct cggattggga ccattaccga cagggaaagg attttacgag 600
atcgcccgaa gcgaatacct tcacataatg ccgacgacat tagctttcga gttcccgcga 660
caaaatttgg gaccacagat tcatttcgtt gggccactgc taccactact agatgataaa 720
atcaccagcg aattcccatc atggtggcag gaagtcacac aaggctccaa agcggttgtg 780
catgtcacac aagggacata tgccaccaat tcagcgaacc taatcagacc ttctatcaat 840
gctctgcgta atgaaagcga cgtgcttctt gttgtaacgt ctcctgatgc agattctgta 900
ttcgccgaca cttcgcaact tccggaaaat gtccgcatag cgcgattcgt tccacacgca 960
ctattattgc cctacgtgaa agtcatgatc actaatgctg gatataacgg cgttcttgcg 1020
tcattgaact tcggcgtccc acttgtctgc gctggtcgca cggaagacaa agcagatgtt 1080
agtagcagag tcgcttggag tggtgctgga atagatctca aaaccgattc cccatctgaa 1140
gtggatatcc gcaatgcggt gaggcgtatt ttagttgaac cggcatacca aaacaatgcc 1200
agaaacatcc aagaagattt ccggaaacac aatagtgctg cagaggcatg tgacctgctg 1260
gagaaactcg caatcgaaaa aaatgtgata gtgagaactt ag 1302

<210> SEQ ID NO 38
<211> LENGTH: 433
<212> TYPE: PRT
<213> ORGANISM: Lipomyces starkeyi

<400> SEQUENCE: 38

Met Lys Phe Leu Ile Ala Thr Gln Pro Phe Thr Gly His Val Asn Pro
1 5 10 15

Met Gln Pro Val Ala Gln Glu Leu Val Gln Arg Gly His Glu Val Val
20 25 30

Trp Leu Thr Gly Glu Glu Phe Arg Ser Lys Val Glu Leu Cys Gly Ala
35 40 45

Arg Phe Met Ala Thr Glu Lys Ser Lys Val Phe Asp Ala Val Pro Leu
50 55 60

Thr Pro Asp Asp Gly Ala Thr Gly Leu Ala Ala Ala Val Ser Ile Leu
65 70 75 80

Arg Arg Leu Phe Ile Asp Arg Ile Val Ala Gln Val Thr Asp Tyr Arg
85 90 95

Gln Val Leu Asp Val Phe Ala Ala Asp Ala Leu Leu Leu Asp Leu Cys
100 105 110

Ser Met Gly Ala Gln Thr Leu Asn Asp Leu Gly Gly Pro Val Tyr Ala
115 120 125

Thr Leu Gly Ile Asn Pro Leu Val Thr Ala Asp Pro Glu Ile Pro Met
130 135 140

Trp Gly Thr Gly Lys Pro Pro Ala Ala Thr Ile Val Asp Arg Met Ile
145 150 155 160

Asn Arg Phe Thr His Phe Met Ser Arg Arg Ile Phe Tyr Ser Lys Leu
165 170 175

Thr Gly Tyr Val Asn Met Gln Arg Lys Ile Leu Gly Leu Gly Pro Leu
180 185 190

Pro Thr Gly Lys Gly Phe Tyr Glu Ile Ala Arg Ser Glu Tyr Leu His
195 200 205

Ile Met Pro Thr Thr Leu Ala Phe Glu Phe Pro Arg Gln Asn Leu Gly
210 215 220

Pro Gln Ile His Phe Val Gly Pro Leu Leu Pro Leu Leu Asp Asp Lys
225 230 235 240

Ile Thr Ser Glu Phe Pro Ser Trp Trp Gln Glu Val Thr Gln Gly Ser
245 250 255

Lys Ala Val Val His Val Thr Gln Gly Thr Tyr Ala Thr Asn Ser Ala
260 265 270

Asn Leu Ile Arg Pro Ser Ile Asn Ala Leu Arg Asn Glu Ser Asp Val
275 280 285

Leu Leu Val Val Thr Ser Pro Asp Ala Asp Ser Val Phe Ala Asp Thr
290 295 300

Ser Gln Leu Pro Glu Asn Val Arg Ile Ala Arg Phe Val Pro His Ala
305 310 315 320

```
Leu Leu Leu Pro Tyr Val Lys Val Met Ile Thr Asn Ala Gly Tyr Asn
                325                 330                 335

Gly Val Leu Ala Ser Leu Asn Phe Gly Val Pro Leu Val Cys Ala Gly
            340                 345                 350

Arg Thr Glu Asp Lys Ala Asp Val Ser Ser Arg Val Ala Trp Ser Gly
        355                 360                 365

Ala Gly Ile Asp Leu Lys Thr Asp Ser Pro Ser Glu Val Asp Ile Arg
    370                 375                 380

Asn Ala Val Arg Arg Ile Leu Val Glu Pro Ala Tyr Gln Asn Asn Ala
385                 390                 395                 400

Arg Asn Ile Gln Glu Asp Phe Arg Lys His Asn Ser Ala Ala Glu Ala
                405                 410                 415

Cys Asp Leu Leu Glu Lys Leu Ala Ile Glu Lys Asn Val Ile Val Arg
            420                 425                 430

Thr


<210> SEQ ID NO 39
<211> LENGTH: 2276
<212> TYPE: DNA
<213> ORGANISM: Lipomyces starkeyi

<400> SEQUENCE: 39

atgtcacacc gcgacgtgaa gcatcatctc ctattcgaga tctcgacaga ggtcgccaat      60

cgaggtgggt ctcagctcgt taatgcatag tcctcgaacg agtccatgct aatgttaccc     120

agtcggcggt atttactccg ttatcaagtc gaaagccccc atcaccaccg ctgaataccg     180

cgacagatac actctcatcg gtccgctgaa ccgcaagagc gtatgtgcgc gtgatgcttg     240

tgtctgatct aaggccccgg tccatactaa cacaacgtac ctcgcaggct gcaatcgagg     300

tcgaagagct cactccaacc gatccctacc ttgtcgagac tctgcggtcc atgtccgagc     360

gtggcgtcca gtatctctac ggacgatggc taattgaagg tggagtaatc ctgcgatgct     420

gttgagcatt accactaacg acgtcattgg caggtgctcc tcgcgtctta cttttcgaaa     480

ccggaccagc cttctctcat ctggacgagt ggaagaccga tctgtggaac gtggctggca     540

tcccaagccc ggttggagac agtgagacca atgaggcggt ggtatttggc tatctcgttg     600

cctggttctt gggagagttt gtctaccacg accgcacgcg agccgttgtt gcccacttcc     660

acgaatggct cgctggagtg gccctgccgc tctgccgtaa gcgtcgtata gatgtcacga     720

cgatcttcac cacccatgcc accttgctcg gtcgctacct gtgcgccggc tcggtagact     780

tctacaacaa ccttcagtac tttgacgtcg acgcagaggc cggtaagcgg ggcatttacc     840

acaggtactg catagaacgt gcggccgccc attcggcaga cgtgtttact accgtgtcgc     900

acatcacggc ctacgagtcc gagcacctgc tcaagcgaaa gccggacggc gttctcccca     960

atggtctaaa tgtcgtcaag ttttctgctg tccacgagtt ccagaatctg catgctgtca    1020

gcaaggccaa gattaatgac tttattcgtg gtcactttta tggtcattat gatttcgatc    1080

tggacaacac gctctacttc ttcacagctg gcagatatga gtataggaat aagggtgtcg    1140

acatgtttat tgagtctctt gctcgtctca atcatcgcct gaagacggag aactcaaaca    1200

agaccgtggt tgcatttatt atcatgcccg cggccacgca ctcatacacg gtagagacac    1260

tcaagggaca ggcggtcatg aaggcacttc acgacactgt caatgagatt caggagagcg    1320

ttggtcggcg gttatttgag cggtcggcga gattcaacga ggactctggc aaagacttct    1380

ctgcagagct taacgagctg ctcacgggcg gcgaaaaagt tctgttgaag cggcgagtct    1440
```

```
ttgcgctgaa gcgccatacg cagccgccca tcgtcacaca caacatggcc gacgacgcga   1500

acgatccaat tctgaaccag atccgacgcg tacagttgtt taacgactca tctgatcgtg   1560

tcaagatcat cttccaccca gagttcttga acagtaataa tcctattctc tcgcttgact   1620

acgacgactt tgtccgtggc tgccatctcg gcgtcttccc ttcgtactac gagccgtggg   1680

gctacactcc agccgaatgt acggtcatgg gcgtcccgtc gatcacgacg aacttgtcag   1740

gatttgggtg ctacatggag gagctcatcg agaacacgtc tgactacggc atttacatcg   1800

tcgaccgtcg atcaaaaggg atcgacgact cgatcaacca actggctgac tacatgtttc   1860

agttctcttt taagtcccgc cgacagcgca tcaaccagcg caaccgcacc gagcgacttt   1920

ccgatctgtt ggattggaaa cgcatggggc ttgagtacat aaaggcccgt cagctggcac   1980

tacggcgtgc gtactcgtcg tcgtttgaga atcaagaggg gttcgaagac ttctttgacg   2040

gcacggagat gaagctctcg cgcccgctgt ctgctcaggc ctcgcctaaa gaccggacgg   2100

gtatgatgac accaggagat tttggatcgc ttcaggaggg ccaggaaggt cttaacactg   2160

atgactatat cgggtttaag ttgcccgacg aggaggacga cgaggcgtat ccgtacccat   2220

tatccctaaa acgacctaac gcgccgtatg tgaatggtaa cggcacgtcc gcgtga       2276


<210> SEQ ID NO 40
<211> LENGTH: 698
<212> TYPE: PRT
<213> ORGANISM: Lipomyces starkeyi

<400> SEQUENCE: 40

Met Ser His Arg Asp Val Lys His His Leu Leu Phe Glu Ile Ser Thr
1               5                   10                  15

Glu Val Ala Asn Arg Val Gly Gly Ile Tyr Ser Val Ile Lys Ser Lys
            20                  25                  30

Ala Pro Ile Thr Thr Ala Glu Tyr Arg Asp Arg Tyr Thr Leu Ile Gly
        35                  40                  45

Pro Leu Asn Arg Lys Ser Ala Ala Ile Glu Val Glu Glu Leu Thr Pro
    50                  55                  60

Thr Asp Pro Tyr Leu Val Glu Thr Leu Arg Ser Met Ser Glu Arg Gly
65                  70                  75                  80

Val Gln Tyr Leu Tyr Gly Arg Trp Leu Ile Glu Gly Ala Pro Arg Val
                85                  90                  95

Leu Leu Phe Glu Thr Gly Pro Ala Phe Ser His Leu Asp Glu Trp Lys
            100                 105                 110

Thr Asp Leu Trp Asn Val Ala Gly Ile Pro Ser Pro Val Gly Asp Ser
        115                 120                 125

Glu Thr Asn Glu Ala Val Val Phe Gly Tyr Leu Val Ala Trp Phe Leu
    130                 135                 140

Gly Glu Phe Val Tyr His Asp Arg Thr Arg Ala Val Val Ala His Phe
145                 150                 155                 160

His Glu Trp Leu Ala Gly Val Ala Leu Pro Leu Cys Arg Lys Arg Arg
                165                 170                 175

Ile Asp Val Thr Thr Ile Phe Thr Thr His Ala Thr Leu Leu Gly Arg
            180                 185                 190

Tyr Leu Cys Ala Gly Ser Val Asp Phe Tyr Asn Asn Leu Gln Tyr Phe
        195                 200                 205

Asp Val Asp Ala Glu Ala Gly Lys Arg Gly Ile Tyr His Arg Tyr Cys
    210                 215                 220
```

-continued

```
Ile Glu Arg Ala Ala Ala His Ser Ala Asp Val Phe Thr Thr Val Ser
225                 230                 235                 240

His Ile Thr Ala Tyr Glu Ser Glu His Leu Leu Lys Arg Lys Pro Asp
                245                 250                 255

Gly Val Leu Pro Asn Gly Leu Asn Val Val Lys Phe Ser Ala Val His
            260                 265                 270

Glu Phe Gln Asn Leu His Ala Val Ser Lys Ala Lys Ile Asn Asp Phe
        275                 280                 285

Ile Arg Gly His Phe Tyr Gly His Tyr Asp Phe Asp Leu Asp Asn Thr
    290                 295                 300

Leu Tyr Phe Phe Thr Ala Gly Arg Tyr Glu Tyr Arg Asn Lys Gly Val
305                 310                 315                 320

Asp Met Phe Ile Glu Ser Leu Ala Arg Leu Asn His Arg Leu Lys Thr
                325                 330                 335

Glu Asn Ser Asn Lys Thr Val Val Ala Phe Ile Ile Met Pro Ala Ala
            340                 345                 350

Thr His Ser Tyr Thr Val Glu Thr Leu Lys Gly Gln Ala Val Met Lys
        355                 360                 365

Ala Leu His Asp Thr Val Asn Glu Ile Gln Glu Ser Val Gly Arg Arg
    370                 375                 380

Leu Phe Glu Arg Ser Ala Arg Phe Asn Glu Asp Ser Gly Lys Asp Phe
385                 390                 395                 400

Ser Ala Glu Leu Asn Glu Leu Leu Thr Gly Gly Glu Lys Val Leu Leu
                405                 410                 415

Lys Arg Arg Val Phe Ala Leu Lys Arg His Thr Gln Pro Pro Ile Val
            420                 425                 430

Thr His Asn Met Ala Asp Asp Ala Asn Asp Pro Ile Leu Asn Gln Ile
        435                 440                 445

Arg Arg Val Gln Leu Phe Asn Asp Ser Ser Asp Arg Val Lys Ile Ile
    450                 455                 460

Phe His Pro Glu Phe Leu Asn Ser Asn Asn Pro Ile Leu Ser Leu Asp
465                 470                 475                 480

Tyr Asp Asp Phe Val Arg Gly Cys His Leu Gly Val Phe Pro Ser Tyr
                485                 490                 495

Tyr Glu Pro Trp Gly Tyr Thr Pro Ala Glu Cys Thr Val Met Gly Val
            500                 505                 510

Pro Ser Ile Thr Thr Asn Leu Ser Gly Phe Gly Cys Tyr Met Glu Glu
        515                 520                 525

Leu Ile Glu Asn Thr Ser Asp Tyr Gly Ile Tyr Ile Val Asp Arg Arg
    530                 535                 540

Ser Lys Gly Ile Asp Asp Ser Ile Asn Gln Leu Ala Asp Tyr Met Phe
545                 550                 555                 560

Gln Phe Ser Phe Lys Ser Arg Arg Gln Arg Ile Asn Gln Arg Asn Arg
                565                 570                 575

Thr Glu Arg Leu Ser Asp Leu Leu Asp Trp Lys Arg Met Gly Leu Glu
            580                 585                 590

Tyr Ile Lys Ala Arg Gln Leu Ala Leu Arg Arg Ala Tyr Ser Ser Ser
        595                 600                 605

Phe Glu Asn Gln Glu Gly Phe Glu Asp Phe Phe Asp Gly Thr Glu Met
    610                 615                 620

Lys Leu Ser Arg Pro Leu Ser Ala Gln Ala Ser Pro Lys Asp Arg Thr
625                 630                 635                 640

Gly Met Met Thr Pro Gly Asp Phe Gly Ser Leu Gln Glu Gly Gln Glu
```

-continued

```
                645                 650                 655

Gly Leu Asn Thr Asp Asp Tyr Ile Gly Phe Lys Leu Pro Asp Glu Glu
            660                 665                 670

Asp Asp Glu Ala Tyr Pro Tyr Pro Leu Ser Leu Lys Arg Pro Asn Ala
        675                 680                 685

Pro Tyr Val Asn Gly Asn Gly Thr Ser Ala
    690                 695


<210> SEQ ID NO 41
<211> LENGTH: 337
<212> TYPE: PRT
<213> ORGANISM: Lipomyces starkeyi

<400> SEQUENCE: 41

Met Val Asp Ser Thr Ala Pro Glu Ile Ser Ala Ser Val Glu Thr Ala
1               5                   10                  15

Val Pro Val Val Ala Asn Gly Gly Ala Lys Ser Ser Ala Phe Val Ala
            20                  25                  30

His Leu Arg Ser Tyr Pro Ile Val Asp Ala Thr Val Ser Tyr Thr Thr
        35                  40                  45

Ser Leu Pro Leu Val Lys Lys Ala Ser Ala Thr Ala Lys Pro Tyr Val
    50                  55                  60

Asp Lys Tyr Val His Pro Ala Val Glu Lys Ala Ala Pro Val Leu Ser
65                  70                  75                  80

Arg Val Asp Lys Leu Gly Asp Thr Thr Leu Ser Lys Val Asp Lys Tyr
                85                  90                  95

Val Pro Ala Leu Arg Thr Thr Ala Ala Pro Asp Ile Pro Gly Thr Val
            100                 105                 110

Ser Lys Ser Val Glu Ser Val Lys Ser Thr Thr His Leu Tyr Thr Glu
        115                 120                 125

Ala Ala Arg Thr Lys Val Asn Asp Thr Val Val Glu Pro Thr Lys Gln
    130                 135                 140

Ala Val Asp Lys Ala Lys Gln Arg Thr Ala Ala Leu Tyr Asp Ala Lys
145                 150                 155                 160

Gly Arg Pro Phe Val Arg Ala Lys Leu Asp Pro Val Leu Ala Pro Leu
                165                 170                 175

Asn Ser Arg Leu Ile Ala Leu Leu Asp Ala Tyr Leu Pro Pro Ala Lys
            180                 185                 190

Ser Tyr Ala Asp Gly Thr Ala Ala Glu Gly Ile Ala Ala Thr Thr Glu
        195                 200                 205

Leu Gly Arg Leu Tyr Leu Ile Gly Thr Asp Ala Val Tyr Arg Val Lys
    210                 215                 220

Pro Val Ile Glu Asp Arg Val Ala Ala Thr Arg Ala His Gly Lys Glu
225                 230                 235                 240

Thr Val Asp Tyr Phe Leu Ser Val Pro Ser Ala Ala Arg Ser His Val
                245                 250                 255

Ile Ser Val Trp Glu Asp Lys Lys Ser Lys Thr Asp Ile Lys Ser Lys
            260                 265                 270

Pro Ile Thr Gly Pro Leu Tyr Val Ser Leu Ser Thr Gly Lys His Leu
        275                 280                 285

Val Phe Glu Val Val Ser Phe Ala Glu Ala Tyr Ala His Glu Lys Val
    290                 295                 300

Gly Lys Val Lys Ser Met Thr Lys Ser Ile Thr Asn Gly His Leu Lys
305                 310                 315                 320
```

```
Lys Ala Asp Ala Pro Ala Pro Ala Glu Ser Thr Pro Glu Val Val Gln
                325                 330                 335

Glu


<210> SEQ ID NO 42
<211> LENGTH: 548
<212> TYPE: PRT
<213> ORGANISM: Oerskovia xanthineolytica

<400> SEQUENCE: 42

Met Pro His Asp Arg Lys Asn Ser Ser Arg Arg Ala Trp Ala Ala Leu
1               5                   10                  15

Cys Ala Ala Val Leu Ala Val Ser Gly Ala Leu Val Gly Val Ala Ala
            20                  25                  30

Pro Ala Ser Ala Val Pro Ala Thr Ile Pro Leu Thr Ile Thr Asn Asp
        35                  40                  45

Ser Gly Arg Gly Pro Ile Tyr Leu Tyr Val Leu Gly Glu Arg Asp Gly
    50                  55                  60

Val Ala Gly Trp Ala Asp Ala Gly Gly Thr Phe His Pro Trp Pro Gly
65                  70                  75                  80

Gly Val Gly Pro Val Pro Val Pro Ala Pro Asp Ala Ser Ile Ala Gly
                85                  90                  95

Pro Gly Pro Gly Gln Ser Val Thr Ile Arg Leu Pro Lys Leu Ser Gly
            100                 105                 110

Arg Val Tyr Tyr Ser Tyr Gly Gln Lys Met Thr Phe Gln Ile Val Leu
        115                 120                 125

Asp Gly Arg Leu Val Gln Pro Ala Val Gln Asn Asp Ser Asp Pro Asn
    130                 135                 140

Arg Asn Ile Leu Phe Asn Trp Thr Glu Tyr Thr Leu Asn Asp Gly Gly
145                 150                 155                 160

Leu Trp Ile Asn Ser Thr Gln Val Asp His Trp Ser Ala Pro Tyr Gln
                165                 170                 175

Val Gly Val Gln Arg Ala Asp Gly Gln Val Leu Ser Thr Gly Met Leu
            180                 185                 190

Lys Pro Asn Gly Tyr Glu Ala Phe Tyr Thr Ala Leu Glu Gly Ala Gly
        195                 200                 205

Trp Gly Gly Leu Val Gln Arg Ala Pro Asp Gly Ser Arg Leu Arg Ala
    210                 215                 220

Leu Asn Pro Ser His Gly Ile Asp Val Gly Lys Ile Ser Ser Ala Ser
225                 230                 235                 240

Ile Asp Ser Tyr Val Thr Glu Val Trp Asn Ser Tyr Arg Thr Arg Asp
                245                 250                 255

Met Val Val Thr Pro Phe Ser His Glu Pro Gly Thr Gln Phe Arg Gly
            260                 265                 270

Arg Val Asp Gly Asp Trp Phe Arg Phe Arg Ser Gly Ser Gly Gln Glu
        275                 280                 285

Val Ala Ala Phe Lys Lys Pro Asp Ala Ser Ser Val Tyr Gly Cys His
    290                 295                 300

Lys Asp Leu Gln Ala Pro Asn Asp His Val Val Gly Pro Ile Ala Arg
305                 310                 315                 320

Thr Leu Cys Ala Ala Leu Val Arg Thr Thr Ala Leu Thr Asn Pro Asn
                325                 330                 335

Gln Pro Asp Ala Asn Ser Ala Gly Phe Tyr Gln Asp Ala Arg Thr Asn
            340                 345                 350
```

```
Val Tyr Ala Lys Leu Ala His Gln Gln Met Ala Asn Gly Lys Ala Tyr
        355                 360                 365

Ala Phe Ala Phe Asp Asp Val Gly Ala His Glu Ser Leu Val His Asp
    370                 375                 380

Gly Asn Pro Gln Ala Ala Tyr Ile Lys Leu Asp Pro Phe Thr Gly Thr
385                 390                 395                 400

Ala Thr Pro Leu Gly Asn Gly Gly Ser Thr Glu Gln Pro Gly Thr Pro
                405                 410                 415

Gly Gly Leu Pro Ala Gly Thr Gly Ala Leu Arg Ile Gly Ser Thr Leu
            420                 425                 430

Cys Leu Asp Val Pro Trp Ala Asp Pro Thr Asp Thr Asn Gln Val Gln
        435                 440                 445

Leu Ala Thr Cys Ser Gly Asn Ala Ala Gln Gln Trp Thr Arg Gly Thr
    450                 455                 460

Asp Gly Thr Val Arg Ala Leu Gly Lys Cys Leu Asp Val Ala Arg Ser
465                 470                 475                 480

Gly Thr Ala Asp Gly Thr Ala Val Trp Ile Tyr Thr Cys Asn Gly Thr
                485                 490                 495

Gly Ala Gln Lys Trp Thr Tyr Asp Ser Ala Thr Lys Ala Leu Arg Asn
            500                 505                 510

Pro Gln Ser Gly Lys Cys Leu Asp Ala Gln Gly Gly Ala Pro Leu Arg
        515                 520                 525

Asp Gly Gln Lys Val Gln Leu Trp Thr Cys Asn Gln Thr Glu Ala Gln
    530                 535                 540

Arg Trp Thr Leu
545


<210> SEQ ID NO 43
<211> LENGTH: 435
<212> TYPE: PRT
<213> ORGANISM: Oerskovia xanthineolytica

<400> SEQUENCE: 43

Met Asp Leu Ala Arg His Arg Ser Leu Thr Pro Pro Arg Asn Leu Ala
1               5                   10                  15

Gly Arg Arg Pro Arg Ala Arg Arg Arg Leu Ala Gly Ala Leu Val Ala
            20                  25                  30

Ala Leu Thr Ala Ala Ala Ala Ala Leu Ala Val Thr Val Pro Ala Thr
        35                  40                  45

Ser Ala Ala Ala Ala Pro Gly Asp Leu Leu Trp Ser Asp Glu Phe Asp
    50                  55                  60

Gly Ala Ala Gly Ser Ala Pro Asn Pro Ala Val Trp Asn His Glu Thr
65                  70                  75                  80

Gly Ala His Gly Trp Gly Asn Ala Glu Leu Gln Asn Tyr Thr Ala Ser
                85                  90                  95

Arg Ala Asn Ser Ala Leu Asp Gly Gln Gly Asn Leu Val Ile Thr Ala
            100                 105                 110

Arg Arg Glu Gly Asp Gly Ser Tyr Thr Ser Ala Arg Met Thr Thr Gln
        115                 120                 125

Gly Lys Tyr Gln Pro Gln Tyr Gly Arg Ile Glu Ala Arg Ile Gln Ile
    130                 135                 140

Pro Arg Gly Gln Gly Ile Trp Pro Ala Phe Trp Met Leu Gly Gly Ser
145                 150                 155                 160

Phe Pro Gly Thr Pro Trp Pro Ser Ser Gly Glu Ile Asp Ile Met Glu
                165                 170                 175
```

-continued

```
Asn Val Gly Phe Glu Pro His Arg Val His Gly Thr Val His Gly Pro
            180                 185                 190

Gly Tyr Ser Gly Gly Ser Gly Ile Thr Gly Met Tyr Gln His Pro Gln
        195                 200                 205

Gly Trp Ser Phe Ala Asp Thr Phe His Thr Phe Ala Val Asp Trp Lys
    210                 215                 220

Pro Gly Glu Ile Thr Trp Phe Val Asp Gly Gln Gln Phe His Arg Val
225                 230                 235                 240

Thr Arg Ala Ser Val Gly Ala Asn Ala Trp Val Phe Asp Gln Pro Phe
                245                 250                 255

Phe Leu Ile Leu Asn Val Ala Val Gly Gly Gln Trp Pro Gly Tyr Pro
            260                 265                 270

Asp Gly Thr Thr Gln Leu Pro Gln Gln Met Lys Val Asp Tyr Val Arg
        275                 280                 285

Val Tyr Asp Asn Gly Ser Gly Ser Ser Asn Pro Gly Asn Pro Gly Thr
    290                 295                 300

Gly Leu Pro Thr Gly Thr Gly Ala Val Arg Ala Ala Asn Gly Met Cys
305                 310                 315                 320

Ile Asp Val Pro Trp Ala Asp Pro Thr Asp Gly Asn Pro Val Gln Ile
                325                 330                 335

Val Thr Cys Ser Gly Asn Ala Ala Gln Thr Trp Thr Arg Gly Ser Asp
            340                 345                 350

Gly Thr Val Arg Ala Leu Gly Lys Cys Leu Asp Val Arg Asp Gly Ser
        355                 360                 365

Thr Thr Arg Gly Ala Ala Val Gln Val Trp Thr Cys Asn Gly Thr Gly
    370                 375                 380

Ala Gln Lys Trp Ala Tyr Asp Ala Gly Ser Lys Ala Leu Arg Asn Pro
385                 390                 395                 400

Gln Ser Gly Leu Cys Leu Asp Ala Thr Gly Gly Ala Pro Leu His Asp
                405                 410                 415

Gly Gln Arg Leu Gln Thr Trp Thr Cys Asn Gly Thr Thr Ala Gln Gln
            420                 425                 430

Trp Thr Leu
        435
```

LIPID BODY COMPOSITIONS, PRODUCTS MADE THEREFROM, METHODS OF MAKING SAME, AND METHODS OF USE

CROSS-REFERENCE TO RELATED APPLICATIONS

Priority is hereby claimed to U.S. Provisional Application 62/935,878, filed Nov. 15, 2019, and U.S. Provisional Application 63/073,679, filed Sep. 2, 2020, each of which is incorporated herein by reference.

STATEMENT REGARDING FEDERALLY SPONSORED RESEARCH

This invention was made with Government support under NSF SBIR grant No. 1632255 awarded by the National Science Foundation. The Government has certain rights in this invention.

SEQUENCE LISTING

The instant application contains a Sequence Listing which has been submitted in ASCII format via EFS-Web and is hereby incorporated by reference in its entirety. The ASCII copy, created on Nov. 13, 2020, is named PCT-201113-Nonprovisional_Patent_Application-SEQUENCE_LISTING_ST25.txt and is 215,394 bytes in size.

FIELD OF THE INVENTION

The invention is directed to lipid bodies and other useful biomaterials derived from engineered hyper-lipogenic yeasts, methods for producing same, and methods of use.

BACKGROUND

There is a clear consumer interest in products that are free of petrochemicals, detergent emulsifiers, and complex chemical compositions, particularly for cosmetics and pharmaceutical compositions. Many cosmetic and skin care products are composed of a number of chemical ingredients needed to make stable emulsions, and many of these ingredients are contraindicated for the purpose of those products. There is also an interest in sustainable products, especially consumer goods made without adverse environmental impacts. Renewable sources of oils for consumer goods can be derived from plant seeds, such as soybean, canola, rapeseed, and oil palm. These triglyceride-based oils are used in pharmaceutical compositions, industrial applications, and biofuels. However, the cost and complexity associated with processing these raw materials is significant, and involves seasonal harvesting, grinding, autoclaving, degumming, solvent isolation, and refining steps to obtain the pure vegetable oils. As a result, many industries need an alternative source of seed oils (Anon 2016). Palm oil is particularly recognized as being environmentally unsustainable due to the extensive tropical deforestation to accommodate more plantations to meet its growing demand, as it is used in half of all consumer goods in the U.S. One solution involves the substitution of single cell oils from organisms such as algae and yeast into the compositions of these products.

Oleaginous yeast and some algae are natural oil producers. On a carbon conversion basis, 2 to 3 times more lipid/g dry weight is generated by microbial sources when compared to seed oils. Algae cultivation for oil has low environmental impact, but cells grow slowly, to relatively low densities, and are difficult to harvest and process. Certain algae can accumulate lipids when cultivated on sunlight and $CO_2$, but carbon fixation by photosynthesis requires a great deal of metabolic energy, so cell growth and lipid accumulation is relatively slow. Some algae can grow heterotrophically on simple organic compounds dissolved in water, which greatly increases their rates of lipid accumulation. Algae, however, do not generally assimilate more complex organic materials such as starch, cellulosic, or hemicellulosic oligomers. On the other hand, heterotrophic Ascomyceteous and Basidiomyceteous oleaginous yeasts and filamentous fungi will readily assimilate these compounds. The growth rates of these organisms on simple or complex dissolved organic materials are much faster than algae under these conditions. Oil-producing yeasts have been isolated and studied over the past 60 years, yet an industrially effective way of recovering yeast oil from oleaginous yeast has eluded individuals skilled in the art with many methods requiring the use of various solvents in processes that have not been proven to be economical (Wang et al. 2016, Wenning et al. 2017, Severa et al. 2014, Nisha et al. 2012, Yu et al. 2015, Ochsenreitheri et al. 2016).

In addition to the oil itself, many current commercial products contain processed plant and animal oils and lipid enclosed structures in stable emulsions or droplets, the latter of which are canonically referred to as liposomes. The term "liposome" commonly refers to a spherical vesicle having at least one lipid bilayer, which usually encloses an aqueous core, but which can be modified to encompass hydrophobic inclusions (Schwendener et al. 2010). Artificial liposomes prepared from egg phosphatidyl choline are typically 85+/−32 nm in diameter prior to fractionation (Ingebrigsten et al. 2002). The outer or hydrophilic sides of liposomes are most often composed of phospholipids, especially phosphatidylcholine derived from egg yolk or soy beans, but may also include other lipids, such as phosphatidylethanolamine or phosphatidylserine. These artificial structures impart stability to emulsions that can be used to maintain a suspension of hydrophobic compounds, which are otherwise not soluble in aqueous solutions. Significant literature and expired patent publications exist related to liposomes dating back to the 1970s. The fatty acids and triglycerides for these lipid-based synthetic structures are generally created by combining chemicals, detergents, emulsifiers, and other agents.

Oleaginous yeasts accumulate their oil in lipid bodies. Lipid bodies are significantly larger than liposomes (generally <2 μm in diameter) and are irregular, lipid-containing intracellular organelles. Lipid bodies have never previously been recognized as a useful free-standing product for commercialization, as alternatives to liposomes for commercial products, or as a useful intermediate composition of matter for solvent-free oil processing. Moreover, methods of generating isolated lipid bodies from either algae or oleaginous yeasts have not existed. While triglyceride oils from yeasts represent an alternative to plant derived oils, if they were extracted from the cells using conventional means such as organic solvent mixtures of chloroform and methanol, these oils would still need to be combined with other emulsifiers and chemical agents to make liposomes. Therefore, yeast derived lipid bodies may be an alternative to plant-based oils and liposomes for certain applications, specifically to meet the growing consumer demand for fewer chemical ingredients and sustainable products from encapsulated oil.

There is a need for the generation and isolation of lipid bodies suitable for industrial and consumer use.

SUMMARY OF THE INVENTION

The invention addresses the aforementioned needs by providing recombinant yeasts and methods for converting a wide range of carbon feedstocks and stillage organics into engineered lipid bodies that can be further processed to isolate lipid bodies, lipids, and other biomaterials.

The recombinant yeasts are specifically bioengineered for rapid lipid body formation and can be used to make enlarged, engineered lipid bodies that can then be used as products themselves or further processed into other products and biological materials.

The present invention describes the genetic modification of oleaginous yeast to increase the intracellular concentration of oil production, and a series of processing steps to obtain single-cell oils, large lipid bodies, and other novel products. The high oil concentrations attained by our novel engineered cells enables efficient recovery of the buoyant cells and lipid bodies through flotation, which consumes much less energy than centrifugation. Hydrolysis of the cell walls by chemical, thermophysical or enzymatic means can recover stable lipid bodies that can be used in compositions that will replace the use of oils in personal care and other products. Novel yeast oil extracts can be obtained through physical, thermophysical, or chemical treatments directly from lipogenic cells or the recovered lipid bodies for use in a wide range of products.

In an exemplary method of making the isolated lipid bodies, yeast cell walls of the recombinant yeasts can be hydrolyzed in heat >50° C. and acid (e.g., sulfuric or phosphoric acid) resulting in spontaneous formation of two phases. The upper tan phase contains the crude lipid bodies, whereas the bottom aqueous phase contains the cell hydrolysate. The lipid bodies can then be washed in pure water. This can be followed by an alkali wash, which removes residual odor and shifts the appearance from tan to white. The lipid bodies can then be washed again and resuspended in a suitable compositions buffer.

The isolated lipid bodies of the invention are drastically larger than lipid bodies isolated from natural, un-modified yeasts. This makes them suitable for a number of useful applications.

The lipid bodies can be used as a platform or intermediate for cosmetic, pharmaceutical, industrial and biofuel products. The engineered lipid bodies are a particularly useful component of skin care products, pharmaceutical compositions involving hydrophobic medicines, consumer goods, food and feed products including aquaculture, and other industrial goods. The isolated lipid bodies of the invention can be applied directly to human skin as a moisturizer or used as a base platform for a wide range of skin and personal care products.

Aspects of the invention provide the ability to produce engineered lipid bodies without influencing the food supply, since the engineered lipid bodies from the recombinant yeast can be cultured in part on inexpensive industrial waste streams derived from ethanol plants or other industrial settings, such as cellulosic hydrolysates of agricultural residues or municipal waste treatment facilities (Leiva-Candia et al. 2014, Gong et al. 2012, Angerbauer et al. 2008, McNeil et al. 2018).

An extension of engineered lipid body technology is the facilitated processing of the isolated engineered lipid bodies to obtain yeast oil using inexpensive oil extraction methods. The identification and processing of biologically derived engineered lipid bodies from genetically modified yeast can facilitate the recovery of a yeast oil that is suitable for biodiesel, other biofuels, and oleochemicals. The yeast oil could meet a significant fraction of the national transportation energy demand and decrease dependency on foreign oil. Alternatively, it could provide a palm oil substitute than can be used in the cosmetic, pharmaceutical and/or food and beverage industries.

Genetic modification of oleaginous yeast described herein provides the ability to produce biologically assembled lipid bodies that are easily isolated and processed into yeast oil in an engineered proportion without the use of solvents. Exemplary aspects of the present invention pertain to the creation of these engineered yeast, the subsequent aqueous processing to isolate lipid bodies, along with solvent or solvent-free oil extraction techniques to isolate the oil contained within these lipid bodies. The development of these technologies has opened broad commercial applications not previously possible with native oleaginous yeasts. Lipid bodies and their applications can also replace the use of synthetic liposomes. Furthermore, the engineered isolated lipid bodies can be used as a product platform for sustainable consumer goods, pharmaceutical compositions, industrial applications, and biofuels. This technology answers the demand of consumers for clean, sustainable, and simple products.

The objects and advantages of the invention will appear more fully from the following detailed description of the preferred embodiment of the invention made in conjunction with the accompanying drawings.

BRIEF DESCRIPTION OF THE DRAWINGS

FIG. 20A: Top view of lipid bodies migrating to a positive pole after chelating copper. FIG. 20B: Side view of lipid bodies that have become neutrally buoyant after chelating copper.

DETAILED DESCRIPTION OF THE INVENTION

Figure 1:
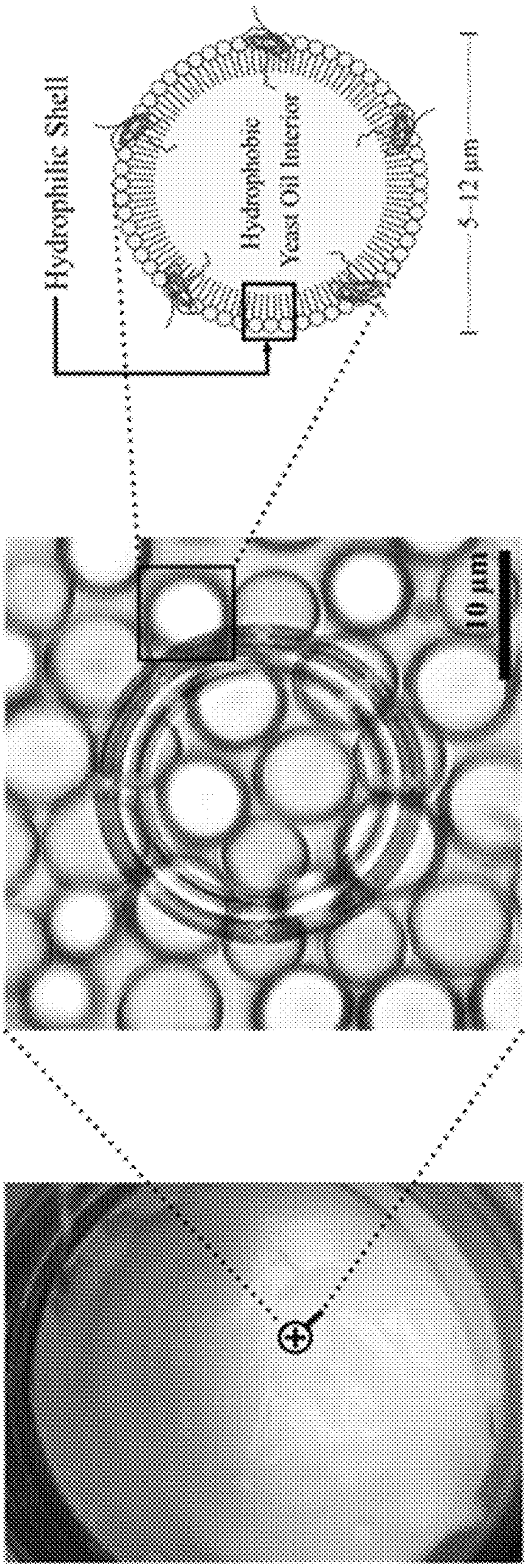
FIG. 1. An exemplary cream compositions of the invention that includes lipid bodies in a water carrier (left); a photograph of lipid bodies relevant to the invention, exemplifying their uniquely large size (middle); and a schema showing the structure and major constituents of the lipid bodies (right).

One aspect of the invention is directed to compositions comprising lipid bodies. As used herein, "lipid body" refers to structures comprising a hydrophobic core comprising lipids such as triacylglycerols, steryl esters, and/or other lipids surrounded by at least one outer layer. The hydrophobic core is referred to herein as the "inner core." The lipid present in the inner core is referred to herein as "core lipid" or "oil." The outer layer is referred to herein as an "envelope." The envelope comprise phospholipid, protein, and/or other materials such as polysaccharide. The phospholipid may predominantly comprise phosphatidylethanolamine. When isolated, lipid bodies can also be designated "lipid droplets" (Uzuka et al. 1975). Lipid bodies or lipid droplets are distinct from synthetic liposomes, which may be most commonly comprised of phospholipid and emulsifiers.

The lipid bodies of the invention are preferably isolated. "Isolated" means that the lipid bodies are not encompassed within an intact cell, such as a yeast cell. Isolated lipid bodies encompass lipid bodies that are isolated from intact cells and exist as-is in their originally isolated state or are modified in some way. Exemplary modifications are described in the following examples and include, without limitation, merging, impregnating with active agents, modifying surface charge, etc. In preferred versions the isolated lipid bodies are yeast lipid bodies, meaning that they are originally produced in, and isolated from, yeast. An indication a lipid body is a yeast lipid body is that the lipid body comprises yeast protein. In some versions, the lipid bodies of the invention comprise isolated lipid bodies that are unmerged. That is, they are not merged after isolation to increase their size. In some versions, the lipid bodies of the invention comprise isolated lipid bodies that are merged. That is, they are merged after isolation to increase their size.

The lipid bodies of the invention are preferably non-synthetic. As used herein, "non-synthetic" refers to lipid bodies produced from constitutive cellular components in vivo (i.e., within a cell, such as a yeast cell), as opposed to entities produced from individual isolated components (e.g., oil, phospholipids, etc.) in vitro. The term "non-synthetic" refers to lipid bodies originally produced from constitutive cellular components in vivo but later modified in some way. Exemplary modifications are described in the following examples and include, without limitation, merging, impregnating with active agents, modifying surface charge, etc. In some versions, the lipid bodies of the invention comprise non-synthetic, isolated lipid bodies that are unmerged. That is, they are not merged after isolation to increase their size. In some versions, the lipid bodies of the invention comprise non-synthetic, isolated lipid bodies that are merged. That is, they are merged after isolation to increase their size.

The lipid bodies of the invention comprise lipid bodies having a larger diameter than lipid bodies isolated from natural yeasts. The lipid bodies of the invention can have a diameter of at least about 5 μm and up to about 60 μm microns or more. For example, the lipid bodies in various versions of the invention can have a diameter of at least about 5 μm, at least about 6 μm, at least about 7 μm, at least about 8 μm, at least about 9 μm, at least about 10 μm, at least about 15 μm, at least about 20 μm, at least about 25 μm, at least about 30 μm, at least about 35 μm, at least about 40 μm, or at least about 45 μm. The lipid bodies in various versions of the invention can have a diameter up to about 10 μm, up to about 15 μm, up to about 20 μm, up to about 25 μm, up to about 30 μm, up to about 35 μm, up to about 40 μm, up to about 45 μm, up to about 50 μm, up to about 55 μm, up to about 60 μm or more. The lipid bodies having these sizes can constitute at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the total number lipid bodies in a given composition. The lipid bodies having these sizes can constitute up to about 5%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, up to about 90%, up to about 95%, or up to about 100% of the total number lipid bodies in a given composition. In some versions, from about 30% to about 80% of the number of lipid bodies in a given composition have a diameter of at least about 5 μm (such as from about 5 μm to about 10 μm or about 15 μm). In some versions, from about 20% to about 50% of the number of lipid bodies in a given composition have a diameter of at least about 6 μm, (such as about 6 μm to about 10 μm or about 15 μm). The lipid bodies in various versions of the invention have a diameter from about 5 to about 12 μm, from about 5 to about 50 μm, or from about 12 to about 50 μm.

In some versions of the invention, the lipid bodies in the composition have an average diameter of at least about 5 μm, at least about 5.5 μm, at least about 6 μm, or at least about 6.5 μm. In some versions, the lipid bodies in the composition have an average diameter up to about 7 μm, up to about 7.5 μm, up to about 8 μm, up to about 8.5 μm, up to about 9 μm, up to about 9.5 μm, up to about 10 μm, or more.

The lipid bodies in some versions have a larger average volume than lipid bodies derived from natural yeasts. In some versions, for example, the lipid bodies in the composition have an average volume of at least about 65 $\mu m^3$, at least about 90 $\mu m^3$, at least about 120 $\mu m^3$, or at least about 150,000 $\mu m^3$. In some versions, the lipid bodies in the composition have an average volume up to about 180,000 $\mu m^3$, up to about 220,000 $\mu m^3$, up to about 270,000 $\mu m^3$, up to about 320,000 $\mu m^3$, up to about 380,000 $\mu m^3$, up to about 450,000 $\mu m^3$, up to about 525,000 $\mu m^3$, or more.

The core lipid of the lipid bodies is preferably present in the lipid bodies in an amount of at least about 30% and up to about 90% or more by weight as determined by gravimetric analysis. In various versions, the core lipid is present in the lipid bodies in an amount of at least about 30%, at least about 35%, at least about 40%, at least about 45%, at least about 50%, at least about 55%, at least about 60%, at least about 65%, at least about 70%, at least about 75%, at least about 80%, or at least about 85% by weight as determined by gravimetric analysis. Alternatively or additionally, the core lipid is present in the lipid bodies in various versions in an amount up to about 60%, up to about 65%, up to about 70%, up to about 75%, up to about 80%, up to about 85%, up to about 90%, up to about 95%, or up to about 99% by weight as determined by gravimetric analysis.

The core lipid in the lipid bodies of the invention is preferably solid at a temperature within a range from about 10° C. to about 30° C., such as a temperature within a range from about 15° C. to about 25° C. Alternatively or additionally, the core lipid in the compositions is preferably liquid at a temperature within a range from about 30° C. to about 60° C., such as a temperature preferably solid at a temperature within a range from about 35° C. to about 55° C. or a range from about 40° C. to about 50° C. The core lipid in the lipid bodies of the invention can have a melting point at a temperature between about 25° C. and about 50° C.

In some versions, the compositions of the invention have a white or off-white color. The white or off-white color is different from the color of crude lipid bodies isolated from yeast, which are typically tan or brown in color. The white or off-white color can be obtained by performing an alkaline wash of the crude lipid bodies, as described in detail below. An objective indicator of the white or off-white color is a spectral absorbance at about 400 nm of less than about 0.32 optical density (OD) units per gram of lipid body wet weight, such as less than about 0.3 OD units per gram of lipid body wet weight, less than about 0.25 OD units per gram of lipid body wet weight, less than about 0.2 OD units per gram of lipid body wet weight, less than about 0.15 OD units per gram of lipid body wet weight, less than about 0.1 OD units per gram of lipid body wet weight, less than about 0.05 OD units per gram of lipid body wet weight, less than about 0.01 OD units per gram of lipid body wet weight, or about 0 OD units per gram of lipid body wet weight. Methods for determining OD units per gram of lipid body wet weight are described in the following examples.

In some versions, the lipid bodies or the composition comprising the lipid bodies exhibit an absorbance at about 230 nm of at least about 0.01 OD units per gram of lipid body wet weight, at least about 0.05 OD units per gram of lipid body wet weight, at least about 0.1 OD units per gram of lipid body wet weight, at least about 0.5 OD units per gram of lipid body wet weight, at least about 1 OD units per gram of lipid body wet weight, at least about 1.5 OD units per gram of lipid body wet weight, at least about 2 OD units per gram of lipid body wet weight, or at least about 2.5 OD units per gram of lipid body wet weight. In some versions, the composition exhibits an absorbance at about 230 nm up to about 1.5 OD units per gram of lipid body wet weight, up to about 2 OD units per gram of lipid body wet weight, up to about 2.5 OD units per gram of lipid body wet weight, up to about 3 OD units per gram of lipid body wet weight, up to about 3.5 OD units per gram of lipid body wet weight, or more.

The compositions of the invention preferably comprise the lipid bodies at a concentration from about 1% or less to about 99% or more by dry weight. In various versions, the compositions of the invention comprise the lipid bodies at a concentration of at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% by dry weight. Alternatively or additionally, the compositions in various versions comprise the lipid bodies at a concentration up to about 5%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, up to about 90%, up to about 95%, or up to about 99% by dry weight. An exemplary range is a concentration from about 30% to about 55% by dry weight.

The compositions of the invention preferably comprise the lipid bodies at a concentration from about 1% or less to about 99% or more by dry weight. In various versions, the compositions of the invention comprise the lipid bodies at a concentration of at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% by dry weight. Alternatively or additionally, the compositions in various versions comprise the lipid bodies at a concentration up to about 5%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, up to about 90%, up to about 95%, or up to about 99% by dry weight. An exemplary range is a concentration from about 30% to about 55% by dry weight.

The composition can have a wide range of solids concentrations. The particular solids concentrations will depend on the desired form of the composition. In some versions, the composition has a solids concentration of at least about 5% w/w, at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, or at least about 80% w/w. In some versions, the composition has a solids concentration up to about 15% w/w, up to about 20% w/w, up to about 25% w/w, up to about 30% w/w, up to about 35% w/w, up to about 40% w/w, up to about 45% w/w, up to about 50% w/w, up to about 55% w/w, up to about 60% w/w, up to about 65% w/w, up to about 70% w/w, up to about 75% w/w, up to about 80% w/w, up to about 85% w/w, up to about 90% w/w, or up to about 95% w/w.

In some versions, the composition of the invention comprises lipid in an amount of at least about 100 g/L, at least about 150 g/L, at least about 200 g/L, at least about 250 g/L, at least about 300 g/L, at least about 350 g/L, at least about 400 g/L, at least about 450 g/L, at least about 500 g/L, at least about 550 g/L, at least about 600 g/L, at least about 650 g/L, at least about 700 g/L, at least about 750 g/L, or at least about 800 g/L. In some versions, the composition of the invention comprises lipid in an amount up to about 150 g/L, up to about 200 g/L, up to about 250 g/L, up to about 300 g/L, up to about 350 g/L, up to about 400 g/L, up to about 450 g/L, up to about 500 g/L, up to about 550 g/L, up to about 600 g/L, up to about 650 g/L, up to about 700 g/L, up to about 750 g/L, up to about 800 g/L, up to about 850 g/L, or up to about 900 g/L. In some versions, at least about 50% by weight, at least about 55% by weight, at least about 60% by weight, at least about 65% by weight, at least about 70% by weight, at least about 75% by weight, at least about 80% by weight, at least about 85% by weight, at least about 90% by weight, at least about 95% by weight, or at least about 99% by weight of the total lipid comprised by the composition is included as part of the lipid droplets.

In some versions, the composition of the invention comprises protein in an amount of at least about 0.01 g/L, at least about 0.05 g/L, at least about 0.1 g/L, at least about 0.5 g/L, at least about 1 g/L, at least about 2 g/L, at least about 3 g/L, at least about 4 g/L, at least about 5 g/L, at least about 6 g/L, at least about 7 g/L, at least about 8 g/L, at least about 9 g/L, at least about 10 g/L, at least about 11 g/L, at least about 12 g/L, at least about 13 g/L, or at least about 14 g/L. In some versions, the composition of the invention comprises protein in an amount up to about 0.5 g/L, up to about 1 g/L, up to about 2 g/L, up to about 3 g/L, up to about 4 g/L, up to about 5 g/L, up to about 6 g/L, up to about 7 g/L, up to about 8 g/L, up to about 9 g/L, up to about 10 g/L, up to about 11 g/L, up to about 12 g/L, up to about 13 g/L, up to about 14 g/L, or up to about 15 g/L. In some versions, at least about 10% by weight, at least about 20% by weight, at least about 30% by weight, at least about 40% by weight, at least about 50% by weight, at least about 55% by weight, at least about 60% by weight, at least about 65% by weight, at least about 70% by weight, at least about 75% by weight, at least about 80% by weight, at least about 85% by weight, at least about 90% by weight, at least about 95% by weight, or at least about 99% by weight of the protein comprised by the composition is included as part of the lipid droplets.

In some versions, the lipid bodies in the composition comprise a lipid:protein ratio by mass from about 25:1 to about 1,000:1, such as from about 50:1 to about 500:1, from about 75:1 to about 300:1, or from about 100:1 to about 250:1.

In preferred versions, the protein in the lipid bodies comprises yeast protein. As used herein, "yeast protein" refers to any protein comprising an amino acid sequence specific to yeast. Determining whether the protein in lipid bodies comprises yeast protein can be performed by isolating the protein from the lipid bodies and determining the sequences and/or identities of the isolated protein by, for example, liquid chromatography tandem mass spectrometry (LC-MS/MS). In some versions, the yeast protein in the lipid bodies comprises protein 212544 from *L. starkeyi*, a yeast homolog or ortholog thereof, or a protein comprising an amino acid sequence at least about 80%, at least about 85%, at least about 90%, at least about 95%, or at least about 99% identical to the amino acid sequence of protein 212544 from *L. starkeyi*. The amino acid sequence of protein 212544 is represented by SEQ ID NO:41. In some versions, the yeast protein in the lipid bodies comprises Oil1 (Bhutada et al. 2018), Sps4 (Garber et al. 1986), or any yeast homolog or ortholog of either of these proteins. In some versions, the yeast protein in the lipid bodies comprises any one or more of squalene epoxidase, sterol-Δ24-methyltransferase, oxidosqualene cyclase, long-chain fatty acid ligases, acylglycerol-3-phosphate dehydrogenase, alcohol acetyltransferase, TAG lipase. See, e.g., Waltermann et al. 2005.

The compositions of the invention can further comprise a carrier for the lipid bodies. The carrier is preferably a liquid, semi-liquid, or a semi-solid. The carrier is preferably a polar or ionic substance. The carrier preferably comprises water. The carrier may further include one or more excipients.

In some versions, the compositions comprise at least 50% w/w water, such as at least about 55% w/w water, at least about 60% w/w water, at least about 65% w/w water, at least about 70% w/w water, at least about 75% w/w water, at least about 80% w/w water, at least about 85% w/w water, at least about 90% w/w water, at least about 95% w/w water, or at least about 99% w/w water.

The carrier may comprise one or more excipients. Exemplary excipients include humectants preservatives, antioxidants, emulsifiers, emollients, stabilizers, and thickening agents.

Exemplary humectants include propylene glycol, hexylene glycol, and butylene glycol, aloe vera gel, alpha hydroxy acids such as lactic acid, egg yolk, egg white, glyceryl triacetate, honey, lithium chloride, molasses, polymeric polyols such as polydextrose, quillaia, sodium hexametaphosphate E452i, sugar alcohols (sugar polyols, e.g., glycerol, sorbitol, xylitol, and maltitol), urea, castor oil, and hyaluronic acid, among others.

Exemplary preservatives include a citrates (e.g., sodium citrate, anhydrous citric acid, or tri-sodium citrate dihydrate), D-gluconolactone, benzoates (e.g., sodium benzoate), sorbates (e.g., potassium sorbate, calcium sorbate and sodium sorbate), propionates, nitrites, antioxidants that inhibit oxidation, sulfites (e.g., sodium sulfite, sodium bisulfite, sodium metabisulfite, potassium bisulfite and potassium metabisulfite), vitamin E (tocopherol), vitamin C (ascorbic acid), butylated hydroxyanisole (BHA), butylated hydroxytoluene (BHT), chelating agents that bind metal ions to prevent oxidation, disodium ethylenediaminetetraacetic acid (EDTA), polyphosphates, and D-gluconolactone, among others.

Exemplary antioxidants include vitamins such as vitamin A, vitamin C, and vitamin E; vitamin cofactors and minerals, such as coenzyme Q10, manganese, and iodide; carotenoid terpenoids, such as alpha-carotene, astaxanthin, beta-carotene, canthaxanthin, cryptoxanthin, lutein, lycopene, and zeaxanthin; phenols or polyphenols. Exemplary phenols or polyphenols include flavonoids, phenolic acids and their esters, and non-flavonoid phenolics. Exemplary flavonoids include flavones, such as apigenin, luteolin, and tangeritin; flavonols, such as isorhamnetin, kaempferol, myricetin, proanthocyanidins, and quercetin; flavanones, such as eriodictyol, hesperetin, and naringenin; flavanols and their polymers, such as catechin, gallocatechin, epicatechin, epigallocatechin, theaflavin, thearubigins, isoflavone phytoestrogens, daidzein, genistein, and glycitein; stilbenoids, such as resveratrol and pterostilbene; and anthocyanins, such as cyanidin, delphinidin, malvidin, pelargonidin, peonidin, petunidin. Exemplary phenolic acids include chicoric acid, chlorogenic acid, cinnamic acid, ellagic acid, ellagitannins, gallic acid, gallotannins, rosmarinic acid, and salicylic acid. Exemplary non-flavonoid phenolics include curcumin, flavonolignans, xanthones, and eugenol.

Exemplary emulsifiers include polysaccharides (e.g., starch), egg yolk, mustard, lecithin, sodium phosphates, mono- and diglycerides, sodium stearoyl lactylate, diacetyl tartaric acid esters of mono- and diglycerides, cellulose, detergents (such as emulsifying wax, polysorbates, and ceteareths.

Exemplary emollients include shea butter, cocoa butter, mineral oil, lanolin, petrolatum, paraffin, beeswax, squalene, plant oils (e.g., coconut, jojoba, sesame, almond, and other plant oils), cetyl alcohol, olive oil (oleic acid), and triethylhexanoin, among others.

Exemplary thickening agents include various polysaccharides and proteins. Examples of polysaccharide thickening agents include starches, microbial and vegetable gums, and sugar polymers. Examples of starches include arrowroot, cornstarch, katakuri starch, potato starch, sago, wheat flour, almond flour, tapioca, and their starch derivatives. Examples of microbial and vegetable gums include alginin, guar gum, locust bean gum, and xanthan gum. Examples of sugar polymers include agar, carboxymethyl cellulose, pectin, and carrageenan. Examples of proteins thickening agents include collagen, egg whites, and gelatin.

The compositions are preferably formulated as stabilized suspensions wherein the lipid bodies remain in suspension for a given period of time at room temperature (e.g., about 20° C.). The stabilized suspension can be achieved, for example, with various thickening agents or emulsifiers. In various versions, the compositions of the invention are formulated to maintain the lipid bodies in suspension for a period of time of at least about 10 days, at least about 20 days, at least about 30 days, at least about 40 days, at least about 50 days, at least about 75 days, at least about 100 days, at least about 200 days, at least about 300 days, at least about a year, at least about two years, or at least about three years at about 20° C.

The composition can be generated by heating the lipid bodies and/or the isolated lipid-body component with or without the carrier at a temperature greater than about 50° C., greater than about 60° C., greater than about 70° C., greater than about 80° C., greater than about 90° C., greater than about 100° C., greater than about 110° C., greater than about 120° C., greater than about 130° C., or greater than about 140° C. and/or up to about 80° C., up to about 90° C., up to about 100° C., up to about 110° C., up to about 120° C., up to about 130° C., up to about 140° C., or up to about 150° C.

The carrier of the compositions can have a pH from about 0.5 or lower to about 12 or more. In some versions, the carrier has a pH from about 0.5 to about 4. In some versions the carrier has a pH from about 4 to about 9. In some versions the carrier has a pH from about 9 to about 12.

The composition can take any number of forms. Depending on the level of dilution or concentration of lipid bodies, the composition can be in a liquid form, a semi-solid form, or a solid form. The liquid and semi-solid forms can be suspensions. An exemplary liquid form includes the hair conditioner described in the following examples. Exemplary semi-solid forms include gels, creams, paste, or ointments, such as the creams described in the following examples. An exemplary solid form includes the solid wax form described in the following examples. Any particular form of a substance for the purposes herein is understood to be the form of the substance at atmospheric pressure (101,325 Pa, 760 mm Hg, 29.9212 inches Hg, or 14.696 psi) and room temperature (23° C.).

Certain embodiments of the present invention include active ingredients. The active ingredients are suitable for use in pharmaceutical compositions and methods of use. The active ingredient can be hydrophilic, lipophilic, amphiphilic, or hydrophobic. Such active ingredients can be any compound or mixture of compounds having therapeutic or other value when administered to an animal, particularly to a mammal, such as drugs, nutrients, cosmeceuticals, diagnostic agents, nutritional agents, and the like. It should be appreciated that the categorization of an active ingredient as hydrophilic or hydrophobic may change, depending upon the particular salts, isomers, analogs, and derivatives used.

In some embodiments, the active ingredient comprise a hydrophobic active ingredient. Hydrophobic active ingredients are compounds with little or no water solubility. Intrinsic water solubilities (i.e., water solubility of the unionized form) for hydrophobic active ingredients are less than about 1% by weight, and typically less than about 0.1% or 0.01% by weight. In a particular aspect of this embodiment, the active ingredient is a hydrophobic drug. In other particular aspects, the active ingredient is a nutrient, a cosmeceutical, a diagnostic agent, or a nutritional agent.

Suitable hydrophobic active ingredients are not limited by therapeutic category, and can be, for example, analgesics, anti-inflammatory agents, anti-helminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Specific, non-limiting examples of suitable hydrophobic active ingredients are: acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, and zopiclone. Of course, salts, isomers and derivatives of the above-listed hydrophobic active ingredients may also be used, as well as mixtures.

In some embodiments, the active ingredient comprises a hydrophilic active ingredient. Amphiphilic compounds are also included within the class of hydrophilic active ingredients. Apparent water solubilities for hydrophilic active ingredients are greater than about 0.1% by weight, and typically greater than about 1% by weight. In a particular aspect of this embodiment, the hydrophilic active ingredient is a hydrophilic drug. In other particular aspects, the hydrophilic active ingredient is a cosmeceutical, a diagnostic agent, or a nutritional agent.

Suitable hydrophilic active ingredients are not limited by therapeutic category, and can be, for example, analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Likewise, the hydrophilic active ingredient can be a cytokine, a peptidomimetic, a peptide, a protein, a toxoid, a serum, an antibody, a vaccine, a nucleoside, a nucleotide, a portion of genetic material, a nucleic acid (e.g., DNA, RNA, mRNA, including nucleic acids that would be included in a DNA or RNA vaccine), or a mixture thereof.

Specific, non-limiting examples of suitable hydrophilic active ingredients include: acarbose; acyclovir; acetyl cysteine; acetylcholine chloride; alatrofloxacin; alendronate; aglucerase; amantadine hydrochloride; ambenomium; amifostine; amiloride hydrochloride; aminocaproic acid; amphotericin B; antihemophilic factor (human), antihemophilic factor (porcine); antihemophilic factor (recombinant), aprotinin; asparaginase; atenolol; atracurium besylate; atropine; azithromycin; aztreonam; BCG vaccine; bacitracin; becalermin; belladona; bepridil hydrochloride; bleomnycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotaxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and clindamycin derivatives; ciprofloxacin; clodronate; colistimethate sodium; colistin sulfate; corticotropin; cosyntropin; cromolyn sodium; cytarabine; dalteparin sodium; danaparoid; desferrioxamine; denileukin diflitox; desmopressin; diatrizoate meglumine and diatrizoate sodium; dicyclomine; didanosine; dirithromycin; dopamine hydrochloride; dornase alpha; doxacurium chloride; doxorubicin; etidronate disodium; enalaprilat; enkephalin; enoxaparin; enoxaprin sodium; ephedrine; epinephrine; epoetin alpha; erythromycin; esmolol hydrochloride; factor IX; famciclovir; fludarabine; fluoxetine; foscarnet sodium; ganciclovir; granulocyte colony stimulating factor, granulocyte-macrophage stimulating factor; growth hormones—recombinant human; growth hormone—bovine; gentamycin; glucagon; glycopyrolate; gonadotropin releasing hormone and synthetic analogs thereof; GnRH; gonadorelin; grepafloxacin; haemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human, insulin lispro; insulin procine; insulin NPH; insulin aspart; insulin glargine; insulin detemir; interferon alpha; interferon beta; ipratropium bromide; ifosfamide; Japanese encephalitis virus vaccine; lamivudine; leucovorin calcium; leuprolide acetate, levofloxacin; lincomycin and lincomycin derivatives; lobucavir; lomefloxacin; loracarbef; mannitol; is measles virus vaccine; meningococcal vaccine; menotropins; mepenzolate bromide; mesalamine; methenamine; methotrexate; methscopolamine; metformin hydrochloride; metoprolol; mezocillin sodium; mivacurium chloride; mumps viral vaccine; nedocromil sodium; neostigmine bromide; neostigmine methyl sulfate; neurontin; norfloxacin; octreotide acetate; ofloxacin; olpadronate; oxytocin; pamidronate disodium; pancuronium bromide; paroxetine; perfloxacin; pentamidine isethionate; pentostatin; pentoxifylline; periciclovir; pentagastrin; pentholamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymyxin B sulfate; pralidoxime chloride; pramlintide, pregabalin; propafenone; propenthaline bromide; pyridostigmine bromide; rabies vaccine; residronate; ribavarin; rimantadine hydrochloride; rotavirus vaccine; salmeterol xinafoate; sinealide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valacyclovir; valsartan; varicella virus vaccine live; vasopressin and vasopressin derivatives; vecuronium bromide; vinblastine; vincristine; vinorelbine; vitamin B12; warfarin sodium; yellow fever vaccine; zalcitabine; zanamivir; zolendronate; zidovudine; pharmaceutically acceptable salts, isomers and derivatives thereof; and mixtures thereof.

In some versions, the active ingredient comprises a UV-absorbing agent. Non-limiting examples of UV-absorbing agents include oxybenzone, avobenzone, octisalate, octocrylene, homosalate, and octinoxate.

Regardless of whether or not the composition includes a UV-absorbing agent, the compositions preferably absorb light at a wavelength within a range from about 100 nm to about 400 nm, such as from about 150 nm to about 350 nm, or from about 190 nm to about 290 nm.

The compositions of the invention can comprise a cationic active ingredient. The cationic active agent can be solubilized in the carrier, bound to the envelope of the lipid bodies, and/or bound to the isolated envelopes. A non-limiting cationic active ingredient includes copper.

The invention is also directed to compositions comprising components isolated from the lipid bodies of the invention. Exemplary components include isolated lipid-body envelopes and isolated lipid-body oil. Such compositions can further include a carrier. Such compositions can further include a cation bound to an isolated lipid-body envelope. Such compositions can comprise an active ingredient bound to the isolated lipid-body envelope. Such compositions can be formulated with any carriers or excipients described herein for lipid bodies.

Another aspect of the invention is directed methods of generating the compositions of the invention.

Such methods can involve disrupting yeast cells containing intracellular lipid bodies to release the lipid bodies therefrom. Disrupting the yeast cells is preferably performed in a manner that maintains the structural integrity of at least a large proportion of the lipid bodies. Maintaining the structural integrity of the lipid bodies can be determined by the lack of detectable significant amounts of—or even any—free oil being released. Exemplary methods of releasing the lipid bodies include cell-wall hydrolysis, enzymatic digestion, bead beating (e.g., using a "bead beater" apparatus (Sitepu et al. 2014) with titanium beads), heating, sonicating, or any combination thereof. Exemplary enzymatic digestion methods are provided herein. Exemplary enzymes that can be used in the enzymatic digestion include yeast lytic enzymes. Exemplary yeast lytic enzymes include β-(1,3)-glucanases, such as those from EC 3.2.1.6 and 3.2.1.39. β-(1,3)-glucanases comprising a Ricin B Lectin binding domain are preferred, such as β-(1,3)-glucanases found in *Cellulosimicrobium cellulans* and *Trichoderma reesei.*

An exemplary method of cell-wall hydrolysis comprises treating the cells with acid. This acid treatment can be performed with heating for various lengths of time. The heating can include heating to temperatures from about 50° C. to about 140° C. or more. The lengths of time can range from about 30 minutes to about 18 hours. In some versions, the heating can comprise autoclaving. The autoclaving can be performed at about 121° C. for about 45 minutes. The acid used to hydrolyze the cells can include sulfuric acid, phosphoric acid, oxalic acid, or citric acid, among others, or any combination thereof. The acid treatment can involve mixing cell suspensions with volumes of the acid. The mixing can include mixing the cell suspensions in 1- to 10-fold volumes of an acid solution. The acid solution in some versions includes the acid in an amount from about 0.1 N to about 3 N. In preliminary experiments, the lipid bodies were released by heat and bead beating or by the combination of heat, bead beating, and 0.2 to 0.5 N sulfuric acid. Surprisingly, control samples that experienced only heat and acid also released lipid bodies. Even more surprisingly, the lipid bodies could be recovered by mixing cell suspensions in 1- to 10-fold volumes of 0.25 to 0.5 N sulfuric acid followed by autoclaving at 121° C. for 45 minutes. Exemplary hydrolysis methods include mixing yeast cell suspensions with about 0.25 N sulfuric acid, about 0.5 N phosphoric acid, about 0.4 N oxalic acid, or about 2 N citric acid at about 50° to about 121° C. for various lengths of time ranging from about 30 min up to about 18 h. The time, temperature, and acidity can be varied to attain hydrolysis of the cell walls and release lipid bodies. All appropriate combinations of these acid hydrolysis steps preserve the lipid bodies.

Due to their large size and low density, the lipid bodies of the invention are easily separated by flotation, centrifugation, or any other means based on their density relative to the surrounding solution. The flotation or isolation by any other means allows for the washing of the lipid bodies to remove the cell wall hydrolysate, nucleic acids, proteins, and other residual yeast and fermentation components. Accordingly, the lipid bodies released from the cells as outlined above can be recovered by centrifugation, with optional crude washing with water. The lipid bodies can be used directly as a product of commerce when a crude washed lipid body is sufficient.

The lipid bodies as isolated above have a tan to brown color, even after washing with water. These crude washed lipid bodies can be made particularly clean and nearly bright white by washing the released lipid bodies with an alkaline buffer. The buffer preferably has a pH from about 9.5 to about 13.5, such as from about 10.5 to about 12.5 or about 11.7. It is suspected that the alkaline washing removes entrained and bound proteins and media. It is preferred to conduct the alkaline wash under reduced temperatures for relatively short, fixed durations, so that saponification reactions of the entrained lipids are minimized. The alkaline wash can include sodium hydroxide, (NaOH), sodium carbonate (washing soda, $Na_2CO_3$), and/or sodium percarbonate ($Na_2CO_3 \cdot 1.5H_2O_2$), as outlined in the following examples.

The lipid bodies are preferably alkaline washed to an extent that results in a white or off-white color, such that the resulting lipid bodies have a lower absorbance at 400 nm than the crude washed lipid bodies.

The alkaline-washed lipid bodies can be recovered as a useful intact commercial product by centrifugation, filtration, evaporation, or any other means of lipid body isolation.

The isolated lipid bodies (whether merely water-washed, alkaline-washed, or non-washed) can be further processed to generate a number of useful biomaterials. The lipid bodies, for example, can be dried to generate a wax-like solid, as described in further detail in the examples. The lipid bodies can also be processed to extract the oil therefrom. Any method can be used to extract the oil from the lipid bodies. In some versions, the oil is extracted using homogenization (2,500 to >35,000 psi) and/or solvents (hexane, chloroform/methanol, or any other similar solvent system) to produce a relatively pure yeast oil. If residual solvents are to be avoided, the lipid bodies can be dried or dried and homogenized or pressed. The drying releases an amount of oil that can be collected. The released oil is comparable to palm-oil and is suitable for skin care and other person care or consumer products. The solvent-free oil extraction obtained by drying is a valuable commercial platforms for a wide range of products.

The yeast cells that generate the intracellular lipid bodies from which the isolated lipid bodies are released are preferably recombinant yeasts. The recombinant yeasts are preferably derived from lipogenic yeasts. A preferred lipogenic yeast is *Lipomyces starkeyi*.

In preferred versions of the invention, the recombinant yeast used to generate the intracellular lipid bodies is a lipogenic yeast, such as *Lipomyces starkeyi* or any other lipogenic yeast, that is genetically modified to express or overexpress a diacylglycerol acyltransferase, a malic enzyme, and a glycerol-3-phosphate acyltransferase.

In some versions, the diacylglycerol acyltransferase comprises the DGA1-1233 variant represented by SEQ ID NO:2, encoded by SEQ ID NO:1, or a protein comprising a sequence at least about 80%, at least about 85%, at least about 90%, or at least about 95% identical to SEQ ID NO:2; the DGA2 represented by SEQ ID NO:4, encoded by SEQ ID NO:3, or a protein comprising a sequence at least about 80%, at least about 85%, at least about 90%, or at least about 95% identical to SEQ ID NO:4; or a combination thereof. The malic enzyme is preferably the ME represented by SEQ ID NO:6, encoded by SEQ ID NO:5, or a protein comprising a sequence at least about 80%, at least about 85%, at least about 90%, or at least about 95% identical to SEQ ID NO:6. The glycerol-3-phosphate acyltransferase is preferably the SCT1 represented by SEQ ID NO:8, encoded by SEQ ID NO:7, or a protein comprising a sequence at least about 80%, at least about 85%, at least about 90%, or at least about 95% identical to SEQ ID NO:8.

In addition to the diacylglycerol acyltransferase, the malic enzyme, and the glycerol-3-phosphate acyltransferase, the recombinant yeast of the invention can also comprise additional modifications. An exemplary additional modification is a modification to express or overexpress an acetyl-CoA carboxylase, such as the Acc1 represented by SEQ ID NO:10, encoded by SEQ ID NO:9, or a protein comprising a sequence at least about 80%, at least about 85%, at least about 90%, or at least about 95% identical to SEQ ID NO:10, particularly an Acc1 variant comprising a serine or threonine at a position corresponding to position 639 of SEQ ID NO:10. Another exemplary additional modification is a modification to express or overexpress a glycerol-3-phosphate dehydrogenase, such as the GPD1 represented by SEQ ID NO:12, encoded by SEQ ID NO:11, or a protein comprising a sequence at least about 80%, at least about 85%, at least about 90%, or at least about 95% identical to SEQ ID NO:12. Another exemplary additional modification is a modification to express or overexpress a glucose-6-phosphate dehydrogenase, such as the ZWF1 represented by SEQ ID NO:14, encoded by SEQ ID NO:13, or a protein comprising a sequence at least about 80%, at least about 85%, at least about 90%, or at least about 95% identical to SEQ ID NO:14. Another exemplary additional modification is a modification to express or overexpress a 6-phosphogluconate dehydrogenase, such as the GND1 represented by SEQ ID NO:16, encoded by SEQ ID NO:15, or a protein comprising a sequence at least about 80%, at least about 85%, at least about 90%, or at least about 95% identical to SEQ ID NO:16. Another exemplary additional modification is a modification to express or overexpress a fatty acid synthase, such as the FAS2.2 represented by SEQ ID NO:18, encoded by SEQ ID NO:17, or a protein comprising a sequence at least about 80%, at least about 85%, at least about 90%, or at least about 95% identical to SEQ ID NO:18, and/or the FAS1.2 represented by SEQ ID NO:20, encoded by SEQ ID NO:19, or a protein comprising a sequence at least about 80%, at least about 85%, at least about 90%, or at least about 95% identical to SEQ ID NO:20. Another exemplary additional modification is a modification to express or overexpress a ATP citrate lyase, such as the ATP citrate lyase alpha subunit represented by SEQ ID NO:22, encoded by SEQ ID NO:19, or a protein comprising a sequence at least about 80%, at least about 85%, at least about 90%, or at least about 95% identical to SEQ ID NO:22, and/or the ATP citrate lyase beta subunit represented by SEQ ID NO:24, encoded by SEQ ID NO:23, or a protein comprising a sequence at least about 80%, at least about 85%, at least about 90%, or at least about 95% identical to SEQ ID NO:24. Another exemplary additional modification is a modification to express or overexpress a glycerol kinase, such as the 1602 variant of GUT1 represented by SEQ ID NO:26, encoded by SEQ ID NO:25, or a protein comprising a sequence at least about 80%, at least about 85%, at least about 90%, or at least about 95% identical to SEQ ID NO:26, or the 1617 variant of GUT1 represented by SEQ ID NO:28, encoded by SEQ ID NO:27, or a protein comprising a sequence at least about 80%, at least about 85%, at least about 90%, or at least about 95% identical to SEQ ID NO:28. Another exemplary additional modification is a modification to express or overexpress a glycerol-3-phosphate dehydrogenase, such as the GUT2 represented by SEQ ID NO:30, encoded by SEQ ID NO:29, or a protein comprising a sequence at least about 80%, at least about 85%, at least about 90%, or at least about 95% identical to SEQ ID NO:30.

These exemplary additional modifications can be included in any combination. An exemplary combination includes expressing or overexpressing a glucose-6-phosphate dehydrogenase with a 6-phosphogluconate dehydrogenase and/or expressing or overexpressing a glycerol kinase with a glycerol-3-phosphate dehydrogenase.

In addition to expressing or overexpressing any one or more of the proteins listed above, the recombinant yeasts of the invention may be modified to reduce or ablate the activity of one or more native or non-native proteins. The recombinant yeasts, for example, may comprise a modification that reduces or ablates the activity of one or more of the following native proteins: acyl-CoA oxidase POX1, the multifunctional enzyme FOX1, UDP-glucose 6 dehydrogenase (UDPGH), Uridine 5'-diphospho-glucuronosyltransferase (UGT), and glycogen synthase. Acyl-CoA oxidases include enzymes falling under EC number 1.3.3.6. An exemplary acyl-CoA oxidase whose activity may be reduced or ablated includes POX1 (SEQ ID NO:32) encoded by POX1 (SEQ ID NO:31) from *L. starkeyi*. Acyl-CoA oxidases catalyze the first step of beta oxidation. An exemplary multifunctional FOX 1 enzyme is the FOX1 from *L. starkeyi* (SEQ ID NO:34), which is encoded by FOX1 (SEQ ID NO:33). This enzyme has both 3-hydroxyacyl-CoA dehydrogenase and enoyl-CoA hydratase activities. An exemplary UDP-glucose 6 dehydrogenase (UDPGH) is the UDPGH from *L. starkeyi* (SEQ ID NO:36), which is encoded by SEQ ID NO:35. An exemplary uridine 5'-diphospho-glucuronosyltransferase (UGT) is the UGT from *L. starkeyi* (SEQ ID NO:38), which is encoded by SEQ ID NO:37. An exemplary glycogen synthase is the glycogen synthase from *L. starkeyi* (SEQ ID NO:40, which is encoded by SEQ ID NO:39. Other suitable proteins whose activity may be reduced or ablated include those comprising amino acid sequences at least about 80%, at least about 85%, at least about 90%, at least about 95%, at least about 97%, or at least about 99% identical to the sequences listed above. Other suitable proteins whose activity may be reduced or ablated include orthologs and paralogs of the proteins listed above. Other suitable proteins whose activity may be reduced or ablated include those comprising amino acid sequences at least about 80%, at least about 85%, at least about 90%, at least about 95%, at least about 97%, or at least about 99% identical to orthologs and paralogs of the proteins listed above.

Lipogenic (oleaginous yeasts), the biochemistry of lipid synthesis by yeasts, enzymes involved in substrate assimilation, genetic engineering, and organic substrate conversion are discussed in US 2018/0245109 A1 and U.S. Pat. No. 10,662,448 The entire content of US 2018/0245109 A1 and U.S. Pat. No. 10,662,448 are incorporated herein by reference in their entireties. In addition to the modifications described herein, the recombinant yeast of the invention can also comprise any other modification described in US 2018/0245109 A1 and U.S. Pat. No. 10,662,448.

The compositions of the invention can be administered to an animal, such as a human, for any of the many purposes described herein. Accordingly, Methods of the invention can include administering a composition of the invention to an animal. The administration can include topical administration, oral administration, and/or parenteral administration.

Some versions include applying a composition of the invention to a site on a surface of an animal. The surface can include the skin, a mucous membrane, a buccal surface, the gums, a surface of the eye, etc. Applying the composition on a site on a surface can deposit envelopes of the lipid bodies and/or isolated envelopes on the site. The envelopes and/or the isolated envelopes can remain deposited on the site for a period of time after the application. The period of time can be at least about 30 minutes, at least about 1 hour, at least about 2 hours, at least about 5 hours, at least about 7 hours, or at least about 10 hours and/or up to about 1 hour, up to about 2 hours, up to about 5 hours, up to about 7 hours, up to about 10 hours, up to about 15 hours, up to about 20 hours, or more.

Consumers increasingly desire pharmaceutical agents, drug delivery platforms, cosmetic, and cosmeceutical compositions from sustainable sources with as few additional chemicals as possible. Topical compositions that minimize chemical exposures and are sustainable are needed as the planet's population grows.

Many diseases can be treated with medicinal compounds, but there are physical limitations in the ability to formulate, particularly hydrophobic drugs, at high doses. Most current compositions for hydrophobic active ingredients require encapsulation, liposomes, or irritating emulsification agents. Personal care products also can contain undesirable chemicals and detergents. Most compositions are complex and have a dozen or more ingredients needed for a useful composition. The present invention addresses the challenge of making compositions that carry high concentrations of hydrophobic substances while maintaining a pleasant aqueous feel.

There is significant medical need for improved oral drugs and vaccines due to consumer dislike of injections. The tolerance of an oral drug carrier system to stomach acid is an important property of oral drugs, which are absorbed in the intestines. Additionally, the present invention addresses important challenges in the preparation of oral and respiratory compositions, which specifically require lipid protection of active ingredients and uniform particles in specific ranges to be effective.

For topical conditions such as burns and open sores covering the damaged tissue is important to facilitate the healing process. Sealing damaged tissue is problematic because the covering and, in some cases, bandages need to be removed, thereby reopening the wound. Finally, the invention addresses compositions that impart a surface sealant to a treated area when used topically that naturally shed over an extended time.

As humans age, natural biological processes, physical, medical, and environmental conditions affect skin quality and appearance (Kvorning et al. 1949). In addition to age, skin conditions can arise due to atmospheric dryness, liver spots, exposure to, salt, sun, water, alterations in diet, changes in weight, and other factors that can affect skin appearance, moisture, pliability, and elasticity (Jiang et al. 2011). The present invention provides compositions to address these conditions.

Similarly, age-related changes in other body parts are also observed, including changes in hair, lips, and other body orifices such as the rectum. In all cases, these changes in epithelial tissues of the body can potentially progress to medical conditions including acne, acne scaring, rosacea, eczema, herpes, sun damage and psoriasis, all of which are hard to treat or cure. In some cases, exposure to sun damage may even progress to melanoma (Gershenwald et al. 2016). Many of the useful medicines that are applied topically require compositions with a degree of hydrophobicity and compatibility with skin and other epithelial body parts. The ability to load active ingredients for addressing anti-aging strategies is an important element in skin care (Ganceviciene et al. 2012). Active ingredients such as vitamin A or retinol are associated with improvements to aging skin (Kafi et al. 2007). However, the loading of drugs into liposomes and emulsions are frequently limited to concentrations of a few percent of active ingredient. This is because the loading capacity equals the mass of the active ingredient divided by the overall mass of a delivery particle, emulsion or micelle, which is limited by the volumetric loading capacity of small entities (generally less than 200 nm), due to the relatively small volume to surface ratio of those delivery approaches (McClements 2015). The invention comprises the uses of engineered biological organelles in compositions because of the engineered lipid bodies' large size (generally in the range of 4,000 nm to 12,000 nm) and associated high loading capacity due to their high volume to surface area ratio. Several additional properties, which are important for compositions of the invention are also described, including a range of robust features such as steam sterilizability and tolerance to gastric pH and more that are important for the compositions of the invention.

Many existing cosmetic and topical pharmaceutical preparations designed to treat skin conditions contain palm oil (U.S. Pat. No. 8,524,292). Compositions disclosed herein use engineered yeast lipid bodies and yeast lipid body oil, which is a palm-oil-biosimilar that is found inside of lipid bodies, as a key property imparting feature of the materials used in the invention.

Compositions of the invention comprise lipid bodies of the invention and/or components thereof, such as lipid body shells, envelopes, and associated biochemicals, including internal or externally added yeast oil along with other exogenous constituents or modifications. These components together or separately impart unique properties and important characteristics that enhance the utility of the compositions containing lipid bodies. Unless otherwise noted, the terms "lipid bodies", "yeast lipid bodies," or "large yeast lipid bodies" as used herein refer to "lipid bodies of the invention." Similarly, unless otherwise noted, the term "formulation(s)" as used herein refers to compositions of the invention that comprise lipid bodies and/or lipid body components.

Lipid bodies and their components provide multiple properties not readily available from other types of composition components, such as liposomes, nanoparticles, or emulsions. Lipid bodies provide a large internal hydrophobic zone with a high volumetric capacity to hold hydrophobic drugs and other ingredients. The lipid bodies also provide a smooth moisturizing matrix that feels aqueous and non-greasy and that can accommodate hydrophilic constituents in the aqueous interstitial layer between the lipid bodies. Lipid bodies, when applied and dried on the skin, provide a sealant property due in part to their encompassing envelope, which remains on the surface of the skin after the lipid body oil and aqueous components have been absorbed. The sealant property can facilitate wound healing, burn repair, enhance the healing of damaged or blistered skin, reduce scar tissue formation and retain both hydrophobic and hydrophilic drugs and other key ingredients.

The lipid bodies can be isolated, refined, bleached, washed with water, saline, acid, or alkali, deodorized, purified, blended, coated with biopolymers, otherwise derivatized, or modified to achieve or take advantage of various properties that are relevant to compositions of the invention. Lipid bodies and lipid-body components, such as the lipid body surface shells and empty shell envelopes, can be chemically or enzymatically modified to impart additional unique properties to the compositions. Lipid bodies of the invention can be used directly or in combination with other substances to obtain novel features and preferred compositions that possess improved functionality. Compositions comprising the lipid bodies and/or lipid-body components can be blended as homogenous materials. The lipid bodies impart desirable features such as moisture retention, longer shelf life, better appearance, improved smell, high-levels of active-ingredient loading and suitable active-ingredient release, and other properties that render enhanced functionality or improved consumer acceptance. These characteristics are uniquely imparted to compositions comprising lipid bodies of the invention.

The compositions of the invention can be used in or as the following: Topical compositions and products, such as beauty agents, personal care products, skin care products, skin creams, lotions, salves, moisturizers, cosmetics, soaps, detergents, shampoos, and deodorants; Drug-delivery vehicles and systems, such as topical drugs, oral drugs and vaccines, cosmeceuticals, therapeutic solutions, parenteral solutions, biologic or biopharmaceutical delivery systems, and wound healing aids; Medicinal compositions and compositions such as anti-inflammatory solutions, pastes, and compositions, oral care products, ophthalmic compositions, vaginal delivery, otitis compositions and pharmaceutical products, and pharmaceutical research reagents for new drug development programs; Films and sprays such as water repellents, insect repellents, sunscreens, sanitizers and foods of various types, including cooking oil, shortening, vegetable ghee margarine, chocolate fats, ice cream fats, confectionary fats, non-dairy creamer, nutritional supplements, synthetic "meat free" compositions and meat substitutes, or as a carrier for food-related flavoring agents; Pet care products, including product compositions and pet and animal feeds and foods; and Other industrial compositions, including lubricants, slip agents, and biodiesel components and generally all those applications and compositions previously available only from palm oil or fractionated or derivatized palm oils.

The invention is directed to compositions comprising the lipid bodies and/or lipid-body components, either alone or in combination with exogenously added constituents, modifications, and/or derivatives.

The lipid bodies of the invention are large lipid bodies isolated from various genetically modified lipogenic yeasts and, optionally, lipid bodies that have been modified after isolation. They can be 5 to 12 microns or more in diameter resulting in volumes of 65 $\mu m^3$ to 525 $\mu m^3$. The lipid-body components isolated from the lipid bodies of the invention include envelopes, oils, and other endogenous biochemical constituents. The lipid bodies, their components, and endogenous constituents alone or in combination with exogenous constituents, coatings, derivatizations, and modifications comprise aspects of the invention.

The lipid bodies' hydrophobic interior contains oil into which hydrophobic drugs or compounds can be loaded. The hydrophilic exterior can carry hydrophilic drugs or compounds in a hydrophilic layer, on the hydrophilic surface or aqueous carrier of the compositions of the invention. The compositions of the invention can accordingly incorporate both hydrophobic and hydrophilic substances, drugs and other beneficial oils, fatty acids, stabilizers, antimicrobial agents, and other compounds. The characteristics of the lipid bodies and lipid-body components impart the ability to carry large quantities of hydrophobic drugs, which normally have an oily feeling, in their interior as active ingredients while maintaining an aqueous, non-greasy, and pleasant feeling when applied to the skin. Advantages for oral applications include acid stability and relative tastelessness.

The compositions of the invention may contain lipid body components, envelops, and associated biochemicals, plus externally added reagents, ingredients, vitamins, nutraceuticals, antioxidants, commercial additives, industrial additives, peptides, drugs or other exogenous constituents, including enzymatic and non-enzymatic protection from oxidation that is known to impact photodamaged skin. Additionally, enzymatic and non-enzymatic antioxidants may play a role in mitigating sun damaged skin and skin aging (Rhie et al. 2001, Shindo et al. 1994).

When used in topical, wound or burn applications, the compositions of the invention can impart key oil-based and/or water-based ingredients to the skin or application area and leave collapsed lipid body envelopes from the lipid bodies on the surface forming a protective seal, which is durable over a number of hours. Skin peel tests demonstrate that the sealing envelopes of the collapsed lipid bodies last for approximately 12 hours as a result of shedding that is analogous to the shedding of skin cells from healthy skin. The shedding of the lipid body envelopes is important to avoid accumulation and undesirable build-up on the skin upon repeated applications.

The lipid-body envelopes provide a stable lubricating property at temperatures up to 200° C. This lubricant property imparts useful features to industrial lubrication and in the operation of consumer devices that require a natural lubrication from a non-animal and non-petrochemical source. An example of mechanical lubrication is the lubrication of syringe plungers and auto-injector cartridge pistons, which are used for delivery of parenteral drugs by injection or for oral dosing in pediatric drug applications.

The internal yeast oil carried inside the lipid bodies or isolated therefrom and added as an additive to the compositions of the invention can provide enhanced functionality to compositions that require additional oiliness for specific purposes in a wide range of product compositions.

In some versions, the compositions of the invention are particularly suited for topical drug compositions and skincare products. Lipid bodies or their components can be blended with other constituents to produce customized compositions with desired properties such as melting point, consistency, stability, constituent release, miscibility, emulsion formation or other desired attributes, qualities, or features. The compositions can be used to treat, for example, a variety of skin and bodily conditions, including adverse and age-related skin or scalp conditions. The compositions can also be used as an effective moisturizer for prolonged maintenance of smooth healthy skin, particularly in cold, dry climates where skin is frequently subjected to chapping and other conditions.

The lipid bodies and lipid-body components address unmet needs and shortcomings of liposomes. First, the relatively low internal volume of conventional liposomes, due to their smaller diameters, results in a much smaller internal volume for carrying hydrophobic ingredients on a per unit basis. Second, their hydrophilic interiors require the use of emulsifiers and detergents to achieve solubility of hydrophobic ingredients. Such components are potential irritants.

The lipid bodies of the invention have an outer durable hydrophilic envelope, that collapses into a barrier once the oil and moisture have been imparted to the skin. The ability this lipid body component to form a seal over the area of composition application is an important property for topical drugs, once the drug, oil or active ingredients are imparted to the skin. The sealing property may play a role in enhanced wound healing compositions. Liposomes and emulsions, in contrast, do not have robust envelopes that can form the protective covering over an area of application.

Important, unique properties of the lipid bodies of the invention for use in compositions of the invention include: (1) their relatively large diameter which gives them a high internal hydrophobic volume; (2) their hydrophilic surface properties resulting in a smooth, non-greasy feel; and (3) their post-application sealing properties attributable to their external envelopes.

Other important properties of the lipid bodies of the invention include: the ability to carry large quantities of hydrophobic drugs, lipids, and hydrophobic active ingredients onto the skin without feeling oily; the ability to be used as a relatively tasteless drug carrier for oral applications and provide the potential of delivering off-flavored drugs in a format that is acceptable to the palate; having envelopes that can be isolated to make additives and lubricants that are heat and friction tolerant in compositions of the invention (these components are also applicable as additives in compositions of various types); the ability to provide compositions of the invention with lipid bodies that collapse after imparting their contents to the skin, yielding an overlapping layer of envelopes that form a clear imperceivably thin protecting seal over the areas into which hydrophobic and hydrophilic ingredients have been applied; the ability to be modified, homogenized, or dehydrated to create envelopes that can be used to enhance compositions of large molecules, biologics, and peptides for transport into the body; the ability for their surface charge state to be altered across a wide range of pH conditions (Some of these charges are useful in unaltered lipid-body compositions, while other charges are formed by chemical or enzymatic treatment of the lipid body surfaces; various charge states of the lipid bodies are associated with rapid repair of skin irritation or dryness, scar prevention, and healing of blisters); tolerance to heat and sterilization by autoclaving (e.g., at 121° C.), making them particularly useful for critical drug applications where subcutaneous injection may be applicable, for example, in vaccine development; stability to acid at pH levels down to 0.5 or lower (such as 0.4), enabling compositions that resist microbial contamination and resistance at gastric pH levels; ow density, which is useful in concentrating hydrophobic chemicals and other industrial applications; bright white color and oxidation resistance, even when heated or treated with acid at high temperatures; odor free, benign interaction with human skin enabling lipid bodies in cosmetic compositions that are non-irritating and well tolerated; smooth, aqueous, and pleasant feel under a wide range of conditions, which enables compositions having a significant interstitial aqueous zone surrounding the exterior of the lipid bodies, which is can carry high concentrations of charged ingredients; melting temperature of internal oil that is a solid at room temperature and below and that melts at body temperature and temperatures above body temperature up to 200° C. or more; high short-wavelength UV absorbance for utility with other sunblock ingredients; utility as a non-Newtonian viscosity modifier (e.g., high viscosity at low shear rates and low viscosity at high shear rates), which can be useful for making the creams and compositions that spread easily but are resistant to dripping or running; ability to form stable suspensions when mixed with, e.g., low concentrations of hydrophilic polymers and starches, despite their low density; the ability to maintain a net charge in compositions of the invention that are applicable to bioelectronics and biosensors; the ability to chelate divalent cations in the compositions of the invention that are useful, for example, in chelating copper in Wilson's disease and other metal-based pathologies; other properties arising from derivatization of lipid bodies for specific purposes in the compositions of the invention, such as the transport of nucleic acids in biological systems and humans in a manner that protect the nucleic acids, genes or other drugs from degradation or hepatic clearance; the lipid bodies are anionic at neutral pH and the charge can be manipulated by the environment around the lipid bodies. Coating, derivatizing and loading lipid bodies with cationic materials and metal ions can achieve variations in their charge state, which can be useful for broadening the range of active ingredients used in the compositions of the invention.

These distinguishing features offer advantages over the prior art. Liposomal delivery systems for topical pharmaceutical, cosmeceutical, and cosmetic ingredients have existed in the patent literature for many years, for example, in US 20050079210A1 and in many scientific publications. The well-established size of liposomes are between 10 and 200 nanometers (0.01 to 0.2 microns) in diameter, typically about 100 nanometers in diameter. No large and stable hydrophobic-interior liposomes with diameters in excess of 2.5 microns have been reported. The lipid bodies, by contrast, can have diameters between 5,000 and 10,000 nanometers (5-10 microns) or larger. The large size of the lipid bodies impart a number of advantages described herein.

According to the general nomenclature, all types of lipid bilayers surrounding an aqueous interior are generally known as liposomes. The methodology for liposome preparation has been known since being first described starting in the late 1960's (Demel et al. 1968, Alving et al. 1971, Bangham et al. 1974, Fishman et al. 1975, Braidman et al. 1976, Patel et al. 1976, Tentsova et al. 1976, Barsoum et al. 1980, Fitfield 1980, Szoka et al. 1980, Mayer et al. 1986, Lopezberestein 1987, Egbaria et al. 1990). Large liposomes, sometimes called unilamellar vesicles are described in U.S. Pat. No. 5,004,611.

The lipid bodies of the invention can be included in compositions comprising or consisting of the lipid bodies and water. In such compositions, the lipid bodies form, in order of increasing concentration from 1% to 80% of lipid bodies by dry weight, a white solution, a spray, a lotion, a cream or paste. A few stabilizing excipients may optionally be further included for long-term shelf-life.

The lipid bodies of the invention, for example, can be formulated as a single-component cream. The lipid bodies form a cream when formulated at a concentration between 33% and 55% by dry weight. An antimicrobial agent, a humectant to prevent crusting, an antioxidant, and pH control can optionally be included to achieve long-term room temperature stability.

Lipid bodies of the invention have a high UV absorbance in the wavelength ranges between 190 nm and 290 nm, with an absorbance maximum at about 230 nm. The skin and eyes are most sensitive to damage by UV light at 265-275 nm wavelength, which is in the lower UVC band that is absorbed by lipid bodies. However, most sunburn is caused by longer wavelengths, because those are more prevalent in sunlight at ground level. Accordingly, compositions containing the lipid bodies have sun blocking absorbance alone that can be enhanced when UV-absorbing agents are added. Examples of UV-absorbing agents include oxybenzone, avobenzone, octisalate, octocrylene, homosalate, and octinoxate.

Many potential additives and active ingredients can be mixed with the lipid bodies or lipid-body components having the potential for skin discoloration. Successful formulation of carotenoids requires an appropriate level of hydrophobicity and compatibility with the components naturally found in skin and other epithelial body parts. The lipid bodies offer properties that can facilitate incorporation of fatty or hydrophobic ingredients.

Vitamin A is associated with carotenoid pigments as found in carrots, red bell peppers, and other pigmented foods. However, carotenoids have a limited application in skin care because of the potential for skin discoloration. Successful formulation of carotenoids requires an appropriate level of hydrophobicity and compatibility with the components naturally found in skin and other epithelial body parts. The lipid bodies offer properties that can facilitate incorporation of fatty or hydrophobic ingredients.

In another example, vitamin E (including such forms as vitamin-E acetate) is an abundant, fat-soluble, lipophilic antioxidant that is important in maintaining healthy skin by preventing damage induced by free radicals and reactive oxygen species (Rhie et al. 2001, Shindo et al. 1994). Topical application of vitamin E effectively increases photoprotection. Vitamin E has very low solubility in water, but lipid bodies can facilitate incorporation of vitamin E as an ingredient in product compositions. Vitamin E can also act as a long-term antioxidant for room temperature shelf life.

Many other potential fatty or hydrophobic additives and active ingredients can be mixed with the lipid bodies, such as the hydrophobic compounds found in vegetable oils, nuts, and green leafy vegetables. Tocotrienols, for example, are similar to tocopherols except these have an unsaturated isoprenoid side chain. As antioxidants, these compounds are suitable additives to cosmeceuticals and personal care products. Specifically, erythema and skin aging effects are treated with topical lotions and emollients containing tocotrienols to address the underlying causes of skin and hair damage, such as free radicals generated by environmental factors. Tocotrienols can be effective in scavenging free radicals from lipid-rich layers of skin and scalp. Keratin in hair is also subject to oxidation by sunlight and harsh chemicals, and traditional remedies use added oil in conditioners or shampoos to ameliorate dry and brittle hair in addition to an antioxidant(s). The use of tocotrienols for treating skin and hair damage is disclosed in U.S. Pat. No. 5,545,398.

The lipid bodies offer properties that can facilitate incorporation of many plant and animal-derived substances. There are many additives and active ingredients that can be mixed with the lipid bodies or lipid-body components either singly or in combination with other additives.

Examples of skin care compositions can be found in U.S. Pat. No. 8,524,292. This patent discloses the use of various palm oil types for the formulation of cosmeceuticals and the utilization of red palm oil and other forms of palm oil, specifically palm stearin, palm olein, fractionated palm oils and blended, homogenized or votated (a type of blending) palm oil as a base for the formulation of skincare products, particularly those containing low but meaningful natural substances including oil isoforms, tocopherols, tocotrienols and carotenoids arising from crude red palm oil. The mixture of miscellaneous hydrophobic material including tocopherols, tocotrienols and various forms of palm oil described in U.S. Pat. No. 8,524,292 illustrates the heterogeneity of palm oil. The lipid bodies can facilitate incorporation of many ingredients in product compositions that currently rely on palm oil.

Goon et al. 2019 provides a review of the importance of palm oils in a broad range of applications for lipid-based compositions and drug delivery systems. Goon et al. also categorizes drug development compositions into the following: Type I, which is defined as any hydrophobic mixture of oil and active ingredients. Type II, which contain surfactants and is defined as self-emulsifying drug delivery systems or SEDDS. Type IIIa, which contains one or more co-surfactants or hydrophilic co-solvents defined as self-micro-emulsifying drug delivery systems or SMEDDS. Type IIIb containing a higher ratio of co-solvent than Type Ma compositions and defined as self-nano-emulsifying drug delivery systems or SNEDDS.

The common feature of these preparations is the use of palm oils. The oil contained within the lipid bodies of the invention can be used as substitutes for the palm oil in any of these delivery systems and related compositions.

The simplicity of the compositions of the invention improves the ability to easily track drug loading and drug delivery to the patient and facilitates the development of analytical quality controls. The properties associated with the compositions of the invention can greatly facilitate topical drug development, manufacturability, and regulatory approvals because the exemplary source of the lipid bodies is a published GRAS yeast, *Lipomyces starkeyi*, which is manufactured in an engineered strain that has a completed EPA review and Regulatory exemption for the intended use in personal care products. *Lipomyces starkeyi* was identified in soil and on human skin as a non-pigmented oleaginous yeast Connell et al. 1953, Connell et al. 1954.

Any engineered hyper-lipogenic yeast harboring lipid bodies with an occupancy in the yeast of greater than 66% oil, to even more than 85% and as much as 95%-98% of the interior of the engineered yeast can be used for producing lipid bodies used in the compositions of the invention.

The lipid bodies can be used in compositions that include the addition of various, surfactants, alcohols, oils, dyes, and hydrophobic substances.

The lipid bodies, when recovered from fermentation, can be easily isolated with little residual odor. This can result in products that are nearly odor free, with only a slight wax scent remaining.

One embodiment of the invention is directed to a biocompatible, cosmeceutical, topical compositions comprising of lipid bodies and/or lipid-body components, such as envelopes, and associated biochemicals, wherein the composition is substantially homogeneous. The composition can replace essential oils in skin, particularly dry skin. Once the composition dries on the skin, lipid-body envelopes form a protective film that helps maintain a durable retention of oil and moisture on the skin. These films shed away from the skin over about 10 hours, as demonstrated by microscopic examination of face peels. This surprising and unique property of such compositions is particularly useful for skin care products and topical drug delivery.

Another embodiment of the present invention is a biocompatible, cosmeceutical, topical composition comprising the lipid bodies blended with yeast oil to alter the aqueous feel and acceptability of the composition when a slightly oily property is desired for the rapid replacement of oil levels in the skin. The composition can contain added yeast oil at levels across a range of mixture ratios, such as from about 10 to 90, w/w % oil or higher to modify the rate and oiliness of a moisturizer or skin softener.

In another embodiment, the lipid bodies are bound to, mixed, blended, emulsified with, or used to dissolve or suspend externally supplied hydrophobic or amphipathic substances. The resulting hydrophobic compositions have utility for research purposes, potential drug development systems and for the creation of a wide range of product compositions in which hydrophobic or semi-hydrophobic active ingredients are desired.

In another embodiment, the lipid bodies are used to bind externally applied hydrophobic or hydrophilic substances, such as hyaluronic acid, in combination with alcohols and surfactants to facilitate hydrophobic compositions, self-assembling microencapsulation compositions, and modified nanoencapsulation compositions useful in drug development and research, including, for example, hydrophobic dyes and/or other compounds. The resulting emulsions, and liposome-like structures are uniquely useful for creating stable hydrophobic compositions that have utility for research purposes, potential drug development systems and for the creation of a wide range of product compositions in which hydrophobic, semi-hydrophobic or amphipathic active ingredients are desired.

The lipid bodies and/or lipid body components can be useful in one or more drug delivery system categories in the following examples in various configurations:

Tablets: Bi-layer, multi-layer, mini, lipid and oil encapsulated tablets.

Capsules: Gel caps and blow-fill-finish configurations, lipid and oil contained within capsules, and time-release compositions.

Powder blends: Microparticle-filled, microsphere-filled; Powders used to make parenteral and intravenous formulations.

Tableting processes containing lipids and oils: Direct compression, dry granulation, wet granulation; Enteric coating.

Ocular Controlled Release containing lipids and oils: Instant release; Sustained release; Enteric or delayed release.

Oral Controlled Release containing lipids and oils: Instant release; Sustained release; Enteric or delayed release based on resistance to gastric acid at pH 0.5.

Respiratory drug formulations, used nasally or inhaled, comprising lipid bodies for the delivery of drug substance.

Rectal Formulations containing lipids and oils: Surface applications; Suppositories; Hemorrhoid creams; Aspirin-based systemic medicines; Anti-epileptics; Anti-nausea drugs and others.

Topical, Liquids, Sprays, Lotions, Creams, containing lipids and oils; Transdermal cream; Topical sprays.

Parenteral-solutions, Injectables, Auto-injector Cartridges, Pre-filled Syringe serum bags, drip formulations, parenteral nutrition.

Other drug delivery systems, containing lipids and oils as appropriate.

The lipid bodies and lipid-body components can be modified by emulsification, saponification, votation, compression, bleaching, alkaline cleaning, acidic cleaning, distillation, cold or cooling fractionation, and other physical or chemical treatments. The modifications can create stable compositions for skin care products, personal care products, soaps, shampoos, drug delivery systems for hydrophobic compositions, drug delivery systems for self-assembling emulsifications and micrometer and sub-micrometer liposomal-like structures, drug delivery systems for medicinal products, pet care products, and other product compositions.

The lipid bodies of the invention can form a moisturizing white cream (FIG. 1), either as a sole ingredient in a carrier (as shown) or in a stabilized composition for a durable shelf-life at room temperature. The lipid bodies can be used directly in product compositions, which are composed of blended reagents or with other components, biochemicals, drugs, emulsification agents, alcohols, co-solvents, and any other appropriate additives to achieve desired compositions and moisturizing base cream for a wide range of products.

The lipid body components refer to any component derived or isolated from the lipid bodies of the invention. These can be used in the compositions of the invention. Exemplary lipid body components include lipid-body envelopes, broken envelope constituents, fragments, oil, and other associated biochemicals, such as protein, phospholipids, lipids, carbohydrates.

The oil contained in the exemplary lipid bodies is a yeast oil that can serve as a palm oil substitute or biosimilar. The term "palm oil" refers to oil recovered from the mesocarp of the fruit of oil palms, primarily the African oil palm *Elaeis guineensis*, and to a lesser extent from the American oil palm *Elaeis* oleifera and the maripa palm *Attalea maripa.*

The compositions of the invention include all compositions made with or comprising the lipid bodies and/or lipid-body components of the invention. The of the invention compositions of the invention may include, in addition to the lipid bodies and/or lipid body components, other ingredients, drugs, and or substances.

In nature, *Lipomyces starkeyi* and other oleaginous yeasts contain less than 45% lipid under the best conditions. The typical yeast oil synthesis rates are less than 0.26 g/l/hour and overall typical yields are less than 20 grams per liter when grown in fermentations. In most cases these yeasts have multiple, very small lipid bodies which can be seen under a microscope at 400× power. These small lipid bodies are not practically isolated or useful in the compositions of the invention.

The yeasts of the invention have product yields that are commercially viable and possess internal single lipid bodies that can occupy around 70%, and up to 95% or greater, of the internal area of the genetically engineered hyper-lipogenic yeast as large lipid bodies. The lipid bodies can be isolated from these strains by homogenization, mechanical disruption, or hydrolysis of yeasts and preparative washings. The isolation and washings of the lipid bodies can include acid hydrolysis, homogenization, and or multiple mild alkaline washes and neutralization steps.

The lipid bodies contain significant amounts of yeast oil that can be isolated by homogenization, hydrolysis, and/or dehydration followed by gravity decanting or, in a preferred manufacturing process, from extraction with suitable solvent, for example iso-hexane, n-hexane, n-pentane, chloroform/methanol or any other suitable solvent. Upon evaporative removal of the solvent, the resulting yeast oil is an unexpectedly pure triglyceride composition that contains the fatty acid content as shown in Table 1. Also shown in Table 1 is a comparison of the yeast oil isolated from yeast containing lipid bodies compared to tropical palm oil.

TABLE 1

The composition of triglyceride fatty acids isolated from lipid bodies of the invention compared to the fatty acid profile in palm oil.

| Fatty Acid Profile of Oil from Exemplary Lipid Bodies of the Invention | | | Fatty Acid |
|---|---|---|---|
| Fatty acid chain length | Fatty acid name | Percent of total fatty acids in exemplary lipid bodies of the invention# | Profile of Palm Oil* Percent of total fatty acids and range in palm oil |
| C12:0 | Lauric Acid | ***0*** | 0.1-1.0 |
| C14:0 | Myristic Acid | ***0.03*** | 0.9-1.5 |
| C16:0 | Palmitic Acid | 40.08-43.0 | 41.8-46.8 |
| C16:1 | Palmitoleic Acid | ***5.08 - 7.0*** | 0.1-0.3 |
| C18:0 | Steric Acid | 4.81-7.0 | 4.2-5.1 |
| C18:1 | Oleic Acid | 35.0-41.42 | 37.3-40.8 |
| C18:2 | Linoleic Acid | ***2 - 8.6*** | 9.1-11.0 |
| C18:3 | Linolenic Acid | 0.01-2 | <0.05-0.6 |
| C20:0 | Arachidic Acid | 0.03 | 0.2-0.7 |

*Kopas et. al. US 8,525292 B2

#: *Increased*; comparable, *decreased*

Figure 10:
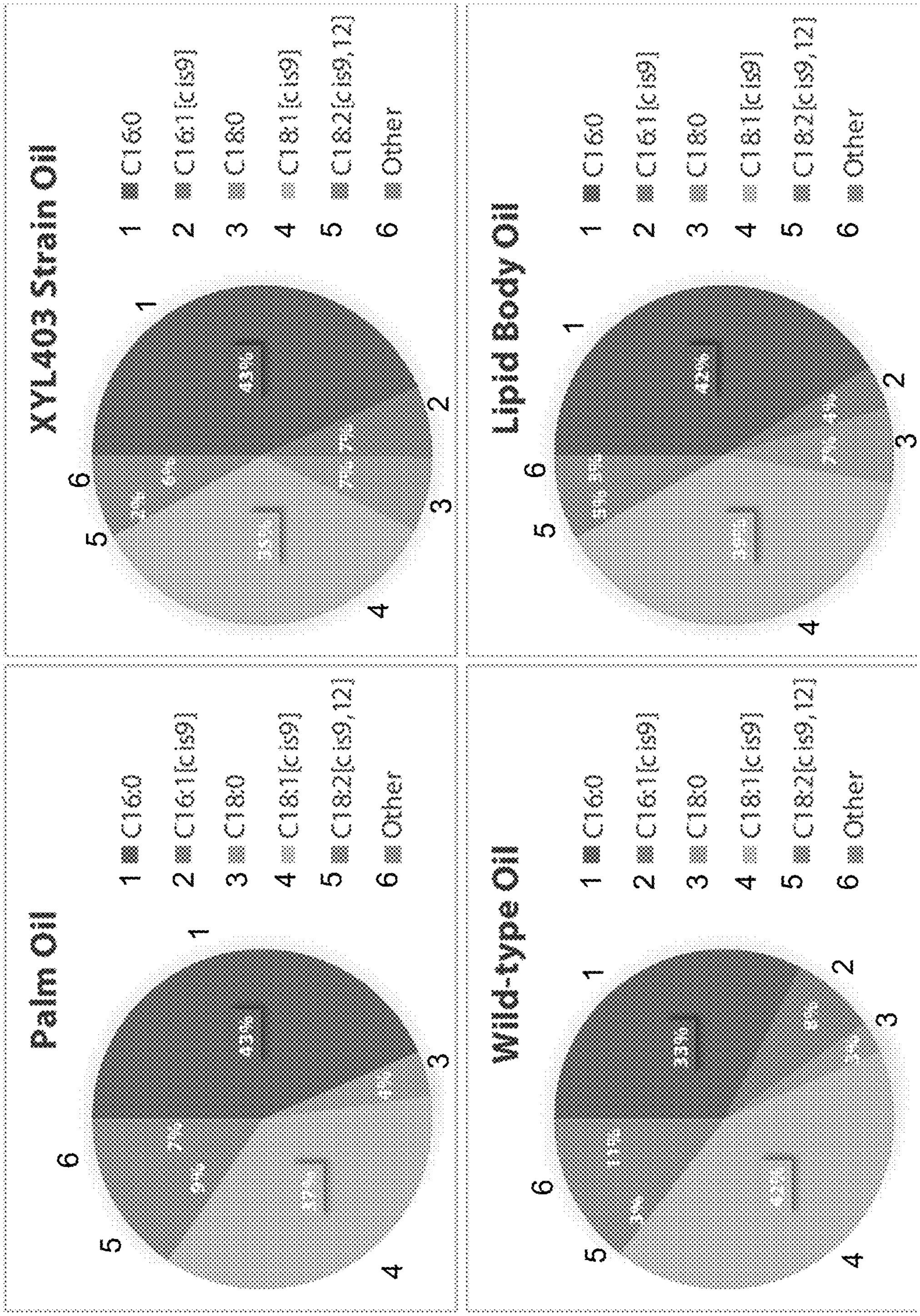
FIG. 10. Lipid compositions of palm oil ("Palm Oil"), oil obtained directly from whole 403 cells ("XYL403 Strain Oil"), oil obtained directly from whole wild-type cells ("Wild-type Oil"), and oil obtained from 403 lipid bodies ("Lipid Body Oil").

The fatty acid profile of oil from lipid bodies of the invention in comparison to palm oil is shown in FIG. 10.

The yeast oil isolated from yeast containing lipid bodies is comparable to palm oil with the exception that the content of palmitoleic acid (C16:1) that occurs in lipid body containing yeast at a level comparable to human skin and is nearly missing (<0.3%) in palm oil. U.S. Pat. No. 8,524,292 highlights the essential fatty acids, particularly palmitoleic acid, at 2-8% of the fatty acids found in skin. The fatty acid profile of the exemplary lipid bodies is similar to human skin. In particular, both contain about 5% palmitoleic acid, an essential fatty acid of skin. This essential fatty acid is almost absent in palm oil. The fatty acid profile of skin is shown in Table 2.

TABLE 2

The profiles of fatty acids of oil isolated from exemplary lipid bodies of the invention compared to lipids found in human skin.

| | Essential fatty acid profile (%) | |
|---|---|---|
| Fatty acid name | Oil of the invention | Human skin lipids* |
| Palmitic Acid | 40.08-43.0 | 30 |
| Palmitoleic Acid | 5.1-7.0 | 8.0 |
| Stearic Acid | 4.8-7.0 | 13.0 |
| Oleic Acid | 35.0-41.4 | 17.0 |
| Linoleic Acid | 0.01-2% | 14.0 |
| Other Lipids, Waxes, Sebum and Cholesterol | ~0-2% | 45% |

*US8,524,292 and Downing et al. 1969

The lipid bodies can impart oil to human skin when applied using the compositions of the invention. Because human skin can frequently be low in essential lipids, skin can be prone to dehydration, dryness, cracking, and other conditions associated with water loss and exposure to the environment. The comparability of the lipids in the lipid bodies to those in human skin makes the lipid bodies useful for treating conditions associated with dry skin. Applying the lipid-body containing creams of the invention to chapped hands makes the skin feel exceptionally smooth and moist and heals chapped skin in a manner not equaled with conventional hand creams. This observation is consistent with the profile of essential skin lipids and supports the suitability of the lipid bodies of the invention for providing the majority of human skin lipids in a proportion approaching the levels found in normal human skin. The lipid bodies can accordingly be used, with or without other ingredients, to restore oil and maintain moisture in skin.

The exemplary oil in lipid bodies have a relatively tight range and dominance of C16:0 and C18:1 lipids and an absence of lower chain saturated fatty acids. The oil from the exemplary lipid bodies are generated in controlled aerobic fermentation, so there are no plant contaminants such as polyphenols, phytophenols, phytoene, beta-carotene, phytofluene, neuroporene, zeacarotene, ubiquinone 10 (CoQ10), lycopene, tocopherol, tocotrienols, squalene, and potential pesticide residues, such as can be found in native tropical palm oils. When any desirable constituent is required in a composition, the composition can be made by adding the individual desired chemical or biochemical to the composition as needed to achieve a particular composition of the invention without the need for excessive co-contaminants, impacts to purify or difficult-to-manage quality controls.

The lipid bodies used in the compositions of the invention can carry hydrophobic chemicals, drugs, and other substances that bind to the hydrophobic interior of the lipid bodies that can be useful in treating skin, for example, lanolin. The use of lipid binding dyes with visible spectrophotometric, microscopic, and/or fluorometric analyses is an excellent and easily quantifiable way to show how hydrophobic substances can bind to the lipid bodies. Examples of dyes that bind to the hydrophobic interior of the lipid bodies include BODIPY, Nile red, and Sudan black. Other actual drug loading and release examples have been demonstrated using HPLC methods and or ultraviolet spectrophotometry to track drug incorporation into the compositions. The uptake and subsequent release of drug compounds provides a strong indication that the lipid bodies can be used as a carriers or vehicles for a range of compositions that incorporate hydrophobic and hydrophilic ingredients, including medicines, fragrances, cosmetic ingredients, coloring agents and many other functional constituents.

The compositions of the invention need not exclude other more conventional compositional materials and systems. The lipid bodies can be modified chemically or enzymatically as type I (hydrophobic blends) or as type II (micro emulsions) containing emulsification agents such as lecithin. In some cases, when variable delivery rates are desired, the lipid bodies can be blended with liposomes in a manner that creates a composition that may not be possible with either platform separately.

The lipid-body components, including envelopes and associated biochemicals, can be mixed with emulsification agents and other detergent-like agents to form other compositions of type III (micro and nano-emulsions) self-assembling emulsions similar to type II but with or without co-solvents (Goon et al. 2019). Examples of drugs that can be formulated with lipid bodies include, Lidocaine, Benzocaine, Colchicine, Betamethasone, Phenytoin, Levadopa, Genistein, Paclitaxel, Aripiprazole, Chloramphenicol, Diclofenac acid, Sodium diclofenac, Ibuprofen, Vitamin E (tocopherols), Fish oils, Glucans, Carotene, Ketoprofen, Docetaxel, Tocopherol acetate, Tocotrienol, and any other suitable hydrophobic or hydrophilic chemicals, drug, drug-delivery systems, food products, cosmeceuticals, cosmetics, skin care agents, personal care products, and other ingredients and composition components either singularly or in combinations with the lipid bodies and or associated components.

Compositions made with lipid bodies may include emulsification agents or commercial reagents, for example, Capmul MCM (mono and di-glycerides of caprylic acid), Capmul PG-8, Captex 200 (mixed diesters of caprylic or capric acids in propylene glycol), Miglyol 812N, PEG 300, Tween 80, Polysorbate 80, Cremophor RH4 and other surfactants and emulsification agents alone or in combination with the compositions of the invention.

Other optional components that may be added to the compositions of the invention may include many types of other oils, for example, aloe vera, apricot oil, avocado oil, apricot kernel oil, fruit oils, borage oil, camellia oil, flower and seed oils of any type, coconut oil, passion fruit oil, safflower oil, rose hip oil, rice bran oil, soya oil, canola oil, olive oil, shea butter oil, sunflower oil, wheat germ oil, tea tree oils, loquat oil, citronene, citrus oils, cannabidiol or CBD oil, and other oils alone or in combination within compositions based on lipid bodies. Additionally, the compositions of the invention may include other charged lipid bodies and or lipid body components, envelopes and associated biochemicals, fatty acids or synthetic chemicals such as organic and inorganic acids.

When important for particular compositions, esterification of fatty acids and alcohols can be made from yeast oils and other oils as straight or branched chain esters composed of either mono, di, tri, and tetra-esters. Depending on the chain length and structural arrangement of the fatty acids and alcohols, esters can be tailored to provide different physical properties and types of emollience that when mixed with lipid bodies can impart the unique properties of lipid bodies to such compositions. For example, straight chain esters from cetylpalmitate and cetylstearyl stearate, which are solid at room temperature, may be used to increase the viscosity of emulsions and impart a dry emollience to the skin in compositions containing lipid bodies providing additional ingredients, yeast oil and or sealant properties that are provided from the lipid bodies.

Liquid branched chain esters, such as isopropyl myristate and cetostearyl ethyl-hexanoate, provide non-occlusive emollience with good spreading properties suitable for the compositions of the invention. Pentaerythrityl tetra-isostearate, a high molecular weight tetra-ester, confers a long-lasting emollience to skin creams and lotions, when in a composition with lipid bodies providing additional ingredients, yeast oil and or sealant properties that are provided from the lipid bodies.

For sun protection compositions that are based on lipid bodies, the choice of emollient influences both the solubility of the protectant and ability of sunscreens to spread evenly. Preferred esters for sunscreen compositions are caprylic or capric triglycerides octyl methoxycinnamate, benzophenone-3, ethylhexyl hydroxystearate, other related benzophenone structures, other aromatic ring structures and esters of C12 through C15 alkyl benzoate when in compositions based on lipid bodies providing additional ingredients, yeast oil and or sealant properties that are provided from the lipid bodies.

Other sunscreen agents such as zinc or titanium metals or other metal salts can be blended into lipid bodies to produce spreadable compositions, which can promote even distribution on the skin and enhance the sun protection performance of a sunblock composition that is based on lipid bodies. Additionally, sunscreens with divalent or trivalent metals such as $Cu2^+$, Fe3, $Co2^+$, $Mn2^+$, $Ti3^+$, $Zn2^+$, and other metals and organic sun blocks can be formulated into lipid bodies either alone or in mixtures. The lipid bodies typically have net negative charge at typical pH's due to phospholipids and hydrophilic surface molecules, which facilitate inorganic sunblock compositions. These compositions can be enhanced by containing lipid bodies providing additional ingredients, yeast oil and or sealant properties are provided from the lipid bodies.

Natural and synthetic waxes can be formulated with lipid bodies and supplemented yeast oil to produce softened waxes, which are normally harder and more brittle with higher melting points than fats. Common waxes used in cosmetics include carnauba wax and beeswax, both of which can be made more pliable by the addition or blending with lipid bodies. Alternatively, synthetic waxes such as ethylene glycol diesters or triesters of long-chain C18 and C16 fatty acids from lipid bodies and associated yeast oil offer functional alternatives to confer rigidity and pliability to stick deodorants and other stick systems by modification of the synthetic wax crystallinity, while maintaining a high melting point. These compositions can be enhanced when containing lipid bodies providing additional ingredients, yeast oil and or sealant properties are provided from the lipid bodies.

Another common wax used in cosmetics is lanolin, which has chemical and physical similarities to the stratum corneum and lipids of human and animal skin. As a result, compositions disclosed herein can be used to help prevent water-loss from skin and maintain moisture with the combination of endogenous and or in combination with exogenous lipids plus the additional emollient and moisturizing properties of lanolin. Additionally, ethoxylated lanolin oils have been found to be effective in reducing the irritating effects of surfactants in detergents and soaps. Thus ethoxylanolin may be useful in improving the quality of lanolin-based soaps and detergents. These compositions can be enhanced by containing lipid bodies providing additional ingredients, yeast oil and or sealant properties are provided from the lipid bodies.

The compositions can be improved with respect oxidative properties by the addition of citric acid as a chelating agent and other agents such as vitamin E acetate. Furthermore, citric acid and D-gluconolactone plus sodium benzoate can provide a significant antimicrobial protection to the compositions.

Commercially available antimicrobial systems of a wide range of types and components are suitably effective when used in combination with the compositions of the invention. Significant shelf-lives have been demonstrated for compositions of the invention that are essentially aqueous mixtures and compositions containing lipid bodies.

It is best to uniformly add anti-oxidants such as vitamin E acetate and citric acid, a chelating agent, to the compositions when the compositions require significant shelf life at room temperature or at least temperatures less than 120° C. to avoid any unwanted localized effects that may arise from non-homogeneous mixing. Additionally, the addition of various starches and modified starches assist in preventing any separation for the aqueous and interstitial components of compositions of the invention.

The compositions of the invention will enhance the utility of many products used in a wide range of applications because of the various properties of lipid bodies. The properties impart features and benefits to standard product compositions comprising a semi-solid, semi-solid, lotions and solution admixtures comprising lipid bodies with or without other lipid body components and associated yeast oil. Key properties are the large size of the lipid bodies of the invention and their resultant high hydrophobic volume, stability under a wide range of pH and temperature conditions, the ability of lipid bodies to form a sealing layer after discharge of ingredients, and their ability to feel aqueous despite being full of oil. Other significant properties and example compositions containing the lipid bodies and components of lipid bodies are described here.

The lipid bodies of the invention have utility where the compositions benefit from an essentially homogeneous state with differences in texture resulting from the effect of temperature on the melting of the lipids within the lipid bodies. In one configuration of the invention compositions can transform from a semi-solid to a liquid due to the melting point of the yeast oil in the lipid bodies. In this case, the compositions can transform from a solid at room temperature to a less solid composition at temperatures above 80° F. (27° C.) and preferably above 85° F. (29° C.) and in some compositions more preferably above 90° F. (32° C.) and most preferably above 95° F. (35° C.). This melting property of lipids within the bodies is associated with a change in viscosity and texture yet the compositions can continue to feel aqueous and smooth, despite the high content of yeast oil inside the lipid bodies or added to the compositions containing lipid bodies, for products, as described in the invention.

The lipid bodies used in the composition may be the direct product isolated by homogenization or by hydrolysis of hyper-lipogenic yeast cells as described herein, followed by washing at various pH's (neutral, acidic, or alkaline) in order to isolate the lipid bodies. Other hydrophobic and hydrophilic partitioning methods are useful in preparing lipid bodies for the compositions in the invention. These processing steps are followed by removal of the solvent by evaporation or washing under a wide range of conditions as long as the lipid bodies do not become dry. Subsequently the lipid bodies can be further processed to make envelopes. Alternatively, lipid bodies can be chemically or enzymatically modified, derivatized or coupled to ligands that are useful for compositions, separations, and other consumer or industrial purposes.

Upon complete drying either in an oven or on the skin, the lipid bodies expel a significant fraction of their oil and the lipid bodies collapse resulting in envelopes or shells along with oil. Following drying the lipid body envelopes are not readily dispersed.

If the lipid bodies are washed and homogenized while wet, the envelopes release oil into aqueous or organic solvent solutions. One dense layer of separated components has a high concentration of lipid body envelopes, which are essentially opened shells. In general, both drying and homogenization disrupt the lipid bodies, which become permanently damaged as they release yeast oil from inside of the lipid bodies. Under these conditions the envelopes are disrupted, and envelopes can be formed.

In another embodiment, the compositions of the invention are obtained by hydrolysis of yeast in which an acid is used to hydrolyze away the cell walls of the yeast and the resulting lipid bodies are isolated by differential density and then washed with an alkaline solution followed by homogenization and solvent extraction followed by solvent evaporation to produce yeast oil that is separated from the lipid bodies envelopes, which can be used in oil-free versions of the compositions of the invention.

In another embodiment, yeast oil can be isolated from yeast containing lipid bodies and the isolated yeast can be added back to the compositions of the invention to increase oiliness or achieve other desirable behaviors in the composition of the invention.

The compositions of the invention may be topical, parenteral, injectable, oral, inhaled and administered as a cleaning composition for any type of object and composition used for medicine and drug delivery systems, pet care, pet medicines, and other acceptable applications of lipid body-based products containing 1% to 100% with or without yeast oil and lipid body components and or including any agent, emulsifier, co-solvent, natural or synthetic additive, flavoring, scent, or colorant as desired for the specific application of the composition.

The compositions of the invention can serve a wide range of drug delivery products, personal care, health care, skin care, hair care, pet care and other products for specific purposes. Of particular interest is the immediate impact on skin moisture and skin soothing, in which lipid bodies and/or lipid bodies are used as they impart significant amounts of hydrophobic ingredients and drug to the user.

The compositions of the invention are surprisingly useful for skin conditions and this material is both pleasant and potentially useful for accelerated wound healing. The moisturizing properties and ability to impart hydrophobic and aqueous compositions to human skin can be beneficial for a number of human conditions that could benefit from the compositions of the invention including dry skin, rashes, sunburn, wind burn, poison ivy, winter-season chapping, skin cracks, inflammatory diseases such as sebaceous gland disorders, e.g. acneiform disorders, such as acne vulgaris, rosacea, seborrhea, dermatoses, lupus erythematosus, systemic lupus, eczema, dermatitis and other skin disorders. Additionally, the compositions may be enhanced by the incorporation of drugs or medicines into the human skin and other medicinal applications to further reduce inflammation through the addition of retinols, lidocaine, benzocaine, Benadryl, aspirin, ibuprofen, Tylenol, or any one or more anti-inflammatory agents, which are suitable for specific conditions for which the lipid bodies based products are being used. Additional ingredients may include nutraceuticals, cosmeceuticals, antioxidants, and any other ingredient that improves the appeal, texture, odor, melting point, or any other property of the compositions. Finally, because of the mild soothing nature of the compositions of the invention, they are particularly suitable as a base for cosmetics and makeup in compositions that can be used day or night on or under makeup.

In practical terms, the compositions of lipid bodies and/or associated components include compositions that can be used to decrease the recovery time associated with skin conditions or reduce the discomforts associated with scar tissue, such as tightness, by maintaining moisture in the healing tissue. When used as an admixture with other antioxidants, antibiotics, or analgesic (for pain), the compositions of the invention can be useful in patients who are either hospitalized or in-home care during recovery from surgery or in compositions useful for soothing bed sores.

In related applications, the compositions of the invention can be the essential component of compositions used to reduce discoloration of scar tissue, discoloration of skin, alleviate parched skin associated with chemotherapy and radiation treatments, to alleviate redness and scaling associated with psoriasis and extremely dry skin as is frequently found at the elbows or soles of the feet.

Because the compositions have a high hydrophobic carrying capacity, they can be effective vehicles for the delivery of carotenoids, vitamin E, retinol, tocotrienols, and other tocopherols and medications to the skin of an individual. They can also retain antimicrobials, such as phenoxyethanol, sodium benzoate, benzalkonium chloride, and others. Similarly, compositions of the invention can be used for antibiotics such as griseofulvin, penicillin, daptomycin, bacitracin, neosporin, streptomycin, vancomycin, and other antibiotics.

The compositions may be applied to an individual's skin within a region in which skin moisturization, softening or soothing is desired. The compositions of the invention may be applied to the skin on the face, including the lips, or a region of inflammation, such as an area around an insect bite. The composition may be applied on a needed basis or as part of an on-going mitigation of an irritation over an extended period of time, such as once a day, multiple times per day, once a week, or other periodic application scheduled as appropriated for the treatment of a skin condition.

Similarly, lipid bodies compositions can be used to impart medicines to the skin, for example, the application of pain reliving agents, lidocaine, benzocaine, gabapentin (neurontin) or other pain control substances as well as localized application of other penetrating drugs formulated with lipid bodies, such as colchicine.

For application of the compositions of the present invention, the compositions of the invention can be used for facial skin and the following regimen is preferred, which involves cleansing the face thoroughly with a mild cleanser, applying compositions of the in a moderate to thin layer, and working the compositions into the skin by applying light pressure and a spreading motion. Makeup may be applied on top of the cream.

The lipid bodies can be used in parenteral treatments, parenteral nutrition, oral applications, inhalation applications, and applications involving other fields of utility including, drug delivery, systems, medicinal applications, pet care, animal health, soaps, detergents, surfactants, industrial lubrication, machinery lubrication, leather conditioners, rubber conditioners, coatings, surface protection, imparting water resistance, and compositions involving the addition of active ingredients, emulsification agents, coloring agents, agents that impart odor, texture or alter the physical properties or melting point of the compositions and other acceptable compositions depending on the desired impact.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

All protein identification (PID) numbers provided herein refer to proteins in the database of the Joint Genome Institute (JGI) of the United States Department of Energy. See, e.g., Jeffries 2013.

It is understood that the invention is not confined to the particular construction and arrangement of parts herein illustrated and described, but embraces such modified forms thereof as come within the scope of the claims. Additionally, engineered lipid bodies exist under a wide range of conditions including as intracellularly, extracellularly, crudely isolated, cleaned, purified or processed to other products both as intact lipid bodies or disassembled lipid bodies, which contain lipids, phospholipids, organellar proteins and dehydrated or packed forms that may be useful.

EXAMPLES

Example 1

Background and Overview

Lipogenic yeasts such as wild-type *L. starkeyi* strains can be used as platform strains for metabolic engineering to produce lipids and lipid bodies. Given that the genome of *L. starkeyi* NRRL Y-11557 has been sequenced (Grigoriev et al. 2012 and DOE JGI 2011), that it can grow on glycerol as a sole carbon source, and that it has a lack of a mucoid morphology in the tested experimental conditions, this public domain strain was selected as the exemplary platform yeast for metabolic engineering and for the development of both engineered yeast and associated engineered lipid bodies. Other wild-type *L. starkeyi* strains listed here and elsewhere, or other lipogenic yeasts, could also be engineered towards this purpose. The existence of an annotated genome for *Lipomyces starkeyi* greatly facilitates cloning and homologous expression. All wild-type strains evaluated have smaller quantities of lipids and small lipid body organelles that have not previously been isolated, purified and recognized as commercially valuable.

Fluorescent dyes such as Nile red or BODIPY (boron-dipyrromethene) can be used in rapid assays for cells or strains of cells showing greater relative lipid body size or accumulation. A series of washes to remove the media from the cells, followed by suspension of the cells in $H_2O$, can eliminate interference due to media components and reduce background fluorescence.

When examining cultures for increased lipid body size or accumulation it is important to distinguish higher levels of lipid due to higher cell density from higher levels of lipid due to higher lipid content per cell. The fluorescence response is therefore normalized to the cell density and confirmation of lipid body size is conducted microscopically.

Gene Cassette Selections and Primer Design

Figure 2:
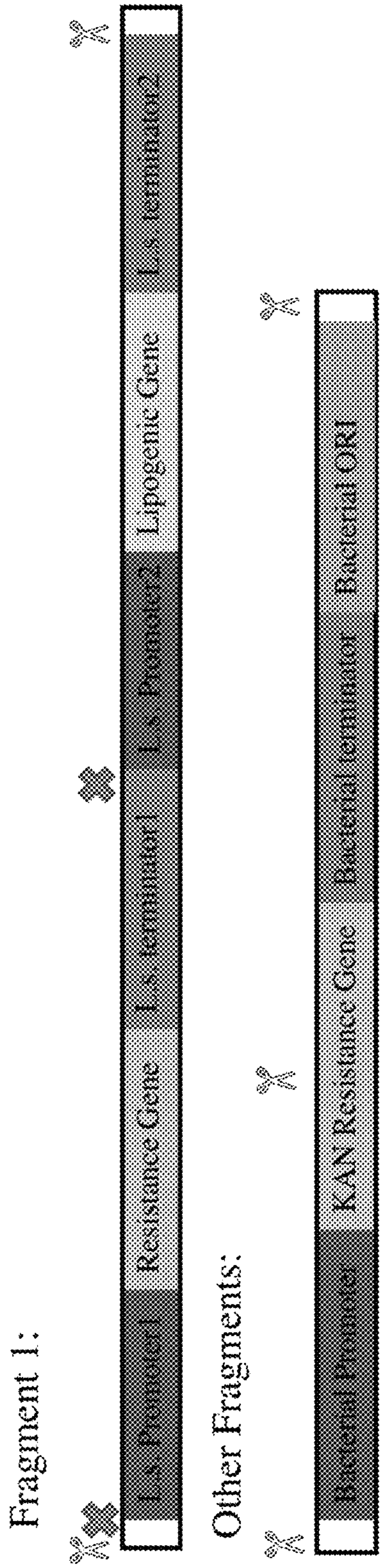
FIG. 2. Schematic diagram of a base vector used for creating genomic integrating cassettes. Restriction digest of a circular vector yields 2-4 fragments, depending on the construct. The integrating fragment contains native *L. starkeyi* promoters and terminators driving expression of a resistance and lipogenic gene. LoxP sequences flank the resistance marker cassette to enable CRE mediated excision. The origin of replication (purple) and kanamycin resistance gene permit propagation and maintenance in *E. coli*, but are not maintained during the selection of transformants. Digest sites are marked with a scissors icon.

Gene cassette integration vectors were designed using a base vector as shown in FIG. 2 and having a sequence identical or similar to the exemplary base vector described in US 2018/0245109. Restriction digest or PCR amplification of a circular vector yielded 2-4 fragments, depending on the construct. The integrating fragment contained native *L. starkeyi* promoters and terminators driving expression of a resistance and lipogenic gene. LoxP sequences flanked the resistance marker cassette to enable CRE mediated excision. The origin of replication and kanamycin resistance gene permitted propagation and maintenance in *E. coli*, but were not maintained during the selection of transformants. Digest sites in FIG. 2 are marked with a scissors icon.

Measures were taken to ensure no antibiotic resistance gene was incorporated in the final yeast strain. The bacterial kanamycin resistance gene was not integrated into the yeast genome if it was interrupted by restriction digestion prior to transformation. The presence of the loxP sites enabled excision of the resistance gene(s) by transient CRE recombinase expression. The LoxP sites themselves were modified (i.e., dead) such that the product after one recombination event resisted further recombination, thereby protecting the genomic integrity of the organism. Genetic tools and selection markers allowed for the removal of antibiotic selection markers, usually by excision or some other selective method. The gene overexpression cassettes therefore included a constitutive promoter, the gene(s) of interest, and one or more transcription terminator regions inserted into one of the multiple cloning sites (MCSs).

Genes were overexpressed to increase lipid body production through enhanced lipogenesis under nutrient-rich conditions. These included the genes described in US 2018/0245109 A1, which include but are not limited to: acetyl-coenzyme-A carboxylase (LsACC1), delta-9 acyl-CoA desaturase (LsOLE1), ATP-citrate lyase alpha and beta subunits (LsACL1/LsACL2), two variants of glycerol kinase (LsGUT1-1602) and (LsGUT1-1617), two variants of diacylglycerol acyltransferase (LsDGA1-1233) and (LsDGA1-1389) having different start sites, and malic enzyme cloned from genomic DNA (LsgME) and cDNA (LscME). Precise promoter, gene, and terminator sequences were selected based on Illumina RNAseq data and knowledge of promoter strength and expression patterns in this organism. All contained a single promoter, gene, and terminator region, with exception to cases in which a bidirectional promoter, natural or synthetic, expresses two genes with different transcription terminator regions. Examples of this included constructs containing GUT1/GUT2 (GPD), ZWF1/GND1, LsAcl1/LsAcl2 and FAS2.2/FAS1.2. In some cases, these sequences were analyzed for the presence of specific restriction digest sites to determine into which one of two MCSs contained in the base vector they would be cloned. This step facilitated future subcloning into other vectors. For example, the diacylglycerol acyltransferase (DGA1) construct was capable of being inserted upstream of the loxP site using the Sbf1 restriction enzyme to linearize the vector. Other constructs were capable of being inserted downstream of the opposing loxP site, using RsrII and AvrII to linearize the vector. In yet a third case, constructs were assembled solely from PCR fragments containing overlapping ends. The desired sequence combinations and restriction enzyme sites were entered into the NEBuilder® assembly tool (nebuilder.neb.com/) with a minimum overlap setting of 20 base pairs to construct the primer sequences for performing the Gibson assembly reaction. Alternatively, this could be done manually without the use of special software.

gDNA Extraction and cDNA Library Creation

A Masterpure™ Yeast DNA Purification Kit (Epicentre, Madison, WI) was used to extract *L. starkeyi* genomic DNA (gDNA). Alternatively, DNA can be isolated using phenol/chloroform extraction followed by ethanol precipitation and resuspension in an aqueous solution. Nitrogen rich (YPD) or nitrogen limited (YPD 70:1 (C:N)) cultures were used for RNA extraction. The YPD 70:1 media contained only 3.64% and 1.82% percent of the yeast extract and peptone as YPD, respectively. A freshly saturated 5 mL culture of *L. starkeyi* grown under constant agitation at 30° C. was pelleted by centrifugation, washed, suspended in 5 mL of sterile $H_2O$, then used to inoculate 50 mL of either YPD or YPD 70:1 media in a 125 mL shaker flask≈0.8 $OD_{600}$ and allowed to incubate overnight at 30° C. under 225 rpm. Cells were observed microscopically to determine lipid production in the YPD 70:1 media as compared to the YPD media, and the $OD_{600}$ was measured to calculate the quantity of cells to use in the RNA extraction protocol. RNA was extracted using an Rneasy Mini Kit (Qiagen), following enzymatic disruption. cDNA was synthesized from these RNA preparations using a QuantiTect® Reverse Transcription Kit (Qiagen), following the instructions of the manufacturer.

PCR of Fragments and Gibson Enzymatic Assembly

A detailed example of how some constructs were created using the Gibson in vitro enzymatic assembly method is provided. A representative base vector (FIG. 2) was linearized with the enzymes listed. Table 3 lists the gene targets, promoters, and terminators employed. All PCR amplifications were performed using Phusion High Fidelity Taq polymerase (NEB) and the manufacturer protocol in either 5× Phusion GC buffer (ACC1) or 5× Phusion buffer (all others). Annealing steps were carried out using the lowest $T_m$ of the primer pair, or the experimentally optimized annealing temperature, where appropriate. The reaction products were analyzed by agarose gel electrophoresis containing ethidium bromide and subsequently visualized and photographed. Successful reactions of identical fragments were pooled and then all samples (including the digested base vector) were subjected to a PCR cleanup column (Qiagen), and then quantified on a Nanodrop 2000 instrument (Thermo Scientific) or a Qubit fluorimeter (Life Technologies). The vector and inserts were then added in equimolar quantities (0.1 pmoles/fragment) in a separate tube, and the final volume adjusted to 20 mL by the addition of 15 mL premade Gibson assembly reaction mix and water. All reactions were allowed to incubate at 50° C. for one hour, and then 5 Ml of the assembly reaction was used to transform 20-30 mL of Endura™ DUO competent cells (Lucigen) using standard techniques. Transformants were selected on LB plates containing kanamycin, and positive candidates were identified by colony PCR and sent for sequencing confirmation.

All vectors were linearized so the entire target gene cassette, including the loxP flanked region, randomly integrates into the *L. starkeyi* genome as one fragment. Linearized DNA was ethanol precipitated and suspended in TE to increase its concentration (>160 Nm) and purity. To transform the cells, a procedure based on the lithium acetate method was used (Calvey et al. 2014, Gietz et al. 2002). A near stationary phase culture of *L. starkeyi* was inoculated into 50 mL YPD to between 0.6 and 0.8 $OD_{600}$ and grown overnight to reach between 2.80 and 3.20 $OD_{600}$. The culture was harvested and washed 1-2 times with 25 mL sterile water, and resuspended to 1.5 mL in sterile water or 0.1M LiAc. Aliquots of 150 mL were dispensed into 1.5 mL tubes and centrifuged. The remaining cell pellet was then suspended in 360 mL transformation mix containing 240 mL 50% w/v PEG 3350, 50 mL boiled ssDNA, 36 mL 1.0 M LiAc, and 36 mL of the desired plasmid DNA (added last). Samples were incubated at 30° C. for 3 hours, heat shocked at 40° C. for 5 minutes, and then centrifuged to remove the transformation suspension. Cells were allowed to recover in 3 mL YPD for 4 hours before being plated onto selective media. After 6 days of growth, transformants were selected, catalogued by size, and streaked onto YPD plates containing the appropriate antibiotic for creating glycerol stocks until characterization.

TABLE 3

Summary of gene targets, promoters, and terminators.

| Target Gene | Full Name | Promoter/Terminator Pairing |
|---|---|---|
| ACC1 | Acetyl-Coenzyme-A-carboxylase | Fructose 1,6-bisphosphate aldolase (promoter and terminator) |
| ACC1(S639A) | Acetyl-Coenzyme-A-carboxylase (S639A) | Fructose 1,6-bisphosphate aldolase (promoter and terminator) |
| ACC1(S1146A) | Acetyl-Coenzyme-A-carboxylase (S1146A) | Fructose 1,6-bisphosphate aldolase (promoter and terminator) |
| ACC1(S639A, S1146A) | Acetyl-Coenzyme-A-carboxylase (S639A, S1146A) | Fructose 1,6-bisphosphate aldolase (promoter and terminator) |
| ACL1/ACL2 | ATP-citrate lyase, alpha and beta subunits | Enolase and promoter, Triose Phosphate Isomerase and ATPase (3900) terminator |
| DGA1(1233) | Diacylglycerol acyltransferase 1 | Translation elongation factor EF-2 alpha promoter, Glyceraldehyde-3-phosphate dehydrogenase terminator |
| DGA1(1389) | Diacylglycerol acyltransferase 1 | Translation elongation factor EF-2 alpha promoter, Glyceraldehyde-3-phosphate dehydrogenase terminator |
| DGA2 | Diacylglycerol acyltransferase 2 | Triose phosphate isomerase promoter, 3-phosphoglycerate kinase terminator |
| FAS1.2/2.2 | Fatty Acid Synthase Complex Subunits 1.2 and 2.2 | Various promoters, Triose phosphate isomerase and ATPase 3900 terminator |
| GDP1 | NAD-dependent Glycerol-3-phosphate dehydrogenase | Pyruvate Kinase promoter and terminator |
| GUT1(1602) | Glycerol Kinase | ATPase 3900 promoter and terminator |
| GUT1(1617) | Glycerol Kinase | ATPase 3900 promoter and terminator |

TABLE 3-continued

| Summary of gene targets, promoters, and terminators. | | |
|---|---|---|
| Target Gene | Full Name | Promoter/Terminator Pairing |
| GUT2 | FAD-dependent Glycerol-3-phosphate dehydrogenase | Pyruvate Kinase promoter and Triose phosphate isomerase terminator |
| cME | Malic Enzyme (cDNA) | Triose phosphate isomerase promoter and terminator |
| OLE1 | Delta-9 acyl Coenzyme A desaturase | Glutamine synthetase promoter and terminator |
| SCT1 | Glycerol 3-phosphate/dihydroxyacetone phosphate sn-1 acyltransferase | Citrate synthase promoter and terminator |
| SLC1 | 1 -acyl-sn-glycerol-3-phosphate acyltransferase | Fructose 1,6-bisphosphate aldolase (promoter and terminator) |
| FOX2 | 3-hydroxyacyl-Coenzyme A dehydrogenase,enoyl-CoA hydratase | N/A, gene knocked out |
| POX1 | Fatty-acyl Coenzyme A oxidase | N/A, gene knocked out |

Yeast Lipid Screening Using Nile Red

Both YPD and Mts were used to screen for lipid accumulation in *L. starkeyi*. Starter cultures were inoculated with the desired transformants in 5 mL tubes containing YPD-NAT or YPD liquid media at 30° C. under constant agitation. This lipid body screening protocol was based on Nile Red fluorescence adapted from a previous study (Sitepu et al. 2012). Samples and appropriate dilutions were then prepared in a 96-well black clear-bottomed plate to contain 100 mL in each well. Nile Red was prepared as a 2 mg/mL stock solution and then diluted to a 2× working concentration (8 μg/mL). Fluorescent signals and $OD_{630}$ readings were read independently from two plate readers (BioTek™ FLx800 and BioWhittaker™ Elx808, respectively). Data was analyzed by normalizing the fluorescent signal to the $OD_{630}$ of the culture. To enable comparisons between different runs, normalized fluorescence was standardized relative to the wild-type culture of each group.

Yeast Lipid Screening Using BODIPY

Starter cultures were inoculated with the desired transformants in 5 mL tubes containing YPD liquid media and grown for 3 days at 30° C. under constant agitation. After outgrowth, 2004 of each culture was added to a tube containing 5 mL of synthetic Thin Stillage (Sts) at a concentration of 0.6 μg/mL of fresh BODIPY (boron-dipyrromethene) dye and monitored by $OD_{630}$ and fluorescence for 72 hours. Data was analyzed by normalizing the fluorescent signal to the $OD_{630}$ of the culture, or by simply summing the raw fluorescence values of each culture throughout the course of the experiment.

Lipid Extraction Analysis

An extraction protocol was used for crude gravimetric assessments of total lipid content based on the classic Bligh and Dyer method (Bligh et al. 1959) (20). First, 2 mL of cell culture was centrifuged at 3,000 rpm for 5 minutes in 15 mL falcon tubes, and the cell pellets frozen at −20° C. until lipid extraction analysis. Thawed cell pellets were suspended in 1 mL $H_2O$ containing 200 mL of concentrated HCl, and the suspension was heated to 90° C. for 1 hour to lyse cells. Lipid was then extracted by addition of 6 mL of a 2:1 (v:v) methanol:chloroform solution and 3 mL of 1M NaCl, followed by vortexing for 5 minutes. Tubes were then centrifuged at 3,000 rpm for 10 minutes to induce phase separation. The lipid-containing lower chloroform layer (≈2 mL) was then carefully removed using a glass Pasteur pipette, and transferred into a clean, pre-weighed, 5 mL glass vial. Finally, the extracted chloroform layer was completely evaporated by incubation in a 40° C. heat block under a constant stream of air for 1 hour. Vials were then re-weighed to determine the mass of extracted total lipids.

Engineering 403 as an NHEJ-Deficient (lig4Δ) Strain for Further Metabolic Engineering The 403 strain was further engineered to facilitate homologous recombination by disrupting the non-homologous end joining (NHEJ) pathway, specifically by deleting the LIG4 locus as described in US 2018/0245109. This greatly facilitates the knockout of other genes that are predicted to increase lipid yields, interfere with lipid catabolism, or even encode genes involved in potentially allergenic antigens. Examples of such genes include the acyl-CoA oxidase POX1, the multifunctional enzyme FOX1, UDP-glucose 6 dehydrogenase (UDPGH), Uridine 5'-diphospho-glucuronosyltransferase (UGT), and glycogen synthase, among others.

Consolidation of Transformed Traits

Not all genes evaluated on an individual basis in US 2018/0245109 A1 increased lipid production. However, various combinations of genes may enhance lipid production or growth synergistically, such as where bottlenecks might be relieved by gene overexpression. Various combinations of genes were therefore tested to determine which combinations resulted in improved lipid production, accumulation, and lipid body size.

Figure 3:
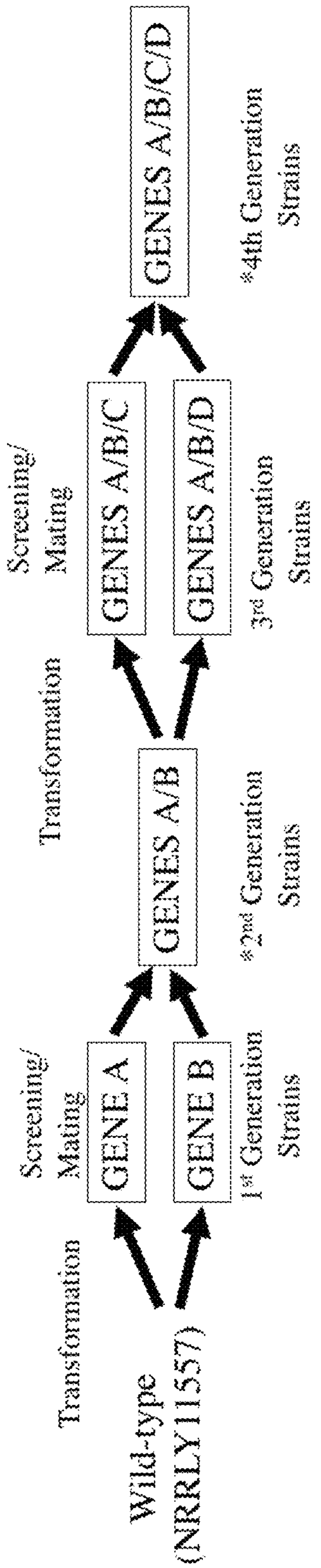
FIG. 3. Schema showing the strategy for creating first-, second-, third-, and fourth-generation engineered strains using several rounds of transformations, mating, and resistance marker removal. Marker removal, deemed "curing", is denoted with an asterisk.
Figure 4:
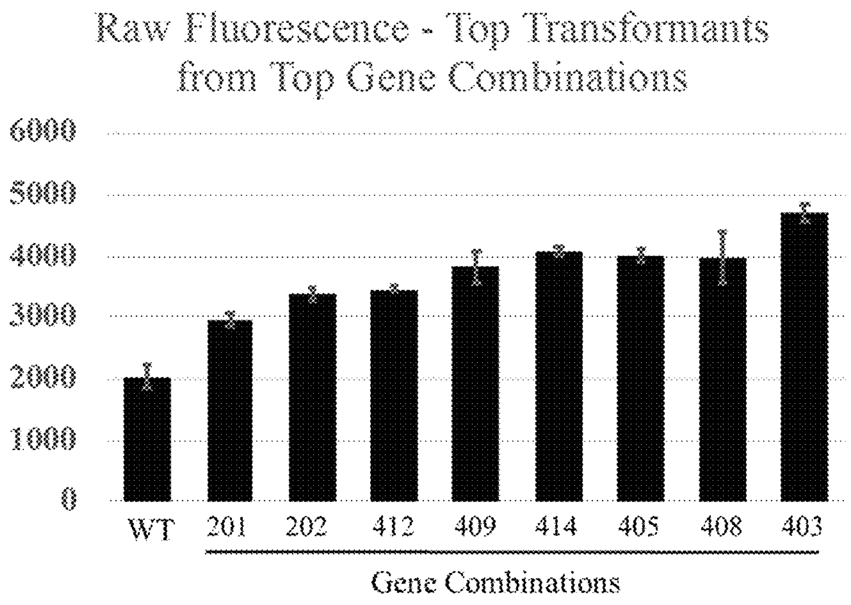
FIG. 4. Effect of combinatorial overexpression of genes on lipid accumulation as deemed by cumulative BODIPY fluorescence compared to the wild-type strain over 4 days of cultivation in sTS. Proteins overexpressed in each strain are as follows: 201 (GUT1, GUT2), 202 (DGA1, DGA2), 412 (GUT1, GUT2, ME, SCT1), 409 (ACL1, ACL2, DGA1, DGA2, SCT1), 414 (ACL1, ACL2, DGA1, DGA2, ME), 405 (DGA1, DGA2, ME, SCT1), 408 (GUT1, GUT2, DGA1, SCT1), and 403 (DGA1, DGA2, ME, SCT1). Strains 403 and 405 differ in the genomic site and/or number of copies of the Malic Enzyme (ME) cassette. The 403 strain was sequenced and has one copy of the Malic Enzyme overexpression construct, plus the native Malic Enzyme locus.

Combinations of gene cassettes from top first-generation lipid producing strains (i.e., strains with a single gene modification) were tested for enhanced lipid accumulation through yeast mating. Progeny were selected by spore isolation or selection on permissive media, granted the parental strains harbored resistances to different antibiotics. Strains derived by mating first-generation strains have two cassettes integrated in the genome, and were considered second-generation strains. Strains that were transformed twice with different cassettes were also considered second-generation strains. The limited number of resistance markers to use in selecting strains required resistance marker removal (curing) of strains to enable further metabolic engineering with additional gene cassettes. Therefore, select second-generation strains were cured and transformed with additional cassettes to create third-generation strains. Third-generation strains were mated to create fourth-generation strains. Fourth-generation strains with prodigious lipid producing properties and capable of generating large intracellular lipid bodies were cured. FIG. 3 provides a diagram describing the creation of a generic fourth-generation strain from the starting wild-type strain. Creation of fifth- and sixth-generation strains followed the same strategy (i.e. transforming a "cured" fourth generation strain with cassettes containing resistance to different antibiotics to create fifth-generation strains, and then mating the fifth-generation strains together to create sixth-generation strains). The progressive improvement in lipid production as deemed by BODIPY fluorescence from select second- and fourth-generation strains are illustrated in FIG. 4.

Figure 5:
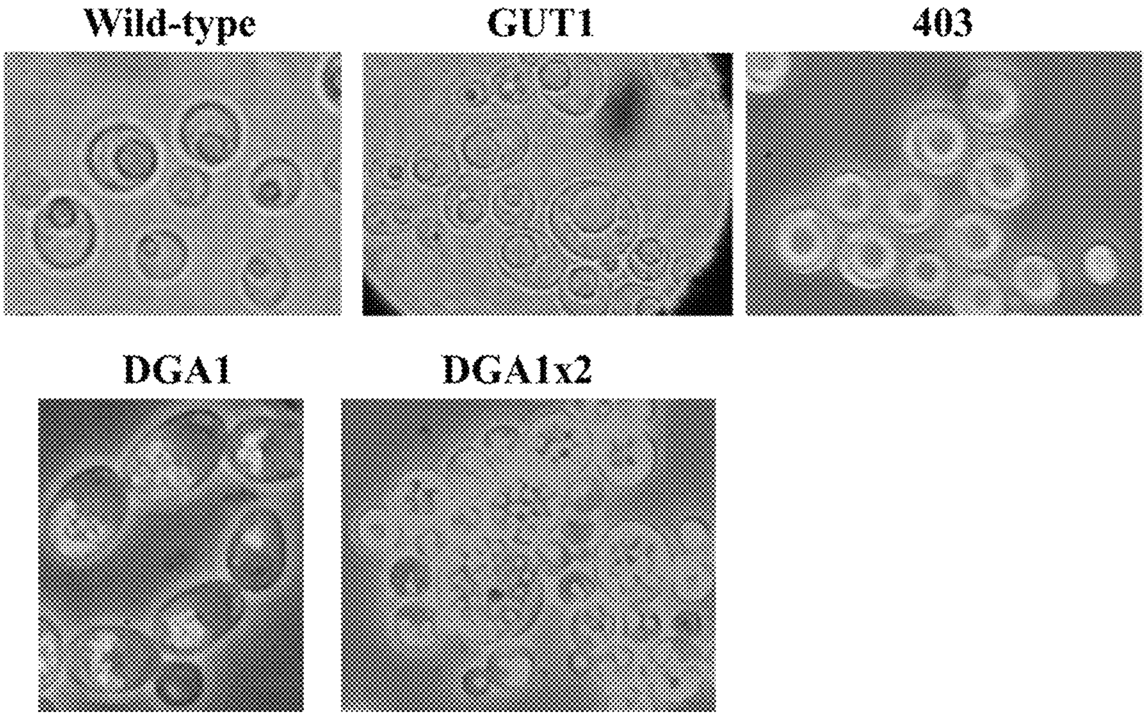
FIG. 5. Manipulation of cellular morphologies and intracellular lipid bodies resulting from overexpression of different proteins. Overexpression of DGA1 by transforming cells once (DGA1) or twice (DGA1 DGA1) with the DGA1 expression cassette results in multiple small intracellular lipid bodies, whereas overexpression of GUT1 alone results in lipid bodies of various sizes and slow growth in media containing glycerol. The 403 strain overexpresses DGA1, DGA2, ME, and SCT1, and results in large uniform lipid bodies suitable for isolation and use in a number of products.

Higher lipid production does not necessarily indicate larger intracellular lipid bodies, as an engineered strain could simply produce more, smaller lipid bodies per cell. Moreover, growth rates of highly lipogenic strains are typically impeded, presumably because lipid bodies restrict the available cytosol and other structures needed for robust protein synthesis. FIG. 5 demonstrates the difference in lipid body morphologies of various strains evaluated, along with isolated lipid bodies. Strain 403 produces lipid bodies that are the desired size and do not significantly decrease cell growth (approximately one large lipid body per cell).

Creation of the 202 and 403 Strains

Strain 202 was genetically modified from wild-type *L. starkeyi* strain NRRLY11557. It overexpressed two endogenous genes related to lipid production driven by native constitutive promoters. Specifically, this strain overexpressed two native genes encoding proteins with acyl transferase activity. These included diacylglycerol transferase 1 (DGA1, Protein ID #6201) driven by the native transcription elongation factor EF-1 alpha promoter (TEF1, Protein ID #63951) and the native glyceraldehyde-3-phosphate terminator (TDH3, Protein ID #68472), and diacylglycerol transferase 2 (DGA2, Protein ID #6231) driven by the native triose phosphate isomerase promoter (TPI, Protein ID #196787) and the native phosphoglycerate kinase terminator (PGK, Protein ID #75322). Vector backbones were obtained by amplification in *Escherichia coli* followed by restriction digests. Amplification of the DNA sequences of interest were created by polymerase chain reaction (PCR) from either cDNA (DGA1) or genomic DNA (DGA2), and PCR fragments and digested vectors were combined using Gibson isothermal assembly. Cassettes were amplified in *Escherichia coli*, linearized by restriction digest, and transformed into *Lipomyces starkeyi* by random genomic integration. Transformations of each cassette were carried out independently in the wild-type strain, and screening revealed top performers of each. These were mated together, and the progeny were selected on plates containing the relevant antibiotics. Resistance genes to these antibiotics were removed using a CRE loxP based strategy, which results in a 34-base pair loxP scar sequence in place of the previously loxP flanked resistance marker cassette. This loxP sequence was not able to undergo further recombination, even in the presence of CRE. Nonetheless, the CRE recombinase gene was also removed during the excision process. Marker and CRE removal was confirmed by loss of resistance to antibiotics used in the original selection and PCR genotyping.

The 202 strain was further genetically modified to create the 403 strain. This strain overexpressed the same genes with the same promoters and terminators as described for the 202 strain in addition to native glycerol-3-phosphate o-acyltransferase 1 (SCT1, Protein ID #235628) driven by the native CIT1 (Protein ID #47067) promoter and terminator and native malic enzyme (Protein ID #72728) driven by the native triose phosphate isomerase (TPI, Protein ID #196787) promoter and terminator. Construction of vector backbones used the same techniques as to make 202 with SCT1 cloned from genomic DNA and malic enzyme cloned from cDNA. Transformations of each cassette were carried out independently in the 202 strain, and screening revealed top performers of each. These were mated and the progeny selected on plates containing the relevant antibiotics. Resistance genes were removed in the same manner as described above and confirmed by loss of resistance to antibiotics used in the original selection and PCR genotyping.

Strain 202 (DGA1+DGA2) Grows Faster Than Strain 403, But Strain 403 Accumulates More Lipid Strains 202 (DGA1, DGA2) and 403 (DGA1, DGA2, ME, and SCT1) were inoculated successively to 5, 25 and 100 mL volumes of yeast extract (10 g/l) and peptone (20 g/l) plus glucose (40 g/l) and xylose (15 g/l) and cultivated at 28° C. in 13-mL tubes, 125-mL baffled Erlenmeyer flasks, and 500-mL baffled Erlenmeyer flasks, respectively, while agitated at 250 rpm with periodic subculture. The densities of the 100-mL cultures were normalized and used as inocula for the bioreactors. Two bioreactors were set up with an initial target volume of 1.0 L with yeast extract (22 g) peptone (44 g) glucose (YPG) medium at an initial concentration of 112.5 g glucose in a final volume of 1 liter. The yeast extract (Fisher) contained 11% w/w N and the peptone (Fisher) contained 15% w/w N. Initial total N in the bioreactor was calculated as 9 g; total carbon (glucose only) as 45 g. Initial C:N ratio was therefore 3.7:1. The experiment was designed to pump into each bioreactor a glucose feed of 225 g glucose in 500 mL of $H_2O$ after 90% of the initial glucose had been consumed. Initial bioreactor operating conditions were pH 5.2 to 5.3, Temp 28° C., DO, 100% saturation, agitation at 600 rpm with 1 v/v·min air sparged. Glucose was pumped into the reactors at 68, 94 and 99 h. At T4 (65 h) and T18 (142 h) samples were withdrawn for dry weight and lipid analysis.

Figure 6A:
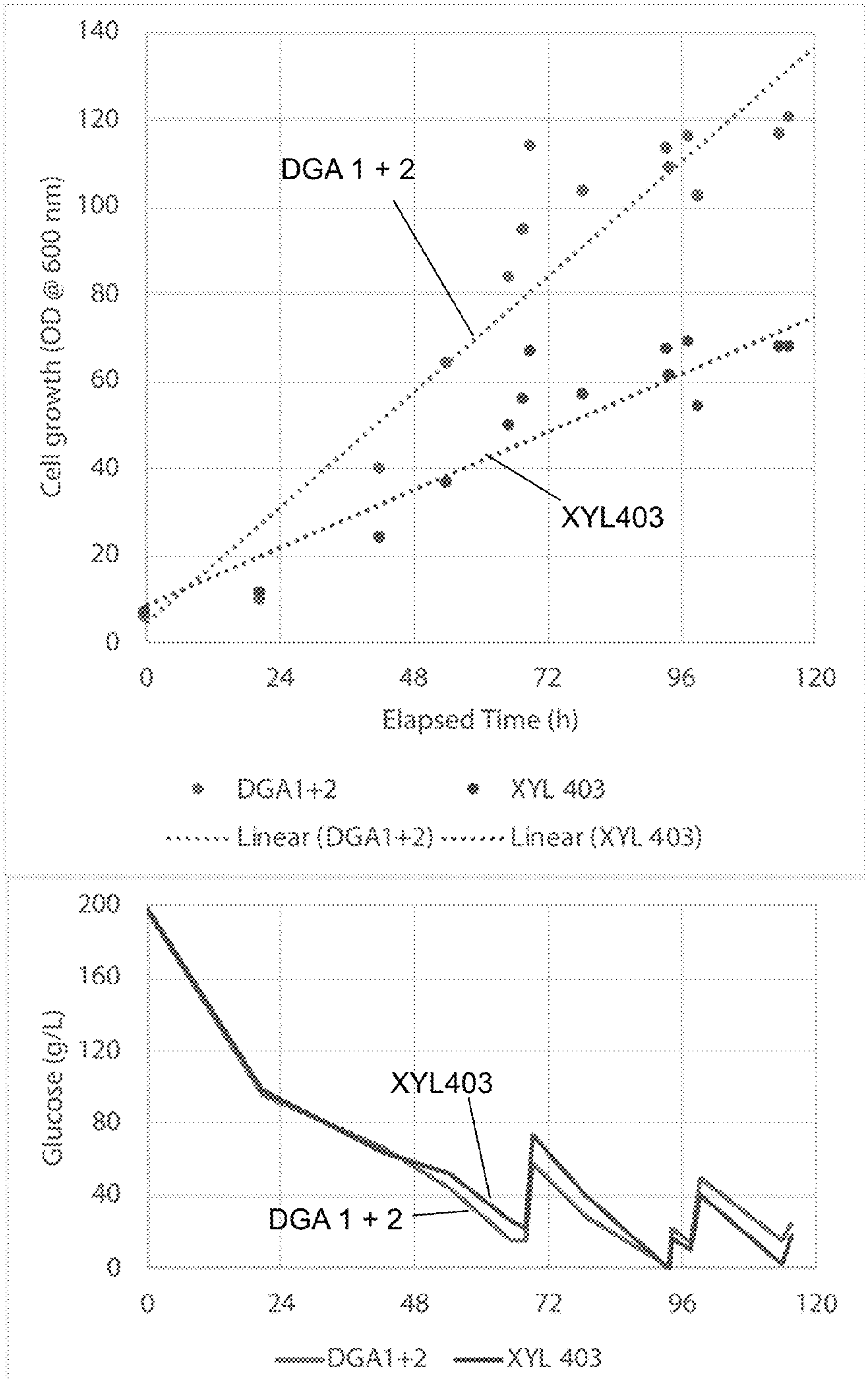
FIG. 6A. Growth rates (top panel) and glucose consumption (bottom panel) of strains 202 (DGA1, DGA2, shown as "DGA1+2") and 403 (DGA1, DGA2, ME, and SCT1, shown as "XYL 403").
Figure 6B:
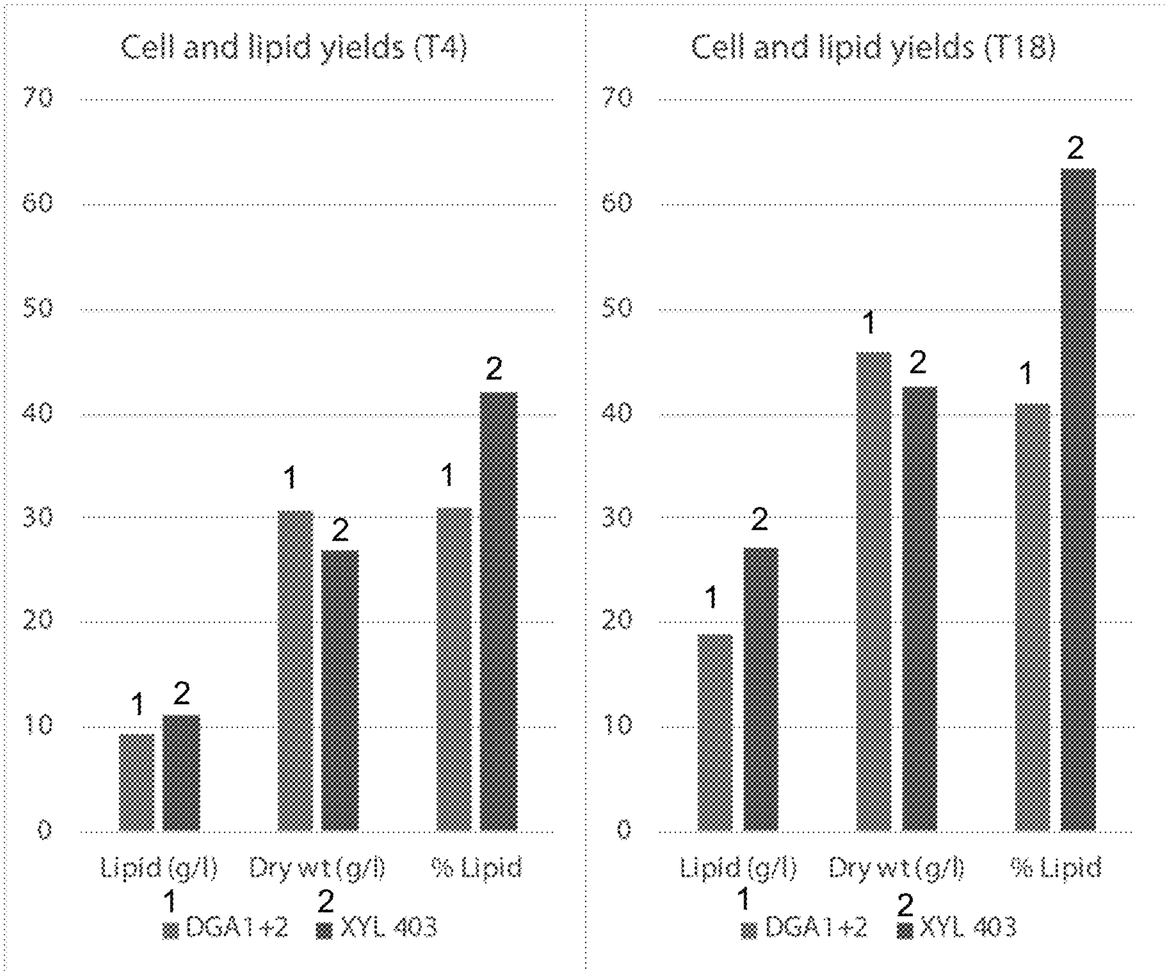
FIG. 6B. Cell and lipid yields of strains 202 (DGA1, DGA2, shown as "DGA1+2") and 403 (DGA1, DGA2, ME, and SCT1, shown as "XYL 403.") at T4 (65 h, left panel) and T18 (142 h, right panel) of growth.

As illustrated in FIG. 6A, the growth rates of the two yeast strains differed by ≈1.7 fold with the 202 and 403 strains attaining a final Ods of 182 and 403, respectively. The optical densities did not correlate directly with dry weight determinations or the lipid contents of the cells (FIG. 6B). At T4, the ratio of OD's for DGA1+2 to Xyl-403 was 1.7:1 while the ratios of their dry weights were 1.14:1. More interestingly, the ratios of their lipid contents were 0.83:1 at T4 and 0.7:1 at T18. The lipid content of the 403 strain was 55% greater than the 202 strain at the end of the experiment.

Fed-Batch Cultivation of the 403 Strain Enables Higher Growth and Lipid Accumulation The 403 strain (DGA1, DGA2, ME, and SCT1) was cultivated in a 13-liter bubble bottle with an initial medium volume of 1.8 liters and an inoculum volume of 200 mL. The medium contained 333 g/l of cerelose (glucose monohydrate) plus 16.1 g/l Lallemand FNI yeast extract. One-third of the cerelose was present at the time of inoculation and two thirds were fed into the reactor after 72 h. This gave a final C:N ratio of 75:1. Cell growth was tracked by measuring packed wet weight, dry weight, and lipid content of cells. At the end of the fermentation, 2980 mL of medium contained 889 g of packed wet cells (≈300 g/L) with a dry weight of 109 g/l and a lipid yield of 68 g/l. The percent lipid concentration in the cells attained as measured by percent dry weight (w/w) was 62%.

Recovery of Lipid Bodies from Whole Broth by Acid Hydrolysis and Flotation

The 403 and 202 strains were cultivated as described above. After cultivation was terminated, the whole broth was transferred to 2-liter glass bottles. Concentrated sulfuric acid was added with mixing to a concentration of 0.5 N, and the acidified broths were autoclaved for 45 min at 212° C. In side experiments, phosphoric acid at 0.5 N was used in place of sulfuric acid. After cooling, two phases emerged. An upper tan layer contained crude lipid bodies, and a lower layer contained cell hydrolysate.

The lipid bodies in the upper layer were examined microscopically. Lipid bodies from the 202 strain were approximately half the diameter of those isolated from the 403 strain.

The pH was adjusted to 7.25 by the addition of 0.5 N NaOH in 32 g/l saline and the lipid bodies were separated from the hydrolysate by centrifugation at 4,000 rpm for 25 min. The dark brown hydrolysate was drawn off from the bottom of the centrifuge bottles. The lipid bodies were suspended in 800 mL of 32 g/l saline and centrifuged a second time at 4,000 rpm for 25 min. The 32 g/l saline provided osmotic support and additional buoyancy that enabled fractionation of larger lipid bodies from the 202 strain from smaller lipid bodies or non-lipogenic cells. No such separation was observed in the 403 cells. We infer from this observation that the higher lipid content of the 403 lipid bodies enables easier separation by flotation. In subsequent trials, washings were carried out with water or physiological saline rather than saline at 32 g/1.

Color and Odor Removal from Lipid Bodies Using Alkaline Wash

Saline or water washes alone did not fully remove a tan color attributed to the hydrolysate in the procedures outlined above. The 403 lipid bodies recovered from the hydrolysate by washing were therefore suspended in 3 to 10 times their volume water or saline, and the pH was raised to 11.2-11.7 by the addition of NaOH (1.0 to 5.0 N). Dilute suspensions (e.g. 10-fold) resulted in more rapid separation of lipid bodies by flotation than in more concentrated suspensions (e.g. 2- to 3-fold), and the initial rise rate from the dilute suspension was significantly faster than the later rate as the lipid bodies became more concentrated at the surface. The alkaline-washed lipid bodies appeared bright and white and did not have any odd odors.

To compare various alkaline washes, 1137 mL of lipid bodies from the 403 strain in 1900 mL $H_2O$ were divided into 3 aliquots of 379 mL each, transferred to 2-liter bottles; made up to 1800 mL with deionized water; adjusted to pH 11.7 with NaOH (5 N), 200 mL of $Na_2CO_3$ (1 M), or $Na_2CO_3$.1.5$H_2O_2$ (0.5 N); and allowed to stand for 18 h. Table 4 outlines the various alkaline wash conditions.

TABLE 4

Comparison of alkaline wash conditions.

| | Conc (M) | vol (mL) | Ph |
|---|---|---|---|
| 5 N NaOH | 5 | 23.5 | 11.7 |
| $Na_2CO_3$ | 1 | 200 | 9.72 |
| $Na_2CO_3$•1.5 $H_2O_2$ | 0.5 | 200 | 9.88 |

The oxygen released by sodium percarbonate was excessive. It resulted in bright, clean lipid bodies and a decolorized solution, but it also disrupted the lipid bodies and left a significant fraction of them as an opalescent suspension. The wash with NaOH at pH 11.7 removed the most color. The lipid bodies resulting from the NaOH wash did not form as compact a layer as observed with the sodium carbonate wash. Also, microscopically, the lipid bodies with the sodium carbonate wash appeared to be larger and more spherical than the lipid bodies washed with either sodium hydroxide at pH 11.7 or with sodium percarbonate at pH 9.88.

In a follow-up experiment, lipid bodies were suspended in an aqueous solution of 1.5% $Na_2CO_3$ and 0.15% $Na_2CO_3$.1.5$H_2O_2$. This yielded bright white lipid bodies with almost no odor and a more compact suspension. In another trial, lipid bodies in a greater than 5:1 lipid body: water suspension were separated from the hydrolysate by washing in 2 to 3 cycles of water, were then suspended in 1.5% $Na_2CO_3$, then adjusted to pH 11.7 briefly at room temperature as they rose to the surface of the container. Following removal of the alkaline wash, the lipid bodies were twice suspended in 4 to 9 volumes of water or physiological saline and the pH was adjusted to 11.2. Following the final wash, the lipid bodies were suspended in two volumes of physiological saline (8.8 g/l) plus sodium citrate, pH 4.5 and 0.5% w/v to 10% w/v glycerol. Higher concentrations of glycerol resulted in a more compact lipid body layer. The resulting lipid body suspension contained between 10% w/w and 60% w/w solids.

Properties of Isolated Lipid Bodies

The physical properties of lipid bodies isolated from the 403 strain and other strains (such as the wild type) were determined by a number of methods.

Packed cell volume: A suspension of lipid bodies were added to a graduated centrifuge tube and centrifuged in a swinging bucket rotor for 15 minutes at 3,000 to 5,000 rpm. The volume of the packed lipid bodies was measured.

Lipid body density (wet): The packed cell volume procedure was carried out in a tared, graduated centrifuge tube, and the tube plus the packed lipid bodies was weighed. The weight of the tube was subtracted, and the resulting weight was divided by the volume.

Percent Solids: A volume of a lipid body composition was placed in a tared aluminum tray. The weight of the tray plus the lipid body composition was determined. The aluminum tray was placed in a drying oven at 50° C. for 3 to 12 h to allow evaporation of the liquid from the composition and weighed again. (Any method that permits evaporation of liquid can be used.) A ratio of the dry weight over the wet weight multiplied by 100 yields the percent solids (w/w) of the original lipid body composition. This is usually repeated in triplicate.

Grams Lipid Per Volume of Lipid Body Composition: An extraction protocol based on the classic Bligh and Dyer method (Bligh et al. 1959) was employed. 2 mL of lipid body composition was frozen at −20° C. for 30 minutes or held until lipid extraction. Thawed lipid bodies were supplemented with 0.5 mL $H_2O$ and 300 Ml of concentrated HCl, and the suspension was heated to boiling for 1 hour to rupture the cell walls and membranes of the lipid bodies. Lipids were extracted by addition of 6 mL of a 2:1 (v:v) methanol:chloroform solution and 3 mL of 1M NaCl, followed by vortexing for 1 minute. Tubes were then centrifuged at 3,000 rpm for 15 minutes to induce phase separation. The lipid-containing lower chloroform layer was then carefully removed using a glass Pasteur pipette, and transferred into a tared aluminum weighing dish. This was greatly facilitated by first removing most of the upper phase. Finally, the extracted chloroform layer was completely evaporated by incubation in a hood under a constant stream of air or in a 50° C. incubator. The aluminum weighing dish was then re-weighed to determine the mass of the total extracted lipids per unit volume of lipid bodies from which lipid was extracted, and reported as grams of lipid per liter of lipid body composition (g/L).

Lipid body diameter and volume: Lipid bodies were suspended in water and placed under a weighted cover slip of a Petroff-Hauser counting chamber (Hausser Scientific, Horsham, PA). A photomicrograph of the lipid body suspension was taken. The dimension of the counting cells was 200 μm on a side. The photomicrograph was calibrated using the dimensions of the counting chamber. Photomicrographs at different magnifications were calibrated by the relative apparent diameter of the oculus ring (ca. 50 μm). The diameters of the lipid bodies in the photomicrograph were measured.

Figure 7:
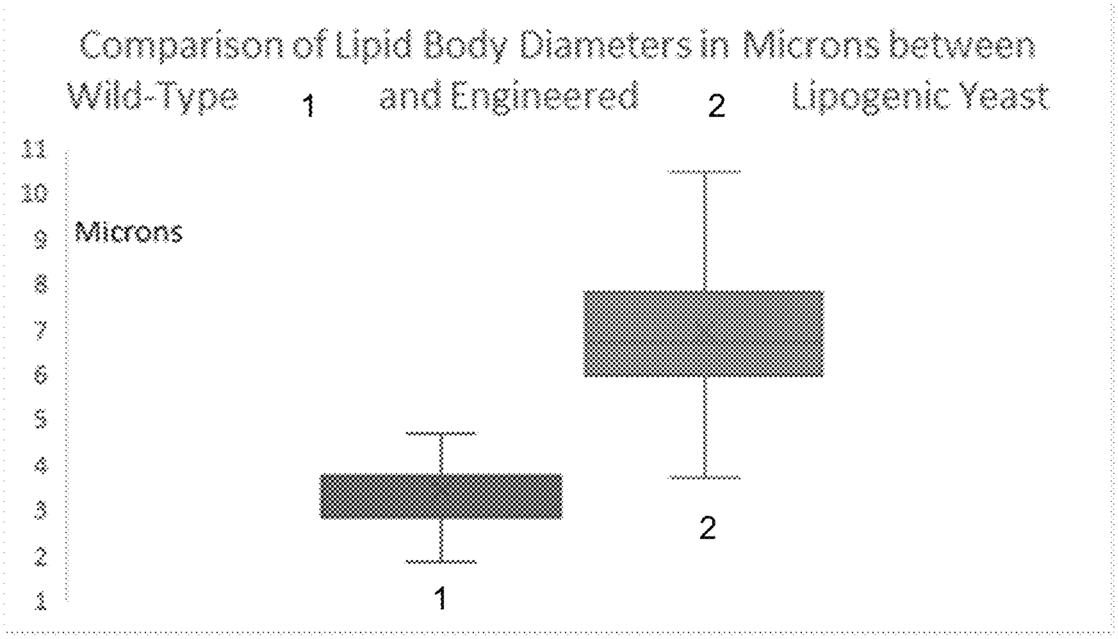
FIG. 7. Comparison of lipid body diameters between those obtained from wild-type *L. starkeyi* and those obtained from the 403 strain (shown as "engineered lipogenic yeast").
Figure 8:
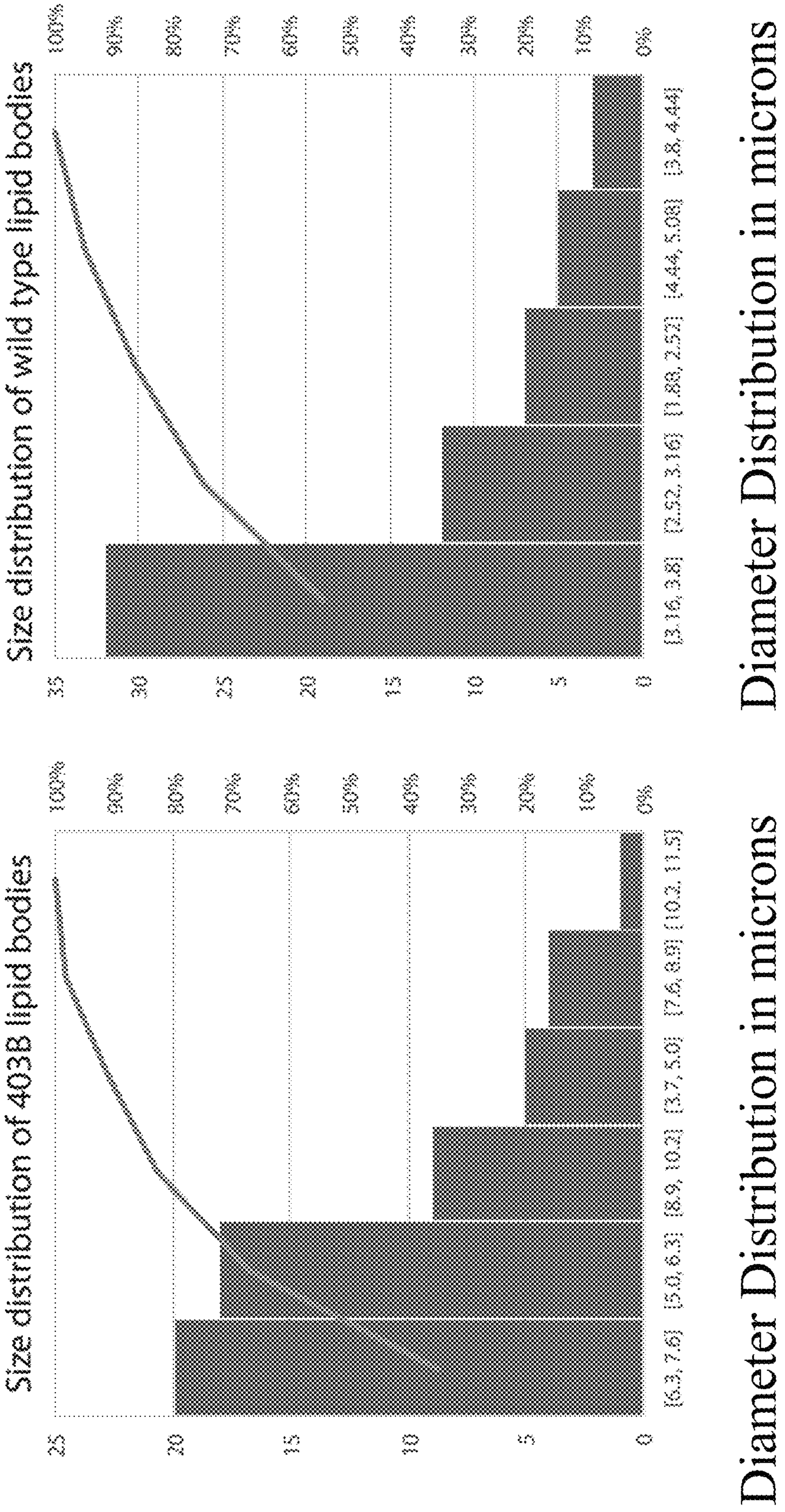
FIG. 8. Size distribution of lipid bodies obtained from the 403 strain (left panel) and those obtained from wild-type *L. starkeyi* (right panel). The Y axis on the left side of each bar graph indicates the percentage of total number of lipid bodies as shown with each individual blue bars. The Y axis on the right side of each bar graph indicates the cumulative percentage of lipid bodies by adding blue bar going from left to right as shown by the orange line. The numbers in brackets under each blue bar on the X axis of each bar graph indicates the diameter range in microns represented by each blue bar. For example, [6.3,7.6], indicates a range of 6.3 μm to 7.6 μm.

The diameters of lipid bodies from wild-type *L. starkeyi* and the 403 strain were determined using the methods outlined above. As shown in FIG. 7, the average diameter of the 403 lipid bodies was much larger (6.9 μm±1.4 μm) than the average diameter of the wild-type lipid bodies (3.417 μm±0.708 μm). The size distribution of lipid bodies from each source is shown in FIG. 8.

Figure 9:
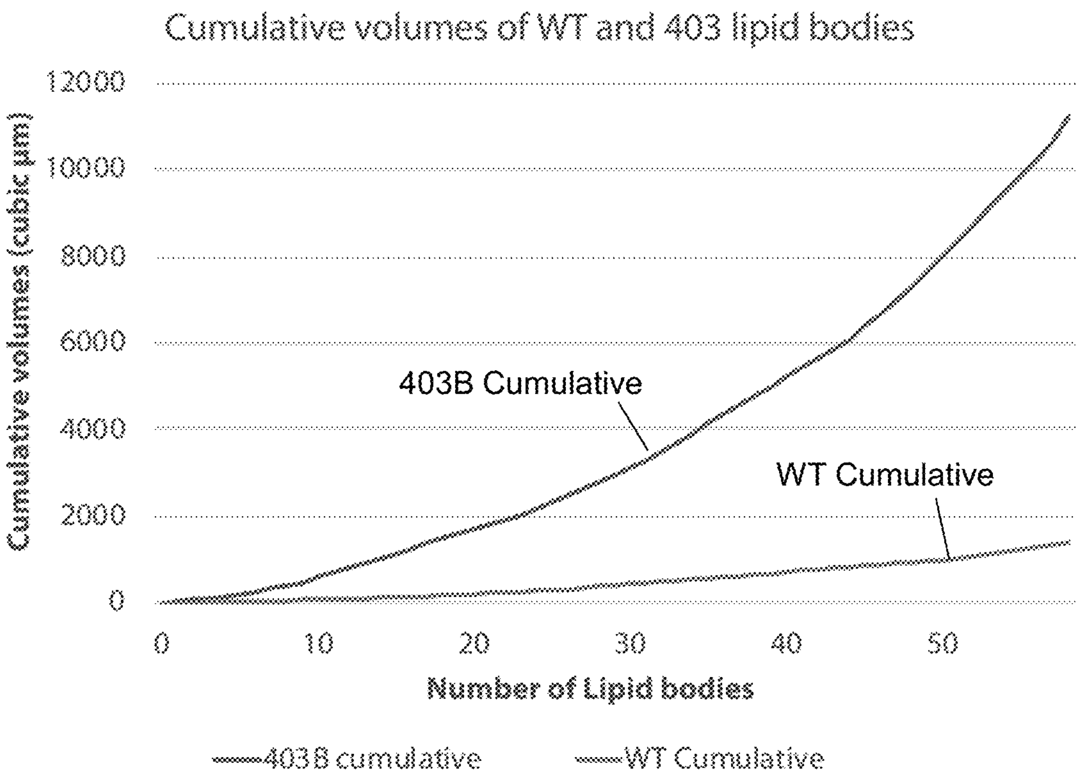
FIG. 9. Cumulative volumes of wild-type and 403 lipid bodies as a function of the number of lipid bodies from each type.

The volumes of the lipid bodies was calculated from the diameters ($4/3\pi r^3$). Because the diameter of the lipid body affects the volume as a function of the cube of the radius, the average volume of the 403 lipid bodies (174.0 $\mu m^3$) greatly exceeded the average volume of the wild-type lipid bodies (20.9 $\mu m^3$). As shown in FIG. 9, the cumulative volume of the 403 lipid bodies also greatly exceeded that of the wild-type cells.

Chloroform/methanol extractions of lipid from lipid bodies that have not been concentrated showed that the lipid body preparations have about 150 g/L lipid. Lipid body preparations having 58% w/w solids (typically condensed from the original lipid body preparations by half) have about 300 g/L lipid.

Protein concentration analyses on lipid body samples yielded between 0.588-1.58 g/L of protein. At a percent solids of about 58% w/w, the lipid body preparations have a protein concentration of about 1.18-3.16 g/L.

From the above data, the lipid body preparations have a lipid:protein ratio at a percent solids of about 58% w/w from about 250:1 to about 95:1.

The relative proportions of fatty acids in the 403 lipid bodies was determined and compared with those in the oils derived from palm oil, wild-type cells, and the 403 strain itself. See FIG. 10. The 403 oil and the lipid body oil derived from the 403 strain differed somewhat due to changes or losses in various fractions during purification of the lipid bodies from the whole cells. Both the characteristics of the 403 strain and the processing of lipid bodies makes the lipid profile different than the wild type, being observed as an increase in saturated fatty acids, and a decrease in most desaturated fatty acids. For example, in one experiment, the lipid profile from 403 lipid bodies was 42% palmitic acid (C16:0), 39% oleic acid (C18:1), 7% stearic acid (C18:0), 5% linoleic acid (C18:2), 4% palmitoleic acid (C16:1), and 3% other fatty acids. By contrast, the wild-type lipid profile (from whole cells) was 33% palmitic acid (C16:0), 42% oleic acid (C18:1), 3% stearic acid (C18:0), 3% linoleic acid (C18:2), 8% palmitoleic acid (C16:1), and 11% other fatty acids by weight.

Figure 11:
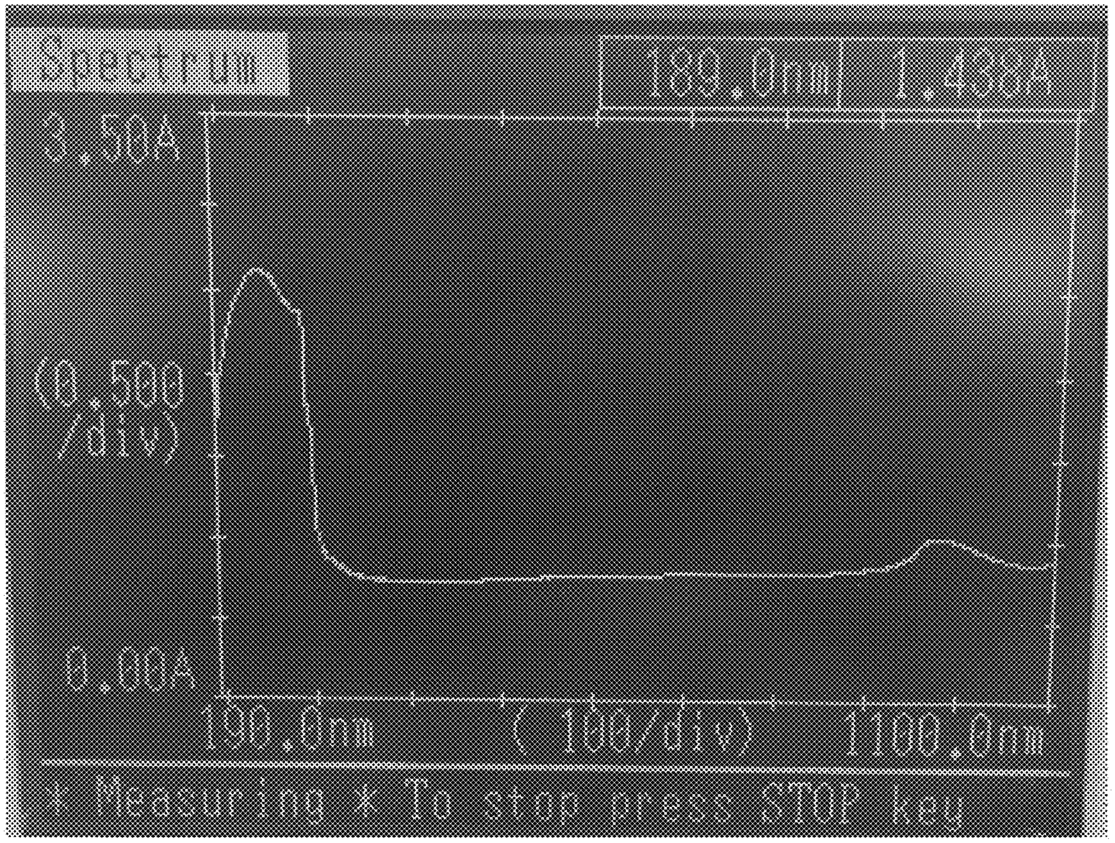
FIG. 11. UV-Vis scan of lipid obtained from a 403-strain lipid body preparation.

UV-Vis scans (190 nm-1100 nm) of 7 different lipid body preparations from the 403 strain were performed. The UV-Vis scans were essentially identical. Two peaks were present; a mild hump around 980 nm and a sharp peak (likely due to the protein present) around 230 nm. A representative scan is shown in FIG. 11.

Method for the Measurement of Residual Color in Isolated Lipid Bodies

Rationale: Lipid body preparations are made white to off white by a combination of aqueous washes at acidic and alkaline pH as described herein. Alkaline washes are particularly effective at removing residual fermentation components, proteins, and colored moieties to generate a white or colorless material.

Method: A quantitative measure of the amount of colored material in lipid bodies can be determined by extracting colored material from water-washed lipid bodies with 0.1 molar potassium hydroxide solution. The amount of extractable colored material is measured by absorbance at 400 nm in a 1.0 cm cuvette and normalized to the wet weight of packed, water-washed lipid bodies (nominally 1.0 gram).

1. Tare a 1.5 mL microfuge tube and add 1.0 to 1.4 mL of a suspension of water-washed lipid bodies. Larger tubes and larger volumes may be applied.
2. Centrifuge tubes at 13,000 to 1600 rpm for 3 to 4 min and pull off the supernatant water with a 1.0 mL syringe and needle (note: lipid bodies will form a layer on the surface); centrifuge a second time for 0.5 to 2 min and pull off the residual water on the bottom; weigh the tube plus wet pellet and subtract the tare weight to obtain the packed wet weight of lipid bodies.
3. Add 1.0 mL of 0.1 M KOH, mix well; centrifuge and remove the aqueous bottom layer. Filter through a 13 mm diameter, 0.22 μm pore size syringe filter into a fresh tube.
4. Measure the optical density of the filtered solution in a 1.0 cm path length cuvette
5. Divide the optical density by the weight of the wet lipid body pellet to obtain the optical density "units" (OD units) per g lipid body wet weight.
6.

Example

Lipid bodies from 403-strain washed once with water

| Tube | 1 | 2 | 3 | 4 | OD/g wet | |
|---|---|---|---|---|---|---|
| Tare | 0.9977 | 0.985 | 0.9896 | 0.9821 | | |
| tare + wet LB | 2.2608 | 2.2902 | 2.2884 | 2.2526 | | |
| Tare + pellet | 1.3494 | 1.3316 | 1.3258 | 1.3667 | | |
| Net pellet | 0.3517 | 0.3466 | 0.3362 | 0.3846 | | |
| OD @400 nm | 1.108 | 1.075 | 1.07 | 1.173 | Ave OD | ± SD |
| OD/g wet | 3.150 | 3.102 | 3.183 | 3.050 | 3.12 | 0.06 |

Lipid bodies from 403-strain washed with water and $Na_2CO_3$

| Tube | 1 | 2 | 3 | 4 | OD/g wet | |
|---|---|---|---|---|---|---|
| Tare | 0.9884 | 0.9882 | 0.9818 | 0.9886 | | |
| tare + wet LB | 1.5195 | 1.4835 | 1.3379 | 1.5053 | | |
| Net wet | 0.5311 | 0.4953 | 0.3561 | 0.5167 | | |
| Net pellet | 0.3666 | 0.3419 | 0.2458 | 0.3567 | | |
| OD @400 run | 0.324 | 0.324 | 0.324 | 0.324 | Ave OD | ± SD |
| | 0.88 | 0.95 | 1.32 | 0.91 | 1.01 | 0.20 |

The extracted color was reduced from 3.12 OD units per g wet wt of lipid bodies to 1.01 OD units per g wet wt of lipid bodies.

Comments:

Extraction with 0.1 M NaOH to 1.0 NaOH can release similar amounts of color. In these experiments, the ratio of NaOH solution to lipid bodies was approximately 3:1. The ratio of solution:lipid bodies can range from 3:1 to 20:1. The lipid bodies have a nominal concentration of from 15% to 55% by dry weight.

The extraction is centrifuged and the color in the aqueous layer is measured spectrophotometrically at 400 nm. Filtration prior to OD reading is performed to avoid contamination of the sample with suspended lipid bodies. If filtration is applied forcefully, the lipid bodies may fragment and yield a slightly turbid suspension. A dilution of lipid bodies in 0.1M KOH range that provides an absorbance reading in the range of 0.05 to 0.8 can provide the most accurate measurement.

The total absorbance at 400 nm is determined accounting and adjusting for dilutions and lipid body weights to yield a maximum residual color released of 3.2 OD absorbance units per gram using packed lipid bodies at 15% to 55% (by dry weight) lipid bodies. The extraction mixture yields a brown to clear solution, which when centrifuged allows the aqueous layer to be measured spectrophotometrically at 400 nm.

Results: An absorbance of 3.2 OD 400 nm per g lipid body wet weight was obtained for crude, water-washed, off-white lipid bodies. There is no minimum color specification or maximum whiteness of lipid body preparations of the invention. Very clean lipid bodies may not yield a measurable color in this quality control test.

Released residual color from 1 gram of packed crude lipid bodies was measured spectrophotometrically in a solution measured spectrophotometrically at 400 nm to quantitate the worse-case residual color remaining in the lipid bodies. The absorbance was about 3.2 Optical Density units per gram wet weight of lipid bodies.

Properties and Uses of Lipid Body Preparations at Various Concentrations

Engineered lipid bodies produced and isolated using the methods described herein form stable emulsions or suspensions when suspended in water at concentrations greater than 25% w/w solids. In approximately 75% w/w suspensions of water and, optionally, other ingredients such as excipients and stabilizers, they form a thin suspension that can be useful as a hair conditioner. When suspended at concentrations greater than 33% w/w solids, along with water and, optionally, other ingredients such as excipients and stabilizers, they form a cream suitable for application to hands. The cream is not greasy and does not leave an oily feeling upon drying—rather it leaves the hands smooth and soft. The lipid bodies form a thin flat layer on the surface of the skin which can constitute a protective coating. At concentrations from approximately 42% w/w to 66% w/w solids, which can include other ingredients such as excipients and stabilizers, the lipid bodies form a cream that can be applied to the face to protect the skin and produce a barrier to preserve moisture. At the higher solids levels, the lipid bodies can be applied in a thick layer to abraded skin, lips, chapped, abraded, cut or fissured skin surfaces to form a protective coating that can help healing when combined with bandages or that can protect against abrasion by medical devices. Application of lipid body cream can reduce itching and irritation.

The engineered lipid bodies are freely miscible with aqueous solutions and can be combined in appropriate ratios with various other agents or ingredients. The agents or ingredients can include excipients and stabilizers. Examples of suitable agents or ingredients include glycerol, hyaluronic acid, vitamin E acetate, sodium benzoate, gluconolactone, retinol, benzoyl peroxide, hydrocortisone, clotrimazole, ketonazole, ecamsule, avobenzone, oxybenzone, titanium dioxide, sulisobenzone, zinc oxide, aloe vera, and others.

Exemplary Cream Preparation

An exemplary cream made from the 403 lipid bodies is made with the materials shown in Table 5. The cream is in the form of a lipid paste. The paste has a pH of 4.5. and is stabilized with an antioxidant agent and an anti-microbial agent in glycerol (10%) in physiological saline. The final cream concentrate is adjusted to 40-60% w/w solids with 10% w/v glycerol and composition stabilizers by evaporation.

TABLE 5

Materials.

| Description | Vendor | Units | Use |
|---|---|---|---|
| Commercial-grade or food-grade yeast extract | Yeast supplier (e.g. Lallemand FNI 100 ag, agglomerated, dry, baker's yeast-sourced | g/L (dry wt equivalence) | 40 g/L × fermentation working volume |
| Cerelose, glucose-hydrate, GMO or non-GMO, | Tate and Lyle or CPC | g/L dry wt | Fed-batch starting at 2.5 g/l/hr increasing until a maximum OD 600 nm. The second phase is a high cerelose feed that triggers lipogenesis |
| Sea Salt (pure food grade or better) | Kirkland, Fisher or equivalent | 0.15 M salt solutions | Used in washes at alkaline and acidic Ph |
| Vitamin E-acetate | Fisher or equivalent, (USP or food grade) | 1.5-2% (w/v) in the final product | 0.45-0.9 grams per liter of fermentation depending on yield |
| Citric Acid | Fisher or equivalent, (USP or food grade) | 3% | 0.15 M concentration in final washes and product |
| Sodium Hydroxide | Fisher or equivalent, (USP or food grade) | As 1-5 N solutions | Used as a 5 N solution |
| GeoGuard-Ultra or D-Gluconolactone SB | Lonza | 2% | Concentration in final product |

TABLE 5-continued

| Materials. | | | |
|---|---|---|---|
| Description | Vendor | Units | Use |
| Soy Peptone | Domo or equiv. | 20% in YPD | Shake flask stage, only |
| Antifoam | Antifoam 204 or equivalent, non-silicone | Sigma | Usage of ~0.1 mL/liter |

Fermentation Process Summary

The 403 strain can be used to produce a lipid body paste that is formed in a two-stage aerobic fermentation. An inoculation level of 10% v/v is desirable but not essential and a synchronized culture is not required for triggering secondary metabolism for lipid synthesis.

The first stage of the fermentation is a primary growth phase, which is carried out through the flask, seed, and early production stages of yeast proliferation. The optimum cerelose feed rates start at 2.5 g/L/hr at the outset of the fermenter with the feed rate building during rapid cell division. The secondary lipogenic phase is triggered by additional carbon in the form of cerelose, which is used to further promote lipogenesis of the cells under reduced aeration. The secondary stage is characterized by a lower oxygen demand, slower growth rate and intracellular lipid formation as large lipid bodies that can be seen microscopically at 400×.

Inoculum Preparation Procedure

An inoculum composed of the 403 strain is prepared from a working cell bank (WCB). The culture is thawed from a frozen WCB vial or an isolated colony on a YPD plate that was generated from a single passage from the WCB. Growth is in modified-YPD medium [20 g/L soy peptone, 20 g/L yeast extract and 40 g/L dextrose] in a 100×500 mL baffled shake flask at 28 C at 300 rpm or faster.

After 48-56 hours, the culture is examined for pure culture status microscopically and then split into two 100×500 mL baffled shake flasks, which are grown at 28° C., at 300 rpm or faster.

At 48-56 hours at 28° C., the flasks are measured for Optical Density (OD600 nm). An $OD_{600}$ in the vicinity of at least 40 is expected. Both flasks are checked microscopically and, if pure, then both flask cultures can be used in the next scale, which can be a 12-Liter production bubble bottle containing 6-liters of medium containing only cerelose and yeast extract for product preparation.

If the 12-liter bottle or intermediate fermenter is still part of the seed train, then expansion with modified-YPD medium is preferred. Other options and larger volume seed fermenters are expected to grow well under any closely related conditions.

Additional scale-up steps use modified-YPD medium. The objective is to achieve at least a 10-20% v/v inoculum for the production fermenter. The best seed stage process will be equipment and facility dependent.

Product stage fermentation uses a simple medium containing only cerelose and yeast extract.

Fermentation Overview

No extraordinary interventions, feeds or control cascades are required. Antifoam (0.5 mL per liter) is preferred during the proliferation stage. Having antifoam control available during first scale-ups will be helpful to determine how much, if any, additional antifoam is required.

With a 10-20% v/v inoculum, proliferative growth under aerobic conditions (1 vvm) is characterized by a declining Ph, dropping to about pH 4.0. but no less than pH 3.0. A generation-time of 6-8 hrs during the primary proliferative stage lasts for up to 3 days and there is consumption of both initial carbon and nitrogen by the yeast. An increasing glucose feed rate based on cell density is desired. Specific feed parameters will be equipment and facility dependent. If the glucose (cerelose) becomes exhausted, then the DO will rise but in most cases this effect is not seen, and it is easily reversed by increasing the cerelose feed rate.

The basic production medium is a yeast extract 40 g/L (Lallemand FNI 100ag agglomerated) and a cerelose feed starting at 2.5 g/L/hr which increases in the second stage of the fermentation until consumption of a total dextrose 350 g/L (Cerelose or dextrose) is complete or until growth slows to less than 1 generation per day. During the fermentation, the pH will decline from 6.5 to 4.5 and can be adjusted with NaOH (not $NH_4OH$) as appropriate.

Generally, a suitable final OD 600 nm of above 100 is reached before glucose exhaustion. With proper adjustment of the growth phase and lipogenic phase, maximum OD 600 readings in excess of 170 can be achieved. If glucose exhaustion is approaching and the OD is sufficient, then it is acceptable to move to the lipogenesis phase earlier than 3 days.

Conversion to the lipogenesis phase can be achieved in several ways. First, the cells can naturally transition into lipogenesis as the cell density increases and oxygen becomes limiting. Second, the cells can be induced to transition by limiting the amount of nitrogen available for growth while providing excess of a readily assimilated carbon source. For example, the excess carbon can be achieved either through the addition a bolus or surfeit of glucose monohydrate (cerelose) up to 350 g/L under reduced aeration (0.25 vvm) or by the gradual addition of cerelose at a rate in excess of its consumption. Following rapid cerelose addition the pH will typically drop so the pH can be adjusted back to 6.5 with a NaOH (other options for adjusting the pH may be acceptable). Adding a carbon source results in a carbon-to-nitrogen ratio ~20:1 or greater. The carbon source may be in excess at the end of the lipogenic fermentation process at 48 hours, and growth may be slower with expected generation times of about 24 hours per cell division during this phase. Alternately, the addition of carbon sources may be tapered off near the end of the fermentation. As nitrogen is depleted or restricted, cell budding will cease, and the cells will become larger. At the end of the fermentation, it is most desirable for >80% of the cells to be homogeneous in size and for their diameters to approximate 10 μm or greater. As cell division stops and cell enlargement continues, the OD 600 will drop while cellular lipid content increases.

During lipogenesis, respiration does not cease, but the capacities of cells to take up oxygen can be limited by the oxygen concentration and residual concentrations of oxygen in the medium can range from less than 1% to greater than 35% of air saturation. Higher cell densities and growth rates can be achieved by increasing the oxygen tension either by pressurizing the bioreactor or by adding supplemental 02.

Contamination checks are done microscopically and verify that the fermenter content is a pure culture. Microscopically, the production of large lipid bodies can be seen in each cell, reaching more than 70% by volume per cell, but in some cases encompassing up to 95% of the intracellular volume.

Hydrolysis Process Steps

Following fermentation cell hydrolysis may be carried out in a separate reactor or in the bioreactor itself. The buoyancy of the lipogenic cells enables partial separation of the cells from the bulk of the medium simply by allowing the culture to stand without agitation. The cells will rise to the top of the reactor and the spent medium can be drawn off either for disposal or recycle. Aside from reducing water and waste disposal and savings in medium constituents, it also reduces the amount of acid required for hydrolysis.

While cells and medium are still in the fermenter at the final volume the oxygen supply is shut off and the agitator is left on. Hydrolysis can be conducted by adding sulfuric acid to 0.25 M or phosphoric acid 0.5 M, followed by heating to a temperature of 75 to 121° C. while mixing for 2 hours. At the lower temperature, heating is continued for up to 18 h and at the higher temperature, the heating can be as short as 1 h. Mixing may be intermittent or absent. Other methods of cell hydrolysis are described elsewhere herein. The hydrolyzed cells are then allowed to stand at 90° C. for an additional 4 to 22 hr with the impeller and air off. During this latter part of the acid hydrolysis, the lipid bodies are allowed to float to the surface.

After the cream rises, the bottom culture medium and cell wall hydrolysate are removed by siphoning or decanting, measured, and recycled or discarded. An estimated volume of the lipid body suspension is made, which is useful information needed as an in-process control and for establishing the approximate wash volumes that will be needed in the next washing steps.

In the low pH wash steps lipid bodies float to the top of a 10-liter bottle in 2 to 4 hours. During the subsequent alkali wash, steps may take up to 6 hours and the rise rate is approximately ⅓ the rate observed at lower pHs.

Following hydrolysis, the lipid bodies are still tan, and the solution is still acidic. The lipid bodies are washed with water in a 10× total dilution after being cooled to 20° C. The goal is to remove cell wall debris and the brown/tan color from the cream.

In the water washes, agitation can be used to break up the lipid bodies to suspend and wash the cream layer. The lipid bodies or cream will rise at initial rates of about 0.25 to 0.5 inches per minute followed by slower rise rates as the lipid bodies accumulate at the top of the vessel. The greater the initial dilution, the faster the initial rise rate. During the water wash, the cream may be taken through rapid short cycles (i.e. after the lipid bodies rise to the top 33% of the volume) or they may be left overnight. Water washing totaling 10× volumes is performed with one or more dilutions with either one 10× exchange or multiple exchanges at lesser volumes. It is acceptable for the flotation to be facilitated by moving the cream layer into a horizontal separation tank (e.g. whey/curd tank) that can speed-up the subsequent flotation steps.

Alkali Washes

The water-washed cream is then washed with alkali in a 10× or greater fold dilution of the cream layer in water adjusted to pH 11.7 with a sodium hydroxide stock solution that is between 1-5 N. FIG. 12D shows the release of additional brown color with the first alkali wash and the whitening of the lipid bodies.

The alkali washes are repeated at pH 11-11.2 as needed until the absorbance at 400 nm is equal to background absorbance of a buffer blank and visual appearance of the lipid bodies is no longer tan. Multiple washes may be required to remove all of the brown color.

Care should be taken during the alkali washes. Alkali at pH 11.7 above 20° C. can hydrolyze the triglyceride fatty acid ester linkages and result in "soap", which forms bubbles. Slow addition of the sodium hydroxide stock solution while mixing is preferred. Wash solutions should be introduced with minimal of air entrainment to avoid bubble formation. Foaming or bubble formation may denature the lipid bodies on the bubble surface, which results in lower yield and lesser quality.

In all alkali wash steps, the sodium hydroxide stock solution is added slowly with agitation at a cool temperature of ~20° C. To reach a 10× wash dilution, more cycles at lower dilution may be required (e.g. two 5-X dilution washes or three 4× dilution washes) to reach the 10×. Flotation of the cream in a 5-X dilution should take 2.5 to 3 hours per cycle at a height of 3 feet during the alkali wash step.

The bottom solution after each cycle is measured and discarded and the floating dilute cream is retained. Removal of the first pH 11.7 wash (minimum of 10× wash) followed by a second 5× or greater dilution will reduce the pH to 11-11.2. A pH of 11-11.2 using a sodium hydroxide solution (1-5 N) is maintained as needed in subsequent washes to achieve a clear bottom without brown color Adding the alkali too fast will cause loss of lipids due to saponification. This will contribute to a white hazy or white turbidity in the discarded bottom once the brown color is gone. There is no corrective action for this phenomenon.

pH Adjustment to pH 4.5 and Buffer Exchange

The lipid bodies achieve a white to off-white color due to the alkali washes. After the alkali washes, the pH is adjusted to 4.5±0.1 with 2 N citric acid and diluted to achieve a 5× dilution. Mixing is performed to suspend the cream, then the cream is allowed to stand to achieve lipid body flotation. The bottom layer is siphoned off, measured, and discarded as in earlier steps. The approximate cream volume is determined.

Once a clear bottom is achieved, it is important to reduce the pH to 4.5 as soon as possible. Lipid bodies should not be left at pH>11 for more than 12 hours at 20° C.

Composition Buffer Exchange, Safety Screening and Bulk Product Final Formulation Next, the washed cream is diluted 6× with a stock bulk product composition buffer at pH 4.5 that is made with 0.15 M sodium chloride (physiologic saline 8.8 g/L), containing 3% w/v sodium citrate, 0.25% w/v sodium benzoate, and 10% w/v glycerol. The suspension is then made acidic to exactly pH 4.5+/−0.1 using citric acid. Mixing is continued for at least 30 minutes and the final pH of 4.5+/−0.1 is verified and adjusted if needed with NaOH or citric acid (as needed) to achieve a pH of 4.5. Perform this correction carefully and only once.

Protective screening is performed. The watery dilute cream is passed through a screened funnel with a tight mesh 100-500 microns (0.5 mm) to ensure removal of sand, glass shards, metal particles and other particulates or globs. The screened suspension is then centrifuged or dried in a scraping bowl vacuum drier, and the final pellicle is harvested in the next step.

Recovery of a concentrated paste as a pellicle involves centrifugation in a swinging bucket centrifuge or decreamer or a bowl scrapping vacuum drier. If a vacuum drier is used, the composition buffer should be adjusted so that at the end of the evaporation the concentration of glycerol is up to 10% w/v and other components return to the correct concentration when the cream achieves a 40% w/w solids concentration. If using centrifugation, then the centrifugation should be about 7000 rpm (approximately 8-10,000 g) for 20-30 minutes conditions for other or larger equipment are not known at this time and will be facility dependent. The harvested concentrated pellicle should be at or slightly exceed 40% w/w solids and 60% w/w water.

The concentrated pellicle is weighed and 2% GeoGuard-Ultra (Lonza) or equivalent (D-Glucolactone SB) and 1% vitamin E-acetate are added, and the cream is checked and adjusted if necessary to pH 4.5+/−0.1 with NaOH (1N) or citric acid (1N).

The solids concentration of 40% w/w is measured and any downward adjustments in concentration can be made using a stock final composition buffer at pH 4.5 containing physiologic saline, 3% w/v sodium citrate, 10% w/v glycerol and 2% w/v GeoGard-Ultra or equivalent. This adjusting buffer specifically excludes additional Vit-E-acetate.

The harvested pellicle is weighed and should have a consistency thicker than yogurt and thinner than whipped cream cheese. The color should be white to off-white and a microscopic purity (under 400× or 1000× power and photographed) is checked for particles and contaminants (e.g. gross cell wall fragments).

If the harvested concentrated pellicle is weighed and is too thick then the final product will be adjusted to 40% w/w/ solids and 60% w/w water, using a composition buffer at 4.5 containing 0.15N sodium chloride (physiologic saline 8.8 g/L), 3% w/v sodium citrate and 2% w/v GeoGuard-Ultra [D-gluconolactone SB (sodium benzoate)].

The paste can be uniformly mixed for 30 minutes followed by pasteurization in an air-tight container at 75° C.+/−10° C. for 2 hours, prior to bottling. If a scraping bowl evaporator is used, then all of these formulation steps can be performed in that unit.

The material is then allowed to cool to room temperature in a closed container in a laminar flow hood or other suitable clean area prior to packaging. Using sterilized tubing and a peristaltic pump, appropriately sized containers are filled with the finished cream using sterile bottles polystyrene bottles or sanitized pales. An air tight seal that is robust enough for shipping is preferred for the packaging. Conventional 5-gallon food-grade pales many be appropriate at approximately 19 Kg per pale.

Notes

The foregoing process is based on production runs from 3 to 45 liters (working volumes). The total quantity of reagents will be scale dependent. Where possible, materials are defined as units per liter. The product and process are robust across a range of fermentation conditions.

The recovery process takes advantage of the unique low-density properties of the cells and lipid bodies. The process was developed to minimize mechanical requirements and centrifugation steps. Alternative cream separation technologies may be applicable.

The product is resistant to heat and freezing when maintained in an air tight container.

The product is sensitive to complete drying, which can irreversibly change the product.

Recovery of Yeast Oil

The lipid bodies from the 403 strain can be used as a source of yeast oil. Recovery of yeast oil from Lipomyces and other oleaginous yeast has posed a significant challenge to the production of yeast derived lipids and the ability to make a palm oil substitute. In one embodiment, the washed large crude engineered lipid bodies can be dried by any manner, and due to their large size and high oil content, a significant portion of yeast oil is unexpectedly released without the use of solvents or mechanical extraction. For example, a clear oil can be collected by spray drying lipid bodies. In another example, a thin layer of lipid bodies is spread onto a surface and sloped surface at 50° C., from which the free oil flows as it is expressed from the drying lipid bodies. The elevated temperature is employed because yeast oil, like palm oil, is a solid at room temperature.

Solid and Semi-Solid Lipid Body Preparations

We unexpectedly generated a unique solid byproduct associated with the residual lipid composition that emerges after drying the 403 lipid bodies. This was obtained after a thin layer of lipid bodies were spread onto a sloped surface and incubated at 50° C. after oil expression. The structure exists with or without yeast oil removal, and it can be used as a thermally stable wax with a temperature tolerance of at least 200° C. before deforming or oxidizing. This lipid material has an unexpectedly high resistance to thermal deformation and oxidation and is useful as a lubricant or specialty packing material, as well as for a range of other commercial and industrial applications, particularly in the area of sustainable lubricants.

In another embodiment, when hydrolyzed or partially hydrolyzed and washed lipid bodies are incubated for 12 to 24 h in 50 to 65° C. in alkali at pH 11.2 to 11.7, a temperature-dependent polymer is extracted from the material. When cooled to less than 25° C., the extracted polymer turns the extractive, alkaline aqueous solvent into a gel. When the gel is heated to greater than 45° C. and the pH is adjusted to less than 8.4, the gel disperses.

Example 2

Exemplary Base Compositions of the Invention

An exemplary base composition of the invention comprises a stable, moisturizing composition, which is either used alone or used as a predominant carrier of other active ingredients or agents in compositions comprised of lipid bodies or lipid body derived components. In one embodiment (1A), the inventors developed a lipid body cream at a defined water content for further compositions using Lipomyces lipid bodies. The lipid bodies were harvested from cells of genetically engineered *Lipomyces starkeyi* strain XYL-403 or XYL-12Lx13L or equivalent strains and were cultivated in bioreactors, as disclosed above. The processing can provide range of qualities from the crudest composition through subsequent processing steps up to the purest grade of lipid bodies. Several grades of lipid bodies are produced during processing and can be used to meet various requirements of specific compositions of the invention. The lipid bodies can be crudely isolated and formulated or highly purified and formulated as required for the specific purpose. For example, an industrial lubrication composition containing lipid bodies as a lubricating ingredient will not require the same level of purity and control expected when lipid bodies are used for an oral or parenteral drug composition.

For simplicity, one embodiment of making purified lipid bodies in the compositions of the invention is presented. In this embodiment, processed lipid bodies are formulated in phosphate buffered saline at pH 6.5-7.5 and sterilized with heat to make a composition that is essentially a simple solution suitable for pharmaceutical purposes.

In another embodiment of the present example, the hyper-lipogenic engineered yeast were grown in fermentations from 2 to 45 liters and the post-harvest process leading to usable lipid bodies. Starting conditions at harvest and yeast cell wall hydrolysis resulted in an initial dry weight that was 26.54% solids in 372 grams of raw lipid body suspension that was stabilized with respect to microbial contamination with citrate and sodium benzoate. The lipid bodies were washed to remove fermentation contaminants and yeast proteins. Final lipid bodies were measured by dry weight and the appropriate amount of excipients were combined as a slurry of 12 g glycerol, 7.2 g sodium citrate, 4.8 g gluconolactone, 2.16 g sea salt, and 1.2 g vitamin E acetate in 100 mL of water to provide the correct final concentration of each excipient once the mixture reached the final lipid body concentration of 52%. During the excipient introduction into the composition or during excipient measurements, the slurry was mechanically mixed at 50 to 60° C. to ensure homogeneity. The volume of the excipients for this single iteration was 88.1 mL. An HPLC check of the composition slurry showed 119 grams/liter of glycerol as a marker for the progress of the evaporation. The lipid body and excipient suspension was evaporated at 50° C. under gentle agitation on a rotary shaker set initially at a slow speed of about 100 rpm to avoid loss through splashing or sloshing. The net wet starting mass of 485 g took 6 hours to reduce to the target of 211 g. The final material was approximately 52% yeast lipid bodies containing about 5% glycerol, 3% sodium citrate, 0.9% sodium chloride from sea salt, 2% D-glucono-lactone, 0.2% sodium benzoate, and 0.5% vitamin-E acetate at a pH of about 4.5. Final checks on dry weight were done in duplicate using a weight to weight method, and a single HPLC analysis was performed to verify the excipient concentrations in which an arbitrary amount of cream near 0.100 grams was placed into a tared microfuge tube and subsequently combined with a calculated amount of water to achieve a 1:10 dilution. This was vortexed and dispensed into an HPLC vial through a filter without centrifugation. The glycerol content was 5.3%, the nominal value being 5%. The composition of the invention comprises lipid bodies in combination with stabilizing ingredients to impart a durable shelf-life and commercial utility in a wide range of industries and markets. The compositions can be adjusted with additional additives and variable amounts of additives to create a stable useful product for any specific purpose.

Composition 2A is a composition that comprises a physiological level of saline and other excipients in a 52% lipid-body composition for use in personal-care and topical drug products.

Composition 2A

| Ingredient | Final Amount [a] |
|---|---|
| Yeast Lipid Bodies | 52% |
| Glycerol | 5% |
| Sodium chloride | 0.9% |
| Sodium citrate | 3% |
| D-gluconolactone | 2% |
| Sodium benzoate | 0.2% |
| Vitamin E acetate | 0.5% |

[a] by dry wt

Composition 2A is a stable composition of the invention that is suitable alone or in combination with other ingredients, drug mixtures, cosmetics, and other compositions of the invention. The composition described in this example has been tested as a hand cream, a face cream, and a carrier for various drugs.

Composition 2B is a composition of the invention that contains glycerol and other excipients in a 52% lipid-body composition for use in personal-care and topical drug products. This composition is identical to Composition 2A except sodium chloride was replaced with water or omitted. This composition is an example of how a modification of Composition 2A can be made, when physiological saline is not needed for incorporation of a drug or active ingredient, depending on the specific product or market of use.

Composition 2B

| Ingredient | Final amount[a] |
|---|---|
| Yeast Lipid Bodies | 52% |
| Glycerol | 5% |
| Sodium citrate | 3% |
| D-gluconolactone | 2% |
| Sodium benzoate | 0.2% |
| Vitamin E acetate | 0.5% |

[a]by dry wt

Composition 2B describes a basic composition used for combinations of other ingredients and other compositions of the invention. Composition 2B was tested as a face cream, and it proved to be tolerated and well received by the subjects.

Composition 2C

| Ingredient | Final amount [a] |
|---|---|
| Yeast Lipid Bodies | 52% |
| Glycerol | 3% |
| Sodium citrate | 3% |
| D-gluconolactone | 2% |
| Sodium benzoate | 0.2% |
| Vitamin E acetate | 0.5% |
| Modified starch | 2% |

[a] by dry wt.

Composition 2C is identical to 2B except that 2% (by dry weight) modified starch (Cargill Star Power Design) was used to inhibit long-term separation by flotation of the lipid bodies in the compositions of the invention. Additionally, glycerol levels were lowered to 3% to reduce transient stickiness as the compositions dried on the skin. This composition comprises a composition that is modified to help maintain a homogeneous mixture and enhanced shelf-life when the composition is prepared for consumer goods, topical drug delivery or any other composition where long-term resistance to component separation or flotation is required. Modifications of this composition are possible depending on the specific consumer product or drug product or markets being addressed by the product. For example, Composition 2C was mixed with lidocaine, an analgesic, which produced a smooth feeling cream that dried and sealed the area of skin that it was applied. Composition 2C describes a basic composition of the invention that can be used for combinations of other ingredients and other compositions.

Example 3

A 52% yeast lipid-body composition of the invention was shown to have direct utility when tested as a face cream on humans. Human test data was obtained using Compositions 2A, 2B, 2C and 3. The data demonstrate the utility of a 52% yeast lipid-body composition of the invention as described in Compositions 2A-2C and 3, when applied to human skin. Initial testing in humans is summarized as follows. The base skin composition comprised of lipid bodies was self-administered by health subjects and the data set was obtained from 579 exposures in 21 individuals in the age range of 28 to 65 with an average use of 27.6 skin treatments per subject. In the various compositions comprising lipid bodies that were stabilized at pH 4-5, testing in human volunteers was conducted as a face cream composition.

This trial suggested that the compositions of the invention were well-tolerated by subjects, who had a general satisfaction with the moisturizing benefits of the composition as a cosmetic skin care product. Any number of variations of the present embodiments can be used directly or used as a base composition for the incorporation of topical or systemic drugs and other active ingredients depending on the specific purposes of the desired compositions.

| Composition 3 | |
|---|---|
| Ingredient | Final amount by dry wt |
| Yeast Lipid Bodies in Water | 52% |
| Glycerol | 5.0% |
| Sodium chloride (optional) | 0.9% |
| Sodium citrate | 3.0% |
| D-gluconolactone | 2.0% |
| Sodium benzoate | 0.2% |

The compositions described in Compositions 2A-2C and 3 were the base compositions that included additives for maintaining long-term cream moisture and microbial stability at room temperature.

Example 4

Yeast XYL-403 was grown under standard fermentation conditions. The yeast will grow under glucose fed-batch conditions or other acceptable carbon sources until a cell concentration has reached 100 or greater optical density units at 600 nm, then the carbon feed is increased until the accumulation or oil in lipid bodies inside of the cell exceeds 50% of the cell volume and, preferably, as much as 85% or greater of the volume inside of the hyper-lipogenic cells. The high-lipid-containing cells can be hydrolyzed with phosphoric acid and the lipid bodies isolated as described herein or the cells can be homogenized to release yeast oil, which is useful as an additive to some compositions of the invention or as a stand-alone yeast oil product for applications that currently use tropical palm oil or similar oils. The composition can comprise lipid bodies along with additional yeast oil or any other modifying oil to cause the composition to be more hydrophobic and to impart a lasting oil sensation on the skin that some individuals find desirable.

As shown in Composition 4A below, compositions of the invention can contain yeast oil, which is a palm-oil-biosimilar. The completed fermentation, containing yeast with internal lipid bodies can be homogenized with a pressure drop homogenizer at an appropriate pressure to lyse the cells and rupture the internal lipid bodies to release the yeast oil into the culture broth. Yeast oil is separated from the homogenates by mixing the material with an equal volume of n-hexane or preferably, iso-hexane, pentane or other appropriate solvent. The yeast oil enters the solvent, which is isolated and then evaporated to produce a pure yeast oil that can be used directly on the skin or added to various compositions that may contain lipid bodies. The yeast oil is essentially water-free and solvent-free following a period in which the oil is held at a temperature between 60° C. and 90° C. to meet residual solvent and moisture specifications. The yeast oil and or lipid bodies can be used directly as a moisturizing agent on the skin in the compositions of the invention.

In the present example the isolated yeast oil composition was used with or without additional stabilizers such as 0.25% vitamin-E acetate as an antioxidant. This yeast oil alone or in compositions of the invention can be used directly as a moisture retention agent and a lipid replenisher for the skin.

| Composition 4A | |
|---|---|
| Ingredient | Final amount by dry wt |
| Yeast Lipid Bodies in Water | 52% |
| Glycerol | 5.0% |
| Sodium chloride (optional) | 0.9% |
| Sodium citrate | 3.0% |
| D-gluconolactone | 2.0% |
| Sodium benzoate | 0.2% |
| Yeast oil from lipid body containing yeast | 0-40% |

When applied to the skin, the combined lipid bodies and yeast oil composition is associated with a supple appearance and significant water repellence for human volunteers who repeatedly used this product composition and who have sensed a smoother skin. The composition comprised of lipid bodies is useful for the protection of skin that is exposed to weather, frequent washing (dish pan hands) or any other consumer or drug product where a protective oil or increased hydrophobicity is required. Any increased level of desired oil-feel can be accomplished by adding various amounts of yeast oil to the compositions of the invention. Additional amounts of added yeast oil in the compositions of the invention can be desirable depending on the specific requirements of the consumer product, industry or market. Compositions of the invention containing added yeast oil were found to be desirable by human test subjects when used as a skin or face cream.

Composition 4B is a composition made only from the yeast oil component of lipid bodies where the composition is modified with increased oil relative to Composition 4A up to the point of containing essentially only the yeast oil component of lipid bodies. The example compositions shown below are with and without Vitamin-E acetate as an antioxidant. This composition comprises the yeast oil component of lipid bodies, where a product composition that is very water resistant is required.

| Composition 4B | |
|---|---|
| Ingredient | Final amount by dry wt |
| Yeast Oil | 99.95% |
| Vitamin E acetate | 0.05% |

Alternatively, the composition can be prepared without an antioxidant, as shown in Composition 4C:

| Composition 4C | |
|---|---|
| Ingredient | Final amount by dry wt |
| Yeast oil | 99.95% |

The embodiment of Composition 4C was found to be desirable as a lipid which melts at body temperature and is a solid at room temperature. The palm oil biosimilar nature of the yeast oil is useful in many applications that currently use tropical palm-oil.

In an embodiment such as Composition 4D, lipid bodies will provide a sealant film. In this embodiment a composition is processed the same as Composition 4A, except the resulting composition contains both yeast oil component of lipid bodies that are mixed 1:1 or 1:2 or any other ratio with lipid bodies in the composition of Composition 4A.

| Composition 4D | |
|---|---|
| Ingredient | Final amount by dry wt |
| Yeast Oil | 50% |
| lipid bodies | 26% |
| Glycerol | 2.5% |
| Sodium chloride | 0.45% |
| Sodium citrate | 1.5% |
| D-gluconolactone | 1.0% |
| Sodium benzoate | 0.1% |
| Vitamin E acetate | 0.25% |

Yeast oil was added to the composition described in Composition 4A and mixed 1:1 with a 52% lipid-body composition to produce a composition that contains 50% yeast oil and 26% lipid bodies with the remainder of the product composition being composed of water and stabilizing excipient as described in Composition 2A. The composition is a blended product that was about 50% yeast oil and 26% lipid bodies. This blended composition can be used directly as a moisturizing agent on the skin and is associated with the appearance of fewer fine wrinkles of the skin as observed by the feedback of 20 human volunteers, who used the product over a period of several weeks. Additionally, this composition can be used as a carrier of hydrophobic drugs in topical and oral applications and in many other applications, products, and markets.

Example 5

Properties and Utility of Creams

In a preferred embodiment the lipid bodies are made into creams containing yeast lipid bodies at sufficient concentrations that will feel smooth when applied to the face, hands or other parts of the skin. The compositions that are prepared as creams with a lipid-body concentration at or above 52%, referred to herein as Composition 5, have been applied to skin and these compositions of the invention dry relatively quickly, typically in less than 5 minutes. Within that time, the yeast oil plus moisture components of compositions are absorbed into the skin. The exterior shell-like structure of the yeast lipid bodies are composed of a thin layer of proteins, phospholipids, glucan-like structures, and other constituents that form a microscopically thin protective layer over the lipid core of the lipid bodies. The emptied lipid body shells form a durable barrier, which can be visualized and quantitated using skin peel methods and a microscope. The duration of retained protection is greater than 50% by area of treated skin at 10 hours as observed in skin peel testing.

When the lipid bodies in various compositions of the invention are applied on the surface of the skin, the moisture and oil are absorbed by the skin and the external shell-like structures of the lipid bodies collapse into pancake-like structures that aggregate as a film to form a protective seal over the skin. This layer along with the oil and other composition constituents can be very soothing on chapped hands, sores, or abrasions. These creams are suitable for use as a base composition for a wide number of topical medicines, cosmetics, personal care products, consumer goods and industrial goods of all type and many other applications, particularly when a durable sealant property is desirable. Here we focus on examples of how the lipid bodies can enhance skin care products, keeping in mind that these are best examples for base composition of many other products using ingredients that can be mixed into the creams having the described sealant properties.

Composition 5 and the other compositions containing lipid bodies are useful when applied to chapped hands or sun-burnt skin or burnt skin. Dry, chapped hands resulting from frequent washing can become irritated, red and sore due to repeated washing or exposure to organic chemicals such as ethanol, acetone, soaps and other agents. Application of yeast lipid body or lipid body plus yeast lipid oil-based compositions can greatly ease itching and soreness of skin irritation. In recent months, the long-term wearing of face masks, nasal accessories on CPAP machines and other areas of direct skin contact by abrasive materials are treatable with the compositions of the invention.

In Composition 5, and other compositions of the invention, a composition containing lipid bodies is useful as lip balm and for potential with or without anti-viral or analgesic drugs for cold for cold sores. Cold sores on lips can often appear in winter months when the skin is exposed to dry air and other irritants. Application of a high concentration of yeast lipid body or yeast lipid oil creams can greatly soothe itching and can be formulated with antiviral compounds or analgesic agents for pain treatment, for example, gabapentin (Nerontin), lidocaine, benzocaine, and others. A preparation of lipid bodies Composition 5 and other compositions of the invention are useful for the treatment of fissures. Mucosal membranes can develop fissures or cracking due to dry air or other irritations. Application of a layer of yeast lipid body or yeast oil-based compositions can soothe itching and promote healing of irritated or inflamed skin. Post shaving application of the compositions of the invention have also proved satisfactory to human subjects in reducing irritation.

Composition 5 and other compositions containing lipid bodies are useful as a treatment for burns and sunburns. First degree burns and sunburns causing redness and irritation can be soothed by the application of a yeast lipid body or yeast oil cream. They are particularly effective with first and second degree burns in which the skin blisters and peels. Additionally, the lipid bodies can be loaded with hydrophobic antifungals, such as fluconazole and other for the treatment or prevention of fungal infections, which are common with severe burns.

Example 6

Examples of Stabilized Compositions

A range of embodiments are described in this example. The lipid bodies and associated component compositions and applications listed above in the invention can be formulated into the stand-alone basic compositions listed below. The best examples of various practical base compositions use antimicrobial stabilizing ingredients in compositions based on lipid bodies.

Many variations to the basic compositions are possible. The following is not intended to limit the range of the compositions of the invention nor to limit the range of product areas addressed by the invention.

The options for various compositions are assembled as a suspension of yeast lipid bodies and information about the starting dry weight and the target concentration, then the final composition preparations are dehydrated to hit the desired final composition targets for all ingredients.

Lipid body concentrations around 20 to 25% solids are further concentrated by evaporation using shaker trays with bowls, or various mixing tanks, or vacuum mixer-driers that can be used to achieve the desired evaporation. The general method to achieve final compositions is evaporation, which will concentrate lipid bodies to a final concentration that is about 50% to 52% by dry weight not including other excipients.

The evaporation bowl or container is mixed at 50 to 350 rpm at 55 to 60° C. either at atmospheric pressure or under partial vacuum in order to concentrate the solids to a final target concentration of 50% to 52% plus the weight (not including) of various excipients for a final dry weight that is 8-12% or higher, depending on the specific additives used in any of the following examples and steps: The yeast lipid body suspension is added to the bowl based on its initial dry solids content and the total wet weight is determined. The total solids is calculated as a product of the percent solids and the total wet weight; Glycerol, anhydrous citric acid and tri-sodium citrate trihydrate along with Polysorbate 80 and other ingredients can be mixed into a concentrated solution and added together in a predetermined ratio; Glucuronolactone and vitamin E acetate are added separately as powders; The mixture is evaporated to a final weight that will yield the following mixtures.

Composition 6A

| Component | Amount (Fraction) |
|---|---|
| Lipid body solids | 0.487 |
| Yeast oil supplement | 0 |
| Water | 0.450 |
| Excipients: | |
| Glycerol | 0.017 |
| Hyaluronic acid | 0.000 |
| Citric acid, anhydrous | 0.005 |
| Tri-sodium citrate dihydrate | 0.008 |
| Polysorbate 80 | 0.009 |
| Gluconolactone | 0.019 |
| Vit. E acetate | 0.005 |
| Total excipients (fraction) | 0.063 |

Composition 6B

| Component | Fraction |
|---|---|
| Lipid body solids | 0.433 |
| Yeast oil supplement | 0.103 |
| Water | 0.400 |
| Excipients: | |
| Glycerol | 0.015 |
| Hyaluronic acid | 0.000 |
| Citric acid, anhydrous | 0.005 |
| Tri-sodium citrate dihydrate | 0.007 |
| Polysorbate 80 | 0.010 |
| Gluconolactone | 0.021 |
| Vit. E acetate | 0.005 |
| Total excipients (fraction) | 0.063 |

Composition 6B is a composition that replaces a portion of the oil in lipid body solids with yeast oil extracted from lipid bodies. This can yield a smoother cream.

Composition 6C

| Component | Fraction |
|---|---|
| Lipid body solids | 0.423 |
| Yeast oil supplement | 0.101 |
| Water | 0.390 |
| Excipients: | |
| Glycerol | 0.030 |
| Hyaluronic acid | 0.002 |
| Citric acid, anhydrous | 0.012 |
| Tri-sodium citrate dihydrate | 0.018 |
| Polysorbate 80 | 0.004 |
| Gluconolactone | 0.016 |
| Vit. E acetate | 0.004 |
| Total excipients (fraction) | 0.086 |

In addition to a yeast oil supplement, the composition in Composition 6C includes hyaluronic acid and a higher concentration of glycerol to reduce separation of lipid bodies from the aqueous layer and to maintain a high humectant level.

Composition 6D

| Component | Fraction |
|---|---|
| Lipid body solids | 0.392 |
| Yeast oil supplement | 0.159 |
| Water | 0.362 |
| Excipients: | |
| Glycerol | 0.028 |
| Hyaluronic acid | 0.003 |
| Citric acid, anhydrous | 0.012 |
| Tri-sodium citrate dihydrate | 0.019 |
| Polysorbate 80 | 0.006 |
| Gluconolactone | 0.015 |
| Vit. E acetate | 0.004 |
| Total excipients (fraction) | 0.083 |

Composition 6D contains a higher concentration of yeast oil supplement to increase the smoothness and hydrophobicity of the cream along with a higher concentration of emulsifier.

| Composition 6E | |
|---|---|
| Component | Fraction |
| Lipid body solids | 0.496 |
| Yeast oil supplement | 0.0 |
| Water | 0.458 |
| Excipients: | |
| Glycerol | 0.0092 |
| STARDESIGN powder | 0.0000 |
| Citric acid, anhydrous | 0.0054 |
| Tri-sodium citrate dihydrate | 0.0083 |
| Gluconolactone | 0.0191 |
| Vit. E acetate | 0.0048 |
| Polysorbate 80 | 0.0000 |
| Total excipients (fraction) | 0.0467 |

Composition 6E is a basic cream containing yeast lipid bodies similar to Composition 1A above. However, in this composition the citric acid concentrations are moderately higher to impart a greater buffering and ionic strength, which are potentially useful for improving antimicrobial stability to the compositions without damaging the feel of the lipid bodies.

| Composition 6F | |
|---|---|
| Component | Fraction |
| Lipid body solids | 0.494 |
| Yeast oil supplement | 0.0 |
| Water | 0.456 |
| Excipients: | |
| Glycerol | 0.0091 |
| STARDESIGN powder | 0.0027 |
| Citric acid, anhydrous | 0.0054 |
| Tri-sodium citrate dihydrate | 0.0083 |
| Gluconolactone | 0.0190 |
| Vit. E acetate | 0.0048 |
| Polysorbate 80 | 0.0000 |
| Total excipients (fraction) | 0.0493 |

Composition 6F is similar to Composition 2A but it also contains a small amount of STARDESIGN powder, a modified starch, to reduce water separation.

| Composition 6G | |
|---|---|
| Component | Fraction |
| Lipid body solids | 0.305 |
| Yeast oil supplement | 0.0 |
| Water | 0.6193 |
| Excipients: | |
| Glycerol | 0.0124 |
| STARDESIGN powder | 0.0217 |
| Citric acid, anhydrous | 0.0073 |
| Tri-sodium citrate dihydrate | 0.0113 |
| Gluconolactone | 0.0185 |
| Vit. E acetate | 0.0046 |
| Polysorbate 80 | 0.0000 |
| Total excipients (fraction) | 0.0757 |

Composition 6G (without yeast oil) is similar to Composition 6F but the amounts of STARDESIGN powder and citric acid are substantially higher.

| Composition 6H | |
|---|---|
| Component | Fraction |
| Lipid body solids | 0.3096 |
| Yeast oil supplement | 0.0469 |
| Water | 0.6155 |
| Excipients | |
| Glycerol | 0.0114 |
| STARDESIGN powder | 0.0199 |
| Citric acid, anhydrous | 0.0081 |
| Tri-sodium citrate dihydrate | 0.0125 |
| Gluconolactone | 0.0185 |
| Vit. E acetate | 0.0046 |
| Polysorbate 80 | 0.0009 |
| Total excipients (fraction) | 0.0750 |

Composition 6H (with yeast oil) contains a small amount of yeast oil supplement along with an emulsifier to increase smoothness and a lower amount of STARDESIGN powder than found in Composition 6G.

| Composition 6I | |
|---|---|
| Component | Fraction |
| Lipid body solids | 0.0 |
| Yeast oil supplement | 0.2695 |
| Water | 0.6288 |
| Excipients: | |
| Glycerol | 0.0129 |
| STARDESIGN powder | 0.0377 |
| Citric acid, anhydrous | 0.0113 |
| Tri-sodium citrate dihydrate | 0.0174 |
| Gluconolactone | 0.0180 |
| Vit. E acetate | 0.0045 |
| Polysorbate 80 | 0.0055 |
| Total excipients (fraction) | 0.1017 |

Composition 6I has been designed to use yeast oil supplement alone without the addition of lipid body solids. It is a semi-transparent cream that is quite smooth, but with more of an oily feel than other compositions. This composition is particularly oil with a lubricating quality on the skin and in applications involving moving parts.

| Composition 6J | | |
|---|---|---|
| Component | Target | Final |
| Lipid body solids | 33% | 29.7% |
| Yeast oil supplement | 0 | 0 |
| Water | 55% | 60.4% |
| Excipients: | | |
| Glycerol* | 2.00% | 1.80% |
| STARDESIGN powder* | 3.50% | 3.15% |
| Citric acid, anhydrous* | 1.18% | 1.06% |
| Tri-sodium citrate dihydrate* | 1.82% | 1.64% |
| Gluconolactone | 2.00% | 1.80% |
| Vit. E acetate | 0.50% | 0.45% |
| Polysorbate 80** | 0.00% | 0.00% |
| Total | 11.0% | 9.91% |

*Based on net water;
**Based on oil content

Composition 6J uses a moderate amount of STARDESIGN powder to stabilize the lipid body suspension at a lower concentration of lipid bodies and without the addition of supplemental yeast oil.

| Composition 6K | | |
|---|---|---|
| Component | Target | Final |
| Lipid body solids | 33% | 31.3% |
| Yeast oil supplement | 5% | 4.4% |
| Water | 51% | 57.1% |
| Excipients: | | |
| Glycerol* | 2.00% | 1.14% |
| STARDESIGN powder* | 3.50% | 2.00% |
| Citric acid, anhydrous* | 1.18% | 0.67% |
| Tri-sodium citrate dihydrate* | 1.82% | 1.04% |
| Gluconolactone | 2.00% | 1.86% |
| Vit. E acetate | 0.50% | 0.46% |
| Polysorbate 80** | 0.10% | 0.09% |
| Total | 11.0% | 7.3% |

*Based on net water;
**Based on oil content

In Composition 6K, a moderate amount of STARDESIGN powder along with Polysorbate 80 is used to stabilize a lower concentration of lipid body solids along with yeast oil to make a smoother preparation.

| Composition 6L | | |
|---|---|---|
| Component | Target | Final |
| Lipid body solids | 0% | 0% |
| Yeast oil supplement | 30% | 20.79% |
| Water | 51% | 69.3% |
| Excipients: | | |
| Glycerol* | 2.05% | 1.42% |
| STARDESIGN powder* | 6.00% | 4.16% |
| Citric acid, anhydrous* | 1.18% | 0.82% |
| Tri-sodium citrate dihydrate* | 1.82% | 1.26% |
| Gluconolactone | 2.00% | 1.80% |
| Vit. E acetate | 0.50% | 0.45% |
| Polysorbate 80** | 0.62% | 0.43% |
| Total | 13.6% | 10.3% |

*Based on net water;
**Based on oil content

Composition 6L uses a higher concentration of STARDESIGN powder to stabilize a preparation that contains no lipid body solids and only a moderate amount of yeast oil. The resultant composition was starchy and prone to separation upon transient heating.

The series of compositions comprising lipid bodies, modified with excipients in a range of concentrations are useful for consumer products, drug delivery systems, and a wide range of industrial and markets applications.

Example 7

Preparation of Antiviral Hydrophobic Surfactant Compositions

Compositions of the invention can be made to enhance the utility of sanitizers, which are typically very drying to the skin. In this example, lipid bodies are formulated to produce an anti-viral composition, although similar applications exist for anti-bacterial, anti-fungal and anti-protozoan sanitizers.

Viruses are not generally susceptible to antibiotics such as antibacterial, antifungal or antiparasitic agents because they target physiological functions unique to the pathogen. Viruses that infect human cells generally bind to surface membrane proteins and then undergo transmembrane transport their DNA or RNA into the target cells where the viral machinery takes over the cell metabolism and forces it to make many copies of itself. Virus infection can be blocked either by preventing contact between the viral surface proteins and the receptor proteins on the target cell or by disrupting the receptor proteins or viral membranes of the virus itself, depending on the specific viral pathogen. The latter is particularly useful as a viral disinfectant. Viral disinfectants are well known, for example, ethanol or isopropyl alcohol. However, these common sanitizing agents are particularly drying to the skin. Utilizing any number of compositions of the invention can offset the drying impact of the sanitizers on human skin.

Animal viruses are generally susceptible to surfactants such as soap. Their outer surface includes a lipid bilayer membrane derived from the cytosolic membrane of their host cell. In another embodiment an antiviral composition comprising lipid bodies is made by adding antiviral substances. Viruses can be destroyed by surfactants and chaotropic agents that break up lipid bilayer membranes of enveloped viruses and dissociate the viral nucleic acids (RNA or DNA) from the vial packaging proteins. In this example, lipid bodies in a base composition are supplemented with a surfactant to achieve an anti-viral composition. Useful surfactants include sodium lauryl sulfate and other detergents at concentrations of less than 10% or alkylation agents such as benzalkonium chloride at concentrations of less than 5%.

The objective of these compositions is to produce a persistent surfactant hand cream that will disrupt viral particles, leave a protective layer on the skin and allow for safe, effective removal of contaminants by washing with soap and water, while slowing the desiccation impact of the antiviral agents. Similar approaches are available for antibacterial and antifungal sanitizers that could benefit from compositions of the invention either as part of the composition or as a follow-up hand moisturizer.

Example 7A

Formulation procedure: Weigh out a quantity of yeast oil; Add Polysorbate 80 equal to one-third of the mass of oil and mix to form an emulsion; Weigh out a quantity of Aloe vera juice equal to the yeast oil plus polysorbate; Add hyaluronic acid equal to 0.5% of the mass of the Aloe vera juice and mix to dissolve; Blend the yeast oil plus polysorbate emulsion with the Aloe vera plus hyaluronic acid to form an even suspension.

Example 7B

Variations to the formulation procedure of Example 7A: The Aloe vera juice may be concentrated prior to mixing with hyaluronic acid; The concentration of hyaluronic acid may be decreased to 2% or increased up to 0.8% to alter thickness of the surfactant cream; Glucuronic acid, sodium benzoate, citric acid, vitamin E and/or STARDESIGN starch may be added; Other antiviral compounds may be added, e.g. ethanol, isopropyl alcohol, benzalkonium chloride and others.

Example 8

In this example, one or more of base Compositions 2-6L, lipid bodies simply sterilized in phosphate buffered physiological saline (PBS), and any other composition described herein are used in combination with other substances, preferably drugs and topical medicinal compositions. In this example, the compositions take up hydrophobic and hydrophilic drugs, which mix uniformly into base compositions. drugs loaded into lipid bodies by the inventors were Lidocaine, Griseofulvin, Benzocaine, Colchicine, Hydroxychloroquine, and many other representative drug substances. The embodiments included drugs for a variety of conditions and administration points, for example, oral, ophthalmic drugs, internal medicines, parenteral and subcutaneous treatments, vaccines, antibiotics, biologics and many other medical applications and compositions, will benefit from the properties of the lipid bodies. Of particular utility is an embodiment that is simply processed, and purified lipid bodies suspended in PBS and which are then steam sterilized at 121° C. This composition was prepared at 27% lipid bodies as measured by dry weight at pH 6.8. The sterile lipid bodies are particularly useful in drug applications, carrier components of vaccines, suitable for coating with cationic biopolymers and suitable for formulation with active drug ingredients for a range of administrations sites. In this embodiment, PBS lipid bodies prepared as described in this example are essentially tasteless and suitable for the development of oral drug forms and oral vaccines.

Example 9

In this example, one or more of base Compositions 2-6L and any other composition described herein, are used in any combination with other substances, preferably cosmetics and cosmeceutical compositions. The lipid body based compositions take up and mix with compounds such as steroids, cholesterol, pigments, dyes, flavors, water insoluble vitamins, hydrophobic peptides, amino acids such as phenyl alanine, polyaromatic compounds and many other generic and brand name substances and ingredients that are useful in preparing compositions for a wide range of pharmaceutical, cosmetics and cosmeceutical applications. Lipid bodies of Compositions 2-6L were washed in a 1:10 mixture of compositions to 95% ethanol and the dehydrated lipid bodies were recovered by centrifugation. The pelleted lipid bodies were resuspended in deionized water and the reduction and effective removal of excipients and particularly the removal of sodium benzoate produced a lipid body suspension which could be filtered through a 0.2 micron syringe filter and the resultant filtrate measured by UV scan from 220-299 nm and determined to have a minimal UV absorbance. Using the experimental composition of washed lipid bodies or suspensions of PBS sterilized lipid bodies, UV absorbing substance could be loaded into the lipid bodies and the filtration used to quantitate the amount of the UV absorbing material that was bound to the lipid bodies. This method proved particularly effective in evaluating the bound vs unbound levels for hydrophobic substances and drug models such as aromatic amino acids, lidocaine, benzocaine, benzoate, Nile red and Sudan black. The resultant compositions of the invention indicated that aromatic and polyaromatic compound load to various degrees into the lipid bodies as a function of their solubility into the internal neutral triglycerides of the compositions.

Example 10

In this example, one or more of base Compositions 2-6L and any other composition described herein are used in any combination with other substances, preferably skin care products and skin healing compositions. In this example, the lipid body based compositions take up and mix with compounds such as lanolin, glycerol, polyglycols, polymers, peptides, oils, vitamins, hyaluronic acid, collagen, peptides, hydrophilic amino acids, non-aromatic amino acids, and many other generic and brand name substances and ingredients that are useful in preparing skin care compositions for a wide range of skin ailments. The lipid body base composition of the invention was capable of being formulated with a range of hydrophilic substances on the hydrophilic surface of lipid bodies and inter-lipid body spaces in example compositions. The method was applied to dehydrated and washed or pure lipid bodies in PBS when there was a significant interstitial space for hydrophilic substances. In some cases, such as lidocaine, the ingredient partitioned into both the hydrophobic interior and the hydrophilic exterior of the compositions.

Example 11

In this example, one or more of base Compositions 2-6L and any other composition described herein are used in any combination with other substances, preferably pet care products and pet veterinary compositions. In this example, the lipid body based compositions take up and mix with compounds such as lice and tick medicines, shampoo, fragrances, odor blocking agents, oils, vitamins, hyaluronic acid, collagen, peptides, amino acids such as phenyl alanine, and many other generic and brand name substances and active ingredients that are useful in preparing pet care compositions for a wide range of pet ailments and pests. The lipid body base compositions of the invention have been developed with Environmental Working Group (EWG) additives in mind so as to maximize the safety of the compositions for pets and humans.

Example 12

In this example, one or more of base Compositions 2-6L, simpler, cruder compositions containing only lipid bodies and or lipid-body envelopes and biochemicals, and any other composition described herein are used in any combination with other substances, preferably with industrial applications such as but not limited to lubrication, sealants, coatings, oils, greases, biofuels, fuels, insulation, conductive compositions, and many other industrial applications. In this example, the lipid body based compositions take up and mix with compounds such as aviation, machinery operation, agriculture, pharmaceutical operations, manufacturing, transportation, and other industrial areas and many other generic and brand name substances and ingredients that are useful in preparing industrial compositions for a wide range of industrial purposes. In this example, yeast containing lipid bodies were dried and oil released by dehydration was removed and the residual lipid body shells were heat resistant up to 200° C. and provided a heat tolerant waxy lubricant, which could be used directly or mixed with other agents to provide an industrially useful lubricant composition of the invention.

Example 13

In this example, one or more of base Compositions 2-6L, simpler compositions containing only lipid bodies and or lipid-body envelopes and biochemicals, and any other composition described herein are used in any combination with other substances, preferably with nanotechnology applications such micro-electronics, biometrics, castings, mold release agents, plastics, polymeric compositions, separation resins, battery elements, photovoltaics, optics, lasers, light filters, whitening agents, dyes, coloring agents, precipitation agents, chelators, organic chemistry reactions and many other physical and chemical or organic chemistry uses, including catalysis, photocatalysis and other compositions that have practical value for many emerging areas of technology. The lipid bodies of the invention are mobile in an electric field established in deionized water. The current flow is on and across the exterior of the lipid bodies with the neutral triglyceride interiors acting as an oil-base resistor to electrical flow. With low levels of divalent cations present, the lipid bodies with their phospholipid exteriors are bridged and aggregate but remain mobile in and electric field, moving toward the positive cathode. The utility of spherical structures in bio-electrical applications are not fully understood at this time. As a proof of lipid body charge state, excess salt was used in the electrical field and the surface charges of lipid bodies are nullified and electrical mobility of the lipid bodies declines.

Example 14

To evaluate drug uptake and delivery into the compositions, several standard analytical methods are used. One method utilized an instrument for UV-VIS spectroscopy. For this example, samples were run on a Perkin-Elmer Lambda 35 UV-VIS Spectrometer with a 4-sided clear quartz cuvette (Fisher) and a 1 mL sample of PBS (Dulbecco's Phosphate Buffered Saline, Sigma) used as the blank before every run.

Another preferred method used a High-Pressure Liquid Chromatography (HPLC) instrument for analysis. Samples were run on an Agilent Technologies 1260 Infinity HPLC in a reverse phase isocratic mode using UV detection at 210 nm and 10 μL of sample injection. The column was a Hypersil Gold column (250×4.6 mm, Thermo Scientific) and the mobile phase was a 1:1 suspension of acetonitrile to aqueous buffer (HPLC grade water) mixed with 5 mM ammonium acetate and 0.02% (of total volume) formic acid. The flow rate was 1.2 mL/min and the column temperature was 22° C. Peak detection and quantitation were determined using ChemStation software and reference standards.

The following non-limiting examples are provided for illustrative purposes and represent the incorporation of drugs in the compositions and their release into aqueous media. The lipid bodies contained approximately 50% lipid and 50% aqueous material. Using these methods, it is shown that many drugs can form useful compositions with unique properties that depend on high loading and unloading volumes.

Example 15

Colchicine, an alkyloid for gout, was determined to form a suitable topical drug composition using the compositions of the invention. Specifically, in this example, an aqueous drug plus lipid-body composition was created.

A 55% aqueous and 45% drug-containing lipid-body composition was prepared by the following procedure. A 2 mg/mL colchicine (TCI, Tokyo Chemical Industry) stock was prepared by vigorous mixing of 20 mg of colchicine and 10 mL Phosphate Buffered Saline (PBS). To 1 g lipid body was added 100 μL of 2 mg/mL colchicine stock followed by vigorous mixing. A 300 mg sample of the resulting topical composition was taken out and placed in the bottom of a 2 mL Eppendorf tube with 1 mL PBS layered on top and incubated for 15 minutes at room temperature without agitation. This mixture was centrifuged for 2 minutes at 14000 RPM in an Eppendorf Centrifuge 5415C to separate the lipid and aqueous layers and once complete, the aqueous layer was removed and stored in a new 2 mL Eppendorf tube at 4C.

Results: UV spectroscopy was run and the peak on the spectrum was at 350 nm with an absorbance of 0.82 and a baseline of 0.57 yielding a total absorbance of 0.25. A total of 5.9 μg/mL was released calculated using the published Extinction Coefficient of ~17 mM units at 350.5 nm. This corresponds to 9.8% drug release from the drug containing lipid body into 1 mL PBS at room temperature. Thus, colchicine can be loaded and released in an aqueous environment from a lipid-body composition. Since colchicine is a potent drug, the resultant level of released drug is believed to be useful for the treatment of gout.

Example 16

In another example, colchicine was loaded into and released from a lipid-body composition containing a larger aqueous fraction. The procedure uses a 62% liquid and 38% drug-containing lipid-body composition that was prepared in a similar manner to Example 18, except a 5 mg/mL stock of colchicine was used (10 mg of colchicine and 2 mL PBS) with 200 μL of PBS added and the homogeneous mixture was allowed to sit in 1 mL PBS at room temperature.

Results: The absorbance of the peak at 350 nm was not readily visible due to extension light scattering and thus a 1/10 dilution in PBS was needed to determine the 350 nm absorbance of 0.22. A total of 51.8 μg/mL drug released corresponds to 34.5% of the total colchicine. By HPLC (350 nm, 2.9 minutes), 61.5 ug/mL released corresponds to 41% colchicine released, which is similar to the value calculated by UV. Thus, colchicine can be loaded and have an enhanced release from a lipid-body composition containing a higher water content than Example 18. Under these conditions, the lipid-body composition retains a pleasant, smooth, and aqueous feeling.

Example 17

Colchicine was loaded into and released from a lipid-body composition containing an even larger aqueous fraction than in Example 19. The procedure and composition is a 67% liquid and 33% drug-containing lipid-body composition prepared in a similar manner to Example 19 except 178 μL of PBS was added.

Results: Due to the high absorbance of the peak at 350 nm, a 1 to 3 dilution followed a 1 to 2 dilution which led to a 350 nm absorbance of 0.16. A total of 22.6 ug/mL of colchicine was released corresponding to 15.1% of the total compound loaded. By HPLC, 38.3 ug/mL or 25.5% of the compound was released, which is almost double that calculated by UV. Thus, colchicine can be loaded and have an enhanced release from higher water content lipid-body compositions than in Examples 18 and 19.

Example 18

Colchicine was loaded as a dry powder into a lipid-body composition and then colchicine was released from a lipid-body composition using a dry starting drug powder. The procedure used 30 mg of colchicine powder, which was vigorously mixed into and with 1 g of lipid bodies. A 300 mg sample was removed and placed in the bottom of a 2 mL Eppendorf tube, 2 mL PBS layered on top and incubated for 15 minutes at room temperature. The sample was centrifuged for 2 minutes at 1400 RPM in an Eppendorf 5415C Centrifuge and the aqueous layer removed and placed in a new 2 mL Eppendorf tube to be run on the UV-VIS spectrophotometer described in Example 17.

Results: Due to large scattering a 200-fold dilution was needed to determine the peak at the 350 nm absorbance of 0.72. A total of 3,390 μg/mL was released, corresponding to 37.6% of the total colchicine present. Thus, colchicine can be loaded as a dry powder and released from a 50% lipid-body composition.

Example 19

In another example, colchicine was loaded as a dry powder into a cream of lipid bodies, plus additional PBS and then the colchicine was released from a lipid body cream and PBS composition using a dry starting drug. The procedure used a sample that was prepared in a similar manner to Example 22, except 33 μL of PBS was added to the PBS mixture and lipid-body composition.

Results: Due to large scattering a 100-fold dilution was needed to obtain a 350 nm absorbance of 1.7 corresponding to 4000 μg/mL released or 44% of the total colchicine. Increasing the volume of the release medium increases the amount of colchicine released. These results support the properties of loading and delivery of topical drugs, which may require dosing control provided by adjusting the lipid body cream and PBS levels in the final topical drug composition.

Example 20

In this example, another drug, hydroxychloroquine, which is used as an antimalarial, amebicide, and also to treat lupus, rheumatoid arthritis, and putatively, Covid-19, can be formulated and benefit from incorporation into lipid bodies. The procedure used a 5 mg/mL stock of hydroxychloroquine (Cayman), which was prepared by vigorously mixing 10 mg of hydroxychloroquine and 2 mL PBS. Then to 1 g of lipid bodies was added 100 uL of 5 mg/mL hydroxychloroquine stock followed by vigorous mixing. A 300 mg sample was removed and placed in the bottom of a 2 mL Eppendorf tube with 1 mL PBS layered on top and incubated for 15 minutes at room temperature. As in earlier examples, the mixture was centrifuged, and the aqueous layer removed for analysis.

Results: Due to the light scattering, a 6-fold dilution was needed to determine the absorbance at 343 nm, which gave a value of 0.65. The concentration from the peak at 343 nm was determined using the stock solution as a reference standard. The released hydroxychloroquine was determined to be 5.66 μg/mL, corresponding to a total hydroxychloroquine release of 10.4%. Thus, hydroxychloroquine can be loaded and released from a hydroxychloroquine lipid-body composition in a therapeutic concentration.

Example 21

Chloroquine, an antimalarial, an amebicide, and used to treat lupus, rheumatoid arthritis, and putatively, Covid-19, was prepared in a lipid-body composition. The procedure used a 5 mg/mL stock solution of chloroquine (Alfa Aesar), which was prepared by vigorously mixing 10 mg chloroquine and 2 mL PBS. Then, to 1 g of lipid bodies, 100 μL of 5 mg/mL chloroquine stock was added and vigorously mixed. A 300 mg sample was removed and placed in the bottom of a 2 mL Eppendorf tube with 1 mL PBS layered on top and incubated and centrifuged as described in earlier examples.

Results: Due to the high light scattering, a 6-fold dilution was performed. This led to an absorbance of 0.40 at 343 nm and a calculated concentration of 12.1 μg/mL, indicating a total chloroquine release of 8.1%. Of note, the absorbance of the peak at 343 nm at a 6-fold dilution was not consistent with the standard, therefore a 1 to 3 dilution was done, which gave an absorbance too high to calculate. Then a 1 to 2 dilution was prepared, and a useful absorbance peak was obtained at 343 nm, giving a value of 0.45 and the baseline 0.05 A, which is a total of 0.40 A. The concentration from the peak at 343 nm was 12.12 mg/mL using the standard and a ratio, and a total release of 8.1%. Thus, chloroquine can be loaded and released from a large yeast lipid-body composition at therapeutic levels.

Example 22

Losartan, an ACE Inhibitor, and a putative Covid-19 treatment was prepared in a lipid-body composition. The procedure used a 5 mg/mL stock of Losartan Potassium Salt (Cayman), which was vigorously mixed after combining 10 mg of Losartan with 2 mL PBS. Then, to 1 g of lipid bodies was added 100 μL of 5 mg/mL Losartan stock and vigorously mixed. A 300 mg sample was removed and placed in the bottom of a 2 mL Eppendorf tube with 1 mL PBS layered on top and incubated and centrifuged as described in previous examples.

Results: The Losartan sample were analyzed by HPLC and spectroscopically, which gave peak heights at 3.9 minutes at 210 nm. The measured value was compared to a 20 mg/mL Losartan reference standard. From the peak heights, the Losartan released into 1 mL PBS had a concentration of 54.4 ug/mL corresponding to a total release of 36.3%. Thus, Losartan can be loaded and released from a Lipid body.

Example 23

Travoprost, a prostaglandin analogue used for glaucoma, was prepared in a lipid-body composition. The procedure (#1) used 1 g of lipid bodies, which was added with 2 μL of Travoprost (25 mg/mL, Cayman Chemical Company) and vigorously mixed. A 300 mg sample was removed and placed in the bottom of an Eppendorf tube with 1 mL PBS layered on top and incubated and processed as before and stored in a 2 mL HPLC vial.

A second procedure used a 10 uL sample of Travoprost stock (25 mg/mL), which was evaporated under nitrogen flow to a final weight of 250 μg. To this concentrate of Travoprost was added 1 g of lipid bodies followed by vigorous mixing. A 100 mg sample was removed and place in an Eppendorf followed by the addition of 1 mL PBS. The remaining steps followed procedure 1, which utilized HPLC analysis.

Results, first procedure: The HPLC results of the Travoprost sample and the 25 μg/mL Travoprost in ethanol sample gave the same peak height of 1.7 at around 4 minutes at 210 nm. With an initial concentration of 50 μg/mL, or a 50% of Travoprost released. Results, second procedure: The HPLC results of Travoprost indicated a 60.7% release. Thus, the drug Travoprost can be loaded and released from lipid bodies under different preparation conditions and concentrations. Compositions include utilizing lipid bodies, which have a diameter larger than 5 μm and are derived from any engineered hyper-lipogenic yeast.

Example 24

In one example, the absorbance at 260 nm was used for determining Lidocaine binding and partitioning into lipid bodies using a UV spectrophotometry. Lipid bodies were cleared of excipients and antimicrobial preservative by undergoing a 1:10 wash in ethanol followed by rehydration in distilled water. To improve the UV signal and minimize turbidity from the lipid bodies, the lipid bodies were filtered through an 0.2 μm filter before measurement. Elimination of the background noise and minimizing dilutions improves the absorbance of UV-absorbing drugs such as lidocaine. The methodology used a lidocaine stock of 50 mg in 950 μL (50 mg/mL), which was used to load various concentrations of lidocaine into the lipid-body compositions of the invention. In this example, 2 μL of a 50 mg/mL stock or 100 μg of lidocaine was mixed with 100 μL of washed lipid bodies in 1M NaCl or in deionized water and incubated 10 minutes before removal of the lipid bodies by 0.2 μm filtration.

The resulting UV absorbances were:

| Concentration of Lidocaine | UV Absorbance | Lidocaine in Aqueous Cream Fraction | Lidocaine Bound to Lipid Bodies |
|---|---|---|---|
| Control: 500 μg Lidocaine without Lipid Bodies and Filtered | 1.06 | 100% | 0% |
| 500 μg Lidocaine in Water | 0.884 | 83% | 16% |
| 500 μg Lidocaine in Salt | 0.76 | 72% | 28% |

The results highlight the ability to influence the partitioning of drug into the lipid body sphere using a high ionic strength imparted by salt, when formulating a large yeast lipid body. Similar results were obtained with phenyl alanine, benzocaine and griseofulvin with some variation depending on the hydrophobicity of each ingredient.

Example 25

In this example, fermentations of different engineered hyper lipogenic *Lipomyces starkeyi* were used to make different diameter lipid bodies. Using the engineered hyper-lipogenic strain XYL-403, compositions of lipid bodies were prepared with a diameter from 6.9+/−1.4 microns, as shown in the figure below, although some size manipulation is possible using fermentation conditions, when measured under a microscope using a calibrated Petroff Hauser counter. Compositions of lipid bodies were prepared with a diameter up to 12 microns using other strains of engineered hyper-lipogenic strains, for example, XYL-610, as measured using a calibrated Petroff Hauser counter and a microscope ocular ring with a 20 micron span under 1000× power. The following photo of lipid bodies was obtained and observed to be approximately 10-12 microns when compared to a 20 μm diameter ocular reference-ring at 1000× power with a phase contrast microscope. These large lipid bodies present a much larger internal hydrophobic volume than commercial liposomes and therefore a greater capacity to carry hydrophobic ingredients.

Example 26

Figure 12A:
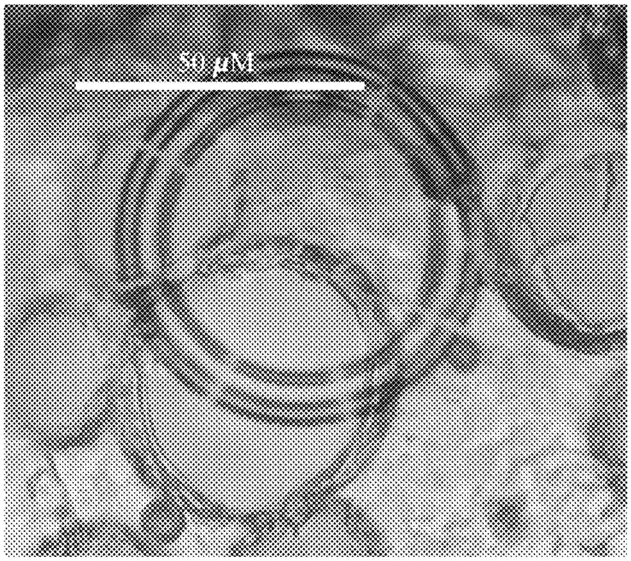
FIGS. 12A-12B. Merged lipid bodies up to 50 microns in diameter in the absence (FIG. 12A) or presence (FIG. 12B) of Sudan black, which stains lipids black.

In this example, fermentations of different engineered hyper lipogenic *Lipomyces starkeyi* were used to create lipid bodies. Using the engineered hyper-lipogenic strain XYL-403, compositions of lipid bodies were prepared with a diameter from 6.9+/−1.4 microns when measured under a microscope using a calibrated Petroff Hauser counter. Following the initial preparation of lipid bodies, the lipid bodies were fused using high levels of salt at 1M NaCl, solvents such as ethanol at 20% (v/v) in water, and application of shear force using centrifugation (FIG. 12A). Homogenization, filtration, or chemical treatments can be used as alternatives to or in additional centrifugation to induce shear force. Thus, compositions utilizing even larger lipid bodies (e.g., between 12 to 50 μm) can be developed using physically modified and merged lipid bodies. The advantages of larger lipid bodies can be extended using high total volumes of drug carrying capacity.

Figure 12B:
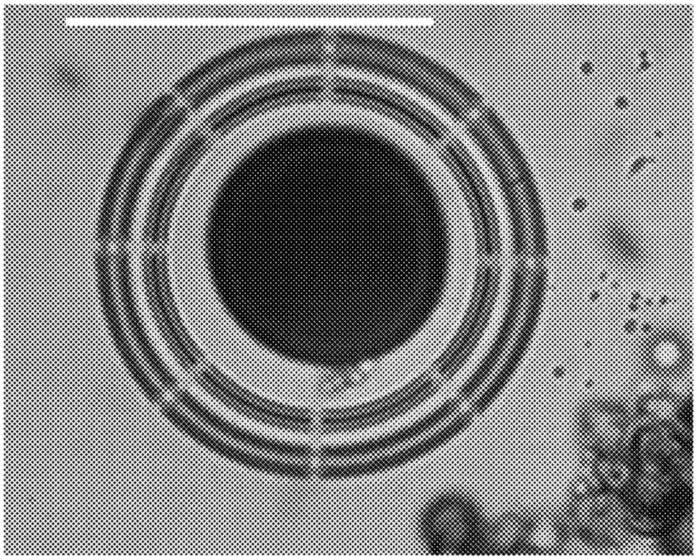

Once such example used Sudan black, which is nearly 100% taken up into the lipid bodies to demonstrate the larger hydrophobic capacity of very large lipid bodies (FIG. 12B). This example opens the possibility of even higher volumetric carrying capacity of lipid-body compositions of the invention when expanded to the upper limit of known diameter.

Example 27

In this example, a composition utilizing lipid body components, envelopes, associated yeast oils and other biochemicals derived from lipid bodies was shown to be possible by the isolation of opened envelopes by passage of a 20% suspension of lipid bodies through a pressure-drop homogenizer. The homogenized solution was centrifuged at high speed in an Eppendorf centrifuge in the presence of a hexane solvent. The yeast oil, which was derived from the lipid bodies was separated into the solvent layer and recovered by evaporation. Following the same centrifugation, the interface was observed to have a layer, which when isolated and examined under a microscope at 400× power was shown to have disrupted envelopes. Additionally, there is a light water interacting layer that is thought to be phospholipid, some protein(s) and other biochemicals, which remain in the bottom aqueous layer as a turbid haze. Finally, heavy solids pelleted to the bottom of the centrifuge tube. This simple process identified multiple components of lipid bodies, which may prove useful when formulated back into the lipid body cream or compositions. To demonstrate this point, the isolated yeast oil was mixed back with a composition at a level of 10, 15 and 40% and mixed to form a homogeneous composition with a somewhat oilier feel.

This example shows that components of lipid bodies can be used independently or in combination with lipid-body compositions to modify the feel and utility of final compositions.

Example 28

Figure 13A:
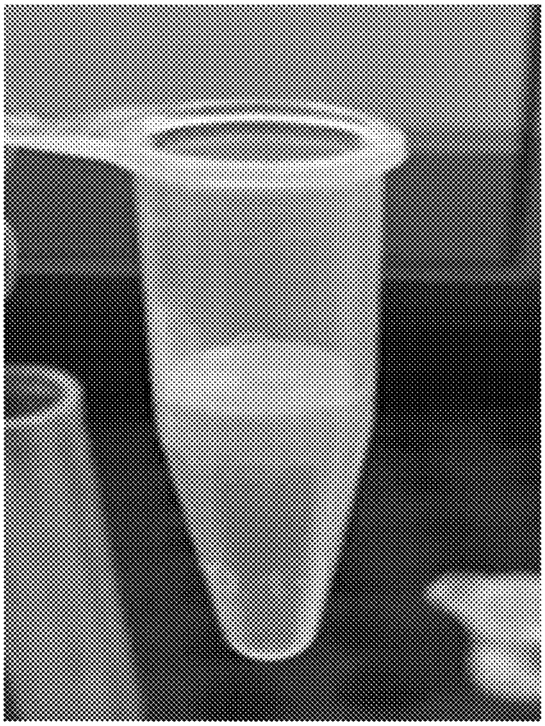
FIGS. 13A-13B. Uptake of hydrophobic dyes by lipid bodies. Lipid bodies were mixed with Nile red (FIG. 13A) or Sudan black (FIG. 13B) and subsequently subjected to flotation.

In this example, lipid bodies at about 50% concentration in base composition of example 1A were subjected to the addition of concentrated Nile red, which had been solubilized in DMSO and used in this example as a surrogate for a hydrophobic compound or hydrophobic drug. The lipid-body composition was mixed with Nile red for 10 minutes and centrifuged. After centrifugation, the lipid bodies separate by flotation and all of the Nile red entered into the lipid bodies. The lipid bodies remain hydrophilic on the exterior of the lipid body spheres and continue to feel aqueous. The observed uptake of Nile red was quantitatively complete, moving the Nile red into the lipid bodies that float upon centrifugation (FIG. 13A).

Figure 13B:
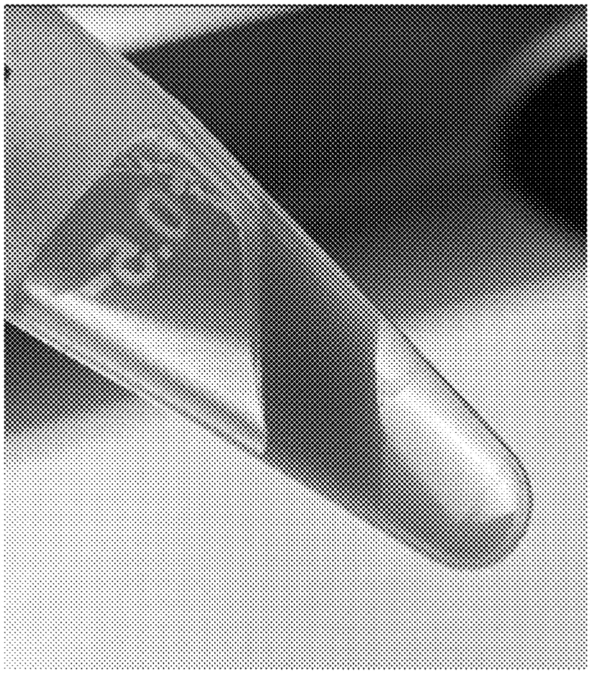

In another version of this example, lipid bodies at approximately 50% by dry weight were mixed with a second hydrophobic model drug compound, Sudan black. After about 10 minutes, the mixture was centrifuged, and the lipid bodies floated with essentially all of the Sudan black loaded into the lipid bodies. This example was used to demonstrate the uptake of a second model compound representing the behavior of hydrophobic materials or drugs as they load into lipid bodies. Similar to the Nile red results, Sudan black is shown to be taken up by lipid bodies (FIG. 13B).

This example shows the ability of the lipid bodies to hold a hydrophobic ingredient.

Example 29

Figure 14A:
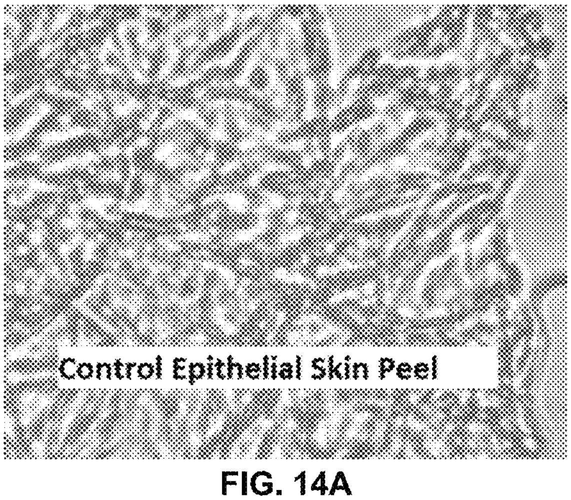
FIGS. 14A-14C. Formation of skin barrier after administration of lipid bodies to skin. Shown are a micrograph of a control epithelial skin peel (FIG. 14A), a micrograph of a skin peel 10 hours after administering lipid bodies of the invention to the skin (FIG. 14B), and a micrograph of yeast lipid bodies overlaying epithelial cells.
Figure 14B:
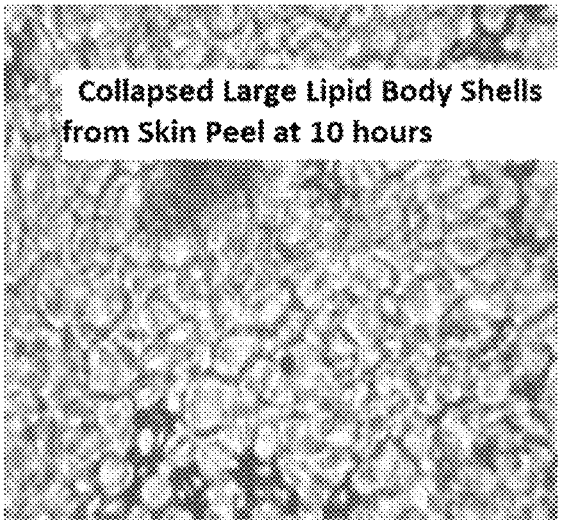
Figure 14C:
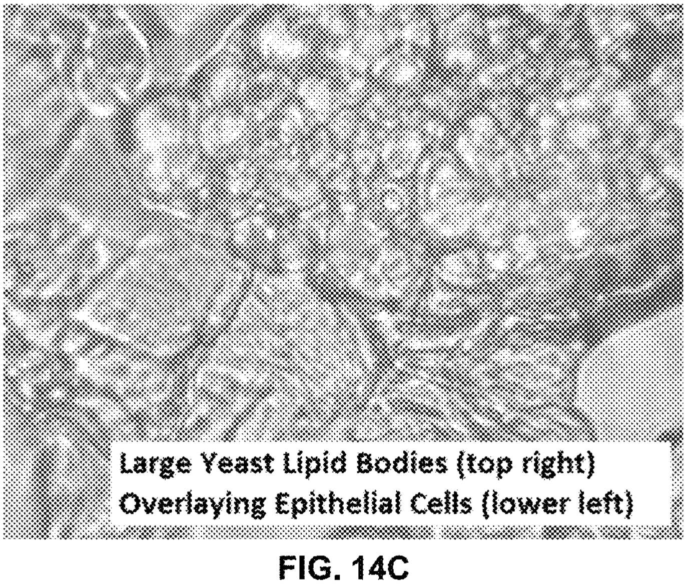

Lipid bodies have a unique property of collapsing and sealing a surface once all other hydrophilic and hydrophobic components are absorbed into a treated surface. Lipid bodies formulated as an approximately 50% lipid body cream were applied uniformly to the face of a test subject. The lipid-body composition was allowed to dry and remain on the skin. After a few minutes, the water and oil components of the composition were absorbed into the skin and a water repellent layer remained as a durable sealant on the skin. After 10 hours, the remaining lipid bodies were removed with clear tape (3M Corp.) and this skin peel was examined at 1000× power under a microscope to observe the durability of the lipid body envelopes as they overlaid epithelial cells from the test subject's face. Lipid bodies, when applied and dried on the skin form pancaked envelopes, which have the property of collapsing to form a sealing surface (FIGS. 14A-C). When the lipid-body compositions discharge of hydrophobic and hydrophilic ingredients, pancaked envelopes form a flexible barrier that is essentially invisible to the naked eye. This example shows that lipid bodies can sealing epithelial cells and promote the protective retention of ingredients, which are absorbed into the skin. This unique property is especially useful in the field of topical drug administration, cosmetic applications and in other fields.

Example 30

Figure 15:
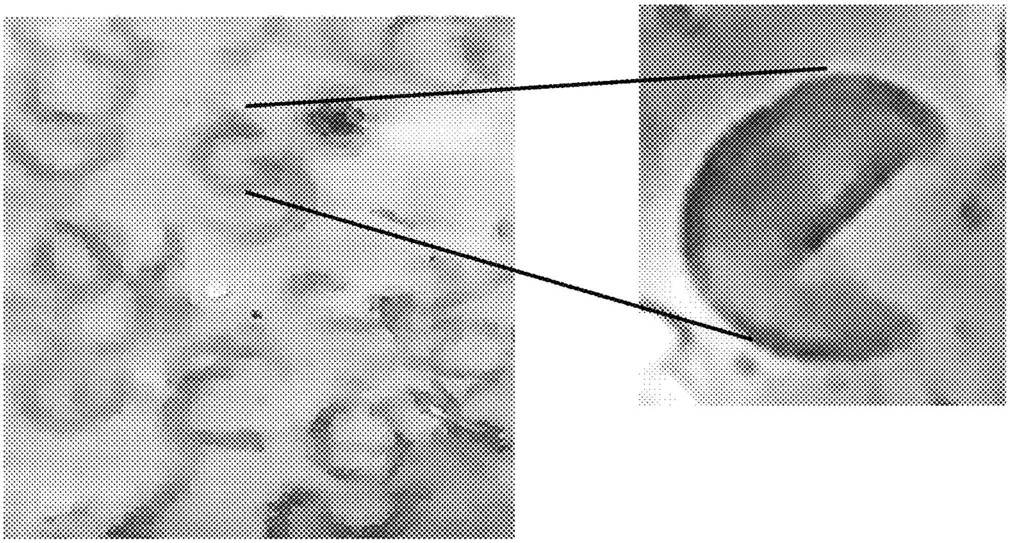
FIG. 15. Micrograph of isolated, opened lipid-body envelopes.

Lipid bodies were formulated to be approximately 50% by dry weight as a cream, which was modified, homogenized or dehydrated to create broken or modified envelopes (FIG. 15) that can be used to enhance the formulation of large molecules, biologics and peptides for transport into the human body at any point of entry. This example applies to compositions containing lipid bodies with or without other lipid body components, such as envelopes. The opened envelope is shown here.

An envelope is the result of homogenizing a yeast lipid body of the invention. The formation of envelopes can then be blended with proteins, peptides, nucleic acids, or adjuvants for vaccines and treated with a biopolymer such a chitosan to product a drug or vaccine delivery system. Once mixed with an active ingredient, the envelopes can be coated or blended with a biopolymer of any type to produce a protected closed entity, which can carry ingredients, including large molecules, nucleotides, and proteins, in a protected state.

Example 31

Figure 17:
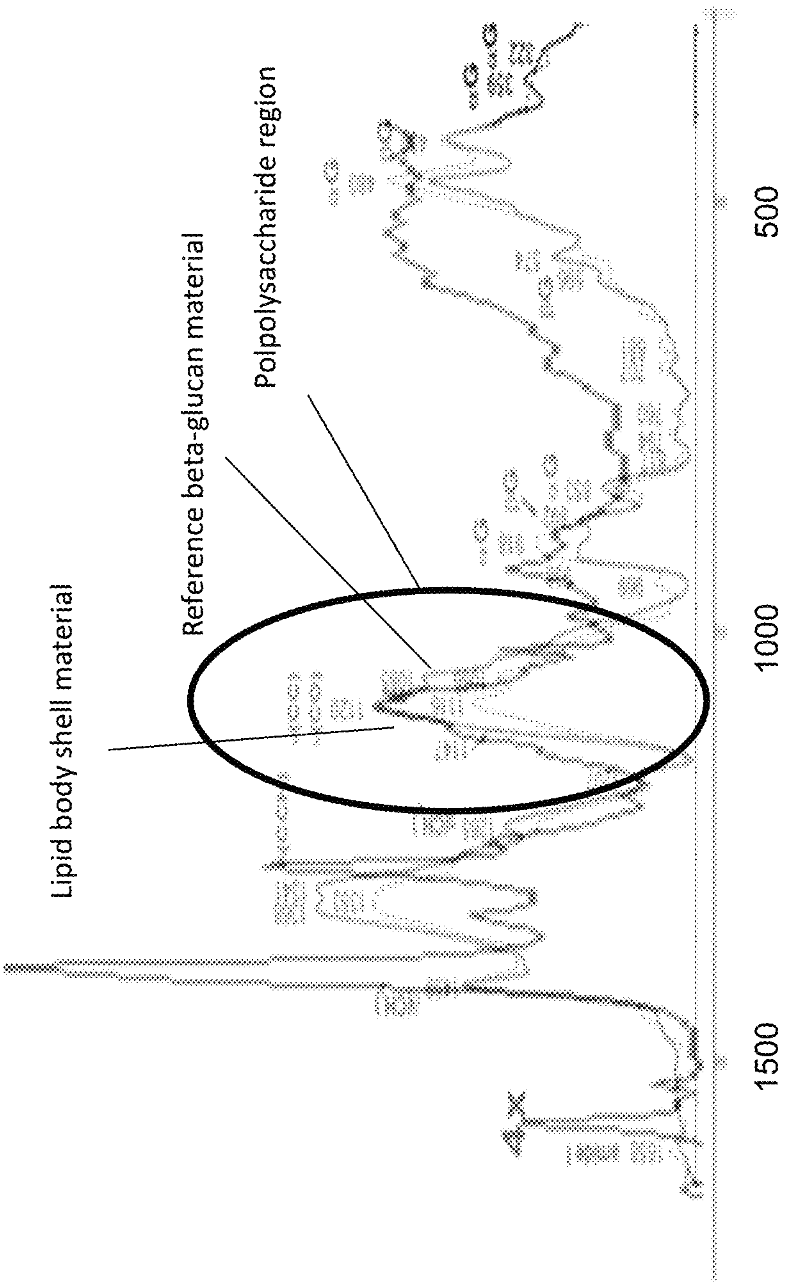
FIG. 17. Raman spectrograph of lipid-body envelope (shell) material and reference beta-glucan material, with the polysaccharide region indicated.

When homogenized yeast lipid bodies are solvent extracted with hexane or pentane, the resulting opened envelope material described in Example 30 can be harvested by centrifugation and dried. The lipid body envelopes were thought to be a mixture of phospholipids, proteins, and glucan-like polysaccharides. Surprisingly, the envelope material of the invention was not consistent with chitin when evaluated by Raman spectrophotometry. The unique envelope material is a hard material that is heat tolerant. Additionally, in the polysaccharide region of a Raman spectra, the spectra are relatively close to a reference yeast beta-glucan (FIG. 17). The beta-glucan identification was further supported by the appearance of free glucan monomers following treatment with lyticase or equivalent beta-1,3 glucanase. These observations show that lipid body envelopes are unique with a robust shell.

Example 32

Figure 16:
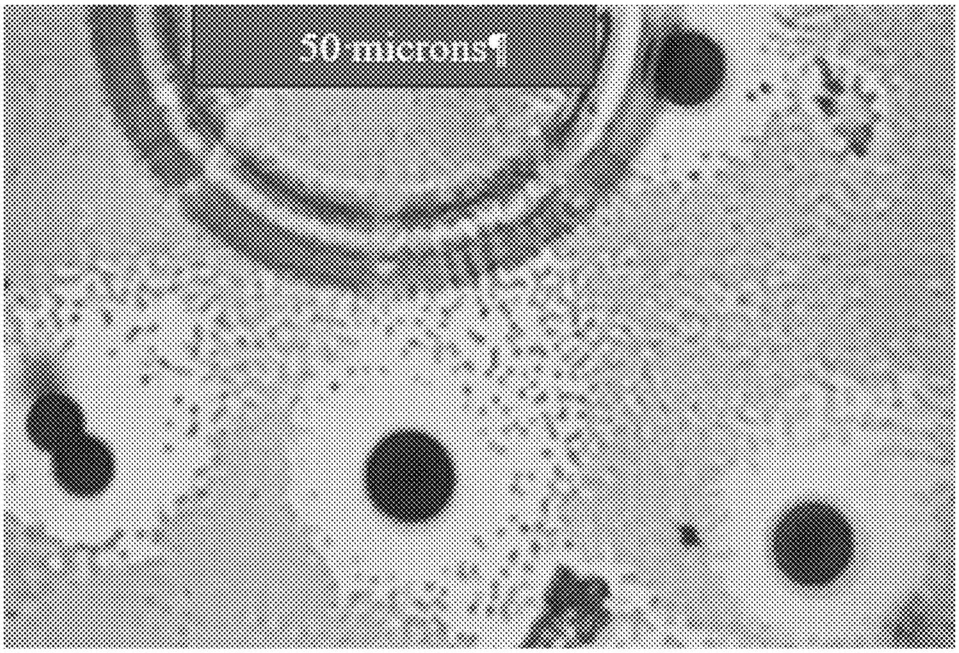
FIG. 16. Micrograph (400×) of lipid bodies subjected to Sudan black in a strong ionic aqueous environment.

In this example, lipid bodies were observed to have properties related to the interplay of hydrophobic and ionic environments. Lipid bodies are surprisingly stable under a wide range of ionic strengths, pH conditions and variable hydrophobicity. To demonstrate the aggressive binding of a hydrophobic substances when applying a strong ionic aqueous environment, lipid bodies were mixed into a 1 M sodium chloride environment. A diluted sample was placed on a microscope slide with a cover slip and a drop of Sudan black was added to the edge of the cover slip and allowed to flow into the lipid bodies that were in the high salt environment. The charged environment was used to drive the model hydrophobic compound, Sudan Black, into the lipid bodies with a surprising effect as shown in FIG. 16.

The aqueous exterior and charge state of lipid bodies across a wide range of pH conditions can be used to enhance drug loading, permitting specialized compositions to exist. Some of these charges are useful in unaltered lipid-body compositions while other charges are formed by chemical or enzymatic treatment of lipid body surfaces with applications for soothing the skin, rapid repair of skin irritation, dryness, scar prevention and healing of blisters when applied by individuals with those conditions. This example shows that modification of the environment of lipid-body compositions can be used to improve drug uptake, particularly hydrophobic drugs such as those used for chemotherapy such as doxorubicin, and inflammatory conditions such as steroid-like compounds.

Example 33

In this example, lipid bodies are released from the engineered yeast by mixing the *Lipomyces starkeyi* with 0.5 M to 1 M phosphoric acid, or 0.25 M to 0.5 M sulfuric acid, or any other acid with equivalent strengths and then placing the lipid bodies at 65° C., or preferably at 80° C., or even more preferably 121° C., for a period of time between 30 minutes and 18 hours, depending on the temperature of treatment. Using the high temperature acid hydrolysis used to isolate lipid bodies, this example illustrates the release of lipid bodies that can be observed because they float above the hydrolyzed yeast debris.

This example demonstrates the heat tolerance of lipid bodies under acid conditions at elevated temperatures, which are useful in the manufacturing of specific compositions of the invention. In fact, the lipid bodies have an ability to be treated at sterilizing temperatures as found in an autoclave e.g. 121° C. This property makes the compositions of the invention particularly useful for critical drug applications, where an aseptic product or subcutaneous injection may be applicable, for example in vaccine development. This example shows the tolerance of lipid bodies to very low pHs.

Example 34

In this example, a deterioration of lipid bodies was observed when dehydrated. Lipid bodies, approximately 75 grams of a 50% lipid body suspension by dry weight were spread on a metal pan and placed into a 65° C. oven and allowed to completely dehydrate overnight. In the drying process, oil was expelled from the lipid bodies and the aqueous portion of the mixture was removed by heat. The expelled oil could be captured by tilting the tray and allowing the oil to pour into a 50 mL test tube. The yield of oil captured in this fashion was approximately half of the yeast oil that could have been isolated by chloroform: methanol extraction. The residual material after heating and oil recovery is also of value, as discussed below.

Example 35

In this example, the residual material which remains after heating, drying, and removal of yeast oil from lipid bodies results in an interesting lubricant material. The dried material has a high lubricity and may be a useful component of industrial lubrication. The material has a slippery waxy feel at a wide range of temperatures. When heated on a hot plate the envelope material does not change in lubricity, color, or texture up to 200° C. Above 240° C., the material begins to turn brown. The lubricity of heat oxidized material was not considered, but this discolored material may still have lubricant properties. Material heated below 200° C. was applied to both sides of a flat metal surface and the resultant lubricant appeared to have a durable and useful property of reducing frictional wear. This example shows that lipid bodies and envelopes, when dried, can be isolated to make a material with significant lubricity for lubricants that are heat and friction tolerant.

Example 36

In this example, lipid-body compositions have extreme acid stability at pH levels at or below 0.9. Similarly, lipid bodies have alkaline tolerance, which facilitates transient removal of impurities, but more importantly this property broadens the useful range of pH conditions from very acidic to pH 9 and transiently to pH 11.7. This range can be used for loading various hydrophobic and hydrophilic ingredients into lipid-body compositions.

Example 37

In this example, the lipid bodies were mixed with 2×-10× levels of water, water plus saline, or water plus citrate, at pH ranges from 1 to 11.7 at room or elevated temperatures. In was noted that some deterioration of yeast oil by saponification was observed at the highest alkaline pHs particularly when combined with elevated temperatures of 50-65° C., so the duration of lipid body exposure was minimized at high pH levels, above 11, at all temperatures. Otherwise the lipid body suspensions exhibit good flotation, particularly when the pH was below 7.5, with initial upward boundary rates of 5 to 7 cm per hour or greater. The flotation rates are somewhat slower at a pH above 8.5. As the compression density of the floating lipid bodies increases during the flotation process, the upward rate of flotation slows. However, the property is particularly useful for washing and formulating by buffer exchange. Flotation in a water plus saline solution can be used to wash the lipid bodies.

In this example, bodies lipid have rapid flotation due to their very low buoyant density, which is useful in concentrating the lipid bodies that are loaded with hydrophobic chemicals and other industrial applications. The property is commercially useful for washing, processing, and buffer exchange steps leading up to and during the production of final compositions. This example shows the utility of the very low buoyant density of lipid bodies for washing and cleaning and isolating lipid bodies from residual reagents and chemicals.

Example 38

In this example, a comparative evaluation was made comparing an existing commercial large liposome to the lipid bodies of the invention. The analysis was conducted using published data from a commercial liposome provider and data gathered by microscopic evaluation of lipid bodies using a Petroff Hauser Counter ocular scaling on a phase contrast microscope at either 400× or 1000× magnification. Additional data was obtained by quantitation of yeast oil levels in lipid bodies, using a solvent extraction followed by gravimetric analysis, which provided confirmation that the lipid bodies have an interior that is predominantly yeast oil, existing as triglycerides when measured by thin layer chromatography. The comparative analysis is shown in Table 6.

TABLE 6

| Impact of Volume on Lipid Content and Drug Loading Potential | Diameter in microns (μm) | Volume (Cubic μm) | Lipid content in 5 mL | Estimated Hydrophobic Drug Loading Capacity |
|---|---|---|---|---|
| Lipid Bodies of the Invention | ~7 microns (6-10 μm) | 174 cubic μm | ~2500 mg | 10-20 mg/mL |
| FormuMax ™ PEGylated liposomes* | 0.1 microns | 0.00052 cubic μm | 220 mg | 1-2 mg/mL |
| Comparative Difference | 6.8 microns per particle | 332,314×-fold delta | 11.4×-fold | 10 × per mL of applied formulation |

*Data from FormuMax Scientific Inc.

A primary observation of this analysis resides in the fact that the lipid bodies have a surprisingly thin but robust envelope that allows them to be large and stable with a significantly larger internal hydrophobic interior due to the engineering of the yeast metabolism as described herein. Large commercial liposomes are relatively small, typically less than 0.2 μm in diameter and they contain a significant amount of phospholipids required to make liposomes or stable emulsions in conventional compositions of hydrophobic ingredients. The lipid bodies of the invention have a significant and unexpectedly large internal hydrophobic volume.

Example 39

Lipid bodies were harvested from engineered *Lipomyces starkeyi* according to the methods described above. Following the initial isolation by hydrolysis, the resulting lipid bodies are tan and have an odor similar to the fermentation medium. When appropriately washed in mild to moderate alkaline conditions, the lipid bodies become bright white using a wide range of basic reagents. In this example, the lipid bodies were washed with 14 g/l sodium carbonate plus 1 g/l of sodium percarbonate at a pH of 8.5 to 9.5. The resulting wash results in the removal of the tan color and residual fermentation smell leaving a bright white and appealing cream.

In a similar example, the lipid bodies were treated with a sodium hydroxide solution which was added slowly with mixing to the lipid bodies until a pH of 11.7 was reached. The mixture was separated by flotation. The product of the sodium hydroxide treatment was a bright white cream with no residual smell from the fermentation medium.

In another version of this example, lipid bodies obtained from the fermentation as described above were mixed with either 14 or 15 g/l of sodium carbonate, 1 g/l of sodium percarbonate to obtain a pH of 8.5-9.5. The treated lipid bodies were made more alkaline by the addition of sodium hydroxide until a pH of 11.5 was obtained. Mixing was allowed to proceed for 10 minutes to 1 hour and then the pH was lowered with citric acid to pH 7.0 or below, until any excessive CO2 was displaced from the mixture. The resulting lipid bodies were bright white without smell and in all cases the result was the same for all cases within this example. The use of additional sodium hydroxide did not remove any more color than just the sodium carbonate and sodium percarbonate treatment. Additionally, raising the pH above 11 can trigger undesirable saponification, unless the intention is to form a soap in a composition. The lipid bodies are visualized as a bright white cream that dominates the appearance of lipid bodies compositions.

This example shows the bright white color of either lipid bodies alone or when formulated for microbial and oxidative stability. The example supports the stability of the lipid bodies under elevated temperatures and acid conditions used in their isolation and subsequent washing. The lipid bodies, produced in each of the cases of this example and in many more preparations, had a near-odorless state with a sooth pleasant aqueous feel, even though they are loaded with yeast oil.

Example 40

In this example, lipid bodies were prepared with approximately a 50% concentration as measured by dry weight in stabilizing excipients that in total make the minimal base composition of lipid bodies. The ~50% lipid body cream was diluted in a stabilizing excipient buffer described in Example 2B to determine what level of interstitial aqueous fraction was possible and still maintain a white appearance and other unique properties of the compositions of the invention. The resulting creams and diluted creams (lotions) were evaluated for visual appearance and microscopic appearance. Additionally, the dilutions were applied to the back of the hands of three test subjects and a consensus opinion about texture was generated. Table 7 shows the dilutions and proportion of interstitial aqueous portions evaluated by feel and consistency.

TABLE 7

| Sample Description | Concentration of lipid bodies | Interstitial Aqueous Fraction | Appearance | Texture description and Feel |
|---|---|---|---|---|
| Starting Formulation (see Example 43) | ~50% | ~50% | White Cream, non-dripping on inversion | Like Soft Cream-Cheese with a smooth feel |
| Dilution 1 | 30-33% | 67-70% | White Cream, non-dripping on inversion | Like Yogurt with a smooth feel |
| Dilution 2 | 18-25% | 75-82% | While Lotion, drips | Like whole milk with a smooth feel |
| Dilution 3 | 12% | 88% | White Lotion, viscous* and drips | Like 2% fat milk with a smooth feel |
| Dilution 4 | 6% | 94% | White Lotion low viscosity drips | Like skim milk with a smooth feel |
| | 3% | 97% | White Thin Lotion, drips | Like skim milk that is diluted 1:2 with water |

*The lipid body suspension is non-Newtonian when measured on a viscometer, values not reported.

The conditions listed in Table 7 have the property of a significant interstitial aqueous zone around the exterior of lipid bodies, while maintaining a solid white appearance, when displayed against a black background. Textures and viscosities vary with dilution, but the color remains a solid white for both creams and lotions down to a 3% concentration of lipid bodies.

Having a wide range of available aqueous fractions, while maintaining a solid white color, is important for the inclusion of hydrophilic ingredients containing lipid bodies. The retention of a solid white appearance important and masking benefits when blending in off-color ingredients. The density of light absorbance was pronounced even in a suspension containing 3% lipid bodies, which appears as a solid color.

Example 41

Figure 18:
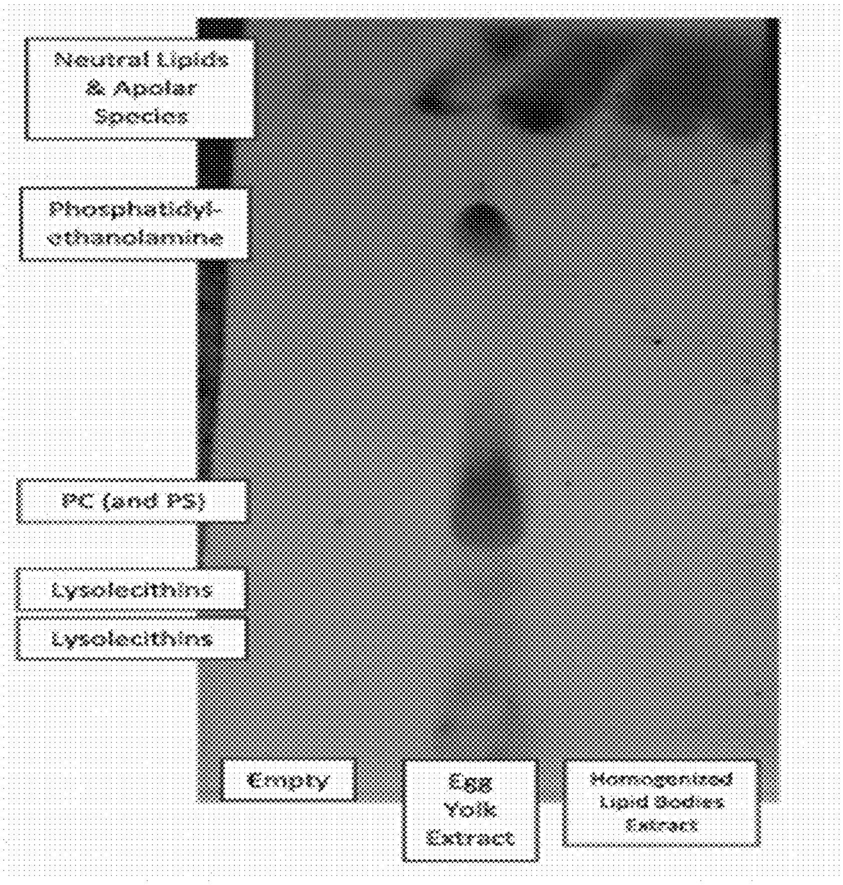
FIG. 18. Analysis of lipid constituents of lipid bodies.

In this example, lipid bodies were prepared as described in Example 43. The alkaline washed and pH adjusted materials were homogenized and extracted with chloroform/methanol extraction to establish the 100% value to total oil. When compared to the dry weight of the lipid bodies in the preparation, the oil content of the large lipid bodies approaches a total oil content of greater than 90% by gravimetric analysis and in some preparations greater than 90%, when considering both triglycerides, phospholipids and lipid containing envelope proteins. The chloroform/methanol extraction is the gold standard for yeast oil measurement. When lipid bodies are extracted with hexane, then the resulting oil level in the lipid bodies appears to be 75-80% of the total gravimetric mass of lipid bodies. In this example, an analysis was conducted to evaluate the relative quantity of envelope phospholipids compared to neutral triglycerides (yeast oil). As a positive control, egg yolk was used to inform the expected locations of various lipid classes. The results suggest that the envelopes and exterior of the lipid bodies contain relatively small amounts of phospholipid when compared to amounts of internal neutral yeast oil as shown in FIG. 18. The presence of low levels of phospholipids was confirmed by lipidomic analysis with LC-MSMS (liquid chromatography-mass spec-mas spec).

The data in this example shows the high level of yeast oil triglycerides (neutral lipids) in the lipid bodies, e.g., an internal lipid content of at least 66% and as much as 90% lipid by gravimetric analysis. The example contributes to the explanation of the relatively small occupancy of the outwardly facing envelopes.

Example 42

Whole yeast containing lipid bodies were homogenized and the yeast oil extracted with pentane, plus an emulsion breaker such as ethanol. The pentane was slowly removed by evaporation at room temperature and the yeast oil formed a solid above the liquid in which it was suspended. The same result can be obtained by first isolating the lipid bodies and then homogenizing them. The yeast oil was then removed and placed on a tin tray and warmed to 40-50° C., after which the yeast oil became a liquid. This is a unique and important property of this component of lipid bodies because of the frequent need to have products melt when applied to the skin or consumed. The following picture demonstrates the melting point transition of the yeast oil component of lipid bodies.

The fact that the lipid bodies have the property of melting at body temperature and above is important for imparting hydrophobic ingredients into the skin as a mobile liquid. Alternatively, there may be instances when restricting mobility of a formulated drug or composition may be required and, in that case, the ingredient will remain in a solid state by maintaining the temperature at or below room temperature. Additionally, lipid bodies can be frozen and melted through multiple cycles providing that free oil is not present that could float to the top of a composition when warmed. The base composition with 50% lipid bodies tolerates multiple cycles of being frozen and thawed without injury to the lipid body spheres.

Example 43

The UV absorbance of lipid bodies (FIG. 11) corresponds to the high light absorbance and reflectance described in Example 44. However, the absorbing wavelengths of lipid bodies are in the UV regions between 290 nm and 190 nm that are important for blocking the harmful rays of the sun. However a valid sunblock composition could be enhanced by using lipid bodies to take-up additional sunblock ingredients, particularly if those ingredients can be facilitated by the hydrophobic or hydrophilic nature of the compositions of the invention that suggest that sunblock agents need only protect against longer wavelength UVC rays when such agents are loaded into the compositions of the invention.

This example shows the utility of lipid bodies in sunblock preparations, such as when sunblock reagents are added. There is a need for safer alternative sunblock reagents that can be made to feel smooth and aqueous.

Example 44

In this example, the viscometric properties were measured in a lipid body-based composition that contained 30% to 50% lipid bodies by dry weight. This observation demonstrates that lipid body cremes exhibit the property of non-Newtonian viscosity. The utility of non-Newtonian viscosity means that compositions of the invention will have a high viscosity at low shear rates, and have a lower viscosity at higher shear rates. This is particularly useful for making the creams and compositions that spread easily but are resistant to dripping.

Example 45

Compositions containing 3% to 50% lipid bodies were mixed with 2% to 5% modified starch (Star-Design Power, Cargill). The resulting compositions had the property of stable suspensions despite low density of lipid bodies, as low as 6% when left to stand for 4 hours. The inhibition of flotation at a fixed level of modified starch at 2% was adequate to maintain the suspension of lipid-body compositions for longer periods of time with increasing lipid body concentrations and or increasing concentrations of modified starch. In this example, lipid-body compositions containing 2% modified starch in a composition with 30% lipid bodies remained suspended without separation for 90 days at room temperature. This example highlights the important shelf-life compositions that are possible when lipid-body compositions include a low concentration of hydrophilic polymers and starches. In another version of this example, hyaluronic acid, glycerol, Polysorbate-80, and non-modified starch can be used to achieve stable suspensions of lipid body containing compositions.

Example 46

Figure 19:
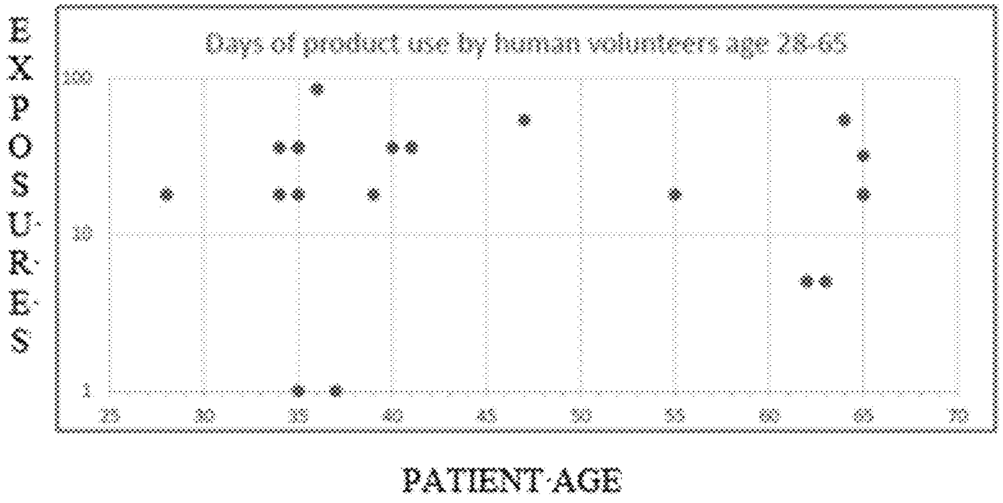
FIG. 19. Results from exposure of patients to an exemplary lipid body-based skin cream of the invention.

As a cosmetic composition, lipid bodies have the property of being relatively benign on human skin and have a demonstrated low irritation level in human exposures. An interim test with a skin cream formulated with approximately 50% lipid body skin cream was performed (FIG. 19) and shows no adverse events or skin irritations. This example shows that the lipid bodies, when used in all types of compositions, are benign and non-irritating on the skin, as shown in this cosmetic composition data above.

Currently the largest commercially available liposomes for hydrophobic drug loading are from FormuMax™ and those are PEGylated liposomes that are 0.1 microns. Table 8 illustrates the relative sized and volumetric values for FormuMax™ hydrophobic PEGylated liposomes in comparison to lipid bodies of the invention.

TABLE 8

Comparison of lipid bodies compared to FormuMax™ Liposomes.

| Impact of Volume on Lipid Content and Drug Loading Potential | Diameter in microns (μm) | Volume (Cubic μm) | Lipid content in 5 mL | Hydrophobic Drug Loading Capacity |
|---|---|---|---|---|
| Lipid bodies of the invention | ~7 microns (6-10 μm) | 174 cubic μm | ~2500 mg | 10-20 mg/mL |
| FormuMax™ PEGylated liposomes* | 0.1 μm | 0.00052 cubic μm | 220 mg | 1-2 mg/mL |
| Comparative Difference | 6.8 microns per particle | 332,314×-fold delta | 11.4×-fold | 10 × per mL |

*Data and Trademark of FormuMax Scientific Inc.

Example 47

Figure 20A:
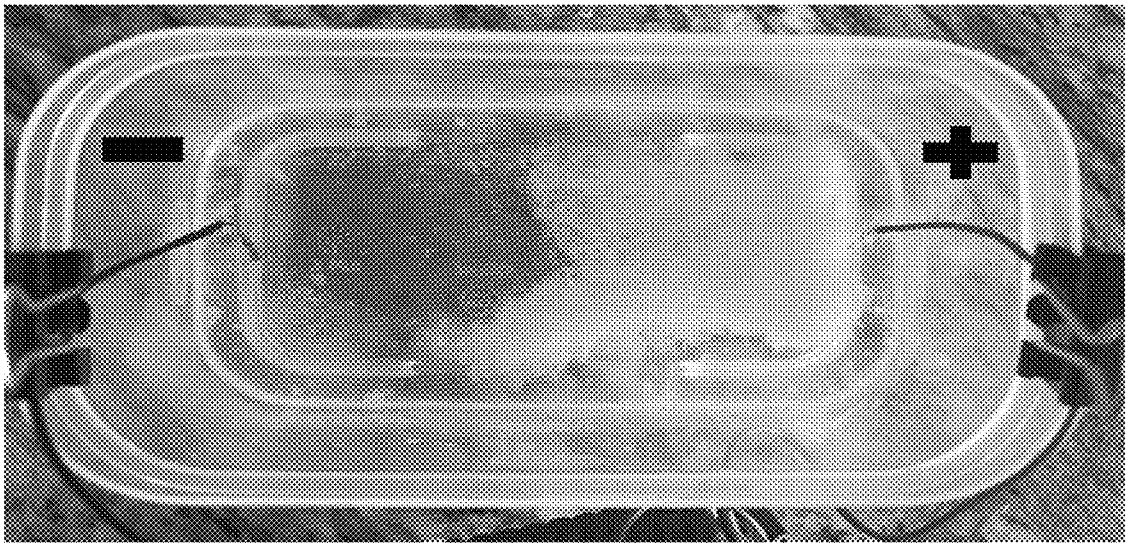
FIGS. 20A and 20B. Properties of lipid bodies chelated to copper.

Lipid bodies were exposed to an electric field using copper electrodes and they migrated toward the positive (cathode) pole (FIG. 20A). During the course of electrophoresis, they accumulated copper. When repeated with simple mixing, the binding of copper was independent of the electrical field. Unexpectedly for a lipid composition, lipid bodies of the invention chelate of copper and perhaps other divalent metals. The chelation of copper by lipid bodies of the invention has medical utility in Wilson's disease and the addition of copper to lipid bodies of the invention increases the density of lipid bodies such that they become neutrally buoyant in water, property that is useful in maintaining stable suspensions of lipid bodies in some applications.

Wilson disease is found worldwide, with an estimated prevalence of 1 case per 30,000 live births in most populations, although data from population screening by molecular sequencing in the United Kingdom suggest a potentially higher prevalence, perhaps as frequent as 1 case in 7021. Assuming a prevalence of 1 in 10,000 to 30,000, approximately one person in 90 carries an abnormal copy of the ATP7B gene. However, in some isolated populations, the prevalence is much higher. One of the highest reported prevalence was from a small mountain village on the island of Crete, where Wilson disease was diagnosed in 1 in 15 births. Excess copper in the diet leads to pathologic accumulation of the metal in the liver, cornea, and brain in patients with insufficient copper transporter proteins.

Figure 20B:
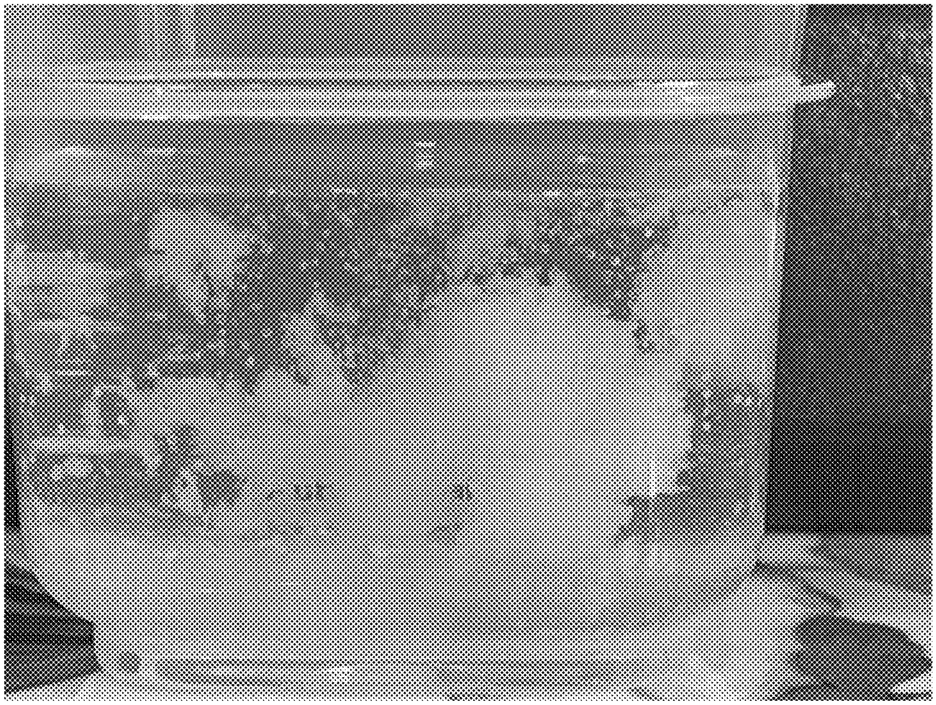

Engineered lipid bodies of the invention effectively chelate copper and become blue from copper, which is displaced from the wire electrodes in an aqueous electrophoresis setting, using in a 12 Volt DC, 1.75-amp system. Upon chelation of copper, the structure and charge properties of lipid bodies remain unchanged, but the density of lipid bodies increases (FIG. 20B).

Example 48

The invention of lipid bodies of the invention that can be manipulated with respect to density is a very useful property for shelf-life stabilization of lipid bodies of the invention suspension in dilute compositions comprising lipid bodies of the invention. Finally, the lipid bodies of the invention can also be loaded with high levels of divalent cations such as copper to achieve an excess of charge, which leads to a change in electrophoretic migration at neutral pH (FIG. 20A). The property of having a net positive charge at neutral pH can facilitate the development of drug and nucleic acid therapeutics comprised of lipid bodies of the invention.

Example 49

Sterile lipid bodies of the invention were found to be essentially tasteless. A 27% lipid bodies of the invention suspension in phosphate buffered saline at neutral pH was tasted and found to have no specific taste other than that of the slightly salty phosphate buffered saline. The property of being tasteless is an important property of lipid bodies of the invention for use in oral drug delivery systems and oral or respiratory vaccines comprising lipid bodies of the invention.

Example 50

Lipid bodies of the invention can be coated with a cationic polymer such as chitosan or specific cationic peptides or cationic sections of larger proteins and ligands. Additionally, lipid bodies of the invention treated with or coupled to cationic peptides can enhance the ability of lipid bodies of the invention to delivery drugs and genes in a manner described by Hashida et al. 2015. Cationic peptides can play a role in transporter-based import across the intestinal mucosal layer or enhance endocytosis across the mucosal layer. Similarly, cardiotoxins can facilitate transport across phospholipid monolayers as described in Bougis et al. 1981. The property of transmucosal transport is a useful property in the development of therapeutic products, which incorporate specific drugs, nucleotides, genes, plasmids and other genetic and immune modulators comprising lipid bodies of the invention as a carrier in such therapeutics.

Example 51

Figure 21:
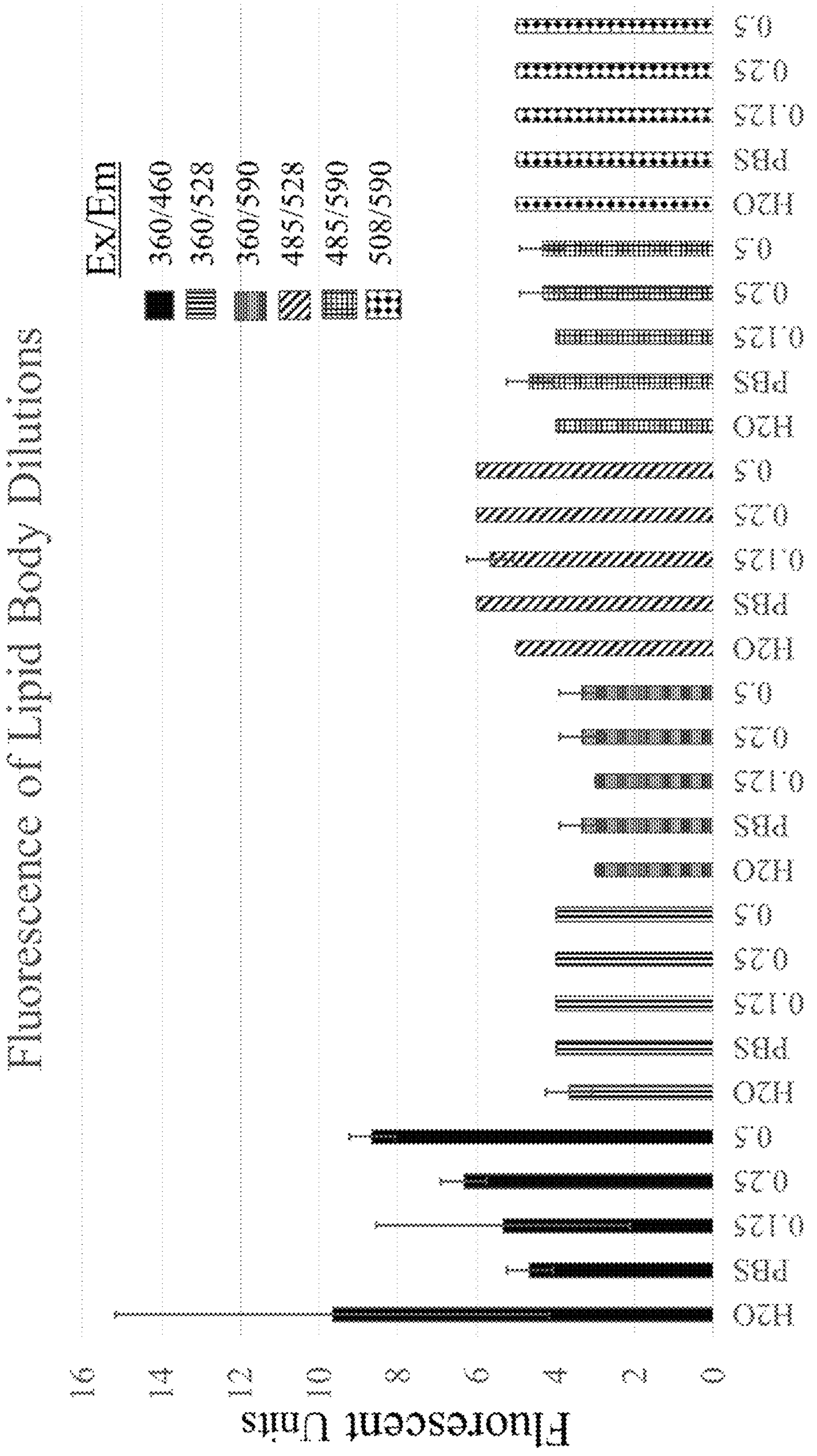
FIG. 21. Intrinsic fluorescence of lipid bodies of the invention.

This example demonstrates intrinsic fluorescence of lipid bodies of the invention. Water ($H_2O$), phosphate buffered saline (PBS) buffer, or lipid bodies at the indicated percent dry weight in PBS (0.125%, 0.25%, and 0.5%) were subjected to six sets of the indicated excitation and emission wavelength pairings. In neither scenario did the lipid bodies display a higher intrinsic fluorescence than both the water or PBS samples, and in most cases were identical to the PBS sample (FIG. 21). In the case of the 360 nm/460 nm excitation and emission pairing, the lipid bodies had a slightly higher intrinsic fluorescence over the PBS sample, but were lower or comparable with the water sample (FIG. 21). These results demonstrate the feasibility of detecting fluorescent compounds or drugs loaded into lipid bodies by monitoring an increase in overall fluorescence at established excitation and emission wavelengths of the lipid body loaded fluorescent compounds or drugs relative to unloaded lipid bodies.

Example 52

Figure 22:
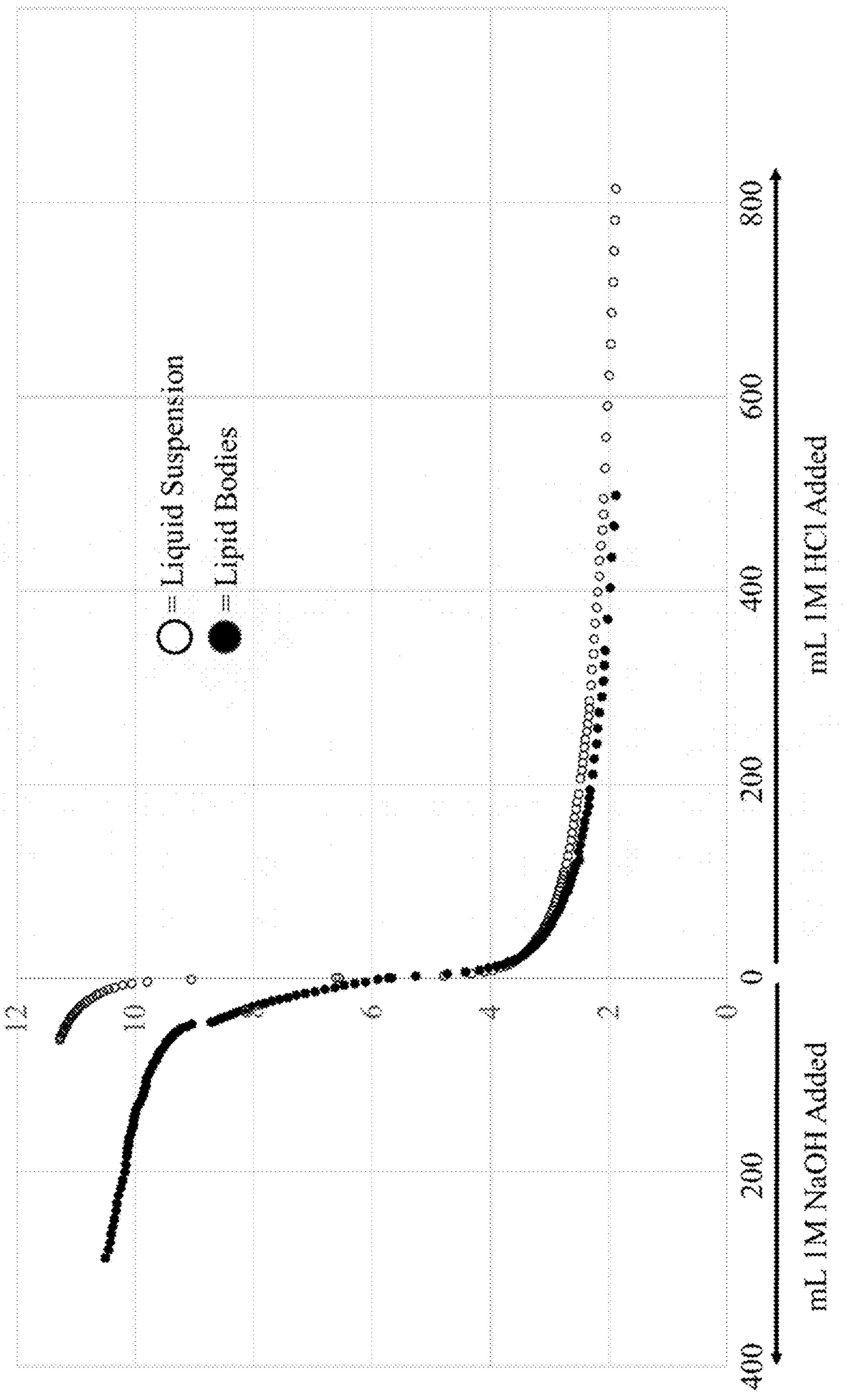
FIG. 22. Titration of lipid bodies of the invention with 1M NaOH or 1M HCl.

This example demonstrates the titration of lipid bodies with 1 M NaOH or 1 M HCl. Water-washed lipid bodies at 10-15% dry weight in water, as well as the water (free of lipid bodies) used to wash the lipid bodies (liquid suspension), were subjected to titration with either 1 M NaOH or 1 M HCl. Titration of the lipid bodies with 1 M NaOH displayed a slight buffering capacity above pH 7 compared to the aqueous wash liquid, and was especially pronounced above pH 9.0 (FIG. 22). However, the titration of lipid bodies with 1 M HCl achieved acidic pH more readily compared to the aqueous resuspension liquid (FIG. 22). A number of explanations could describe this behavior, such as saponification of lipid bodies under alkaline pH conditions, and the displacement of free water by lipid bodies allowing sharper changes in pH where no buffering capacity is present. These results demonstrate a unique titration profile of lipid bodies compared to the liquid in which they are suspended.

Example 53

Enzymatic Treatments

Cell lysis is among the most difficult process steps for recovering oil from yeast, especially for the recovery of highly purified lipid free from odor and color. The present examples show a scalable process for lipid body recovery that involves hydrolysis with 0.5 M phosphoric acid and heating at 90 to 121° C. followed by washing. The oil itself can be recovered by direct high-pressure homogenization of the cells following alkali treatment and organic extraction. This process yields a high-quality oil, but it depends on the use of a very high-pressure and expensive homogenization system.

Beta-(1,3)-glucanases digest the cell walls of yeasts. These are often known as yeast cell wall degrading enzymes (YCWDE) or yeast lytic enzymes (YLE). Originally, yeast cell wall degrading enzymes were derived from snail gut (Giaja 1914, Uzuka et al. 1975). Many different microbial sources were later described (Kitamura et al.). Such enzymes have been used to make yeast protoplasts from viable cells to transform cells with DNA (Marchand et al. 2007), to release endogenous or heterologous enzymes (Andrews et al. 1987 *Trends in Biotechnology*) or to extract carotenoids (Michelon et al. 2012), among other uses.

The enzymes produced by *Oerskovia xanthineolytica* (Jeffries et al. 1981, Mann et al. 1978) (aka: *Arthrobacter luteus* (Kitamura et al. 1971, Kanedo et al. 2014), *Cellulosimicrobium cellulans*) include at least three enzymes, two of which possess the Ricin B Lectin binding domain, which enables these enzymes to attach to the yeast cell walls and release pentameric oligosaccharides from the cell walls (Jeffries et al. 1981). A continuous cultivation process allows rapid and economical production of YLE from *O. xanthineolytica* (Andrews et al. 1987 *Biotechnol Bioeng*).

Yeast Lytic Enzymes

Bacterial endo-1,3-β-glucanases (EC 3.2.1.6 and 3.2.1.39) are integral for assimilating fungal cell walls as a food source in nature, because they catalyze the hydrolysis of cell wall β-1,3-glucosidic linkages (Tanabe et al. 2011). Bacteria from the species *Cellulosimicrobium cellulans*, previously known as *Oerskovia xanthineolytica* and *Arthrobacter luteus*, produces yeast cell wall degrading enzymes. These bacteria are various strains of high GC nocardioid actinomyces.

Three genes encoding endo-β-1,3-glucanases from two *C. cellulans* have been cloned and characterized (Ferrer 2006). The βglII and βglIIA genes from strain DSM 10297 (also known as *O. xanthineolytica* LL G109) encode proteins of 40.8 and 28.6 kDa, respectively, whereas the β-1,3-glucanase gene from strain ATCC 21606 (also known as *A. luteus* 73-14) encode a 54.5 kDa protein (GenBank: BAA04892.1). βglII and βglIIA have catalytic domains assigned to GH family 16 of glycosyl hydrolases, whereas the catalytic domain from the 54.5 kDa glucanase belongs to GH family 64. both βglII and the 54.5 kDa β-1,3-glucanase are multi-domain proteins, having a lectin-like C-terminal domain that has been assigned to GH family 13 of carbohydrate binding modules, and that confers to β-1,3-glucanases the ability to lyse viable yeast cells.

In cloned, nuclease and protease-free formulations, yeast cell wall degrading enzymes are used to release protoplasts from *S. cerevisiae* and other yeasts (Ferrer 2006). One characteristic of the principal enzyme known to produce yeast protoplasts (β-1,3-glucanase I) is its capacity to rapidly solubilize insoluble laminarin and produce laminaripentaose. Because of the oligomeric nature of this product, few reducing groups are formed, but the ricin binding domain enables it to readily attack yeast cell walls. Enzymes belonging to this class are known from *C. cellulans* (Tanabe et al. 2011) (*Oerskovia xanthineolytica*) (Jeffries et al. 1981, Mann et al. 1978), *Arthrobacter* sp. YCWD3 (Doi et al. 1986), *Arthrobacter luteus* (Tanabe et al. 2011, Watanabe et al. 2014, Aono et al. 1995, Nakabayashi et al. 1998), and *Streptomyces matensis* (Shrestha et al. 2011. A second enzyme, β-1,3-glucanase II, attacks oligomeric β-1,3-glucans and reduces them to glucose, and β-1,3-linked dimeric oligosaccharides. It can also release trimeric β-1,3-β-1,6-branched oligomers.

A number of methods for producing yeast lytic enzymes have been described. See DeWi et al. 2016 for the production of β-glucanase production by *Bacillus circulans*. None of the three GH-16 β-1,3-glucanases found in *Bacillus circulans* include the Ricin B Lectin domain that enables binding to yeast cell walls; hence they are predicted to be less effective than the enzyme from *C. cellulans*. See Ferracini-Santos et al. 2008 for the production of alkaline protease from *Cellulosimicrobium cellulans*. See Mann et al. 1978 for the production of yeast lytic activities from *O. xanthineolytica*. See Andrews et al. 1987 (*Biotechnol Bioeng*) for the induction of yeast lytic enzymes in *O. xanthineolytica*. See Andrews et al. 1987 (*Trends in Biotechnology*).

Strain, Media, and Cultivation of *C. cellulans* to Produce Yeast Lytic Enzyme

There were two motives of this example: (1) to dispose of the acid hydrolysate and/or (2) eliminate the need for acid hydrolysis by replacing phosphoric acid with a yeast cell wall degrading enzyme (YCWDE).

The strain of *Cellulosimicrobium cellulans* used herein to demonstrate the utility of yeast lytic enzymes for recovery of lipid bodies and oil was NRRL B-4567, which corresponds to ATCC 21606, but other strains possessing the appropriate enzymes may be used. Strain NRRL B-4567 was used by Ferrer et al. 2006. A sequencing project for this strain has been announced by Peking University (*Cellulosimicrobium cellulans* strain: ATCC 21606 Genome sequencing and assembly; NCBI Accession PRJNA505736). An assembly is available (NCBI Accession ASM523930v1).

This strain has at least one glycosyl hydrolase GH64 "Ricin-type beta-trefoil lectin domain protein", which releases laminaripentose ([β-D-glucosyl-(1,3)]$_4$-)β-D-glucosyl and which rapidly breaks down the β-D-(1,3/1,6)-glucan in the yeast cell walls (NCBI Accession WP_137279716.1, *Cellulosimicrobium cellulans*, family GH64 ricin-type beta-trefoil lectin domain protein; SEQ ID NO:42). It also has at least one glycosyl hydrolase (GH16) "Family 16 glycosylhydrolase", which hydrolyses the laminaripentose to glucose. Both of these proteins have the Ricin B Lectin binding domain, which enables the enzymes to attach to the yeast cell walls (NCBI Accession WP 137281286.1, *Cellulosimicrobium cellulans*, family GH16 glycosylhydrolase; SEQ ID NO:43).

In these examples, *C. cellulans* NRRL B-4567 is used as the producer organism and autolyzed nutritional yeast (AY) yeast glucan (YG) and/or a phosphoric acid hydrolysate of *L. starkeyi* (LS Hyd) as medium components. The AY, YG and LS Hyd media were all adjusted to between 6.8 and 7.2 prior to inoculation. AY medium contained the components shown in Table 9. The YG medium contained the components shown in Table 10.

TABLE 9

AY medium.

| Component | Amount (g) |
|---|---|
| Peptone | 2.5 |
| Yeast extract | 2.5 |
| $K_2HPO_4$ | 1.3 |
| Glucose | 0.5 |
| Autolysed yeast | 10.0 |
| $DH_2O$ QS | 1.0 L |
| pH | 6.93 |

TABLE 10

YG medium.

| Component | Amount (g) |
|---|---|
| $K_2HPO_4$ | 0.65 |
| $KH_2PO_4$ | 2.5 |
| $(NH4)_2SO_4$ | 0.5 |
| NaCl | 2.5 |
| $MgSO_4 \cdot 7H_2O$ | 0.12 |
| yeast extract | 1.5 |
| β-glucan | 10.0 |
| Water | 1.0 L |

The LS Hyd was used directly after adjusting the pH of the phosphoric acid hydrolysate from 1.2 to between 6.9 and 7.1 by the addition of KOH. The starting $H_3PO_4$ concentration was relatively high (ca. 56 g/l or 0.5 M), so the medium prepared from the hydrolysate was strongly buffered and did not shift significantly during the fermentation.

Assays

The presence of yeast lytic activity can be assayed by the methods of Dewi et al. 2016, Jeffries et al. 1981, or others. Substrates may comprise live yeasts suspended in a buffered osmotic support such as 1- or 2-M KCl, sorbitol, or some other osmotic support with or without supplemental dithiothreitol. Yeast lytic activity may be quantified by optical density readings before and after osmotic shock, from which one can measure the rate or extent of yeast lysis. Activity may also be assayed using isolated yeast cell walls, beta-(1,3)-glucan isolated from yeast or other sources as the substrate. Enzyme activity may be quantified by measuring the release of reducing sugars using the DNS or Nelson-Somogyi methods or by separating the products of the enzymatic hydrolysis on an HPLC column. Other dye-release methods from appropriate substrates may also be used to assess activity.

Preparation of Lytic Enzyme

The LS Hyd was used directly after adjusting the pH of the phosphoric acid hydrolysate from 1.2 to between 6.9 and 7.1 by the addition of KOH. The starting $H_3PO_4$ concentration was relatively high (ca. 56 g/l or 0.5 M), so the medium prepared from the hydrolysate was strongly buffered and did not shift significantly during the fermentation. LS Hyd medium alone produces an active Lipomyces lytic enzyme after 96 h of incubation in a flat-bottom 125 mL Erlenmeyer at 28° C., shaken at 250 rpm. The LS Hyd substrate is high in phosphate and nutrients and does not reliably produce large titers of yeast lytic enzymes. Moreover, the large amount of residual hydrolyzed yeast proteins and wall material make the LSHyd *C. cellulans* lytic enzyme complex and when used to recover lipid bodies or oil, the product is contaminated with the hydrolysate degradation products and proteins.

The AY medium was made up as indicated, autoclaved and distributed to baffled 125 mL Erlenmeyer flasks, inoculated with a small amount of NRRL B-4567 from a fresh plate and incubated with shaking at 250 to 350 rpm, 28° C. for 24 to 48 h. Samples are removed after 7, 12, 18, 24 and 48 h and tested for their abilities to hydrolyze 1% yeast glucan and to release lipid bodies from whole cell broth. In this example, the pH of the reaction mixture comprising 5, 10 or 20% AY enzyme preparation ranged from 5.5 to 7.5. Reaction mixtures with the pH at 7.0 had higher activity than reaction mixtures at pH 5.5. The temperature of incubation ranged from 30° C. to 50° C. The reaction mixtures incubated at 50° C. had higher activity than reaction mixtures at 30° C.

The YG medium was likewise made up as indicated, distributed to baffled Erlenmeyer flasks, autoclaved, inoculated with NRRL B-4567 and incubated with shaking at 250 to 350 rpm, 28° C. for 24 to 48 h. Samples were removed after 7, 12, 18, 24 and 48 h and tested for their abilities to hydrolyze 1% yeast glucan and to release lipid bodies from whole cell broth. The cell lytic activities were similar to those observed with AY medium. Samples from the AY and YG cultures were also examined microscopically. NRRL B-4567 initially grows with a thin filamentous morphology. With time, the filaments grow thicker and break into rods, which then progress to the stage of small spherical cells. The optimal time for cell transfer to larger scale is when the cells are in the rod stage.

Release of Lipid Bodies

For the purposes of this example, release of lipid bodies was assessed by direct inspection of cell suspensions, microscopically, or by HPLC of the cell-free assay medium following treatment of highly lipogenic *Lipomyces starkeyi* with enzyme preparations. In the first instance, enzyme preparations were added to whole broth containing highly lipogenic cells in which the pH ranged from 5.0 to 7.5. Alternately, the cells may be suspended in water, physiological saline or 1 M KCl along with a 0.1 to 0.025 M phosphate buffer of the corresponding pH. The concentration of lipogenic cells used as a substrate can range from 10% to 50% on a volumetric basis. The cell suspension plus the enzyme with or without additional buffer or osmotic support is incubated at 37 to 50° C. for 2 to 24 h and the cells are examined directly, microscopically or by separating the supernatant lipid bodies from the enzyme plus buffer reaction mixture and measuring the amount of glucose and oligosaccharides released. The concentration of crude enzyme broth can range from 1% to 20% of the reaction volume depending on the cell concentration, the enzymatic activity and the length of the incubation.

In direct observation, active preparations caused the lipid bodies to clump and go to the surface of the vessel. In small-volume assays of 5 mL, the lipid bodies clumped at the top of the tube. This can be discerned either by the length of time that it takes for the layer of cells at the top of the tube to be disrupted by mixing or by the rapidity with which the cells rise to the surface following mixing. In both cases, the enzyme-treated cells or lipid bodies are compared to cells in a control tube that receives either buffer without enzyme or a heat-killed enzyme preparation. This result can be observed with 5, 50, 250, 500 and 1000 mL reaction mixtures or larger. The reaction rate is accelerated if mixing is applied during the incubation. Following enzymatic treatment, the lipid bodies can be separated from the hydrolysate by dilution and washing with water or physiological saline. The lipid bodies rise to the surface and the hydrolysate can be drawn off from the lower level.

In microscopic observation, the enzymatically prepared lipid bodies appear smooth and unlike untreated cells they do not contain intracellular constituents. The lipid bodies tend to clump together and form flat surfaces with adjacent lipid bodies. Prior to washing fragments of intracellular constituents can be seen microscopically.

HPLC analysis of the cell-free, lipid body-free reaction medium reveals the accumulation of glucose, disaccharide and higher oligosaccharides in the reaction medium as compared to the cell suspensions incubated without enzyme or active enzyme.

Experimental Determination of pH and Temperature for Enzymatic Hydrolysis

Enzymatic cell wall lysis and release of lipid bodies can be done optimally in whole broth following cultivation of the lipogenic cells and adjustment of the broth to pH 7.0. The crude enzyme preparation is added to the cell suspension and the broth is again adjusted to the optimal pH as necessary. The broth plus enzyme is agitated without aeration and the temperature is raised to 50° C. Samples are periodically removed and assessed microscopically or by centrifugation and HPLC analysis of the cell-free broth. Typically, a final fermentation may contain 30% cells by packed volume, which will require dilution prior to recovery of the lipid bodies.

Scale Up

The fermentation can be scaled up in a fed-batch mode. In this example, 25 to 50 mL of AY or YG medium in a 125 to 250 mL baffled or flat-bottom Erlenmeyer flask is inoculated with NRRL B-4567 for 15 to 20 h. The inoculum is then transferred to a 3-liter bioreactor pH 5.3 and agitated at 200 to 700 rpm with 1 L air per L medium per minute (1 v/v min). The AY or YG medium is fed into the reactor slowly so as to keep the culture under glucose limitation. After 20 to 24 h, the reactor is harvested, the suspended cells are removed by centrifugation and the enzyme preparation is stabilized by refrigeration or the addition of 0.1% sodium benzoate.

Properties of the Lipid Bodies Following Isolation

Following washing and isolation, the enzymatically prepared lipid bodies are osmotically more fragile than lipid bodies prepared using phosphoric acid hydrolysis. They appear to have a thinner membrane and a more hydrophobic surface.

Breakage using low pressure homogenization: The enzymatically treated lipid bodies may be homogenized immediately following incubation at 50° C. One aspect of their physical properties is that they can be disrupted more readily at a lower homogenization pressure than whole cells either with or without treatment with alkali. Their subsequent extraction with hexane or pentane and ethanol yields a clean oil without the formation of a rag layer or particulates.

Release of lipid from enzymatic lipid bodies following osmotic shock: If the enzymatically treated lipid bodies are suspended in a strong osmotic medium such as 15 g/L of sodium carbonate plus 1 g/L of sodium percarbonate plus 55 g/L of sodium citrate and then immediately diluted into a 10-fold volume of water, they will rupture and release their contents Production of Lipid Body Creams from Enzymatically Recovered Lipid Bodies When the enzymatically treated lipid bodies are used to make a cream, the texture of the cream is such that it is smoother and does not readily separate. The resulting enzymatically treated lipid bodies may be suitable for formulation with more hydrophilic constituents than the phosphoric acid treated lipid bodies.

Example 54

A summary of the some conclusions from the foregoing examples is as follows.

The lipid bodies of the invention can have a diameter larger than 5 μm, a diameter from 5 μm to 12 μm, and/or can be merged to have a diameter of 12 to 50 μm or more.

The lipid bodies can be processed to generate isolated components thereof, such as envelopes, yeast oils and other lipid body components or biochemicals.

The lipid bodies and/or any one or more components thereof can be formulated to generate compositions of the invention for drug delivery, consumer products, industrial products, and other products.

The compositions of the invention can be formulated in the form of pastes, creams, lotions, and solutions.

The compositions of the invention can include from 1% to 99% lipid bodies, when measured as a percent dry weight of the formulation The compositions of the invention can be formulated in an aqueous mixture that can carry hydrophobic drugs, lipids, and hydrophobic active ingredients on the interior of the lipid bodies, while simultaneously carrying large quantities of hydrophilic drugs in the exterior of the lipid bodies.

The compositions of the invention can be applied to the skin without feeling oily.

The compositions of the invention comprising lipid bodies of the invention, when applied to the skin, collapse to form a sealing and protectant surface once the lipid bodies in the composition discharge their content. The compositions quickly dry on human skin after the discharge of hydrophobic and hydrophilic ingredients, drugs, and additives, impart a durable protecting layer from the exterior envelopes. The collapse of the lipid body envelopes can seal and retain any ingredients discharged by the composition. This can occur for a period of at least 10 hours. Such compositions can be used as topical drug compositions in the field of topical drug administration and other medical or veterinary fields. These compositions can be important replacements for liposomes and emulsions, which fail to provide retention and protection of treated areas.

The lipid bodies can be modified, charge manipulated, homogenized, and/or dehydrated to create envelopes.

The envelopes can be included in compositions of the invention with or without intact lipid bodies to serve as modified surfaces that can change the types of active ingredients loaded in the compositions. The envelopes can enhance the formulation of large molecules, biologics, and/or peptides for transport into the human body at any point of entry.

The lipid bodies and/or envelopes in the compositions of the invention can have an adjustable and modified surface charge state across a wide range of pH conditions, permitting improved product compositions for specific applications. Some of these charge modifications are useful in unaltered lipid-body compositions. Other charges are formed by chemical or enzymatic treatment of lipid body surfaces. Compositions with lipid bodies or lipid-body envelopes with modified surface charge states can include anti-inflammatory drugs, steroid-like compounds, or other active ingredients. The compositions can contain both hydrophobic and hydrophilic active ingredients. The compositions can be used as a topical composition for soothing the skin, rapid repair of skin irritation, burns, dryness, scar prevention and healing of blisters when applied by individuals with those conditions.

The lipid bodies have tolerance to heat and the ability to be sterilized by autoclaving at 121° C. This makes the lipid bodies particularly useful for critical drug applications, such as subcutaneous injection or vaccines.

The compositions of the invention can include lipid bodies supplemented with yeast oils and/or exterior envelopes that can be isolated by dehydration. Such compositions of the invention have significant lubricity and can be used as industrial or medical lubricants that are heat and friction tolerant.

The lipid bodies of the invention have extreme acid stability to pH levels at or below 0.9, making acidic product compositions and industrial compositions possible.

The lipid bodies of the invention have mild alkaline tolerance, which facilitates transient stability to pH levels at or above 9 to about 12. This is useful in conducting chemical modifications of lipid bodies containing product compositions for medical compositions, consumer care products, cleaners, and de-oiling purposes by the creation of saponified product compositions.

The lipid bodies of the invention have low buoyant density, which is useful in concentrating hydrophobic chemicals and other commercial applications for industrial compositions, such as compositions for the concentration and cleanup of hydrophobic toxic substances and other environmental uses.

Lipid bodies having a diameter 5-12 microns or greater provide internal capacity much greater than conventional liposomes and emulsions and can be used in for medicinal or veterinary product compositions where emulsifiers are undesirable or potentially irritating.

The lipid bodies and compositions thereof can be bright white and oxidation resistant, even when heated or treated with acid at high temperatures. This property is useful in compositions in which oxidation needs to be avoided, either for performance or consumer acceptance.

The lipid bodies and compositions thereof can have a solid white color and a smooth aqueous and pleasant feel under a wide range of conditions and dilutions. This can be a valuable characteristic in many consumer products, medical compositions, and industrial compositions.

The compositions of the invention can include a significant interstitial and surface aqueous zone around the exterior of lipid bodies. This can be important for carrying high concentrations of charged ingredients, hydrophilic drugs, and moisture to areas of application.

The lipid bodies of the invention can have internal lipid contents of at least 66% and as much as 90% or higher, when considering both triglycerides and phospholipids, that are useful as biochemical components and/or for loading hydrophobic drugs in medicinal compositions.

The encapsulated oil in the lipid bodies have a melting temperature at approximately human body temperature and above. The external addition of yeast oil isolated from the lipid bodies imparts a soft-to-liquid texture to elevated-temperature compositions and a softer or even liquid state when warmed above body temperatures. Such compositions can be useful in consumer goods, medical compositions, personal-care compositions, and industrial compositions, where a temperature sensitive state and texture transition to a more liquid state is important for the performance of the composition.

The encapsulated oil in the lipid bodies is a solid at room temperature and below. This property can be exploited to impart a solid texture to room-temperature compositions and a softer or even liquid state when warmed to body temperatures. Such compositions can be useful in consumer goods, medical compositions, personal-care compositions, and industrial compositions, where a temperature-sensitive state and texture transition to a more solid state, for example ice cream or deodorant sticks, is important for the performance of the composition.

The lipid bodies have high UV absorbance. This property makes the lipid bodies useful for sunblock compositions or other compositions in which UV absorbance is important. The sunblock compositions can include the lipid bodies as the sole UV absorbing agent or can include the lipid bodies in addition to other UV absorbing agents. Sunblock compositions that include additional UV absorbing agents have native UV absorbance and enhanced UV absorbance.

The lipid bodies have a higher viscosity at low shear rates and a lower viscosity at high shear rates, a characteristic of non-Newtonian viscosity modifiers. This is a property useful for making the creams and compositions that spread easily but are resistant to dripping. The compositions of the invention can include lipid bodies with or without other viscosity modifiers or ingredients.

The lipid bodies can be formulated as stable suspensions, despite the low density of lipid bodies, when mixed with low concentrations of hydrophilic polymers, starches, or other reagents. Such compositions can be useful for applications in which a lack of separation of the composition components is preferred.

The lipid bodies and components thereof can be odor free as a result of purifying the lipid bodies using water, acids, bases, and microbial stabilizers, and can be combined with or without antimicrobial agents, to both remove yeast smell from the lipid bodies and components thereof and prevent the development of unwanted smells in the final compositions.

The lipid bodies are benign on human skin and have demonstrated low irritation level, when used in compositions of the invention that come into contact with human skin. This hypoallergenic quality of can be important in many medical compositions, veterinary compositions, personal care product compositions, and industrial compositions that may come into contact with human skin.

The lipid bodies can serve as a source of palm-oil-substitute, which is a fundamental feedstock material and basic for many product compositions, for example, in drug delivery systems, medicinal applications, nutritional uses, industrial uses, personal care, skin care, pet care, and many other formulated products.

Topical compositions of the invention have the property of sealing the area of skin where it has been applied. The durability of the sealing and protection of the area of application is durable with minimal shedding over an extended period of time exceeding 4-hours, and in some cases over 10-hours and in some cases over 12-24 hours to help maintain skin moisture and lipid retention in human skin, hair or other tissues without undesirable accumulation.

The lipid bodies and lipid-body components can be easily combined with a wide range of ingredients of all types to make acceptable compositions for a wide range of products across industries. The added ingredients can be hydrophobic, amphiphilic and/or hydrophilic.

The lipid bodies can be composed of at least 50% yeast oil and as much as 98% yeast oil. The yeast oil is capable of being used in product compositions that currently utilize palm oil or palm oil derivatives or fractionations of palm oil, where consumer preference is to use a palm-free product compositions for environmental or other reasons.

The compositions of the invention can enhance skin care and wound healing aids, particularly moisturizers for skin. The compositions of the invention can be used to restore lipids to and heal dry skin, burnt skin, and protected skin. These applications are complemented by the unique protective film from the lipid bodies, which is formed when the lipid bodies impart their lipids to the skin.

The lipid bodies can be formulated in water-repellent compositions, which can be used in any industry where water resistance and lubrication is appropriate.

The lipid bodies can be formulated without chemical emulsifiers or other chemicals frequently associated with personal care and cosmetic products. Product compositions comprised solely of lipid bodies have the property of easy mixing at elevated pasteurizing and or sterilizing temperatures. The pasteurized lipid bodies can be used in the sanitary production of medicines, nutrients, snacks, animal nutrition, parenteral nutrition, food emulsifications, nutritional water-resistant foods, aquaculture feeds, and thermally stable oils for cooking, frying, baking, microwavable food compositions, and ready-to-use food compositions.

The easy combination and mixability of the lipid bodies lends them to generating compositions for oral care, ocular care, mouth washes, topical and oral anti-infectives, antibiotics, antifungals and other medical applications to other body parts including inhalation therapies, intestinal therapies and composition for the movement of drug through the stomach. Such compositions can include, in addition to lipid bodies, other drug emulsifications, drug compositions that require various levels of hydrophobicity and or hydrophilicity, and, in some cases, product compositions that protect against light, moisture, oxidation, radiation, and/or sun-exposure.

The compositions of the invention can include other oils, vegetable oils, synthetic oils, biochemicals, RNA, DNA, peptides, dyes, colorants, vaccine antigens and adjuvants, carbohydrates, sugars, fibers, cellulose or other substance or combination of substances.

The compositions of the invention can deliver amphipathic substance, steroids, hormones, carotenoids, vitamins, nutraceuticals, cosmeceuticals, essential fatty acids, essential lipids, essential amino acids, other amino acids, RNA, DNA, oligonucleotides, synthetic genes and other nutritional, medical or cosmetic applications and or research reagents.

The lipid bodies and/or lipid-body components can modify skin care products that are capable of impacting the skin or skin wrinkles, rashes, inflammations, irritations, blisters, dry skin remediations, sunburn, sun blocks, and any medical condition appearing or experienced on the skin. The resulting composition can include night creams, day creams, cosmetics, cosmetic bases, beauty agents, hair and scalp gels, conditioners, anti-fungal treatments, and deodorants.

The lipid bodies and/or lipid-body components are capable of impacting facial skin appearance, skin wrinkles, rashes, inflammations, irritations, blisters, dry skin remediations, sunburn, sun blocks, and any medical or cosmetic condition appearing or experienced on the facial skin.

The lipid bodies can be combined with or without other liposome products, nanoparticles, macro emulsification, hydrophobic carrier, micro emulsification reagents or nano-emulsification agents with or without co-solvents and other solvents. The compositions can be used as insecticides, herbicides, algaecides, pesticides in general, rodenticide, sanitization of water systems, sanitization of water towers, cleaning agents, clearing heat exchangers and boiler tubes, sanitization of cooling towers, ship bottom paints containing time-release anti-fouling agents, other marine compositions and other similar product applications.

The compositions of the invention can be used in product compositions for electronics, insulation, capacitance, resistance, optical properties, radio frequency modulation, corrosion resistance, lubricity at high temperatures and other industrial applications.

Compositions of the invention comprising the lipid bodies or components thereof can be used for research and scientific compositions. The lipid bodies and/or lipid-body components can be modified or derivatized with other chemicals or ligands for making separations media or chromatographic resins, membranes, films, coatings, reflectance modifiers, transmission modifiers, clear films, colored films, opacity on glass or crystals, and any other industrial or research applications or used in product compositions for marine, outer-space, on Mars, on the Moon and in all composition applications for micro-electronics, high-power electrical systems related insulation, capacitance, resistance, optical properties, radio frequency modulation, corrosion resistance, lubricity at high temperatures and other industrial applications.

REFERENCES

Alving, C. R., and S. C. Kinsy, Preparation and properties of liposomes in LA and LAC states *Immunochemistry*, vol. 8, no. 4, pp. 325-343, 1971, doi: 10.1016/0019-2791(71)90155-8.

Angerbauer, C., Siebenhofer, M., Mittelbach, M. & Guebitz, G. M. Conversion of sewage sludge into lipids by *Lipomyces starkeyi* for biodiesel production. *Bioresource Technology* 99, 3051-3056 (2008).

Andrews, B. A. & Asenjo, J. A. Enzymatic lysis and disruption of microbial cells. *Trends in Biotechnology* 5, 273-277 (1987).

Andrews, B. A. & Asenjo, J. A. Continuous-culture studies of synthesis and regulation of extracellular beta(1-3) glucanase and protease enzymes from *Oerskovia xanthineolytica. Biotechnol Bioeng* 30, 628-637 (1987).

Anon, Edn. Jul. 29, 2016 (U.S. Energy Information Administration, 2016).

Aono, R., Hammura, M., Yamamoto, M. & Asano, T. Isolation of extracellular 28- and 42-kilodalton beta-1,3-glucanases and comparison of three beta-1,3-glucanases produced by *Bacillus circulans* IAM1165. *Appl Environ Microbiol* 61, 122-129 (1995).

Athenstaedt, K. YALI0E32769g (DGA1) and YALI0E16797g (LRO1) encode major triacylglycerol synthases of the oleaginous yeast *Yarrowia lipolytica. Biochimica Et Biophysica Acta-Molecular and Cell Biology of Lipids* 1811, 587-596 (2011).

Bangham A. D., M. W. Hill, and N. G. A. Miller, *Preparation and use of liposomes as models of biological membranes* (Korn, Edward D.). 1974, pp. 1-68.

Barcia-Vieitez, R. & Ramos-Martinez, J. I. The Regulation of the Oxidative Phase of the Pentose Phosphate Pathway: New Answers to Old Problems. *Iubmb Life* 66, 775-779 (2014).

Barsoum I. S. and M. Reich, "Liposomes as carriers of antibacterial agents" *Abstracts of the Annual Meeting of the American Society for Microbiology*, vol. 80, pp. 430-ABSTRACT 430, 1980.

Bartolo-Aguilar, Y. et al. Autolysis of *Pichia pastoris* induced by cold. *AMB Express* 7, 9 (2017).

Becker, J. et al. Metabolic flux engineering of L-lysine production in *Corynebacterium glutamicum*—over expression and modification of G6P dehydrogenase. *Journal of Biotechnology* 132, 99-109 (2007).

Beer, M. U., Arrigoni, E. & Amado, R. Extraction of oat gum from oat bran: Effects of process on yield, molecular weight distribution, viscosity and (1->3)(1->4)-beta-D-glucan content of the gum. *Cereal Chemistry* 73, 58-62 (1996).

Beopoulos, A. et al. Identification and characterization of DGA2, an acyltransferase of the DGAT1 acyl-CoA:diacylglycerol acyltransferase family in the oleaginous yeast *Yarrowia lipolytica*. New insights into the storage lipid metabolism of oleaginous yeasts. *Applied Microbiology and Biotechnology* 93, 1523-1537 (2012).

Bhutada G, Kavšček M, Hofer F, Gogg-Fassolter G, Schweiger M, Darnhofer B, Kordiš D, Birner-Gruenberger R, Natter K. Characterization of a lipid droplet protein from *Yarrowia lipolytica* that is required for its oleaginous phenotype. *Biochim Biophys Acta Mol Cell Biol Lipids.* 2018 October; 1863(10):1193-1205.

Bignell, G. R., Bruce, I. J. & Evans, I. H. Amylolytic enzymes of *Lipomyces starkeyi*: purification and size-determination. *Biotechnology Letters* 22, 1713-1718 (2000).

Bligh and Dyer. A rapid method of total lipid extraction and purification. *Canadian Journal of Biochemistry and Physiology* 37(8):911-7 (1959).

Boulton, C. A. & Ratledge, C. Use of transition studies in continuous cultures of *Lipomyces starkeyi*, an oleaginous yeast, to investigate the physiology of lipid accumulation. *Journal of general microbiology* 129, 2871-2876 (1983).

Bougis P., H. Rochat, G. Pieroni, and R. Verger, "Penetration of phospholipid monolayers by cardiotoxins" (in English), Biochemistry, Article vol. 20, no. 17, pp. 4915-4920, 1981.

Braidman I. and G. Gregoriadis, "Preparation of glucocerebroside beta-glucosidase for entrapment in liposomes and treatment of patients with adult Gauchers disease" *Biochemical Society Transactions*, vol. 4, no. 2, pp. 259-261, 1976.

Calvey, C. H., Willis, L. B. & Jeffries, T. W. An optimized transformation protocol for *Lipomyces starkeyi. Current Genetics* 60, 223-230 (2014).

Calvey, C. H., Su, Y. K., Willis, L. B., McGee, M. & Jeffries, T. W. Nitrogen limitation, oxygen limitation, and lipid accumulation in *Lipomyces starkeyi. Bioresource Technology* 200, 780-788 (2016).

Cannella, D. & Jorgensen, H. Do New Cellulolytic Enzyme Preparations Affect the Industrial Strategies for High Solids Lignocellulosic Ethanol Production? *Biotechnology and Bioengineering* 111, 59-68 (2014).

Cardenas, J. & Da Silva, N. A. Engineering cofactor and transport mechanisms in *Saccharomyces cerevisiae* for enhanced acetyl-CoA and polyketide biosynthesis. *Metabolic Engineering* 36, 80-89 (2016).

Chen, L., Zhou, X. S., Fan, W. M. & Zhang, Y. X. Expression, purification and characterization of a recombinant *Lipomyces starkeyi* dextranase in *Pichia pastoris. Protein Expression and Purification* 58, 87-93 (2008).

Choi, J. W. & Da Silva, N. A. Improving polyketide and fatty acid synthesis by engineering of the yeast acetyl-CoA carboxylase. *Journal of Biotechnology* 187, 56-59 (2014).

Collett, J. R., Meyer, S. & Jones, S. Preliminary economics for hydrocarbon fuel production from cellulosic sugars. (2014).

Connell G. H. and C. E. Skinner, "The external surface of the human body as a habitat for nonfermenting nonpigmented yeasts" *Journal of Bacteriology*, vol. 66, no. 6, pp. 627-633, 1953.

Connell G. H., C. E. Skinner, and R. C. Hurd, "*Lipomyces starkeyi* on the skin surface of the human body" *Mycologia*, vol. 46, no. 1, pp. 12-15, 1954.

Courchesne, N. M. D., Parisien, A., Wang, B. & Lan, C. Q. Enhancement of lipid production using biochemical, genetic and transcription factor engineering approaches. *J Biotechnol* 141, 31-41 (2009).

Demel R. A., S. C. Kinsky, C. B. Kinsky, and Vandeenen. L. L. M., "Effects of temperature and cholesterol on glucose permeability of liposomes prepared with natural and synthetic lecithins" *Biochimica Et Biophysica Acta*, vol. 150, no. 4, pp. 655-665, 1968.

Dewi, R., Mubarik, N. & Suhartono, M. Medium optimization of beta-glucanase production by *Bacillus subtilis* SAHA 32.6 used as biological control of oil palm pathogen. *Emirates Journal of Food and Agriculture* 28, 116-125 (2016).

Doi, K. & Doi, A. Cloning and expression in *Escherichia coli* of the gene for an *Arthrobacter* beta-(1-3)-glucanase. *J Bacteriol* 168, 1272-1276 (1986).

Egbaria K. and N. Weiner, "Liposomes as topical drug delivery system" *Advanced Drug Delivery Reviews*, vol. 5, no. 3, pp. 287-300, 1990.

Esposito, S. Nitrogen Assimilation, Abiotic Stress and Glucose 6-Phosphate Dehydrogenase: The Full Circle of Reductants. *Plants-Basel* 5 (2016).

Evans, C. T. & Ratledge, C. Possible regulatory roles of ATP-citrate lyase, malic enzyme and AMP deaminate in lipid accumulation by *Rhodosporidium toruloides* CBS-14. *Canadian Journal of Microbiology* 31, 1000-1005 (1985).

Ferracini-Santos, L. & Sato, H. H. Production of alkaline protease from *Cellulosimicrobium cellulans. Braz J Microbiol* 40, 54-60 (2009).

Ferrer, P. et al. Nucleotide sequence of a beta-1,3-glucanase isoenzyme IIA gene of *Oerskovia xanthineolytica* LL G109 (*Cellulomonas cellulans*) and initial characterization of the recombinant enzyme expressed in *Bacillus subtilis*. *Journal of Bacteriology* 178, 4751-4757 (1996).

Ferrer, P. et al. Molecular cloning of a lytic beta-1,3-glucanase gene from *Oerskovia xanthineolytica* LLG109. A beta-1,3-glucanase able to selectively permeabilize the yeast cell wall. *Annals of the New York Academy of Sciences* 782, 555-565 (1996).

Ferrer, P. Revisiting the *Cellulosimicrobium cellulans* yeast-lytic beta-1,3-glucanases toolbox: a review. *Microb Cell Fact* 5, 10 (2006).

Fifield R., "Liposomes—bags of biological potential" *New Scientist*, vol. 88, no. 1223, pp. 150-153, 1980.

Fishman Y. and N. Citri, "L-Asparaginase entrapped in liposomes—preparation and properties" *FEBS Letters*, vol. 60, no. 1, pp. 17-20, 1975.

Flores, C. L., and Gancedo, C. *Yarrowia lipolytica* mutants devoid of pyruvate carboxylase activity show an unusual growth phenotype, Eukaryot. *Cell* 4 (2005) 356-364.

Gallagher, A. M., Kelly, C. T. & Fogarty, W. M. A novel extracellular carbohydrase produced by *Lipomyces tetrasporus*. *Applied Microbiology and Biotechnology* 35, 455-460 (1991).

Ganceviciene R., A. I. Liakou, A. Theodoridis, E. Makrantonaki, and C. C. Zouboulis, "Skin anti-aging strategies," (in eng), *Dermatoendocrinol*, vol. 4, no. 3, pp. 308-319, 2012.

Garay, L. A. et al. Eighteen new oleaginous yeast species. *Journal of industrial microbiology & biotechnology* 43, 887-900 (2016).

Garber A T, Segall J. The SPS4 gene of *Saccharomyces cerevisiae* encodes a major sporulation-specific Mrna. *Mol Cell Biol.* 1986 December; 6(12):4478-85.

Gershenwald J. E., A. C. Halpern, and V. K. Sondak, "Melanoma Prevention-Avoiding Indoor Tanning and Minimizing Overexposure to the Sun," *Jama—Journal of the American Medical Association*, vol. 316, no. 18, pp. 1913-1914, November 2016.

Giaja, J. The effect of some ferments on carbon hydrates of yeast. *Comptes Rendus Seances Soc. Biol. Fil.* 77, 2-4 (1914).

Gibson, D. G. et al. Enzymatic assembly of DNA molecules up to several hundred kilobases. *Nature Methods* 6, 343-U341 (2009).

Gietz, R. D., and R. A. Woods, Transformation of yeast by lithium acetate/single stranded carrier DNA/polyethylene glycol method. *Methods in Enzymology* 350:87-96 (2002).

Gomma, A. E., Lee, S. K., Sun, S. M., Yang, S. H. & Chung, G. Improvement in Oil Production by Increasing Malonyl-CoA and Glycerol-3-Phosphate Pools in *Scenedesmus quadricauda*. *Indian Journal of Microbiology* 55, 447-455 (2015).

Goon D. E., S. Kadir, N. Ab Latip, S. Ab Rahim, and M. Mazlan, "Palm Oil in Lipid-Based Formulations and Drug Delivery Systems," *Biomolecules*, vol. 9, no. 2, February 2019.

Gong, Z. W. et al. Co-fermentation of cellobiose and xylose by *Lipomyces starkeyi* for lipid production. *Bioresource Technology* 117, 20-24 (2012).

Gomer, C. et al. Genetic engineering and production of modified fatty acids by the non-conventional oleaginous yeast *Trichosporon oleaginosus* ATCC 20509. Green Chemistry 18, 2037-2046 (2016).

Hamid, A. A., Mokhtar, N. F., Taha, E. M., Omar, O. & Yusoff, W. M. W. The role of ATP citrate lyase, malic enzyme and fatty acid synthase in the regulation of lipid accumulation in *Cunninghamella* sp 2A1. *Annals of Microbiology* 61, 463-468 (2011).

Hammond, E. G., Johnson, L. A., Su, C., Wang, T. & White, P. J. Soybean oil. Bailey's Industrial Oil and Fat Products (2005).

Hashida M., S. Kawakami, and F. Yamashita, "Lipid carrier systems for targeted drug and gene delivery," (in English), *Chem. Pharm. Bull.*, Review vol. 53, no. 8, pp. 871-880, August 2005.

Holdsworth, J. E. & Ratledge, C. Lipid turnover in oleaginous yeasts. *Journal of General Microbiology* 134, 339-346 (1988).

Holdsworth, J. E., Veenhuis, M. & Ratledge, C. Enzyme activities in oleaginous yeasts accumulating and utilizing exogenous or endogenous lipids. *Journal of General Microbiology* 134, 2907-2915 (1988).

Huang, C. et al. Bioconversion of Corncob Acid Hydrolysate into Microbial Oil by the Oleaginous Yeast *Lipomyces starkeyi*. *Applied Biochemistry and Biotechnology* 172, 2197-2204 (2014).

Ingebrigtsen, L. & Brandt, M. Determination of the size distribution of liposomes by SEC fractionation, and PCS analysis and enzymatic assay of lipid content. *AAPS PharmSciTech* 3, E7-E7 (2002).

Jeffries, T. W. *Lipomyces starkeyi* NRRL Y-11557 Genome Sequencing Project. *European Nucleotide Archive* (2013).

Jeffries, T. W. Effects of nitrate on fermentation of xylose and glucose by *Pachysolen tannophilus*. *Bio-Technology* 1, 503-506 (1983).

Jeffries T. W., Eveleigh D. E., Macmillan J. D., Parrish F. W., & Reese E. T. (1977) Enzymatic hydrolysis of walls of yeast cells and germinated fungal spores. *Biochimica Et Biophysica Acta* 499(1): 10-23.

Jeffries, T. W. & Macmillan, J. D. Action patterns of (1→3)-β-d-glucanases from *Oerskovia xanthineolytica* on laminaran, lichenan, and yeast glucan. *Carbohydr. Res.* 95, 87-100 (1981).

Jiang Z. X. and J. Delacruz, "Appearance benefits of skin moisturization," *Skin Research and Technology, vol.* 17, no. 1, pp. 51-55, February 2011.

Kafi R. et al., "Improvement of naturally aged skin with vitamin A (retinol)," *Archives of Dermatology*, vol. 143, no. 5, pp. 606-612, May 2007.

Kandror, O., Bretschneider, N., Kreydin, E., Cavalieri, D. & Goldberg, A. L. Yeast adapt to near-freezing temperatures by STRE/Msn2,4-dependent induction of trehalose synthesis and certain molecular chaperones. *Molecular Cell* 13, 771-781 (2004).

Kaneko, T., Kitamura, K. & Yamamoto, Y. Susceptibilities of Yeasts to Yeast Cell Wall Lytic Enzyme of *Arthrobacter luteus*. *Agricultural and Biological Chemistry* 37, 2295-2302 (2014).

Kang, H. K. et al. Cloning and characterization of a dextranase gene from *Lipomyces starkeyi* and its expression in *Saccharomyces cerevisiae*. *Yeast* 22, 1239-1248 (2005).

Kildegaard, K. R. et al. Engineering and systems-level analysis of *Saccharomyces cerevisiae* for production of 3-hydroxypropionic acid via malonyl-CoA reductase-dependent pathway. *Microbial Cell Factories* 15 (2016).

Kim, Y. et al. Composition of corn dry-grind ethanol by-products: DDGS, wet cake, and thin stillage. *Bioresource Technology* 99, 5165-5176 (2008).

Kitamura, K., Kaneko, T. & Yamamoto, Y. Lysis of viable yeast cells by enzymes of *Arthrobacter luteus*. *Arch Biochem Biophys* 145, 402-404 (1971).

Kochetkov, N. K. et al. Polysaccharides from Lipomyces 0.8 The structure of the extracellular polysaccharides from *Lipomyces starkeyi Bioorganicheskaya Khimiya* 5, 408-417 (1979).
Kruger, J. S. et al. Recovery of Fuel-Precursor Lipids from Oleaginous Yeast. *ACS Sustainable Chemistry & Engineering* 6, 2921-2931 (2018).
Kvorning S. A. and E. Kirk, "The correlation between the clinical appearance of the skin and the skin lipid secretion in middle-aged and old individuals" *Journals of Gerontology*, vol. 4, no. 2, pp. 113-120, 1949.
Lee, S. Y. et al. Demonstration of two independent dextranase and amylase active sites on a single enzyme elaborated by *Lipomyces starkeyi* KSM 22. *Journal of Microbiology and Biotechnology* 13, 313-316 (2003).
Leigh S., "Pro-liposome compositions," U.S. Pat. No. 5,004, 611, 1991.
Leiva-Candia, D. E. et al. The potential for agro-industrial waste utilization using oleaginous yeast for the production of biodiesel. *Fuel* 123, 33-42 (2014).
Li, Z. et al. Overexpression of malic enzyme (ME) of *Mucor circinelloides* improved lipid accumulation in engineered *Rhodotorula glutinis. Appl Microbiol Biotechnol* (2012).
Liu, L. P. et al. Efficient microbial oil production on crude glycerol by *Lipomyces starkeyi* AS 2.1560 and its kinetics. *Process Biochemistry* 58, 230-238 (2017).
Lodder, J., Acomina & Kreger-Van Rij, N. J. W. The yeasts—a taxonomic study. (1952).
Lopezberestein G., "Liposomes as carriers of antimicrobial agents" *Antimicrobial Agents and Chemotherapy*, vol. 31, no. 5, pp. 675-678, May 1987.
Mann, J. W., Jeffries, T. W. & Macmillan, J. D. Production and ecological significance of yeast cell wall-degrading enzymes from oerskovia. *Appl Environ Microbiol* 36, 594-605 (1978).
Marchand, G. et al. Alternative methods for genetic transformation of Pseudozyma *antarctica*, a basidiomycetous yeast-like fungus. *Journal of Microbiological Methods* 70, 519-527 (2007).
Mayer L. D., M. B. Bally, M. J. Hope, and P. R. Cullis, "Techniques for encapsulating bioactive agents into liposomes" *Chemistry and Physics of Lipids*, vol. 40, no. 2-4, pp. 333-345, June-July 1986.
McClements D. J., *Nanoparticle- and microparticle-based delivery systems. Encapsulation, protection and release of active compounds* (Nanoparticle- and microparticle-based delivery systems. Encapsulation, protection and release of active compounds). 2015, pp. xxvi-546.
McNeil, B. A. & Stuart, D. T. *Lipomyces starkeyi*: an emerging cell factory for production of lipids, oleochemicals and biotechnology applications. *World Journal of Microbiology & Biotechnology* 34 (2018).
Michelon, M., de Matos de Borba, T., da Silva Rafael, R., Burkert, C. A. V. & de Medeiros Burkert, J. F. Extraction of carotenoids from Phaffia rhodozyma: A comparison between different techniques of cell disruption. *Food Science and Biotechnology* 21, 1-8 (2012).
Mitra, D. et al. Value-added oil and animal feed production from corn-ethanol stillage using the oleaginous fungus *Mucor circinelloides. Bioresource Technology* 107, 368-375 (2012).
Moritz, B., Striegel, K., De Graaf, A. A. & Sahm, H. Kinetic properties of the glucose-6-phosphate and 6-phosphogluconate dehydrogenases from *Corynebacterium glutamicum* and their application for predicting pentose phosphate pathway flux in vivo. *European journal of biochemistry/FEBS* 267, 3442-3452 (2000).
Naganuma, T., Uzuka, Y., Tanaka, K. & Iizuka, H. Differences in enzyme activities of *Lipomyces starkeyi* between cells accumulating lipid and proliferating cells. *Journal of basic microbiology* 27, 35-42 (1987).
Nakabayashi, M. et al. Structure of the gene encoding laminaripentaose-producing β-1,3-glucanase (LPHase) of *Streptomyces matensis* DIC-108. *Journal of Fermentation and Bioengineering* 85, 459-464 (1998).
Nisha, A., Sankar, K. U. & Venkateswaran, G. Supercritical CO2 extraction of *Mortierella alpina* single cell oil: Comparison with organic solvent extraction. *Food Chemistry* 133, 220-226 (2012).
Ochsenreitheri, K., Gluck, C., Stressler, T., Fischer, L. & Syldatk, C. Production Strategies and Applications of Microbial Single Cell Oils. *Frontiers in Microbiology* 7 (2016).
Oguro, Y. et al. Multicopy integration and expression of heterologous genes in the oleaginous yeast, *Lipomyces starkeyi. Bioscience Biotechnology and Biochemistry* 79, 512-515 (2015).
Ohnishi, J., Katahira, R., Mitsuhashi, S., Kakita, S. & Ikeda, M. A novel gnd mutation leading to increased L-lysine production in *Corynebacterium glutamicum. FEMS Microbiology Letters* 242, 265-274 (2005).
Okada, T. et al. Structure of the gene encoding β-1,3-glucanase B of *Bacillus circulans* WL-12. *Journal of Fermentation and Bioengineering* 80, 229-236 (1995).
Pan, L.-X. et al. Isolation of the oleaginous yeasts from the soil and studies of their lipid-producing capacities. *Food Technol. Biotechnol* 47, 215-220 (2009).
Papanikolaou, S., Chevalot, I., Komaitis, M., Aggelis, G. & Marc, I. Kinetic profile of the cellular lipid composition in an oleaginous *Yarrowia lipolytica* capable of producing a cocoa-butter substitute from industrial fats. *Antonie Van Leeuwenhoek International Journal of General and Molecular Microbiology* 80, 215-224 (2001).
Patel H. M. and B. E. Ryman, "Oral administration of insulin by encapsulation within liposomes" *FEBS Letters*, vol. 62, no. 1, pp. 60-63, 1976.
Punpeng, B., Nakata, Y., Goto, M., Teramoto, Y. & Hayashida, S. A novel raw-starch digesting yeast alpha amylase from *Lipomyces starkeyi. Journal of Fermentation and Bioengineering* 73, 108-111 (1992).
Rangasamy, D. & Ratledge, C. Genetic Enhancement of Fatty Acid Synthesis by Targeting Rat Liver ATP:Citrate Lyase into Plastids of Tobacco. *Plant Physiology* 122, 1231-1238 (2000).
Ratledge, C. Lipid biotechnology—a wonderland for the microbial physiologist. *Journal of the American Oil Chemists Society* 64, 1647-1656 (1987).
Ratledge, C. Regulation of lipid accumulation in oleaginous micro-organisms. *Biochemical Society Transactions* 30, 1047-1050 (2002).
Ratledge, C. Fatty acid biosynthesis in microorganisms being used for Single Cell Oil production. *Biochimie* 86, 807-815 (2004).
Ratledge, C. The role of malic enzyme as the provider of NADPH in oleaginous microorganisms: a reappraisal and unsolved problems. *Biotechnol. Lett.* 36, 1557-1568 (2014).
Rhie G. E. et al., "Aging- and photoaging-dependent changes of enzymic and nonenzymic antioxidants in the epidermis and dermis of human skin in vivo," *Journal of Investigative Dermatology, vol.* 117, no. 5, pp. 1212-1217, November 2001.

Riley R, et al. (2016) Comparative genomics of biotechnologically important yeasts. *Proceedings of the National Academy of Sciences* 113(35): 9882-9887.

Rippa, M., Giovannini, P. P., Barrett, M. P., Dallocchio, F. & Hanau, S. 6-phosphogluconate dehydrogenase: the mechanism of action investigated by a comparison of the enzyme from different species. *Biochimica Et Biophysica Acta-Protein Structure and Molecular Enzymology* 1429, 83-92 (1998).

Ruenwai, R., Cheevadhanarak, S. & Laoteng, K. Overexpression of acetyl-CoA carboxylase gene of *Mucor rouxii* enhanced fatty acid content in *Hansenula polymorpha*. Mol Biotechnol 42, 327-332 (2009).

Ryu, S. J. et al. Purification and partial characterization of a novel glucanhydrolase from *Lipomyces starkeyi* KSM 22 and its use for inhibition of insoluble glucan formation. *Bioscience Biotechnology and Biochemistry* 64, 223-228 (2000).

Saenge, C., Cheirsilp, B., Suksaroge, T. T. & Bourtoom, T. Potential use of oleaginous red yeast *Rhodotorula glutinis* for the bioconversion of crude glycerol from biodiesel plant to lipids and carotenoids. *Process Biochemistry* 46, 210-218 (2011).

Schwendener, R. A. & Schott, H. Liposome formulations of hydrophobic drugs. *Methods in molecular biology* (Clifton, Ni) 605, 129-138 (2010).

Severa, G., Kumar, G. & Cooney, M. J. Corecovery of Lipids and Fermentable Sugars from *Rhodosporidium toruloides* Using Ionic Liquid Cosolvents: Application of Recycle to Batch Fermentation. *Biotechnology Progress* 30, 1239-1242 (2014).

Shi, S. B., Chen, Y., Siewers, V. & Nielsen, J. Improving Production of Malonyl Coenzyme A-Derived Metabolites by Abolishing Snfl-Dependent Regulation of Acc1. *Mbio* 5 (2014).

Shindo Y., E. Witt, D. Han, W. Epstein, and L. Packer, "Enzymic and non-enzymic antioxidants in epidermis and dermis of human skin," (in eng), *J Invest Dermatol*, vol. 102, no. 1, pp. 122-4, January 1994, doi: 10.1111/1523-1747.

Shrestha, K. L. et al. Characterization and identification of essential residues of the glycoside hydrolase family 64 laminaripentaose-producing-beta-1,3-glucanase. *Protein Eng Des Sel* 24, 617-625 (2011).

Sikl, D., Masler, L. & Bauer, S. Extracellular polysaccharides of *Lipomyces starkeyi* Lodder et Kreuger van Rij. Isolation and structural features of galactomannan *Collection of Czechoslovak Chemical Communications* 33, 1157-& (1968).

Sitepu, et al. An improved high-throughput Nile red fluorescence assay for estimating intracellular lipids in a variety of yeast species. *Journal of Microbiological Methods* 91:321-328 (2012).

Sitepu, I. R. et al. Oleaginous yeasts for biodiesel: Current and future trends in biology and production. *Biotechnology Advances* 32, 1336-1360 (2014).

Signori, L. et al. Assessing an effective feeding strategy to optimize crude glycerol utilization as sustainable carbon source for lipid accumulation in oleaginous yeasts. *Microbial Cell Factories* 15 (2016).

Spier, F., Buffon, J. G. & Burkert, C. A. V. Bioconversion of Raw Glycerol Generated from the Synthesis of Biodiesel by Different Oleaginous Yeasts: Lipid Content and Fatty Acid Profile of Biomass. *Indian Journal of Microbiology* 55, 415-422 (2015).

Steyn, A. J. C., Marmur, J. & Pretorius, I. S. Cloning, sequence analysis and expression in yeasts of a cDNA-containing a *Lipomyces kononenkoae* alpha-amylase encoding gene. *Gene* 166, 65-71 (1995).

Szoka F. J. and D. Papahadjopoulos, "Comparative properties and methods of lipid vesicles liposomes" in Mullins, L. J., (Annual Review of Biophysics and Bioengineering, 1980, pp. P467-508.

Tai, M. & Stephanopoulos, G. Engineering the push and pull of lipid biosynthesis in oleaginous yeast *Yarrowia lipolytica* for biofuel production. *Metabolic Engineering* 15, 1-9 (2013).

Tanabe, Y. & Oda, M. Molecular characterization of endo-1,3-beta-glucanase from *Cellulosimicrobium cellulans*: effects of carbohydrate-binding module on enzymatic function and stability. *Biochim Biophys Acta* 1814, 1713-1719 (2011).

Tang, W., Zhang, S., Wang, Q., Tan, H. & Zhao, Z. K. The isocitrate dehydrogenase gene of oleaginous yeast *Lipomyces starkeyi* is linked to lipid accumulation. *Can J Microbiol* 55, 1062-1069 (2009).

Tang, X. L., Feng, H. X. & Chen, W. N. Metabolic engineering for enhanced fatty acids synthesis in *Saccharomyces cerevisiae. Metabolic Engineering* 16, 95-102 (2013).

Tang, X. L. & Chen, W. N. Investigation of fatty acid accumulation in the engineered *Saccharomyces cerevisiae* under nitrogen limited culture condition. *Bioresource Technology* 162, 200-206 (2014).

Tchakouteu, S. S. et al. Lipid production by yeasts growing on biodiesel-derived crude glycerol: strain selection and impact of substrate concentration on the fermentation efficiency. *Journal of Applied Microbiology* 118, 911-927 (2015).

Tentsova A. I., N. S. Kovaleva, E. A. Yarova, and N. N. Ivkov, "Liposomes and the possibilities of their use in pharmacy and pharmacology" *Farmatsiya* (Moscow), vol. 25, no. 3, pp. 82-85, 1976.

Uzuka, Yasuyuki; Kanamori, Takeshi; Koga, Tetsuro; Tanaka, Kentaro; Naganuma, Takafumi. Isolation and Chemical Composition of Intracellular Oil Globules from the Yeast *Lipomyces starkeyi. J. Gen. Appl. Microbiol.,* 21, 157-168 (1975).

Van Rossum, H. M., Kozak, B. U., Pronk, J. T. & van Maris, A. J. A. Engineering cytosolic acetyl-coenzyme A supply in *Saccharomyces cerevisiae*: Pathway stoichiometry, free-energy conservation and redox-cofactor balancing. *Metabolic Engineering* 36, 99-115 (2016).

Velasco, P., Sieiro, A. M., Ibarguren, I., Ramosmartinez, J. I. & Barcia, R. The Modulation of the Oxidative Phase of the Pentose-Phosphate Pathway in Mouse Liver. *International Journal of Biochemistry & Cell Biology* 27, 1015-1019 (1995).

Vicente, G. et al. Direct transformation of fungal biomass from submerged cultures into biodiesel. *Energy & Fuels* 24, 3173-3178 (2010).

Waltermann M, Steinbüchel A. Neutral lipid bodies in prokaryotes: recent insights into structure, formation, and relationship to eukaryotic lipid depots. *J Bacteriol.* 2005 June; 187(11):3607-19.

Wang, Z. P., Xu, H. M., Wang, G. Y., Chi, Z. & Chi, Z. M. Disruption of the MIG1 gene enhances lipid biosynthesis in the oleaginous yeast *Yarrowia lipolytica* ACA-DC 50109. *Biochimica Et Biophysica Acta-Molecular and Cell Biology of Lipids* 1831, 675-682 (2013).

Wang, W. et al. Fatty alcohol production in *Lipomyces starkeyi* and *Yarrowia lipolytica. Biotechnology for Biofuels* 9 (2016).

Wang, J. C., Xu, R. H., Wang, R. L., Hague, M. E. & Liu, A. Z. Overexpression of ACC gene from oleaginous yeast *Lipomyces starkeyi* enhanced the lipid accumulation in *Saccharomyces cerevisiae* with increased levels of glycerol 3-phosphate substrates. *Bioscience Biotechnology and Biochemistry* 80, 1214-1222 (2016).

Watanabe, T. et al. Expression in *Escherichia coli* of the *Bacillus circulans* WL-12 Structural Gene for β-1,3-Glucanase A. *Agricultural and Biological Chemistry* 53, 1759-1767 (2014).

Wei, T., Sufang, Z., Qian, W., Haidong, T. & Zongbao Kent, Z. The isocitrate dehydrogenase gene of oleaginous yeast *Lipomyces starkeyi* is linked to lipid accumulation. *Canadian Journal of Microbiology* 55, 1062-1069 (2009).

Wenning, L., Yu, T., David, F., Nielsen, J. & Siewers, V. Establishing very long-chain fatty alcohol and wax ester biosynthesis in *Saccharomyces cerevisiae. Biotechnology and Bioengineering* 114, 1025-1035 (2017).

Wilkie, A. C., Riedesel, K. J. & Owens, J. M. Stillage characterization and anaerobic treatment of ethanol stillage from conventional and cellulosic feedstocks. *Biomass & Bioenergy* 19, 63-102 (2000).

Wynn, J. P., bin Abdul Hamid, A. & Ratledge, C. The role of malic enzyme in the regulation of lipid accumulation in filamentous fungi. *Microbiology* 145 (Pt 8), 1911-1917 (1999).

Wynn, J. P., Hamid, A. B. A. & Ratledge, C. The role of malic enzyme in the regulation of lipid accumulation in filamentous fungi. *Microbiology-Uk* 145, 1911-1917 (1999).

Xavier, M. C. A., Coradini, A. L. V., Deckmann, A. C. & Franco, T. T. Lipid production from hemicellulose hydrolysate and acetic acid by *Lipomyces starkeyi* and the ability of yeast to metabolize inhibitors. *Biochemical Engineering Journal* 118, 11-19 (2017).

Xuan, J. W., Fournier, P. & Gaillardin, C. Cloning of the Lys5 gene encoding saccharopine dehydrogenase from the yeast *Yarrowia lipolytica. Current Genetics* 14, 15-21 (1988).

Yen, H.-W., Yang, Y.-C. & Yu, Y.-H. Using crude glycerol and thin stillage for the production of microbial lipids through the cultivation of *Rhodotorula glutinis. Journal of Bioscience and Bioengineering* 114, 453-456 (2012).

Yu, X. C., Dong, T., Zheng, Y. B., Miao, C. & Chen, S. L. Investigations on cell disruption of oleaginous microorganisms: Hydrochloric acid digestion is an effective method for lipid extraction. *European Journal of Lipid Science and Technology* 117, 730-737 (2015).

Yu, X. C., Zheng, Y. B., Dorgan, K. M. & Chen, S. L. Oil production by oleaginous yeasts using the hydrolysate from pretreatment of wheat straw with dilute sulfuric acid. *Bioresource Technology* 102, 6134-6140 (2011).

Zha, J., Shen, M. H., Hu, M. L., Song, H. & Yuan, Y. J. Enhanced expression of genes involved in initial xylose metabolism and the oxidative pentose phosphate pathway in the improved xylose-utilizing *Saccharomyces cerevisiae* through evolutionary engineering. *Journal of Industrial Microbiology & Biotechnology* 41, 27-39 (2014).

Zhang, Y., Adams, I. P. & Ratledge, C. Malic enzyme: the controlling activity for lipid production? Overexpression of malic enzyme in *Mucor circinelloides* leads to a 2.5-fold increase in lipid accumulation. *Microbiology-Sgm* 153, 2013-2025 (2007).

Zhang, Y., Wang, Z. Y., He, X. P., Liu, N. & Zhang, B. R. New industrial brewing yeast strains with ILV2 disruption and LSD1 expression. *International Journal of Food Microbiology* 123, 18-24 (2008).

Zhang, M., Galdieri, L. & Vancura, A. The Yeast AMPK Homolog SNF1 Regulates Acetyl Coenzyme A Homeostasis and Histone Acetylation. *Molecular and Cellular Biology* 33, 4701-4717 (2013).

Zhao, X., Kong, X. L., Hua, Y. Y., Feng, B. & Zhao, Z. B. Medium optimization for lipid production through co-fermentation of glucose and xylose by the oleaginous yeast *Lipomyces starkeyi. European Journal of Lipid Science and Technology* 110, 405-412 (2008).

Zhou, Y. J. J. et al. Production of fatty acid-derived oleochemicals and biofuels by synthetic yeast cell factories. *Nature Communications* 7 (2016).

Zhu, Z. W. et al. in *Nature Communications*, Vol. 3 (2012).

We claim:

1. A composition comprising isolated yeast lipid bodies, wherein:

each lipid body comprises an envelope surrounding an inner core;

the envelope comprises phospholipid, protein, and polysaccharide;

the inner core comprises lipid;

the lipid bodies comprise a set of lipid bodies having a diameter of at least 5 μm:

the lipid bodies are non-synthetic;

the lipid bodies comprise yeast protein; and the yeast protein comprises a protein comprising an amino acid sequence at least 95% identical to SEQ ID NO:41.

2. The composition of claim 1, wherein a number of the lipid bodies in the set is at least 30% of a total number of the lipid bodies in the composition.

3. The composition of claim 1, wherein the lipid bodies comprise a subset of the lipid bodies within the set, wherein the lipid bodies in the subset have a diameter of at least 6 μm.

4. The composition of claim 3, wherein a number of the lipid bodies in the subset is at least 20% of a total number of the lipid bodies in the composition.

5. The composition of claim 1, wherein the lipid bodies in the composition have an average diameter from 5 μm to 10 μm.

6. The composition of claim 1, wherein the set of the lipid bodies comprises lipid bodies having a diameter of at least 12 μm.

7. The composition of claim 1, wherein the lipid in the inner core of the lipid bodies has a melting point at a temperature between 25° C. and 50° C.

8. The composition of claim 1, wherein the lipid bodies absorb light at a wavelength within a range from 190 nm to 290 nm.

9. The composition of claim 1, further comprising a carrier for the lipid bodies, wherein the carrier comprises water.

10. The composition of claim 1, further comprising a carrier for the lipid bodies, wherein the carrier comprises an excipient.

11. The composition of claim 10, wherein the excipient comprises one or more of a humectant, a preservative, an antioxidant, an emulsifier, an emollient, and a thickening agent.

12. The composition of claim 1, wherein the composition is in the form of a cream or a paste.

13. The composition of claim 1, wherein the composition further comprises an active ingredient.

14. The composition of claim 13, wherein the active ingredient comprises a hydrophobic active ingredient.

15. The composition of claim 14, wherein the hydrophobic active ingredient is disposed within the inner core of the lipid bodies.

16. The composition of claim 13, wherein the active ingredient comprises a hydrophilic active ingredient.

17. The composition of claim 1, wherein the composition comprises a hydrophobic active ingredient disposed within the inner core of the lipid bodies and a hydrophilic active ingredient disposed within a carrier or adhered to the envelopes of the lipid bodies.

18. The composition of claim 1, wherein the composition further comprises a cation bound to the envelope of the lipid bodies.

19. A method of preparing the composition of claim 1, the method comprising disrupting yeast cells containing intracellular lipid bodies to release the lipid bodies therefrom.

20. The method of claim 19, further comprising culturing a recombinant lipogenic yeast to generate the intracellular lipid bodies, wherein the recombinant yeast is genetically modified to overexpress a DGA1, a DGA2, a malic enzyme, and an SCT1.

21. The method of claim 19, wherein the disrupting the yeast cells comprises hydrolyzing the yeast cells with acid.

22. The method of claim 19, wherein the disrupting the yeast cells comprises enzymatic digestion of the yeast cells with a yeast lytic enzyme.

23. The method of claim 19, further comprising washing the released lipid bodies with an alkaline buffer having a pH from 10.5 to 12.5 to thereby generate alkaline-washed lipid bodies.

24. The method of claim 23, wherein the alkaline-washed lipid bodies have a lower absorbance at 400 nm than the released lipid bodies.

25. A method comprising administering the composition of claim 1 to an animal.

26. The method of claim 25, wherein the administering comprises at least one of topical administration, oral administration, and parenteral administration.

27. The method of claim 25, wherein the administering comprises applying the composition to a site on a surface of an animal.

28. The method of claim 27, wherein the applying deposits the envelopes of the lipid bodies on the site.

29. The method of claim 28, wherein the envelopes remain deposited on the site for a period of at least one hour after the applying.

30. The method of claim 27, wherein the surface comprises skin.

31. The composition of claim 1, wherein the composition exhibits an absorbance at 400 nm of less than 0.32 OD units per gram of lipid body wet weight.

32. The composition of claim 1, wherein:

a number of the lipid bodies in the set is at least 30% of a total number of the lipid bodies in the composition;

the lipid bodies comprise a subset of the lipid bodies within the set, wherein the lipid bodies in the subset have a diameter of at least 6 μm;

a number of the lipid bodies in the subset is at least 20% of a total number of the lipid bodies in the composition;

the lipid bodies in the composition have an average diameter from 5 μm to 10 μm; and the set of the lipid bodies comprises lipid bodies having a diameter of at least 12 μm.

* * * * *